(12) United States Patent
Mukasa et al.

(10) Patent No.: US 12,145,987 B2
(45) Date of Patent: *Nov. 19, 2024

(54) METHOD FOR DEPLETING CYTOTOXIC T CELLS USING AN ANTI-LAG-3 ANTIBODY COMPOSITION

(71) Applicant: Daiichi Sankyo Company, Limited, Tokyo (JP)

(72) Inventors: Ryuta Mukasa, Taito-ku (JP); Naoki Kiyosawa, Shinagawa-ku (JP); Shinnosuke Yamada, Kawasaki (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 886 days.

This patent is subject to a terminal disclaimer.

(21) Appl. No.: 16/651,531

(22) PCT Filed: Oct. 4, 2018

(86) PCT No.: PCT/JP2018/037139
§ 371 (c)(1),
(2) Date: Mar. 27, 2020

(87) PCT Pub. No.: WO2019/070013
PCT Pub. Date: Apr. 11, 2019

(65) Prior Publication Data
US 2020/0262917 A1    Aug. 20, 2020

(30) Foreign Application Priority Data
Oct. 5, 2017  (JP) .................................. 2017-194945

(51) Int. Cl.
| C07K 16/28 | (2006.01) |
| A61K 39/00 | (2006.01) |
| A61P 37/06 | (2006.01) |
| C07K 16/46 | (2006.01) |

(52) U.S. Cl.
CPC ...... *C07K 16/2803* (2013.01); *A61K 39/0008* (2013.01); *A61P 37/06* (2018.01); *C07K 16/46* (2013.01); *A61K 2039/505* (2013.01); *A61K 2039/577* (2013.01); *C07K 2317/51* (2013.01); *C07K 2317/515* (2013.01)

(58) Field of Classification Search
None
See application file for complete search history.

(56) References Cited

U.S. PATENT DOCUMENTS

| 10,647,769 B1 | 5/2020 | Mukasa et al. |
| 2010/0233183 A1 | 9/2010 | Triebel et al. |
| 2011/0150892 A1 | 6/2011 | Thudium et al. |
| 2014/0093511 A1 | 4/2014 | Lonberg et al. |
| 2014/0286935 A1 | 9/2014 | Hamblin et al. |
| 2015/0259420 A1 | 9/2015 | Triebel et al. |

FOREIGN PATENT DOCUMENTS

| JP | 2010526052 A | 7/2010 |
| JP | 2012-500006 A | 1/2012 |
| JP | 2015-527880 A | 9/2015 |
| JP | 2016-516681 A | 6/2016 |
| JP | 2017-516489 A | 6/2017 |
| JP | 6865758 B2 | 4/2021 |
| WO | 2014/140180 A | 9/2014 |
| WO | 2016/090329 A2 | 6/2016 |
| WO | 2016/090329 A3 | 6/2016 |
| WO | 2016/116626 A1 | 7/2016 |
| WO | 2016200782 A1 | 12/2016 |

OTHER PUBLICATIONS

Yasunaga, M., et al., "Immunoregulation by IL-7R-targeting antibody-drug conjugates: overcoming steroid-resistance in cancer and autoimmune disease", Scientific Reports, Sep. 6, 2017, 7, 10735, 1-14.
Pardoll, D.M., "The blockade of immune checkpoints in cancer immuotherapy", Nature, Apr. 2012, 12, 252-264.
Steward-Tharp, S.M., et al., "New insights into T cell biology and T cell-directed therapy for autoimmunity, inflammation, and immunosuppression", Ann. N.Y. Acad. Sci., 2009, 2009, 1183(2010), 123-148.
Hodge, G., et al., "Steroid Resistant CD8+CD28null NKT-Like Pro-inflammatory Cytotoxic Cells in Chronic Obstructive Pulmonary Disease", Frontiers in Immunology, Dec. 2016, vol. 7, Article 617, 6 pages.
Kataoka, T. et al., "Explore the cytotoxic mechanisms of lymphocytes—Analysis using small-molecule probes," Chemistry and biological, vol. 37, No. 3, 1888, pp. 176-184.
Matsuzaki, J., "Basic and Clinical Applications of LAG-3 Molecules," Cancer for Immunotherapy, Roswell Park Cancer Institute, 13 pages.
Ohara, T., "Tumor necrosis factor Inhibitory Therapy Corrects Abnormal Peripheral T Cells Differentiation (increased terminal differentiated effector memory T Cells) in Individuals with Rheumatoid Arthritis," 2008, Dokkyo Journal of Medical Sciences, vol. 35, No. 1, T99-T119, 37 pages.
Atamaniuk, J., et al., "Overexpression of G Protein-Coupled Receptor 5D in the Bone Marrow Is Associated With Poor Prognosis in Patients With Multiple Myeloma," European Journal of Clinical Investigation 42(9):953-960, Sep. 2012.

(Continued)

*Primary Examiner* — Daniel E Kolker
*Assistant Examiner* — Estella M. Gustilo
(74) *Attorney, Agent, or Firm* — Christensen O'Connor Johnson Kindness PLLC

(57) ABSTRACT

Provided is a composition for cytotoxic T cell depletion, comprising an anti-LAG-3 antibody or a binding fragment thereof having the properties described in (i) to (iii) below: (i) having in vitro ADCC activity; (ii) reducing, in a low fucose form, the number of LAG-3 positive cells in vivo; and (iii) binding to activated human T cells. Also provided are methods for depleting cytotoxic T cells using the disclosed anti-LAG-3 antibody or binding fragment thereof.

12 Claims, 35 Drawing Sheets
(4 of 35 Drawing Sheet(s) Filed in Color)
Specification includes a Sequence Listing.

(56) References Cited

OTHER PUBLICATIONS

Cohen, Y., et al., "GPRC5D Is a Promising Marker for Monitoring the Tumor Load and to Target Multiple Myeloma Cells," Hematology 18(6):347-350, Nov. 2013.

Gershoni, J.M., et al., "Epitope Mapping-The First Step in Developing Epitope-Based Vaccines," in Adis International Limited, New Zealand (ed.), BioDrugs 21(3):145-156, Jan. 1, 2007.

Rudikoff, S., et al., "Single Amino Acid Substitution Altering Antigen-Binding Specificity," Proceedings of the National Academy of Sciences of the United States of America, Immunology 79:1979-1983, Mar. 1982.

Strohl, W.R., "Optimization of Fc-Mediated Effector Functions of Monoclonal Antibodies," Current Opinion in Biotechnology 20:685-691, Dec. 2009.

Matsuzaki, J., "Basic Biology and Clinical Application of LAG-3," Figure 1, Center for Immunotherapy, Roswell Park Cancer Institute, 70(3):360-365, 2015.

Strioga, M., et al., "CD8+ CD28) and CD8+ CD57+ T cells and their role in health and disease," Blackwell Publishing Ltd, Immunology, 134, 17-32.

Pérez De La Lastra, J.M., et al., "Epitope Mapping of 10 Monoclonal Antibodies Against the Pig Analogue of Human Membrane Cofactor Protein (MCP)," Immunology 96(4):663-670, Apr. 1999.

R&D Systems, Catalog No. FAB6300A, "Human GPR5D APC-Conjugated Antibody" (Abstract), Oct. 2015 (Rev. Feb. 2018) <https://resources.mndsystems.com/pdfs/datasheets/fab6300a.pdf>, 1 page.

Matsuzaki, J., "Basic and Clinical Application of LAG-3 Molecules," Advanced Medicine, 2015, 70(3): 360-365.

Huard, B., et al., "Characterization of the major histocompatibility complex class II binding site on LAG-3 protein," Proc. Natl. Acad. Sci. USA, vol. 94, pp. 5744-5749, May 1997.

Notice of Reasons for Refusal as mailed on Apr. 20, 2023, issued by the Japan Patent Office (JPO) in corresponding Japanese Application No. 2019-547003, filed Oct. 4, 2018, 5 pages.

Figure 3
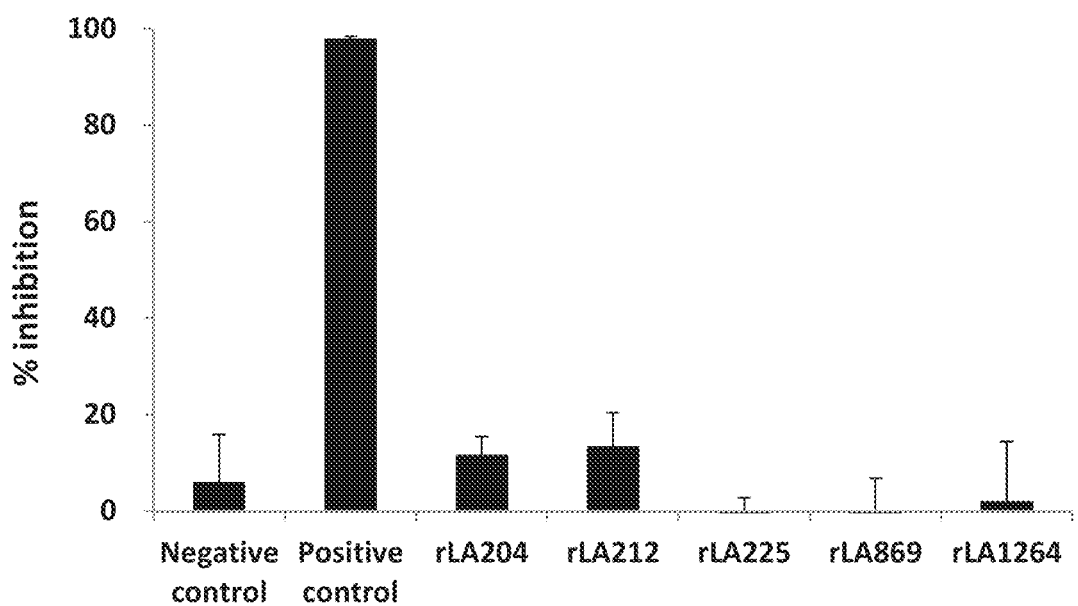
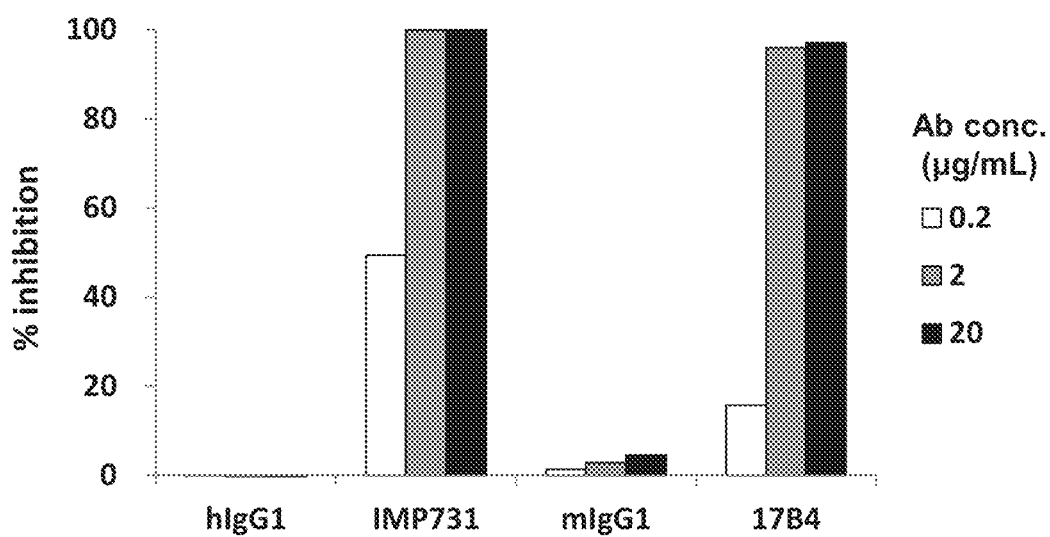

Figure 5
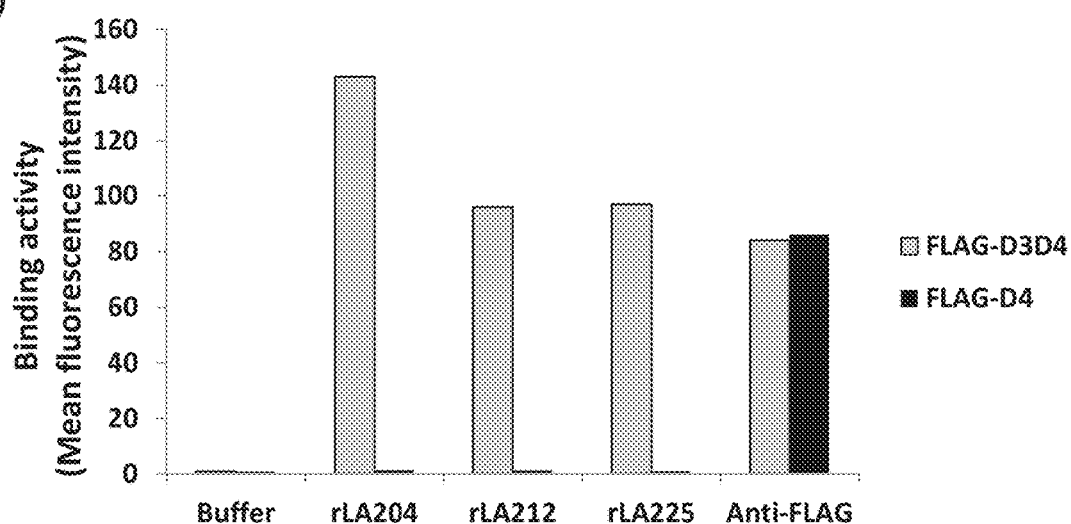
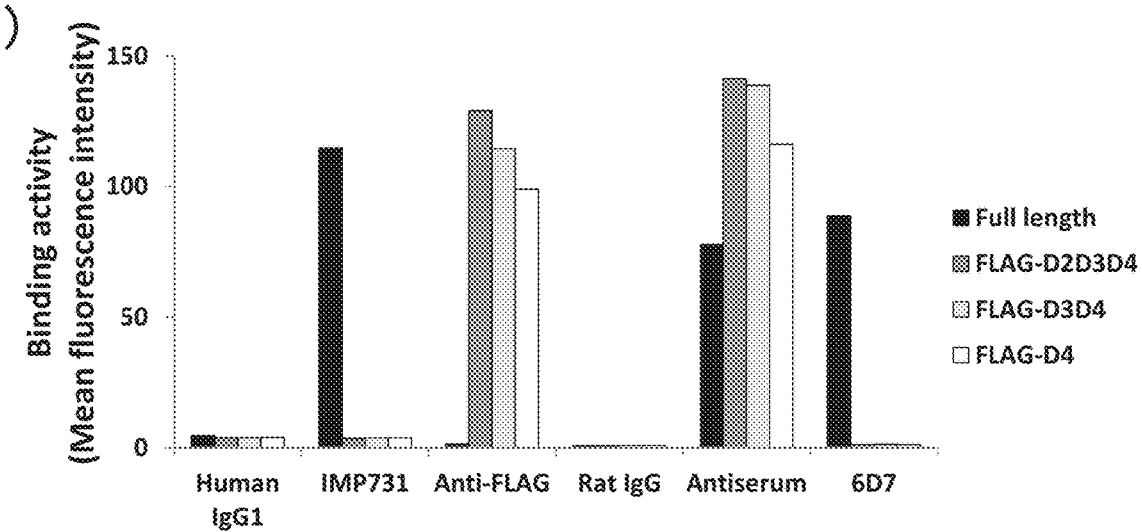

Figure 7

|  | ANTIBODY NAME | KD (nM) |
|---|---|---|
| 1 | hLA212_H2/L1 | 0.11 |
| 2 | hLA212_H2/L2 | 0.12 |
| 3 | hLA212_H2/L3 | 0.15 |
| 4 | hLA212_H2/L4 | 0.096 |
| 5 | hLA212_H2/L5 | 0.12 |
| 6 | hLA212_H3/L1 | 0.092 |
| 7 | hLA212_H3/L2 | 0.062 |
| 8 | hLA212_H3/L3 | 0.10 |
| 9 | hLA212_H3/L4 | 0.076 |
| 10 | hLA212_H3/L5 | 0.10 |

Figure 16
GAGGTAGAGCTGGTGGAGTCTGGGGGCGGCTTAGTGCAGCCTGGAAGGTCCATGAAACTCTCCTGTGCAG
CCTCAGGATTCACTTTCAGAACCTATGGCATGGCCTGGGTCCGCCAGGCTCCAACGAAGGGTCTGGAGTGG
GTCGCATCCATTAGTACTGGTGGTGGTAGCACTTACTATCGCGACTCCGTGAAGGGCCGATTCACTATCTCC
AGAGATAATGCAAAAAGCACCCTATACCTGCAAATGGACAGTCTGAGGTCTGAGGACACGGCCACTTATTA
CTGTACAACAGATCTAATTAACTACCCGGGTATAGGGGGGTTTGCTTTCTGGGGCCAAGGCACTCTGGTCA
CTGTCTCTTCA
VARIABLE REGION (1-366)
  (SEQ ID NO: 1)

Figure 17
EVELVESGGGLVQPGRSMKLSCAASGFTFRTYGMAWVRQAPTKGLEWVASISTGGGSTYYRDSVKGRFTISRD
NAKSTLYLQMDSLRSEDTATYYCTTDLINYPGIGGFAFWGQGTLVTVSS
VARIABLE REGION (1-122)
  (SEQ ID NO: 2)

Figure 18
AACATTGTGATGACCCAGTCTCCCAAATCCATGTCCATATCAGTAGGAGACAGGGTCACCATGAACTGCAA
GGCCAGTCAGAATGTGTATAATAATATAGCCTGGTATCAACAGAAGCCAGGGAAATCTCCTAAACTGTTGA
TCTACTATGCATCTAACCGGTACACTGGGGTCCCTGATCGCTTCACAGGCAGTGGCTCTGGGACAGATTTCA
CTCTCACCATCCATAGTGTGCAAGCTGAAGATGCAGCCTTTTATTACTGTCAGCGTCTTTACAATTCTCCTCC
GACGTTCGGTGGAGGCACCAAGCTGGAATTGAAACGGGCT
VARIABLE REGION (1-327)
  (SEQ ID NO: 3)

Figure 19
NIVMTQSPKSMSISVGDRVTMNCKASQNVYNNIAWYQQKPGKSPKLLIYYASNRYTGVPDRFTGSGSGTDFTL
TIHSVQAEDAAFYYCQRLYNSPPTFGGGTKLELKRA
VARIABLE REGION (1-109)
  (SEQ ID NO: 4)

Figure 20
GAGGTGCAGCTGGTGGAGTCTGGGGGAGGCTTAGTGCAGCCTGGAAGGTCCCTGAAACTCTCCTGTGCAG
CCTCAGGATTCACTTACCGTAGCTATGTCATGGCCTGGGTCCGCCAGGCTCCAACGAGGGGTCTGGAGTGG
GTCGCATCCATTAGTACTGGTGGTGGTAACACTTACTATCGAGACTCCGTGAAGGGCCGATTCACTATCTCC
AGAGATAATGCAAAGAACACCCTATACCTACAAATGGACAGTCTGAGGTCTGAGGACACGGCCACTTATTA
CTGTGCAGAAGACATGAGTAATTCGGGATACGGGCTCTTTGATTACTGGGGCCAAGGAGTCATGGTCACAG
TCTCCTCA
VARIABLE REGION (1-363)
  (SEQ ID NO: 5)

Figure 21
EVQLVESGGGLVQPGRSLKLSCAASGFTYRSYVMAWVRQAPTRGLEWVASISTGGGNTYYRDSVKGRFTISRD
NAKNTLYLQMDSLRSEDTATYYCAEDMSNSGYGLFDYWGQGVMVTVSS
VARIABLE REGION (1-121)
  (SEQ ID NO: 6)

Figure 2 2
AACATTGTGATGACCCAGTCTCCCAAATCCATGTCCATATCAGTAGGAGACAGGGTCACCATGAACTGCAA
GGCCGGTCAGAATGTGGATAATAATATAGCCTGGTATCAAAAGAAACCAGGGCAGTCTCCTAAACTGTTGA
TCTACTATGCATCTAACCGGAACACTGGGGTCCCTGATCGCTTCACAGGCGGTGGATATGGGACAGATTTC
ACTCTCACCATCAATAGTGTGCAAGCTGAAGATGCAGCCTTTTATTACTGTCAGCGTATTTCCAATTCTCCGT
ACACGTTTGGCGCTGGGACCGAGCTGGAACTGAAACGGGCT
VARIABLE REGION (1-327)
 (SEQ ID NO: 7)

Figure 2 3
NIVMTQSPKSMSISVGDRVTMNCKAGQNVDNNIAWYQKKPGQSPKLLIYYASNRNTGVPDRFTGGGYGTDFT
LTINSVQAEDAAFYYCQRISNSPYTFGAGTELELKRA
VARIABLE REGION (1-109)
 (SEQ ID NO: 8)

Figure 2 4
GAGGTGCAGCTGGTGGAGTCTGGGGGAGGCTTAGTGCAGCCTGGAAGGTCCATGAAACTCTCCTGTGTAG
CCTCAGGATTCACTTTCAGTAACTATTACATGGCCTGGGTCCGCCAGGCTCCAACGAAGGGTCTGGAGTGG
GTCGCATCCATTAGTACTGGTGGTGGTAACACTTACTATCGAGACTCCGTGAAGGGCCGATTCACTATCTCC
AGAGATAATGCAAAAAGCACCCTATACCTGCAAATGGACAGTCTGAGGTCTGAGGACACGGCCACTTATTA
CTGTGCAAGACCCCCATATGGCTATAACTACGGTTGGTTTACTTACTGGGGCCAAGGCACTCTGGTCACTGT
CTCTTCA
VARIABLE REGION (1-363)
 (SEQ ID NO: 9)

Figure 2 5
EVQLVESGGGLVQPGRSMKLSCVASGFTFSNYYMAWVRQAPTKGLEWVASISTGGGNTYYRDSVKGRFTISRD
NAKSTLYLQMDSLRSEDTATYYCARPPYGYNYGWFTYWGQGTLVTVSS
VARIABLE REGION (1-121)
 (SEQ ID NO: 1 0)

Figure 2 6
GACATCCAGATGACACAGTCTCCAGCTTCCCTGTCTGCATCTCTGGGAGAAACTGTCACCATCGAATGTCGA
GCAAGTGAGGACATTCACAATGGTTTAGTATGGTATCAGCAGAAGCCAGGGAAATCTCCTCAGCTCCTGAT
CTATAATGCAAATAGTATGCATACTGGGGTCCCATCACGGTTCAGTGGCAGTGGATCTGGTACACAGTATTC
TCTCAAGATAAACAGCCTGCAGTCTGAAGATGTCGCAAGTTATTTCTGTCAACAGTATTACAATTATCCTCG
GACGTTCGGTGGAGGCACCAAGCTGGAATTGAAACGGGCT
VARIABLE REGION (1-327)
 (SEQ ID NO: 1 1)

Figure 2 7
DIQMTQSPASLSASLGETVTIECRASEDIHNGLVWYQQKPGKSPQLLIYNANSMHTGVPSRFSGSGSGTQYSLKI
NSLQSEDVASYFCQQYYNYPRTFGGGTKLELKRA
VARIABLE REGION (1-109)
 (SEQ ID NO: 1 2)

Figure 28
GAGGTGCAGCTGGTGGAGTCTGGGGGAGGCTTAGTGCAGCCTGGAAGGTCCCTGAAACTCTCCTGTGCAG
CCTCAGGATTCACTTATCGTACCTATGTCATGGCCTGGGTCCGCCAGGGTCCAACGCAGGGTCTGGAGTGG
GTCGCATCCATTAGTACTGGTGGTGTTAGCACTTATTATCGAGACTCCGTGAAGGGCCGATTCACTATCTCC
AGAGATAATGCAAAAAACACCCTATACTTGCAAATGGACAGTCTGAGGTCTGAGGACACGGCCACTTATTA
CTGTGCAAAAGACATGTTGAATGGTTATAACTCTCAGGGGCTTTTTGATTACTGGGGCCAAGGAGTCATGG
TCACAGTCTCCTCA
VARIABLE REGION (1-369)
  (SEQ ID NO: 1 3)

Figure 29
EVQLVESGGGLVQPGRSLKLSCAASGFTYRTYVMAWVRQGPTQGLEWVASISTGGVSTYYRDSVKGRFTISRD
NAKNTLYLQMDSLRSEDTATYYCAKDMLNGYNSQGLFDYWGQGVMVTVSS
VARIABLE REGION (1-123)
  (SEQ ID NO: 1 4)

Figure 30
AACATTGTGATGACCCAGTCTCCCAAATCCATGTCCATATCAGTGGGAGACAGGGTCACCATGAACTGCAG
GGCCAGTCAGAATGTGGATAATACTATAGCCTGGTATCAACAGAAACCAGGGCAGTCTCCTAAACTGTTGA
TCTACTTTGCATCTGACCGGTACACTGGGGTCCCTGATCGCTTCACAGGCGGTGGATATGGGACAGATTTCA
CTCTCACCATCAATAGTGTGCAAGCTGAAGATGCAGCCTTTTATTACTGTCAGCGTATTTACAATTCTCCACT
CACGTTCGGTTCTGGGACCAAGCTGGAGATCAGACGGGCT
VARIABLE REGION (1-327)
  (SEQ ID NO: 1 5)

Figure 31
NIVMTQSPKSMSISVGDRVTMNCRASQNVDNTIAWYQQKPGQSPKLLIYFASDRYTGVPDRFTGGGYGTDFTL
TINSVQAEDAAFYYCQRIYNSPLTFGSGTKLEIRRA
VARIABLE REGION (1-109)
  (SEQ ID NO: 1 6)

Figure 32
GAGGTGCAGCTGGTGGAATCTGGGGGAGGCTTAGTGCAGCCTGGAAGGTCCCTGAAACTCTCCTGTGCAG
CCTCAGGATTCACTTTCAGTTCCTATTACATGGCCTGGGTCCGCCAGGCTCCAACGAAGGGTCTGGAGTGG
GTCGCATACATCAGTAATGGTGGTTATAGCACTTACTATCGAGACTCCGTGAAGGGCCGATTCACTATCTCC
AGAGAAAATGCAAAAAGCACCCTTTACCTGCAAATGGACAGTCTGAGGTCTGAGGACACGGCCACTTATTA
CTGTACAATCACAGATCATTCGGGGTACAGGTTTACTTACTGGGGCCAAGGCACTCTGGTCACTGTCTCTTC
A
VARIABLE REGION (1-357)
  (SEQ ID NO: 1 7)

Figure 33
EVQLVESGGGLVQPGRSLKLSCAASGFTFSSYYMAWVRQAPTKGLEWVAYISNGGYSTYYRDSVKGRFTISREN
AKSTLYLQMDSLRSEDTATYYCTITDHSGYRFTYWGQGTLVTVSS
VARIABLE REGION (1-119)
  (SEQ ID NO: 1 8)

Figure 34
GACATCCAGATGACCCAGTCTCCTTCACTCCTGTCAGCATCTGTGGGAGACAGAGTCACTCTCAGCTGCAAA
GCAAGTCAGAGTATTTACAACAGCTTAGCCTGGTATCAGCAAAAACTTGGAGAAGCTCCCAAACTCCTCATA
TATGATGCAAACAGTTTGCAAACGGGCATCCCATCAAGGTTCAGTGGCAGTGGATCTGGTACAGATTTCAC
ACTCACCATCAGCAGCCTGCAGCCTGAAGATGTTGCCACATATTTCTGCCAGAAGTATTATAGCGGGAACAC
GTTTGGAGCTGGGACCAAGCTGGAACTGAAACGGGCT
VARIABLE REGION (1-324)
(SEQ ID NO: 1 9)

Figure 35
DIQMTQSPSLLSASVGDRVTLSCKASQSIYNSLAWYQQKLGEAPKLLIYDANSLQTGIPSRFSGSGSGTDFTLTISS
LQPEDVATYFCQKYYSGNTFGAGTKLELKRA
VARIABLE REGION (1-108)
(SEQ ID NO: 2 0)

Figure 36
gcctccggactctagagccaccATGGTGCTGCAGACCCAGGTGTTCATCTCCCTGCTGCTGTGGATCTCCGGCGCGT
ACGGCGATATCGTGATGATTAAACGTACGGTGGCCGCCCCTCCGTGTTCATCTTCCCCCCCTCCGACGAGC
AGCTGAAGTCCGGCACCGCCTCCGTGGTGTGCCTGCTGAATAACTTCTACCCCAGAGAGGCCAAGGTGCAG
TGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCT
GCGAGGTGACCCACCAGGGCCTGAGCTCCCCCGTCACCAAGAGCTTCAACAGGGGGGAGTGTtaggggcccgt
ttaaacgggggaggcta
(SEQ ID NO: 2 1)

Figure 37
gcctccggactctagagccaccATGAAACACCTGTGGTTCTTCCTCCTGCTGGTGGCAGCTCCCAGATGGGTGCTGA
GCCAGGTGCAATTGTGCAGGCGGTTAGCTCAGCCTCCACCAAGGGCCCAAGCGTCTTCCCCCTGGCACCCT
CCTCCAAGAGCACCTCTGGCGGCACAGCCGCCCTGGGCTGCCTGGTCAAGGACTACTTCCCCGAACCCGTG
ACCGTGAGCTGGAACTCAGGCGCCCTGACCAGCGGCGTGCACACCTTCCCCGCTGTCCTGCAGTCCTCAGG
ACTCTACTCCCTCAGCAGCGTGGTGACCGTGCCCTCCAGCAGCTTGGGCACCCAGACCTACATCTGCAACGT
GAATCACAAGCCCAGCAACACCAAGGTGGACAAGAGAGTTGAGCCCAAATCTTGTGACAAAACTCACACAT
GCCCACCCTGCCCAGCACCTGAACTCCTGGGGGGACCCTCAGTCTTCCTCTTCCCCCCAAAACCCAAGGACA
CCCTCATGATCTCCCGGACCCCTGAGGTCACATGCGTGGTGGTGGACGTGAGCCACGAAGACCCTGAGGTC
AAGTTCAACTGGTACGTGGACGGCGTGGAGGTGCATAATGCCAAGACAAAGCCCCGGGAGGAGCAGTACA
ACAGCACGTACCGGGTGGTCAGCGTCCTCACCGTCCTGCACCAGGACTGGCTGAATGGCAAGGAGTACAA
GTGCAAGGTCTCCAACAAAGCCCTCCCAGCCCCCATCGAGAAAACCATCTCCAAAGCCAAAGGCCAGCCCC
GGGAACCACAGGTGTACACCCTGCCCCCATCCCGGGAGGAGATGACCAAGAACCAGGTCAGCCTGACCTG
CCTGGTCAAAGGCTTCTATCCCAGCGACATCGCCGTGGAGTGGGAGAGCAATGGCCAGCCCGAGAACAAC
TACAAGACCACCCCTCCCGTGCTGGACTCCGACGGCTCCTTCTTCCTCTACAGCAAGCTCACCGTGGACAAG
AGCAGGTGGCAGCAGGGCAACGTCTTCTCATGCTCCGTGATGCATGAGGCTCTGCACAACCACTACACCCA
GAAGAGCCTCTCCCTGTCTCCGGGCAAAtgagatatcgggcccgtttaaacgggggaggcta
(SEQ ID NO: 2 2)

Figure 38

ATGAAACACCTGTGGTTCTTCCTCCTGCTGGTGGCAGCTCCCAGATGGGTGCTGAGCGAGGTGCAGCTGGT
GGAGTCTGGGGGAGGCTTAGTGCAGCCTGGAAGGTCCCTGAAACTCTCCTGTGCAGCCTCAGGATTCACTT
ACCGTAGCTATGTCATGGCCTGGGTCCGCCAGGCTCCAACGAGGGGTCTGGAGTGGGTCGCATCCATTAGT
ACTGGTGGTGGTAACACTTACTATCGAGACTCCGTGAAGGGCCGATTCACTATCTCCAGAGATAATGCAAA
GAACACCCTATACCTACAAATGGACAGTCTGAGGTCTGAGGACACGGCCACTTATTACTGTGCAGAAGACA
TGAGTAATTCGGGATACGGGCTCTTTGATTACTGGGGCCAAGGAGTCATGGTCACAGTCAGCTCAGCCTCC
ACCAAGGGCCCAAGCGTCTTCCCCCTGGCACCCTCCTCCAAGAGCACCTCTGGCGGCACAGCCGCCCTGGG
CTGCCTGGTCAAGGACTACTTCCCCGAACCCGTGACCGTGAGCTGGAACTCAGGCGCCCTGACCAGCGGCG
TGCACACCTTCCCCGCTGTCCTGCAGTCCTCAGGACTCTACTCCCTCAGCAGCGTGGTGACCGTGCCCTCC
AGCAGCTTGGGCACCCAGACCTACATCTGCAACGTGAATCACAAGCCCAGCAACACCAAGGTGGACAAGAG
AGTTGAGCCCAAATCTTGTGACAAAACTCACACATGCCCACCCTGCCCAGCACCTGAACTCCTGGGGGGACC
CTCAGTCTTCCTCTTCCCCCCAAAACCCAAGGACACCCTCATGATCTCCCGGACCCCTGAGGTCACATGCGTG
GTGGTGGACGTGAGCCACGAAGACCCTGAGGTCAAGTTCAACTGGTACGTGGACGGCGTGGAGGTGCATA
ATGCCAAGACAAAGCCCCGGGAGGAGCAGTACAACAGCACGTACCGGGTGGTCAGCGTCCTCACCGTCCT
GCACCAGGACTGGCTGAATGGCAAGGAGTACAAGTGCAAGGTCTCCAACAAAGCCCTCCCAGCCCCCATCG
AGAAAACCATCTCCAAAGCCAAAGGCCAGCCCCGGGAACCACAGGTGTACACCCTGCCCCCATCCCGGGAG
GAGATGACCAAGAACCAGGTCAGCCTGACCTGCCTGGTCAAAGGCTTCTATCCCAGCGACATCGCCGTGGA
GTGGGAGAGCAATGGCCAGCCCGAGAACAACTACAAGACCACCCCTCCCGTGCTGGACTCCGACGGCTCCT
TCTTCCTCTACAGCAAGCTCACCGTGGACAAGAGCAGGTGGCAGCAGGGCAACGTCTTCTCATGCTCCGTG
ATGCATGAGGCTCTGCACAACCACTACACCCAGAAGAGCCTCTCCCTGTCTCCGGCAAA
SIGNAL SEQUENCE (1-57), HEAVY CHAIN VARIABLE REGION (58-420), HEAVY CHAIN
CONSTANT REGION (421-1410)
(SEQ ID NO: 23)

Figure 39

MKHLWFFLLLVAAPRWVLSEVQLVESGGGLVQPGRSLKLSCAASGFTYRSYVMAWVRQAPTRGLEWVASISTG
GGNTYYRDSVKGRFTISRDNAKNTLYLQMDSLRSEDTATYYCAEDMSNSGYGLFDYWGQGVMVTVSSASTKG
PSVFPLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFLYSKLTVDKSRWQQGN
VFSCSVMHEALHNHYTQKSLSLSPGK
SIGNAL SEQUENCE (1-19), HEAVY CHAIN VARIABLE REGION (20-140), HEAVY CHAIN
CONSTANT REGION (141-470)
(SEQ ID NO: 24)

Figure 40

ATGGTGCTGCAGACCCAGGTGTTCATCTCCCTGCTGCTGTGGATCTCCGGCGCGTACGGCAACATTGTGATG
ACCCAGTCTCCAAATCCATGTCCATATCAGTAGGAGACAGGGTCACCATGACTGCAAGGCCGGTCAGAA
TGTGGATAATAATATAGCCTGGTATCAAAAGAAACCAGGGCAGTCTCCTAAACTGTTGATCTACTATGCATC
TAACCGGAACACTGGGGTCCCTGATCGCTTCACAGGCGGTGGATATGGGACAGATTTCACTCTCACCATCA
ATAGTGTGCAAGCTGAAGATGCAGCCTTTTATTACTGTCAGCGTATTTCCAATTCTCCGTACACGTTTGGCGC
TGGGACCGAGCTGGAACTGAAACGGGCTGTGGCCGCCCCTCCGTGTTCATCTTCCCCCCTCCGACGAGC
AGCTGAAGTCCGGCACCGCCTCCGTGGTGTGCCTGCTGAATAACTTCTACCCCAGAGAGGCCAAGGTGCAG
TGGAAGGTGGACAACGCCCTGCAGTCCGGGAACTCCCAGGAGAGCGTGACCGAGCAGGACAGCAAGGAC
AGCACCTACAGCCTGAGCAGCACCCTGACCCTGAGCAAAGCCGACTACGAGAAGCACAAGGTGTACGCCT
GCGAGGTGACCCACCAGGGCCTGAGCTCCCCCGTCACCAAGAGCTTCAACAGGGGGGAGTGT
SIGNAL SEQUENCE (1-60), LIGHT CHAIN VARIABLE REGION (61-387), LIGHT CHAIN
CONSTANT REGION (388-702)
(SEQ ID NO: 25)

Figure 4 1
MVLQTQVFISLLLWISGAYGNIVMTQSPKSMSISVGDRVTMNCKAGQNVDNNIAWYQKKPGQSPKLLIYYASN
RNTGVPDRFTGGGYGTDFTLTINSVQAEDAAFYYCQRISNSPYTFGAGTELELKRAVAAPSVFIFPPSDEQLKSGT
ASVVCLLNNFYPREAKVQWKVDNALQSGNSQESVTEQDSKDSTYSLSSTLTLSKADYEKHKVYACEVTHQGLSSP
VTKSFNRGEC
SIGNAL SEQUENCE (1-20), LIGHT CHAIN VARIABLE REGION (21-129), LIGHT CHAIN
CONSTANT REGION (130-234)
(SEQ ID NO: 2 6)

Figure 4 2
ATGAAACACCTGTGGTTCTTCCTCCTGCTGGTGGCAGCTCCCAGATGGGTGCTGAGCGAAGTGCAGCTGGT
GGAATCTGGCGGCGGACTGGTGCAGCCTGGCGGATCTCTGAGACTGAGCTGTGCCGCCAGCGGCTTCACC
TACCGGTCTTACGTGATGGCCTGGGTGCGCCAGGCCCCTGGAAAAGGACTGGAATGGGTGGGATCCATCA
GCACCGGCGGAGGCAACACCTACTACCGGGATAGCGTGAAGGGCCGGTTCACCATCAGCCGGGACAACGC
CAAGAACACCCTGTACCTGCAGATGAACAGCCTGCGGGCCGAGGACACCGCCGTGTACTATTGCGCCGAG
GATATGAGCAACAGCGGCTACGGCCTGTTCGACTACTGGGGCCAGGGAACCCTCGTGACCGTCAGCTCAGC
CTCCACCAAGGGCCCAAGCGTCTTCCCCCTGGCACCCTCCTCCAAGAGCACCTCTGGCGGCACAGCCGCCCT
GGGCTGCCTGGTCAAGGACTACTTCCCCGAACCCGTGACCGTGAGCTGGAACTCAGGCGCCCTGACCAGCG
GCGTGCACACCTTCCCCGCTGTCCTGCAGTCCTCAGGACTCTACTCCCTCAGCAGCGTGGTGACCGTGCCCT
CCAGCAGCTTGGGCACCCAGACCTACATCTGCAACGTGAATCACAAGCCCAGCAACACCAAGGTGGACAAG
AGAGTTGAGCCCAAATCTTGTGACAAAACTCACACATGCCCACCCTGCCCAGCACCTGAACTCCTGGGGGG
ACCCTCAGTCTTCCTCTTCCCCCCAAAACCCAAGGACACCCTCATGATCTCCCGGACCCCTGAGGTCACATGC
GTGGTGGTGGACGTGAGCCACGAAGACCCTGAGGTCAAGTTCAACTGGTACGTGGACGGCGTGGAGGTG
CATAATGCCAAGACAAAGCCCCGGGAGGAGCAGTACAACAGCACGTACCGGGTGGTCAGCGTCCTCACCG
TCCTGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGCCAGCCCCGGGAACCACAGGTGTACACCCTGCCCCCATCCCG
GGAGGAGATGACCAAGAACCAGGTCAGCCTGACCTGCCTGGTCAAAGGCTTCTATCCCAGCGACATCGCCG
TGGAGTGGGAGAGCAATGGCCAGCCCGAGAACAACTACAAGACCACCCCTCCCGTGCTGGACTCCGACGG
CTCCTTCTTCCTCTACAGCAAGCTCACCGTGGACAAGAGCAGGTGGCAGCAGGGCAACGTCTTCTCATGCTC
CGTGATGCATGAGGCTCTGCACAACCACTACACCCAGAAGAGCCTCTCCCTGTCTCCCGGCAAA
SIGNAL SEQUENCE (1-57), HEAVY CHAIN VARIABLE REGION (58-420), HEAVY CHAIN
CONSTANT REGION (421-1410)
(SEQ ID NO: 2 7)

Figure 4 3
MKHLWFFLLLVAAPRWVLSEVQLVESGGGLVQPGGSLRLSCAASGFTYRSYVMAWVRQAPGKGLEWVGSIST
GGGNTYYRDSVKGRFTISRDNAKNTLYLQMNSLRAEDTAVYYCAEDMSNSGYGLFDYWGQGTLVTVSSASTKG
PSVFPLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFLYSKLTVDKSRWQQGN
VFSCSVMHEALHNHYTQKSLSLSPGK
SIGNAL SEQUENCE (1-19), HEAVY CHAIN VARIABLE REGION (20-140), HEAVY CHAIN
CONSTANT REGION (141-470)
(SEQ ID NO: 2 8)

Figure 44

ATGAAACACCTGTGGTTCTTCCTCCTGCTGGTGGCAGCTCCCAGATGGGTGCTGAGCGAAGTGCAGCTGGT
GGAATCTGGCGGCGGACTGGTGCAGCCTGGCGGATCTCTGAGACTGAGCTGTGCCGCCAGCGGCTTCACC
TACCGGTCTTACGTGATGGCCTGGGTGCGCCAGGCCCCTGGAAAAGGACTGGAATGGGTGGCCAGCATCA
GCACCGGCGGAGGCAACACCTACTACCGGGATAGCGTGAAGGGCCGGTTCACCATCAGCCGGGACAACGC
CAAGAACACCCTGTACCTGCAGATGGACAGCCTGCGGGCCGAGGATACCGCCGTGTACTACTGTGCCGAG
GACATGAGCAACAGCGGCTACGGCCTGTTCGACTACTGGGGCCAGGGAACCCTCGTGACCGTCAGCTCAG
CCTCCACCAAGGGCCCAAGCGTCTTCCCCCTGGCACCCTCCTCCAAGAGCACCTCTGGCGGCACAGCCGCCC
TGGGCTGCCTGGTCAAGGACTACTTCCCCGAACCCGTGACCGTGAGCTGGAACTCAGGCGCCCTGACCAGC
GGCGTGCACACCTTCCCCGCTGTCCTGCAGTCCTCAGGACTCTACTCCCTCAGCAGCGTGGTGACCGTGCCC
TCCAGCAGCTTGGGCACCCAGACCTACATCTGCAACGTGAATCACAAGCCCAGCAACACCAAGGTGGACAA
GAGAGTTGAGCCCAAATCTTGTGACAAAACTCACACATGCCCACCCTGCCCAGCACCTGAACTCCTGGGGG
GACCCTCAGTCTTCCTCTTCCCCCCAAAACCCAAGGACACCCTCATGATCTCCCGGACCCCTGAGGTCACATG
CGTGGTGGTGGACGTGAGCCACGAAGACCCTGAGGTCAAGTTCAACTGGTACGTGGACGGCGTGGAGGT
GCATAATGCCAAGACAAAGCCCCGGGAGGAGCAGTACAACAGCACGTACCGGGTGGTCAGCGTCCTCACC
GTCCTGCACCAGGACTGGCTGAATGGCAAGGAGTACAAGTGCAAGGTCTCCAACAAAGCCCTCCCAGCCCC
CATCGAGAAAACCATCTCCAAAGCCAAAGGCCAGCCCCGGGAACCACAGGTGTACACCCTGCCCCCATCCC
GGGAGGAGATGACCAAGAACCAGGTCAGCCTGACCTGCCTGGTCAAAGGCTTCTATCCCAGCGACATCGCC
GTGGAGTGGGAGAGCAATGGCCAGCCCGAGAACAACTACAAGACCACCCCTCCCGTGCTGGACTCCGACG
GCTCCTTCTTCCTCTACAGCAAGCTCACCGTGGACAAGAGCAGGTGGCAGCAGGGCAACGTCTTCTCATGCT
CCGTGATGCATGAGGCTCTGCACAACCACTACACCCAGAAGAGCCTCTCCCTGTCTCCGGCAAA
SIGNAL SEQUENCE (1-57), HEAVY CHAIN VARIABLE REGION (58-420), HEAVY CHAIN
CONSTANT REGION (421-1410)
(SEQ ID NO: 2 9)

Figure 45

MKHLWFFLLLVAAPRWVLSEVQLVESGGGLVQPGGSLRLSCAASGFTYRSYVMAWVRQAPGKGLEWVASIST
GGGNTYYRDSVKGRFTISRDNAKNTLYLQMDSLRAEDTAVYYCAEDMSNSGYGLFDYWGQGTLVTVSSASTKG
PSVFPLAPSSKSTSGGTAALGCLVKDYFPEPVTVSWNSGALTSGVHTFPAVLQSSGLYSLSSVVTVPSSSLGTQTYI
CNVNHKPSNTKVDKRVEPKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKALPAPIEKTISKAKGQPREPQ
VYTLPPSREEMTKNQVSLTCLVKGFYPSDIAVEWESNGQPENNYKTTPPVLDSDGSFFLYSKLTVDKSRWQQGN
VFSCSVMHEALHNHYTQKSLSLSPGK
SIGNAL SEQUENCE (1-19), HEAVY CHAIN VARIABLE REGION (20-140), HEAVY CHAIN
CONSTANT REGION (141-470)
(SEQ ID NO: 3 0)

Figure 46

ATGGTGCTGCAGACCCAGGTGTTCATCTCCCTGCTGCTGTGGATCTCCGGCGCGTACGGCGACATCCAGAT
GACCCAGAGCCCTAGCAGCCTGAGCGCCAGCGTGGGCGACAGAGTGACCATCACCTGTAAAGCCGGCCAG
AACGTGGACAACAATATCGCCTGGTATCAGCAGAAGCCCGGCCAGGCCCCTAAGCTGCTGATCTACTACGC
CAGCAACCGGAACACCGGCGTGCCCAGCAGATTTTCTGGCAGCGGCTCCGGCACCGACTTCACCCTGACAA
TCAGCAGCCTGCAGCCCGAGGACTTCGCCACCTACTACTGCCAGAGAATCAGCAACAGCCCCTACACCTTCG
GCCAGGGCACCAAGGTGGAAATCAAGCGTACGGTGGCCGCCCCTCCGTGTTCATCTTCCCCCCCTCCGAC
GAGCAGCTGAAGTCCGGCACCGCCTCCGTGGTGTGCCTGCTGAATAACTTCTACCCCAGAGAGGCCAAGGT
GCAGTGGAAGGTGGACAACGCCCTGCAGTCCGGGAACTCCCAGGAGAGCGTGACCGAGCAGGACAGCAA
GGACAGCACCTACAGCCTGAGCAGCACCCTGACCCTGAGCAAAGCCGACTACGAGAAGCACAAGGTGTAC
GCCTGCGAGGTGACCCACCAGGGCCTGAGCTCCCCCGTCACCAAGAGCTTCAACAGGGGGGAGTGT
SIGNAL SEQUENCE (1-60), LIGHT CHAIN VARIABLE REGION (61-387), LIGHT CHAIN
CONSTANT REGION (388-702)
(SEQ ID NO: 3 1)

Figure 47
MVLQTQVFISLLLWISGAYGDIQMTQSPSSLSASVGDRVTITCKAGQNVDNNIAWYQQKPGQAPKLLIYYASNR
NTGVPSRFSGSGSGTDFTLTISSLQPEDFATYYCQRISNSPYTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGLSSPVTK
SFNRGEC
SIGNAL SEQUENCE (1-20), LIGHT CHAIN VARIABLE REGION (21-129), LIGHT CHAIN
CONSTANT REGION (130-234)
(SEQ ID NO: 3 2)

Figure 48
ATGGTGCTGCAGACCCAGGTGTTCATCTCCCTGCTGCTGTGGATCTCCGGCGCGTACGGCGACATCCAGAT
GACCCAGAGCCCTAGCAGCCTGAGCGCCAGCGTGGGCGACAGAGTGACCATCACCTGTAAAGCCGGCCAG
AACGTGGACAACAATATCGCCTGGTATCAGCAGAAGCCCGGCCAGAGCCCCAAGCTGCTGATCTACTACGC
CAGCAACCGGAACACCGGCGTGCCCAGCAGATTTTCCGGCAGCGGCTACGGCACCGACTTCACCCTGACAA
TCAGCAGCCTGCAGCCCGAGGACTTCGCCACCTACTACTGCCAGAGAATCAGCAACAGCCCCTACACCTTCG
GCCAGGGCACCAAGGTGGAAATCAAGCGTACGGTGGCCGCCCCCTCCGTGTTCATCTTCCCCCCCTCCGAC
GAGCAGCTGAAGTCCGGCACCGCCTCCGTGGTGTGCCTGCTGAATAACTTCTACCCCAGAGAGGCCAAGGT
GCAGTGGAAGGTGGACAACGCCCTGCAGTCCGGGAACTCCAGGAGAGCGTGACCGAGCAGGACAGCAA
GGACAGCACCTACAGCCTGAGCAGCACCCTGACCCTGAGCAAAGCCGACTACGAGAAGCACAAGGTGTAC
GCCTGCGAGGTGACCCACCAGGGCCTGAGCTCCCCCGTCACCAAGAGCTTCAACAGGGGGGAGTGT
SIGNAL SEQUENCE (1-60), LIGHT CHAIN VARIABLE REGION (61-387), LIGHT CHAIN
CONSTANT REGION (388-702)
(SEQ ID NO: 3 3)

Figure 49
MVLQTQVFISLLLWISGAYGDIQMTQSPSSLSASVGDRVTITCKAGQNVDNNIAWYQQKPGQSPKLLIYYASNR
NTGVPSRFSGSGYGTDFTLTISSLQPEDFATYYCQRISNSPYTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTHQGLSSPVT
K SFNRGEC
SIGNAL SEQUENCE (1-20), LIGHT CHAIN VARIABLE REGION (21-129), LIGHT CHAIN
CONSTANT REGION (130-234)
(SEQ ID NO: 3 4)

Figure 50
ATGGTGCTGCAGACCCAGGTGTTCATCTCCCTGCTGCTGTGGATCTCCGGCGCGTACGGCAACATCCAGAT
GACCCAGAGCCCCAGCAGCCTGTCTGCCAGCGTGGGCGACAGAGTGACCATCACATGCAAGGCCGGCCAG
AACGTGGACAACAATATCGCCTGGTATCAGAAGAAGCCCGGCCAGTCCCCCAAGCTGCTGATCTACTACGC
CAGCAACCGGAACACCGGCGTGCCCGACAGATTTTCCGGCGGAGGCTACGGCACCGACTTCACCCTGACCA
TCAGCTCCCTGCAGCCCGAGGACTTCGCCTTCTACTACTGTCAGCGGATCAGCAACAGCCCCTACACCTTCG
GCCAGGGCACCAAGGTGGAAATCAAGCGTACGGTGGCCGCCCCCTCCGTGTTCATCTTCCCCCCCTCCGAC
GAGCAGCTGAAGTCCGGCACCGCCTCCGTGGTGTGCCTGCTGAATAACTTCTACCCCAGAGAGGCCAAGGT
GCAGTGGAAGGTGGACAACGCCCTGCAGTCCGGGAACTCCAGGAGAGCGTGACCGAGCAGGACAGCAA
GGACAGCACCTACAGCCTGAGCAGCACCCTGACCCTGAGCAAAGCCGACTACGAGAAGCACAAGGTGTAC
GCCTGCGAGGTGACCCACCAGGGCCTGAGCTCCCCCGTCACCAAGAGCTTCAACAGGGGGGAGTGT
SIGNAL SEQUENCE (1-60), LIGHT CHAIN VARIABLE REGION (61-387), LIGHT CHAIN
CONSTANT REGION (388-702)
(SEQ ID NO: 3 5)

Figure 5 1
MVLQTQVFISLLLWISGAYGNIQMTQSPSSLSASVGDRVTITCKAGQNVDNNIAWYQKKPGQSPKLLIYYASNR
NTGVPDRFSGGGYGTDFTLTISSLQPEDFAFYYCQRISNSPYTFGQGTKVEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQGLSSPV
TKSFNRGEC
SIGNAL SEQUENCE (1-20), LIGHT CHAIN VARIABLE REGION (21-129), LIGHT CHAIN
CONSTANT REGION (130-234)
(SEQ ID NO: 3 6)

Figure 5 2
ATGGTGCTGCAGACCCAGGTGTTCATCTCCCTGCTGCTGTGGATCTCCGGCGCGTACGGCGACATCCAGAT
GACCCAGAGCCCCAGCAGCATGAGCATCAGCGTGGGCGACAGAGTGACCATGACCTGCAAGGCCGGCCAG
AACGTGGACAACAATATCGCCTGGTATCAGAAGAAGCCCGGCCAGTCCCCCAAGCTGCTGATCTACTACGC
CAGCAACCGGAACACCGGCGTGCCCAGCAGATTTTCTGGCAGCGGCTCCGGCACCGACTTCACCCTGACAA
TCAGCAGCGTGCAGCCCGAGGACTTCGCCACCTACTACTGCCAGAGAATCAGCAACAGCCCCTACACCTTCG
GCCAGGGCACCAAGCTGGAACTGAAGCGTACGGTGGCCGCCCCCTCCGTGTTCATCTTCCCCCCCTCCGAC
GAGCAGCTGAAGTCCGGCACCGCCTCCGTGGTGTGCCTGCTGAATAACTTCTACCCCAGAGAGGCCAAGGT
GCAGTGGAAGGTGGACAACGCCCTGCAGTCCGGGAACTCCCAGGAGAGCGTGACCGAGCAGGACAGCAA
GGACAGCACCTACAGCCTGAGCAGCACCCTGACCCTGAGCAAAGCCGACTACGAGAAGCACAAGGTGTAC
GCCTGCGAGGTGACCCACCAGGGCCTGAGCTCCCCCGTCACCAAGAGCTTCAACAGGGGGGAGTGT
SIGNAL SEQUENCE (1-60), LIGHT CHAIN VARIABLE REGION (61-387), LIGHT CHAIN
CONSTANT REGION (388-702)
(SEQ ID NO: 3 7)

Figure 5 3
MVLQTQVFISLLLWISGAYGDIQMTQSPSSMSISVGDRVTMTCKAGQNVDNNIAWYQKKPGQSPKLLIYYASN
RNTGVPSRFSGSGSGTDFTLTISSVQPEDFATYYCQRISNSPYTFGQGTKLELKRTVAAPSVFIFPPSDEQLKSGTA
SVVCLLNNFYPREAKVQWKVDNALQSGNSQESVTEQDSKDSTYSLSSTLTLSKADYEKHKVYACEVTHQGLSSPV
TKSFNRGEC
SIGNAL SEQUENCE (1-20), LIGHT CHAIN VARIABLE REGION (21-129), LIGHT CHAIN
CONSTANT REGION (130-234)
(SEQ ID NO: 3 8)

Figure 5 4
ATGGTGCTGCAGACCCAGGTGTTCATCTCCCTGCTGCTGTGGATCTCCGGCGCGTACGGCAACATCCAGAT
GACCCAGAGCCCCAGCAGCATGAGCATCAGCGTGGGCGACAGAGTGACCATGACCTGCAAGGCCGGCCAG
AACGTGGACAACAATATCGCCTGGTATCAGAAGAAGCCCGGCCAGTCCCCCAAGCTGCTGATCTACTACGC
CAGCAACCGGAACACCGGCGTGCCCGACAGATTTTCCGGCGGAGGCTACGGCACCGACTTCACCCTGACAA
TCAGCAGCGTGCAGCCCGAGGACGCCGCCTTCTACTACTGTCAGCGGATCAGCAACAGCCCCTACACCTTC
GGCCAGGGCACCAAGCTGGAACTGAAGCGTACGGTGGCCGCCCCCTCCGTGTTCATCTTCCCCCCCTCCGA
CGAGCAGCTGAAGTCCGGCACCGCCTCCGTGGTGTGCCTGCTGAATAACTTCTACCCCAGAGAGGCCAAGG
TGCAGTGGAAGGTGGACAACGCCCTGCAGTCCGGGAACTCCCAGGAGAGCGTGACCGAGCAGGACAGCA
AGGACAGCACCTACAGCCTGAGCAGCACCCTGACCCTGAGCAAAGCCGACTACGAGAAGCACAAGGTGTA
CGCCTGCGAGGTGACCCACCAGGGCCTGAGCTCCCCCGTCACCAAGAGCTTCAACAGGGGGGAGTGT
SIGNAL SEQUENCE (1-60), LIGHT CHAIN VARIABLE REGION (61-387), LIGHT CHAIN
CONSTANT REGION (388-702)
(SEQ ID NO: 3 9)

Figure 55
MVLQTQVFISLLLWISGAYGNIQMTQSPSSMSISVGDRVTMTCKAGQNVDNNIAWYQKKPGQSPKLLIYYASN
RNTGVPDRFSGGGYGTDFTLTISSVQPEDAAFYYCQRISNSPYTFGQGTKLELKRTVAAPSVFIFPPSDEQLKSGT
ASVVCLLNNFYPREAKVQWKVDNALQSGNSQESVTEQDSKDSTYSLSSTLTLSKADYEKHKVYACEVTHQGLSSP
VTKSFNRGEC
SIGNAL SEQUENCE (1-20), LIGHT CHAIN VARIABLE REGION (21-129), LIGHT CHAIN
CONSTANT REGION (130-234)
(SEQ ID NO: 40)

Figure 56
GFTFRTYGMA
(SEQ ID NO: 41)

Figure 57
SISTGGGSTYYRDSVKG
(SEQ ID NO: 42)

Figure 58
DLINYPGIGGFAF
(SEQ ID NO: 43)

Figure 59
KASQNVYNNIA
(SEQ ID NO: 44)

Figure 60
YASNRYT
(SEQ ID NO: 45)

Figure 61
QRLYNSPPT
(SEQ ID NO: 46)

Figure 62
GFTYRSYVMA
(SEQ ID NO: 47)

Figure 63
SISTGGGNTYYRDSVKG
(SEQ ID NO: 48)

Figure 64
DMSNSGYGLFDY
(SEQ ID NO: 49)

Figure 65
KAGQNVDNNIA
(SEQ ID NO: 50)

Figure 66
YASNRNT
  (SEQ ID NO: 51)

Figure 67
QRISNSPYT
  (SEQ ID NO: 52)

Figure 68
GFTFSNYYMA
  (SEQ ID NO: 53)

Figure 69
SISTGGGNTYYRDSVKG
  (SEQ ID NO: 54)

Figure 70
PPYGYNYGWFTY
  (SEQ ID NO: 55)

Figure 71
RASEDIHNGLV
  (SEQ ID NO: 56)

Figure 72
NANSMHT
  (SEQ ID NO: 57)

Figure 73
QQYYNYPRT
  (SEQ ID NO: 58)

Figure 74
GFTYRTYVMA
  (SEQ ID NO: 59)

Figure 75
SISTGGVSTYYRDSVKG
  (SEQ ID NO: 60)

Figure 76
DMLNGYNSQGLFDY
  (SEQ ID NO: 61)

Figure 77
RASQNVDNTIA
  (SEQ ID NO: 62)

Figure 78
FASDRYT
  (SEQ ID NO: 63)

Figure 79
QRIYNSPLT
  (SEQ ID NO: 64)

Figure 80
GFTFSSYYMA
  (SEQ ID NO: 65)

Figure 81
YISNGGYSTYYRDSVKG
  (SEQ ID NO: 66)

Figure 82
TDHSGYRFTY
  (SEQ ID NO: 67)

Figure 83
KASQSIYNSLA
  (SEQ ID NO: 68)

Figure 84
DANSLQT
  (SEQ ID NO: 69)

Figure 85
QKYYSGNT
  (SEQ ID NO: 70)

Figure 86
CTCCAGAGTTCCAGGTCACGGTGACTGGC
  (SEQ ID NO: 71)

Figure 87
TCAGTAACACTGTCCAGGACACCATCTC
  (SEQ ID NO: 72)

Figure 88
TATACCGTCGACCTCTAGCTAGAGCTTGGC
  (SEQ ID NO: 73)

Figure 89
GCTATGGCAGGGCCTGCCGCCCCGACGTTG
  (SEQ ID NO: 74)

Figure 90
CCAGATGGGTGCTGAGCGAGGTGCAGCTGGTGGAGTCTGGGGGAGG
(SEQ ID NO: 75)

Figure 91
CTTGGTGGAGGCTGAGCTGACTGTGACCATGACTCCTTGGCCCCAG
(SEQ ID NO: 76)

Figure 92
ATCTCCGGCGCGTACGGCAACATTGTGATGACCCAGTCTCCCAAATCC
(SEQ ID NO: 77)

Figure 93
GGAGGGGGCGGCCACAGCCCGTTTCAGTTCCAGCTCGGTCCCAGC
(SEQ ID NO: 78)

Figure 94
ATGTGGGAGGCTCAGTTCCTGGGCTTGCTGTTTC
(SEQ ID NO: 79)

Figure 95
GCCCGAGCCCGAGCCCGAGCCGGAGCAGCTCTGA
(SEQ ID NO: 80)

Figure 96
GAGTATGTGTTGACTGGTTGATAACTATCG
(SEQ ID NO: 81)

Figure 97
GCCATGACAGATTAGCCATGTCTGCAGCAC
(SEQ ID NO: 82)

Figure 98
CAGGACCTTTTTCTAACCTCCCTTGGAGGGCTGGGGAGGCCCGGGCCATAGAGGAG
(SEQ ID NO: 83)

Figure 99
CCTGGAGCCGAGGCAGCCAGCAGGTCTCAGCAGCTCCGCCCGCCCGCCCGCCCGCC
(SEQ ID NO: 84)

Figure 100
ATGTGGGAGGCTCAGTTCCTGGGCTTGCTGTTTCTGCAGCCGCTTTGGGTGGCTCCAGTGAAGCCTCTCCAG
CCAGGGGCTGAGGTCCCGGTGGTGTGGGCCCAGGAGGGGGCTCCTGCCCAGCTCCCCTGCAGCCCCACAA
TCCCCCTCCAGGATCTCAGCCTTCTGCGAAGAGCAGGGGTCACTTGGCAGCATCAGCCAGACAGTGGCCCG
CCCGCTGCCGCCCCGGCCATCCCCTGGCCCCCGGCCCTCACCGGCGGCGCCCTCCTCCTGGGGGCCCAG
GCCCCGCCGCTACACGGTGCTGAGCGTGGGTCCCGGAGGCCTGCGCAGCGGGAGGCTGCCCCTGCAGCCC
CGCGTCCAGCTGGATGAGCGCGGCCGGCAGCGCGGGGACTTCTCGCTATGGCTGCGCCCAGCCCGGCGCG
CGGACGCCGGCGAGTACCGCGCCGCGGTGCACCTCAGGGACCGCGCCCTCTCCTGCCGCCTCCGTCTGCGC
CTGGGCCAGGCCTCGATGACTGCCAGCCCCCAGGATCTCTCAGAGCCTCCGACTGGGTCATTTTGAACTGC
TCCTTCAGCCGCCCTGACCGCCCAGCCTCTGTGCATTGGTTCCGGAACCGGGGCCAGGGCCGAGTCCCTGTC
CGGGAGTCCCCCCATCACCACTTAGCGGAAAGCTTCCTCTTCCTGCCCCAAGTCAGCCCCATGGACTCTGGG
CCCTGGGGCTGCATCCTCACCTACAGAGATGGCTTCAACGTCTCCATCATGTATAACCTCACTGTTCTGGGTC
TGGAGCCCCCAACTCCCTTGACAGTGTACGCTGGAGCAGGTTCCAGGGTGGGGCTGCCCTGCCGCCTGCCT
GCTGGTGTGGGGACCCGGTCTTTCCTCACTGCCAAGTGGACTCCTCCTGGGGGAGGCCCTGACCTCCTGGT
GACTGGAGACAATGGCGACTTTACCCTTCGACTAGAGGATGTGAGCCAGGCCCAGGCTGGGACCTACACCT
GCCATATCCATCTGCAGGAACAGCAGCTCAATGCCACTGTCACATTGGCAATCATCACAGTGACTCCCAAAT
CCTTTGGGTCACCTGGATCCCTGGGGAAGCTGCTTTGTGAGGTGACTCCAGTATCTGGACAAGAACGCTTT
GTGTGGAGCTCTCTGGACACCCCATCCCAGAGGAGTTTCTCAGGACCTTGGCTGGAGGCACAGGAGGCCCA
GCTCCTTTCCCAGCCTTGGCAATGCCAGCTGTACCAGGGGGAGAGGCTTCTTGGAGCAGCAGTGTACTTCA
CAGAGCTGTCTAGCCCAGGTGCCCAACGCTCTGGGAGAGCCCCAGGTGCCCTCCCAGCAGGCCACCTCCTG
CTGTTTCTCATCCTTGGTGTCCTTTCTCTGCTCCTTTTGGTGACTGGAGCCTTTGGCTTTCACCTTTGGAGAAG
ACAGTGGCGACCAAGACGATTTTCTGCCTTAGAGCAAGGGATTCACCCTCCGCAGGCTCAGAGCAAGATAG
AGGAGCTGGAGCAAGAACCGGAGCCGGAGCCGGAGCCGGAACCGGAGCCCGAGCCCGAGCCCGAGCCG
GAGCAGCTC
(SEQ ID NO: 85)

Figure 101
MWEAQFLGLLFLQPLWVAPVKPLQPGAEVPVVWAQEGAPAQLPCSPTIPLQDLSLLRRAGVTWQHQPDSGP
PAAAPGHPLAPGPHPAAPSSWGPRPRRYTVLSVGPGGLRSGRLPLQPRVQLDERGRQRGDFSLWLRPARRAD
AGEYRAAVHLRDRALSCRLRLRLGQASMTASPPGSLRASDWVILNCSFSRPDRPASVHWFRNRGQGRVPVRES
PHHHLAESFLFLPQVSPMDSGPWGCILTYRDGFNVSIMYNLTVLGLEPPTPLTVYAGAGSRVGLPCRLPAGVGT
RSFLTAKWTPPGGGPDLLVTGDNGDFTLRLEDVSQAQAGTYTCHIHLQEQQLNATVTLAIITVTPKSFGSPGSLG
KLLCEVTPVSGQERFVWSSLDTPSQRSFSGPWLEAQEAQLLSQPWQCQLYQGERLLGAAVYFTELSSPGAQRSG
RAPGALPAGHLLLFLILGVLSLLLLVTGAFGFHLWRRQWRPRRFSALEQGIHPPQAQSKIEELEQEPEPEPEPEPEP
EPEPEPEQL
(SEQ ID NO: 86)

Figure 105
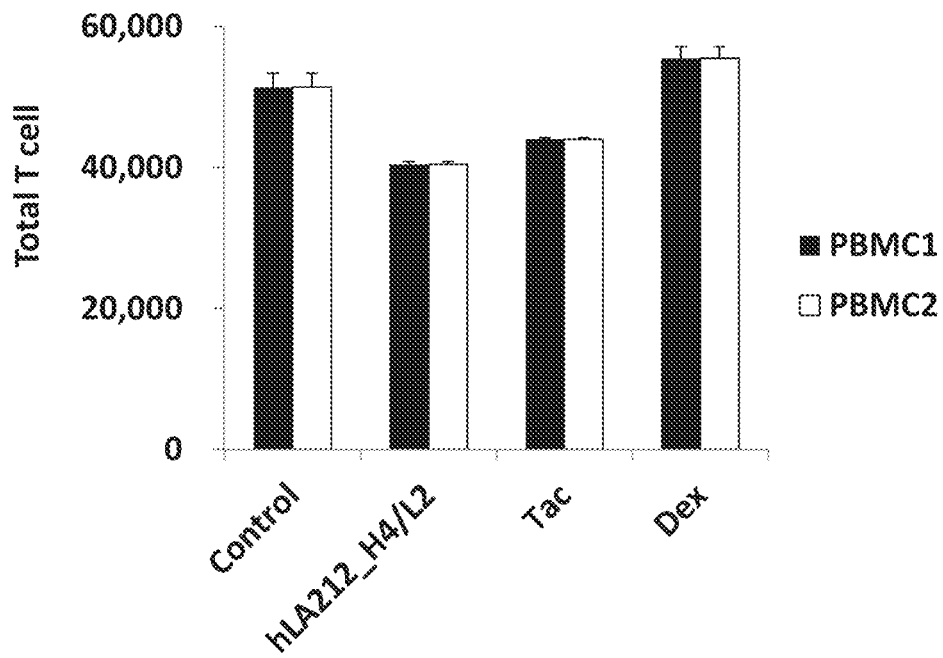
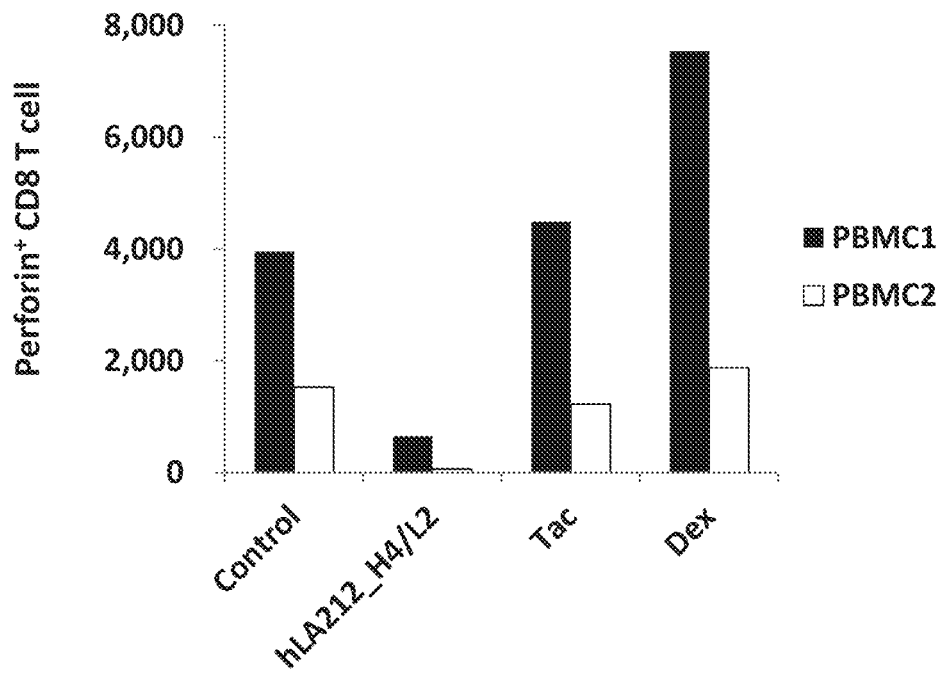

Figure 106
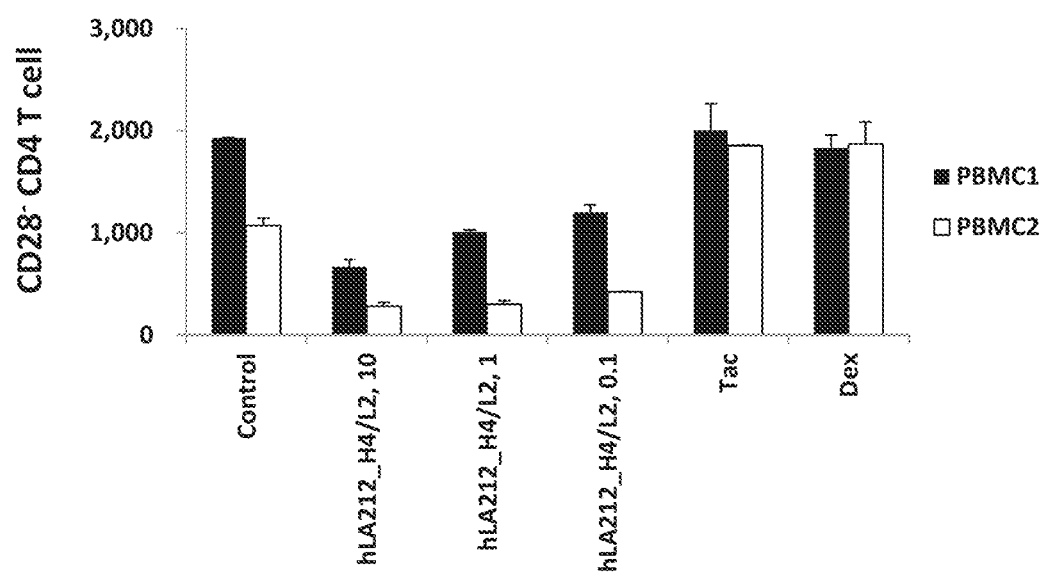
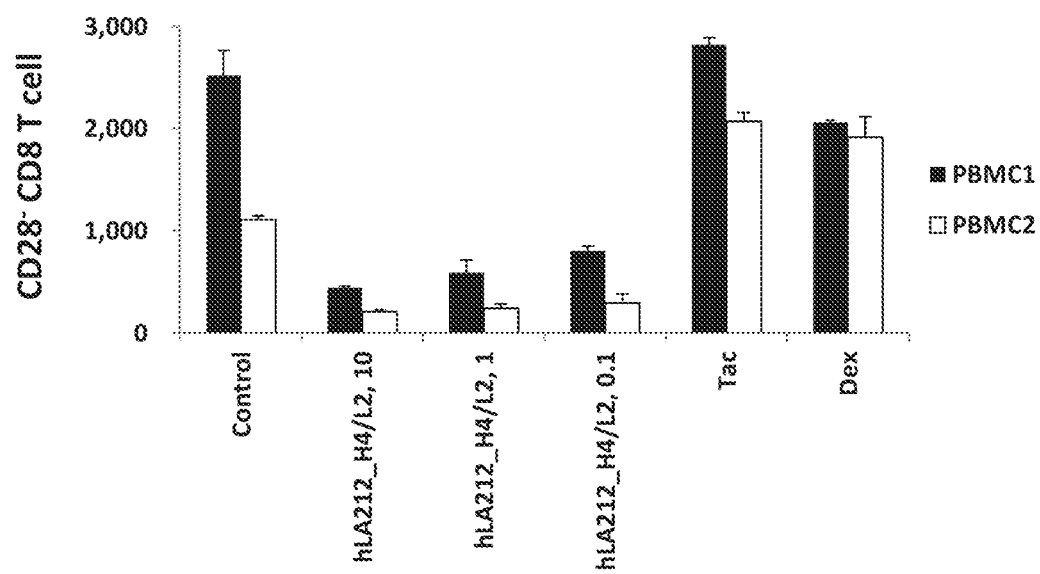

Figure 107
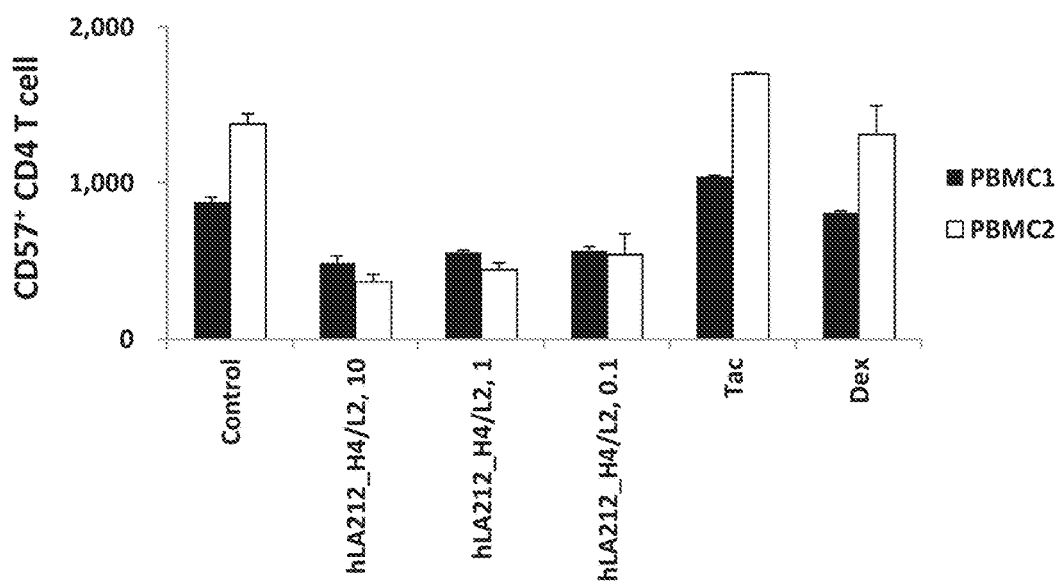
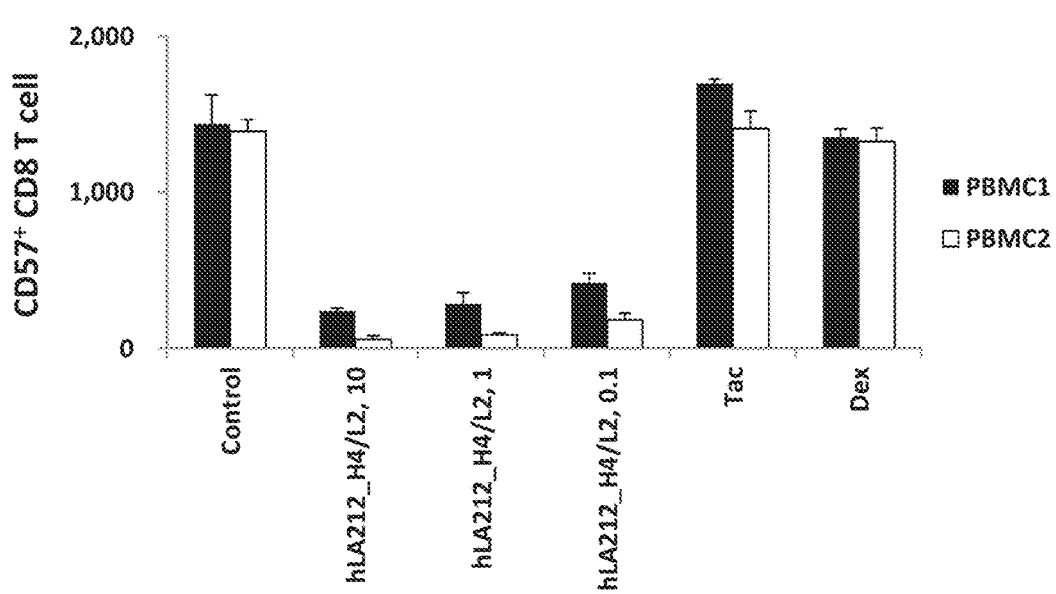

ured (Patent Literature 2).

METHOD FOR DEPLETING CYTOTOXIC T CELLS USING AN ANTI-LAG-3 ANTIBODY COMPOSITION

CROSS REFERENCE TO RELATED APPLICATIONS

This application is the U.S. national phase of PCT/JP2018/037139 filed on Oct. 4, 2018, which claims priority to Japanese Application No. 2017-194945 filed on Oct. 5, 2017, each of which is expressly incorporated herein by reference in its entirety.

STATEMENT REGARDING SEQUENCE LISTING

The sequence listing associated with this application is provided in text format in lieu of a paper copy and is hereby incorporated by reference into the specification. The name of the text file containing the sequence listing is 1660-P96USPNP_Seq_List_20230515_ST25. The text file is 119,263 bytes; was created on May 15, 2023; and is being submitted via Patent Center.

TECHNICAL FIELD

The present invention relates to, for example, a composition for cytotoxic T cell depletion, comprising an antibody, a binding fragment thereof, or the like, use of the antibody, the binding fragment thereof, or the like for cytotoxic T cell depletion, and a method for depleting cytotoxic T cells, comprising the step of administering the antibody, the binding fragment thereof, or the like.

BACKGROUND ART

T lymphocytes (T cells) are cells that play a central role in the immune response, and therefore T cells having various antigen specificities, which are said to number from 10 million to one billion clones, are present in vivo, in order to deal with diverse antigens. When an antigen invades the body, only a very limited number of clones specific to the antigen out of such enormous T cell repertoires are proliferated and activated to work to defend the body through cytokine production and cytotoxic activity, etc. In autoimmune diseases, various pathological conditions are considered to be triggered by abnormal immune responses to some self-antigens. Even under such situations, most other clones that do not have such antigen specificity are not proliferated and activated and instead remain in a resting state. Therefore, selective removal of only activated T cells can suppress immunity specifically, without affecting most T cells having other antigen specificities and thus can be a useful treatment or prevention method against autoimmune diseases, rejection of transplants, allergic diseases, etc. Meanwhile, in a situation where T cells that negatively regulate the immune system, such as regulatory T cells, are mainly activated, removal of such cells can be a useful treatment or prevention method against malignant tumors, chronic infections, etc.

LAG-3 (CD223) is a single-pass transmembrane molecule that belongs to the immunoglobulin superfamily and is known to be expressed selectively in activated T cells (Non Patent Literature 1). It is reported that, when rabbit antiserum having complement-dependent cytotoxic (CDC) activity against the rat LAG-3 molecule is administered to a rat allogeneic heart transplant model, LAG-3 positive cells in a graft decrease, so that the period to the rejection of the graft is slightly extended (Non Patent Literature 2). It is also reported that anti-human LAG-3 chimeric antibody A9H12 having cross-reactivity with baboons and exhibiting antibody-dependent cell-mediated cytotoxic (ADCC) activity suppresses the delayed-type hypersensitivity reaction of baboons, though its dose response is unclear (Non Patent Literature 3), and humanized antibodies thereof were produced (Patent Literature 2).

LAG-3 is known to bind to major histocompatibility complex (or, major histocompatibility gene complex) (MHC) class II molecules, thereby transmitting some inhibitory signals to T cells to regulate the T cell function negatively (Non Patent Literature 1). For binding of LAG-3 to MHC class II molecules, N-terminal domains 1 and 2 of the four extracellular immunoglobulin-like domains of LAG-3 are considered to be important (Non Patent Literature 4), and it is also reported that such suppression of T cell function via LAG-3 is cooperatively exerted with other signals that suppress the T cell function via the PD-1 molecule, etc. (Non Patent Literature 5). In fact, novel cancer treatment methods for activating immune cell function by inhibiting the T cell suppression function of LAG-3 to attack cancer cells have been actively developed in recent years (Non Patent Literatures 6 and 7). Therefore, in the case of applying a LAG-3 antibody that depletes LAG-3 positive cells by ADCC activity, etc., to autoimmune diseases, an antibody having no activity of inhibiting the T cell suppression function inherent to LAG-3 is considered more desirable, since there is thus no risk that autoimmune diseases instead get worse due to abnormal activation of the immune system. In both the anti-rat LAG-3 rabbit antiserum having CDC activity and the anti-human LAG-3 chimeric antibody A9H12 exhibiting ADCC activity (IMP731: Patent Literatures 1 and 2) described above, LAG-3 positive cells are not completely depleted (Non Patent Literatures 2 and 3), and thus the possibilities of side effects due to abnormal reaction of the remaining T cells that have not been depleted and negative influences on the suppression of autoimmune diseases are assumed.

Among T cell subsets, CD4+(positive) CD28-(negative) T cells, CD8+CD28– T cells, CD4+CD57+ T cells, and CD8+CD57+ T cells are cytotoxic T cell groups highly expressing perforin, granzyme B, etc. (Non Patent Literatures 12 and 13). Although steroid drugs are widely used for the treatment of diseases of the immune system, there exists a steroid refractory population of patients with diseases of the immune system such as asthma or chronic obstructive pulmonary disease (COPD) (Non Patent Literature 14). In recent years, the cytotoxic T cells as mentioned above have been reported as one of main inflammatory cells involved in the pathological conditions of certain autoimmune diseases (Non Patent Literatures 12 and 15). The cytotoxic T cells have a high cytotoxic action, while resistance to the anti-inflammatory action brought about by steroid treatment or apoptosis induction has been reported (Non Patent Literature 16).

CITATION LIST

Patent Literature

Patent Literature 1: US 2011/0070238 A1
Patent Literature 2: WO 2014/140180

Non Patent Literature

Non Patent Literature 1: Triebel, F., LAG-3: a regulator of T-cell and DC responses and its use in therapeutic vaccination., Trends Immunol., December 2003; Vol. 24 (No. 12): p. 619-22

Non Patent Literature 2: Haudebourg, T. et al., Depletion of LAG-3 positive cells in cardiac allograft reveals their role in rejection and tolerance., Transplantation, December 2007; Vol. 84 (No. 11): p. 1500-06

Non Patent Literature 3: Haudebourg, T. et al., Antibody-mediated depletion of lymphocyte-activation gene-3 (LAG-3 (+))-activated T lymphocytes prevents delayed-type hypersensitivity in non-human primates, Clin. Exp. Immunol., May 2011; Vol. 164 (No. 2): p. 265-74

Non Patent Literature 4: Huard, B. et al., Characterization of the major histocompatibility complex class II binding site on LAG-3 protein, Proc. Natl. Acad. Sci. U.S.A., May 27, 1997; Vol. 94 (No. 11): p. 5744-49

Non Patent Literature 5: Okazaki, T. et al., PD-1 and LAG-3 inhibitory co-receptors act synergistically to prevent autoimmunity in mice, J. Exp. Med., Feb. 7, 2011; Vol. 208 (No. 2): p. 395-407

Non Patent Literature 6: Nguyen, L. T. and Ohashi, P. S., Clinical blockade of PD1 and LAG3—potential mechanisms of action, Nat. Rev. Immunol., January 2015; Vol. 15 (No. 1): p. 45-56

Non Patent Literature 7: Turnis, M. E. et al., Inhibitory receptors as targets for cancer immunotherapy, Eur. J. Immunol. July 2015; Vol. 45 (No. 7): p. 1892-905

Non Patent Literature 8: Huard, B. et al., T cell major histocompatibility complex class II molecules down-regulate CD4+ T cell clone responses following LAG-3 binding, Eur. J. Immunol., May 1996; Vol. 26 (No. 5): p. 1180-06

Non Patent Literature 9: Macon-Lemaitre, L and Triebel, F, The negative regulatory function of the lymphocyte-activation gene-3 co-receptor (CD223) on human T cells, Immunology, June 2005; Vol. 115 (No. 2): p. 170-08

Non Patent Literature 10: Li, M. et al., Reconstitution of human Fc gamma RIII cell type specificity in transgenic mice, J. Exp. Med., May 1, 1996; Vol. 183 (No. 3): p. 1259-63

Non Patent Literature 11: Miller, Stephen D. et al., Experimental Autoimmune Encephalomyelitis in the Mouse, Current Protocols in Immunology, Chapter 15 (UNIT 15.1), Wiley, 2010: p. 15.1.1-15.1.20

Non Patent Literature 12: STRIOGA, M. et al., CD8+ CD28− and CD8+CD57+ T cells and their role in health and disease, Immunology, 2011; Vol. 134 (No. 1): p. 17-32

Non Patent Literature 13: Maly K, Schirmer M, The story of CD4+CD28− T cells revisited: solved or still ongoing?, J. Immunol. Res., 2015; Vol. 2015: Material No. 348746

Non Patent Literature 14: Barnes, P., Corticosteroid resistance in patients with asthma and chronic obstructive pulmonary disease, J. Allergy Clin. Immunol., 2013; Vol. 131 (No. 3): p. 636-645

Non Patent Literature 15: Broux, B, et al., Pathogenic features of CD4+CD28− T cells in immune disorders, Trends. Mol. Med., 2012; Vol. 18 (No. 8): p. 446-453

Non Patent Literature 16: Hodge, G. and Hodge, S., Steroid Resistant CD8+CD28null NKT-Like Pro-inflammatory Cytotoxic Cells in Chronic Obstructive Pulmonary Disease, Front. Immunol., 2016; Vol. 7: p. 617

SUMMARY OF INVENTION

Technical Problem

It is intended to provide a composition for depleting cytotoxic T cells, etc.

Solution to Problem

The present invention relates to:
(1) a composition for cytotoxic T cell depletion, comprising an anti-LAG-3 antibody or a binding fragment thereof having the properties described in (i) to (iii) below:
(i) having in vitro ADCC activity;
(ii) reducing, in a low fucose form, the number of LAG-3 positive cells in vivo; and
(iii) binding to activated human T cells;
(2) the composition according to (1), wherein the cytotoxic T cell is selected from the group consisting of: a perforin positive T cell, a granzyme B positive T cell, a CD28 negative and CD4 positive T cell, a CD28 negative and CD8 positive T cell, a CD57 positive and CD4 positive T cell, and a CD57 positive and CD8 positive T cell;
(3) the composition according to (1) or (2), wherein the cytotoxic T cell is LAG-3 positive;
(4) the composition according to any one of (1) to (3), wherein the anti-LAG-3 antibody or the binding fragment thereof binds to domain 3 of human LAG-3 and has the properties described in (i) to (iii) below:
(i) suppressing, in a low fucose form, experimental autoimmune encephalomyelitis in vivo;
(ii) allowing human LAG-3 to bind to human major histocompatibility complex class II molecules in the presence of the antibody or the binding fragment thereof; and
(iii) allowing human LAG-3 to exert a human T cell suppression function in the presence of the antibody or the binding fragment thereof;
(5) the composition according to any one of (1) to (4), for use in the treatment or prevention of an immunosuppressant resistant disease associated with cytotoxic T cells;
(6) the composition according to (5), wherein the immunosuppressant is a steroid;
(7) the composition according to (5), wherein the immunosuppressant is a calcineurin inhibitor;
(8) the composition according to any one of (1) to (7), wherein the antibody or the binding fragment thereof is a chimeric antibody, a humanized antibody, or a human antibody, or a binding fragment thereof;
(9) the composition according to (4), wherein the antibody or the binding fragment thereof comprises: a light chain comprising CDRL1 having the amino acid sequence represented by SEQ ID NO: 50 or FIG. 65, CDRL2 having the amino acid sequence represented by SEQ ID NO: 51 or FIG. 66 and CDRL3 having the amino acid sequence represented by SEQ ID NO: 52 or FIG. 67, and a heavy chain comprising CDRH1 having the amino acid sequence represented by SEQ ID NO: 47 or FIG. 62, CDRH2 having the amino acid sequence represented by SEQ ID NO: 48 or FIG. 63 and CDRH3 having the amino acid sequence represented by SEQ ID NO: 49 or FIG. 64;

(10) the composition according to (9), wherein the antibody or the binding fragment thereof is a humanized antibody or a binding fragment thereof;

(11) the composition according to (10), wherein the antibody or the binding fragment thereof comprises: a heavy chain comprising an amino acid sequence derived from the amino acid sequence represented by SEQ ID NO: 28 or FIG. 43 with the amino acid corresponding to position 68 being either Gly or substituted with Ala, and the amino acid corresponding to position 103 being either Asn or substituted with Asp, and a light chain comprising an amino acid sequence derived from the amino acid sequence represented by SEQ ID NO: 32 or FIG. 47 with the amino acid corresponding to position 21 being either Asp or substituted with Asn, the amino acid corresponding to position 31 being either Leu or substituted with Met, the amino acid corresponding to position 33 being either Ala or substituted with Ile, the amino acid corresponding to position 41 being either Ile or substituted with Met, the amino acid corresponding to position 58 being either Gln or substituted with Lys, the amino acid corresponding to position 63 being either Ala or substituted with Ser, the amino acid corresponding to position 80 being either Ser or substituted with Asp, the amino acid corresponding to position 85 being either Ser or substituted with Gly, the amino acid corresponding to position 87 being either Ser or substituted with Tyr, the amino acid corresponding to position 98 being either Leu or substituted with Val, the amino acid corresponding to position 103 being either Phe or substituted with Ala, the amino acid corresponding to position 105 being either Thr or substituted with Phe, the amino acid corresponding to position 124 being either Val or substituted with Leu, and the amino acid corresponding to position 126 being either Ile or substituted with Leu;

(12) the composition according to (10) or (11), wherein the antibody or the binding fragment thereof comprises: a light chain variable region amino acid sequence comprising amino acid 21 to amino acid 129 of an amino acid sequence selected from the group consisting of SEQ ID NOs: 32, 34, 36, 38, and 40, and a heavy chain variable region amino acid sequence comprising amino acid 20 to amino acid 140 of an amino acid sequence selected from the group consisting of SEQ ID NOs: 28 and 30;

(13) the composition according to any one of (10) to (12), wherein the antibody or the binding fragment thereof comprises:
 a light chain amino acid sequence comprising amino acid 21 to amino acid 234 of an amino acid sequence selected from the group consisting of SEQ ID NOs: 32, 34, 36, 38, and 40, and a heavy chain amino acid sequence comprising amino acid 20 to amino acid 470 of an amino acid sequence selected from the group consisting of SEQ ID NOs: 28 and 30;

(14) the composition according to any one of (10) to (13), wherein the antibody or the binding fragment thereof is selected from the group consisting of [i] to [x] below:
 [i] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 34 (FIG. 49);
 [ii] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 32 (FIG. 47);
 [iii] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 36 (FIG. 51);
 [iv] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 34 (FIG. 49);
 [v] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 36 (FIG. 51);
 [vi] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 38 (FIG. 53);
 [vii] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 40 (FIG. 55);
 [viii] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 32 (FIG. 47);
 [ix] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 38 (FIG. 53); and
 [x] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 40 (FIG. 55);

(15) the composition according to (14), comprising an antibody or a binding fragment thereof comprising: a light chain variable region and a heavy chain variable region comprising amino acid sequences having 95% or higher identity respectively to the amino acid sequences of the light chain variable region and the heavy chain variable region of the antibody or the binding fragment thereof according to (14);

(16) the composition according to (14), comprising an antibody or a binding fragment thereof comprising: a light chain variable region amino acid sequence encoded by a nucleotide sequence of a second nucleic acid molecule that hybridizes under stringent conditions to a first nucleic acid molecule having a nucleotide sequence encoding the amino acid sequence of the light chain variable region of the antibody or the binding fragment thereof according to (14) or a nucleotide sequence complementary thereto, and a heavy chain variable region amino acid sequence encoded by a nucleotide sequence of a fourth nucleic acid molecule that hybridizes under stringent conditions to a third nucleic acid molecule having a nucleotide sequence encoding the amino acid sequence of the heavy chain variable region of the antibody or the binding fragment thereof according to (14) or a nucleotide sequence complementary thereto;

(17) the composition according to (14), comprising an antibody or a binding fragment thereof having a property described in (i) or (ii) below:
(i) binding to a site on domain 3 of human LAG-3 that is recognized by the antibody or the binding fragment thereof according to (14); or
(ii) competing with the antibody or the binding fragment thereof according to (14) for binding to domain 3 of human LAG-3;

(18) the composition according to any one of (1) to (17), wherein the antibody or the binding fragment thereof is in a low fucose form;

(19) the composition according to any one of (1) to (18), wherein the antibody or the binding fragment thereof is obtained by a method for producing the antibody or the binding fragment thereof, comprising the step of culturing a cell comprising a nucleic acid molecule comprising a nucleotide sequence encoding the amino acid sequence thereof or a vector comprising the nucleic acid molecule, or a cell producing the antibody or the binding fragment thereof;

(20) the composition according to any one of (1) to (3), wherein the presence of the antibody or the binding fragment thereof allows human LAG-3 to exert no human T cell suppression function;

(21) the composition according to any one of (1) to (3) and (20), wherein human LAG-3 does not bind to human major histocompatibility complex class II molecules in the presence of the antibody or the binding fragment thereof;

(22) the composition according to (20) or (21), wherein the antibody or the binding fragment thereof is in a low fucose form;

(23) an anti-LAG-3 antibody or a binding fragment thereof that is used for cytotoxic T cell depletion and has the properties described in (i) to (iii) below:
(i) having in vitro ADCC activity;
(ii) reducing, in a low fucose form, the number of LAG-3 positive cells in vivo; and
(iii) binding to activated human T cells;

(24) use of an anti-LAG-3 antibody or a binding fragment thereof having the properties described in (i) to (iii) below for cytotoxic T cell depletion:
(i) having in vitro ADCC activity;
(ii) reducing, in a low fucose form, the number of LAG-3 positive cells in vivo; and
(iii) binding to activated human T cells;

(25) a method for depleting cytotoxic T cells, comprising administering an anti-LAG-3 antibody or a binding fragment thereof having the properties described in (i) to (iii) below:
(i) having in vitro ADCC activity;
(ii) reducing, in a low fucose form, the number of LAG-3 positive cells in vivo; and
(iii) binding to activated human T cells;

(26) the composition according to any one of (1) to (22), for use in combination with additional drugs;

(27) a pharmaceutical composition for the treatment or prevention of a disease associated with perforin positive, granzyme B positive, CD28 negative and CD4 positive, CD28 negative and CD8 positive, CD57 positive and CD4 positive, and/or CD57 positive and CD8 positive cytotoxic T cells, comprising an anti-LAG-3 antibody or a binding fragment thereof having the properties described in (i) to (iii) below:
(i) having in vitro ADCC activity;
(ii) reducing, in a low fucose form, the number of LAG-3 positive cells in vivo; and
(iii) binding to activated human T cells;

(28) the pharmaceutical composition according to (27), wherein the treatment or prevention comprises determining that a cytotoxic T cell contained in a biological sample or a cell membrane fraction thereof is perforin positive, granzyme B positive, CD28 negative and CD4 positive, CD28 negative and CD8 positive, CD57 positive and CD4 positive, and/or CD57 positive and CD8 positive;

(29) the pharmaceutical composition according to (28), wherein the biological sample is derived from an individual who suffers from the disease associated with cytotoxic T cells or for whom it is desired to avoid suffering from the disease associated with cytotoxic T cells;

(30) the pharmaceutical composition according to any one of (27) to (29), wherein the disease associated with cytotoxic T cells is idiopathic pulmonary fibrosis, chronic obstructive pulmonary disease (COPD), multiple sclerosis, Graves' disease, ankylosing spondylitis, pars planitis, asthma, rheumatoid arthritis, polymyositis or dermatomyositis, inclusion body myositis, acute coronary syndrome, systemic lupus erythematosus, lupus nephritis, scleroderma, Crohn's disease, ulcerative colitis, aplastic anemia, myelodysplastic syndrome, Sjogren's syndrome, Wegener's granulomatosis, psoriasis, type 2 diabetes, host-versus-graft reaction, chronic hepatitis B, and/or sarcoidosis;

(31) the pharmaceutical composition according to any one of (27) to (30), wherein the disease associated with cytotoxic T cells is LAG-3 positive;

(32) the pharmaceutical composition according to any one of (27) to (31), wherein the anti-LAG-3 antibody or the binding fragment thereof binds to domain 3 of human LAG-3 and has the properties described in (i) to (iii) below:
(i) suppressing, in a low fucose form, experimental autoimmune encephalomyelitis in vivo;
(ii) allowing human LAG-3 to bind to human major histocompatibility complex class II molecules in the presence of the antibody or the binding fragment thereof; and
(iii) allowing human LAG-3 to exert a human T cell suppression function in the presence of the antibody or the binding fragment thereof;

(33) the pharmaceutical composition according to any one of (27) to (32), wherein the disease associated with cytotoxic T cells is immunosuppressant resistant;

(34) the pharmaceutical composition according to (33), wherein the immunosuppressant is a steroid;

(35) the pharmaceutical composition according to (33), wherein the immunosuppressant is a calcineurin inhibitor;

(36) the pharmaceutical composition according to any one of (27) to (35), wherein the antibody or the binding fragment thereof is a chimeric antibody, a humanized antibody, or a human antibody, or a binding fragment thereof;

(37) the pharmaceutical composition according to any one of (27) to (36), wherein the antibody or the binding fragment thereof comprises: a light chain comprising CDRL1 having the amino acid sequence represented by SEQ ID NO: 50, CDRL2 having the amino acid sequence represented by SEQ ID NO: 51 and CDRL3 having the amino acid sequence represented by SEQ ID NO: 52, and a heavy chain comprising CDRH1 having the amino acid sequence represented by SEQ ID NO: 47, CDRH2 having the amino acid sequence represented by SEQ ID NO: 48 and CDRH3 having the amino acid sequence represented by SEQ ID NO: 49;

(38) the pharmaceutical composition according to (37), wherein the antibody or the binding fragment thereof is a humanized antibody or a binding fragment thereof;

(39) the pharmaceutical composition according to (38), wherein the antibody or the binding fragment thereof comprises: a heavy chain comprising an amino acid sequence derived from the amino acid sequence represented by SEQ ID NO: 28 with the amino acid corresponding to position 68 being either Gly or substituted with Ala, and the amino acid corresponding to position 103 being either Asn or substituted with Asp, and a light chain comprising an amino acid sequence derived from the amino acid sequence represented by SEQ ID NO: 32 with the amino acid corresponding to position 21 being either Asp or substituted with Asn, the amino acid corresponding to position 31 being either Leu or substituted with Met, the amino acid corresponding to position 33 being either Ala or substituted with Ile, the amino acid corresponding to position 41 being either Ile or substituted with Met, the amino acid corresponding to position 58 being either Gln or substituted with Lys, the amino acid corresponding to position 63 being either Ala or substituted with Ser, the amino acid corresponding to position 80 being either Ser or substituted with Asp, the amino acid corresponding to position 85 being either Ser or substituted with Gly, the amino acid corresponding to position 87 being either Ser or substituted with Tyr, the amino acid corresponding to position 98 being either Leu or substituted with Val, the amino acid corresponding to position 103 being either Phe or substituted with Ala, the amino acid corresponding to position 105 being either Thr or substituted with Phe, the amino acid corresponding to position 124 being either Val or substituted with Leu, and the amino acid corresponding to position 126 being either Ile or substituted with Leu;

(40) the pharmaceutical composition according to (38) or (39), wherein the antibody or the binding fragment thereof comprises
a light chain variable region amino acid sequence comprising amino acid 21 to amino acid 129 of an amino acid sequence selected from the group consisting of SEQ ID NOs: 32, 34, 36, 38, and 40, and a heavy chain variable region amino acid sequence comprising amino acid 20 to amino acid 140 of an amino acid sequence selected from the group consisting of SEQ ID NOs: 28 and 30;

(41) the pharmaceutical composition according to any one of (38) to (40), wherein the antibody or the binding fragment thereof comprises: a light chain amino acid sequence comprising amino acid 21 to amino acid 234 of an amino acid sequence selected from the group consisting of SEQ ID NOs: 32, 34, 36, 38, and 40, and a heavy chain amino acid sequence comprising amino acid 20 to amino acid 470 of an amino acid sequence selected from the group consisting of SEQ ID NOs: 28 and 30;

(42) the pharmaceutical composition according to any one of (38) to (41), wherein the antibody or the binding fragment thereof is selected from the group consisting of [i] to [x] below:

[i] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 34 (FIG. 49);

[ii] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 32 (FIG. 47);

[iii] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 36 (FIG. 51);

[iv] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 34 (FIG. 49);

[v] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 36 (FIG. 51);

[vi] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 38 (FIG. 53);

[vii] an antibody or a binding fragment thereof comprising a heavy chain having an amino acid sequence consisting of amino acid positions 20 to 470 of SEQ ID NO: 28 (FIG. 43) and a light chain having an amino acid sequence consisting of amino acid positions 21 to 234 of SEQ ID NO: 40 (FIG. 55);

[viii] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 32 (FIG. 47);

[ix] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 38 (FIG. 53); and

[x] an antibody or a binding fragment thereof comprising a heavy chain having an amino acid sequence consisting of amino acid positions 20 to 470 of SEQ ID NO: 30 (FIG. 45) and a light chain having an amino acid sequence consisting of amino acid positions 21 to 234 of SEQ ID NO: 40 (FIG. 55);

(43) the pharmaceutical composition according to (42), comprising an antibody or a binding fragment thereof comprising: a light chain variable region and a heavy chain variable region comprising amino acid sequences having 95% or higher identity respectively to the amino acid sequences of the light chain variable region and the heavy chain variable region of the antibody or the binding fragment thereof according to (42);

(44) the pharmaceutical composition according to (42), comprising an antibody or a binding fragment thereof comprising a light chain variable region amino acid sequence encoded by a nucleotide sequence of a second nucleic acid molecule that hybridizes under stringent conditions to a first nucleic acid molecule having a nucleotide sequence encoding the amino acid sequence of the light chain variable region of the antibody or the binding fragment thereof according to (42) or a nucleotide sequence complementary thereto, and a heavy chain variable region amino acid sequence encoded by a nucleotide sequence of a fourth nucleic acid molecule that hybridizes under stringent conditions to a third nucleic acid molecule having a nucleotide sequence encoding the amino acid sequence of the heavy chain variable region of the antibody or the binding fragment thereof according to (42) or a nucleotide sequence complementary thereto;

(45) the pharmaceutical composition according to (42), comprising an antibody or a binding fragment thereof having a property described in (i) or (ii) below:
(i) binding to a site on domain 3 of human LAG-3 that is recognized by the antibody or the binding fragment thereof according to (42); or
(ii) competing with the antibody or the binding fragment thereof according to (42) for binding to domain 3 of human LAG-3;

(46) the pharmaceutical composition according to any one of (27) to (45), wherein the antibody or the binding fragment thereof is in a low fucose form;

(47) the pharmaceutical composition according to any one of (27) to (46), wherein the antibody or the binding fragment thereof is obtained by a method for producing the antibody or the binding fragment thereof, comprising the step of culturing a cell comprising a nucleic acid molecule comprising a nucleotide sequence encoding the amino acid sequence thereof or a vector comprising the nucleic acid molecule, or a cell producing the antibody or the binding fragment thereof;

(48) the pharmaceutical composition according to any one of (27) to (31), wherein the presence of the antibody or the binding fragment thereof allows human LAG-3 to exert no human T cell suppression function;

(49) the pharmaceutical composition according to any one of (27) to (31) and (48), wherein human LAG-3 does not bind to human major histocompatibility complex class II molecules in the presence of the antibody or the binding fragment thereof;

(50) the pharmaceutical composition according to (48) or (49), wherein the antibody or the binding fragment thereof is in a low fucose form;

(51) the pharmaceutical composition according to any one of (27) to (50), for use in combination with additional drugs;

(52) a method for treating or preventing a disease associated with perforin positive, granzyme B positive, CD28 negative and CD4 positive, CD28 negative and CD8 positive, CD57 positive and CD4 positive, and/or CD57 positive and CD8 positive cytotoxic T cells, comprising the step of administering the composition according to any one of (1) to (22) or the pharmaceutical composition according to any one of (27) to (51) to an individual who suffers from the disease associated with cytotoxic T cells or for whom it is desired to avoid suffering from the disease associated with cytotoxic T cells;

(53) the method according to (52), wherein the disease associated with cytotoxic T cells is immunosuppressant resistant;

(54) the method according to (53), wherein the immunosuppressant is a steroid;

(55) the method according to (53), wherein the immunosuppressant is a calcineurin inhibitor;

(56) the method according to any one of (52) to (55), further comprising the step of determining whether or not a biological sample containing cytotoxic T cells or a cell membrane fraction thereof is perforin positive, granzyme B positive, CD28 negative and CD4 positive, CD28 negative and CD8 positive, CD57 positive and CD4 positive, and/or CD57 positive and CD8 positive;

(57) the method according to (56), wherein the biological sample is derived from the individual who suffers from the disease associated with cytotoxic T cells or for whom it is desired to avoid suffering from the disease associated with cytotoxic T cells; and the like.

Advantageous Effects of Invention

The composition provided by the present invention depletes cytotoxic T cells and thus can be used for the treatment and/or prevention of diseases associated with cytotoxic T cells (mentioned later).

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 3A is a diagram showing the inhibitory activity of the rat anti-LAG-3 antibodies (rLA204, rLA212, rLA225, rLA869, and rLA1264) in a LAG-3/MHC class II binding test. Rat IgG2b was used as a negative control, and a rat anti-LAG-3 antibody that has been separately developed and recognizes domain 1 of LAG-3 was used as a positive control, respectively. Each antibody was evaluated at 10 μg/mL. FIG. 3B is a diagram showing that the human chimeric anti-LAG-3 antibody IMP731, which is a known antibody, exhibits inhibitory activity in the LAG-3/MHC class II binding test. 17B4, which is a commercially available mouse anti-human LAG-3 antibody, also exhibited inhibitory activity.

FIG. 5A is a diagram showing the results of testing the human LAG-3 binding epitope of rat anti-LAG-3 antibodies (rLA204, rLA212 and rLA225) by flow cytometry. The vertical axis represents the mean fluorescence intensity measured by flow cytometry. The binding of anti-FLAG antibody, used as a positive control, is also shown. Each antibody was evaluated at 10 µg/mL.

FIG. 5B is a diagram showing the results of testing the human LAG-3 binding epitope of the human chimeric anti-LAG-3 antibody IMP731, which is a conventional antibody in the Citation List, by flow cytometry. The vertical axis represents the mean fluorescence intensity measured by flow cytometry. The antiserum obtained from the rat immunized in Example 1)-1 was used at 500-fold dilution as antiserum. Each of the other antibodies was evaluated at 10 µg/mL. 6D7 is the rat anti-LAG-3 antibody that was developed in Example 2)-6 and recognizes domain 1 of LAG-3.

FIG. 7 is a table showing the binding ability of humanized anti-LAG-3 antibodies as dissociation constants.

FIG. 16 is a nucleotide sequence encoding the amino acid sequence of the heavy chain variable region of the rLA204 antibody (SEQ ID No: 1).

FIG. 17 is the amino acid sequence of the heavy chain variable region of the rLA204 antibody (SEQ ID No: 2).

FIG. 18 is a nucleotide sequence encoding the amino acid sequence of the light chain variable region of the rLA204 antibody (SEQ ID No: 3).

FIG. 19 is the amino acid sequence of the light chain variable region of the rLA204 antibody (SEQ ID No: 4).

FIG. 20 is a nucleotide sequence encoding the amino acid sequence of the heavy chain variable region of the rLA212 antibody (SEQ ID No: 5).

FIG. 21 is the amino acid sequence of the heavy chain variable region of the rLA212 antibody (SEQ ID No: 6).

FIG. 22 is a nucleotide sequence encoding the amino acid sequence of the light chain variable region of the rLA212 antibody (SEQ ID No: 7).

FIG. 23 is the amino acid sequence of the light chain variable region of the rLA212 antibody (SEQ ID No: 8).

FIG. 24 is a nucleotide sequence encoding the amino acid sequence of the heavy chain variable region of the rLA225 antibody (SEQ ID No: 9).

FIG. 25 is the amino acid sequence of the heavy chain variable region of the rLA225 antibody (SEQ ID No: 10).

FIG. 26 is a nucleotide sequence encoding the amino acid sequence of the light chain variable region of the rLA225 antibody (SEQ ID No: 11).

FIG. 27 is the amino acid sequence of the light chain variable region of the rLA225 antibody (SEQ ID No: 12).

FIG. 28 is a nucleotide sequence encoding the amino acid sequence of the heavy chain variable region of the rLA869 antibody (SEQ ID No: 13).

FIG. 29 is the amino acid sequence of the heavy chain variable region of the rLA869 antibody (SEQ ID No: 14).

FIG. 30 is a nucleotide sequence encoding the amino acid sequence of the light chain variable region of the rLA869 antibody (SEQ ID No: 15).

FIG. 31 is the amino acid sequence of the light chain variable region of the rLA869 antibody (SEQ ID No: 16).

FIG. 32 is a nucleotide sequence encoding the amino acid sequence of the heavy chain variable region of the rLA1264 antibody (SEQ ID No: 17).

FIG. 33 is the amino acid sequence of the heavy chain variable region of the rLA1264 antibody (SEQ ID No: 18).

FIG. 34 is a nucleotide sequence encoding the amino acid sequence of the light chain variable region of the rLA1264 antibody (SEQ ID No: 19).

FIG. 35 is the amino acid sequence of the light chain variable region of the rLA1264 antibody (SEQ ID No: 20).

FIG. 36 is a nucleotide sequence encoding the amino acid sequences of the human light chain secretion signal and the human K chain constant region (SEQ ID No: 21).

FIG. 37 is a nucleotide sequence encoding the amino acid sequences of the human heavy chain secretion signal and the human IgG1 constant region (SEQ ID No: 22).

FIG. 38 is a nucleotide sequence encoding the amino acid sequence of the heavy chain of the cLA212 antibody (SEQ ID No: 23).

FIG. 39 is the amino acid sequence of the heavy chain of the cLA212 antibody (SEQ ID No: 24).

FIG. 40 is a nucleotide sequence encoding the amino acid sequence of the light chain of the cLA212 antibody (SEQ ID No: 25).

FIG. 41 is the amino acid sequence of the light chain of the cLA212 antibody (SEQ ID No: 26).

FIG. 42 is a nucleotide sequence encoding the amino acid sequence of the heavy chain H2 of the hLA212 antibody (SEQ ID No: 27).

FIG. 43 is the amino acid sequence of the heavy chain H2 of the hLA212 antibody (SEQ ID No: 28).

FIG. 44 is a nucleotide sequence encoding the amino acid sequence of the heavy chain H3 of the hLA212 antibody (SEQ ID No: 29).

FIG. 45 is the amino acid sequence of the heavy chain H3 of the hLA212 antibody (SEQ ID No: 30).

FIG. 46 is a nucleotide sequence encoding the amino acid sequence of the light chain L1 of the hLA212 antibody (SEQ ID No: 31).

FIG. 47 is the amino acid sequence of the light chain L1 of the hLA212 antibody (SEQ ID No: 32).

FIG. 48 is a nucleotide sequence encoding the amino acid sequence of the light chain L2 of the hLA212 antibody (SEQ ID No: 33).

FIG. 49 is the amino acid sequence of the light chain L2 of the hLA212 antibody (SEQ ID No: 34).

FIG. 50 is a nucleotide sequence encoding the amino acid sequence of the light chain L3 of the hLA212 antibody (SEQ ID No: 35).

FIG. 51 is the amino acid sequence of the light chain L3 of the hLA212 antibody (SEQ ID No: 36).

FIG. 52 is a nucleotide sequence encoding the amino acid sequence of the light chain L4 of the hLA212 antibody (SEQ ID No: 37).

FIG. 53 is the amino acid sequence of the light chain L4 of the hLA212 antibody (SEQ ID No: 38).

FIG. 54 is a nucleotide sequence encoding the amino acid sequence of the light chain L5 of the hLA212 antibody (SEQ ID No: 39).

FIG. 55 is the amino acid sequence of the light chain L5 of the hLA212 antibody (SEQ ID No: 40).

FIG. 56 is the amino acid sequence of the heavy chain CDRH1 of the rLA204 antibody (SEQ ID No: 41).

FIG. 57 is the amino acid sequence of the heavy chain CDRH2 of the rLA204 antibody (SEQ ID No: 42).

FIG. 58 is the amino acid sequence of the heavy chain CDRH3 of the rLA204 antibody (SEQ ID No: 43).

FIG. 59 is the amino acid sequence of the light chain CDRL1 of the rLA204 antibody (SEQ ID No: 44).

FIG. 60 is the amino acid sequence of the light chain CDRL2 of the rLA204 antibody (SEQ ID No: 45).

FIG. 61 is the amino acid sequence of the light chain CDRL3 of the rLA204 antibody (SEQ ID No: 46).

FIG. 62 is the amino acid sequence of the heavy chain CDRH1 of the rLA212 antibody (SEQ ID No: 47).

FIG. 63 is the amino acid sequence of the heavy chain CDRH2 of the rLA212 antibody (SEQ ID No: 48).

FIG. 64 is the amino acid sequence of the heavy chain CDRH3 of the rLA212 antibody (SEQ ID No: 49).

FIG. 65 is the amino acid sequence of the light chain CDRL1 of the rLA212 antibody (SEQ ID No: 50).

FIG. 66 is the amino acid sequence of the light chain CDRL2 of the rLA212 antibody (SEQ ID No: 51).

FIG. 67 is the amino acid sequence of the light chain CDRL3 of the rLA212 antibody (SEQ ID No: 52).

FIG. 68 is the amino acid sequence of the heavy chain CDRH1 of the rLA225 antibody (SEQ ID No: 53).

FIG. 69 is the amino acid sequence of the heavy chain CDRH2 of the rLA225 antibody (SEQ ID No: 54).

FIG. 70 is the amino acid sequence of the heavy chain CDRH3 of the rLA225 antibody (SEQ ID No: 55).

FIG. 71 is the amino acid sequence of the light chain CDRL1 of the rLA225 antibody (SEQ ID No: 56).

FIG. 72 is the amino acid sequence of the light chain CDRL2 of the rLA225 antibody (SEQ ID No: 57).

FIG. 73 is the amino acid sequence of the light chain CDRL3 of the rLA225 antibody (SEQ ID No: 58).

FIG. 74 is the amino acid sequence of the heavy chain CDRH1 of the rLA869 antibody (SEQ ID No: 59).

FIG. 75 is the amino acid sequence of the heavy chain CDRH2 of the rLA869 antibody (SEQ ID No: 60).

FIG. 76 is the amino acid sequence of the heavy chain CDRH3 of the rLA869 antibody (SEQ ID No: 61).

FIG. 77 is the amino acid sequence of the light chain CDRL1 of the rLA869 antibody (SEQ ID No: 62).

FIG. 78 is the amino acid sequence of the light chain CDRL2 of the rLA869 antibody (SEQ ID No: 63).

FIG. 79 is the amino acid sequence of the light chain CDRL3 of the rLA869 antibody (SEQ ID No: 64).

FIG. 80 is the amino acid sequence of the heavy chain CDRH1 of the rLA1264 antibody (SEQ ID No: 65).

FIG. 81 is the amino acid sequence of the heavy chain CDRH2 of the rLA1264 antibody (SEQ ID No: 66).

FIG. 82 is the amino acid sequence of the heavy chain CDRH3 of the rLA1264 antibody (SEQ ID No: 67).

FIG. 83 is the amino acid sequence of the light chain CDRL1 of the rLA1264 antibody (SEQ ID No: 68).

FIG. 84 is the amino acid sequence of the light chain CDRL2 of the rLA1264 antibody (SEQ ID No: 69).

FIG. 85 is the amino acid sequence of the light chain CDRL3 of the rLA1264 antibody (SEQ ID No: 70).

FIG. 86 is primer RG2AR3 (SEQ ID No: 71).

FIG. 87 is primer RKR5 (SEQ ID No: 72).

FIG. 88 is primer 3.3-F1 (SEQ ID No: 73).

FIG. 89 is primer 3.3-R1 (SEQ ID No: 74).

FIG. 90 is primer 212H-F (SEQ ID No: 75).

FIG. 91 is primer 212H-R (SEQ ID No: 76).

FIG. 92 is primer 212L-F (SEQ ID No: 77).

FIG. 93 is primer 212L-R (SEQ ID No: 78).

FIG. 94 is oligonucleotide LAG-3-H1 (SEQ ID No: 79).

FIG. 95 is oligonucleotide LAG-3-H2 (SEQ ID No: 80).

FIG. 96 is oligonucleotide LAG-3-H3 (SEQ ID No: 81).

FIG. 97 is oligonucleotide LAG-3-H4 (SEQ ID No: 82).

FIG. 98 is oligonucleotide LAG-3-H5 (SEQ ID No: 83).

FIG. 99 is oligonucleotide LAG-3-H6 (SEQ ID No: 84).

FIG. 100 is a nucleotide sequence encoding the amino acid sequence of human LAG-3 (SEQ ID No: 85).

FIG. 101 is the amino acid sequence of human LAG-3 (SEQ ID No: 86).

FIG. 105 is a diagram showing that the LAG-3 antibody selectively depletes perforin positive CD8 T cells. Cells obtained by stimulating human PBMCs with Dynabeads Human T-Activator CD3/CD28 in the presence of the humanized anti-LAG-3 antibody hLA212_H4/L2, tacrolimus (Tac), or dexamethasone (Dex) for 4 days were analyzed by flow cytometry (multiple staining). Results when PBMCs derived from two donors were used are shown (PBMC1 and PBMC2). FIG. 105A shows the total number of T cells, and FIG. 105B shows the number of perforin positive CD8 T cells.

FIG. 106 is a diagram showing that the LAG-3 antibody depletes CD28 negative T cells. Cells obtained by stimulating human PBMCs with Dynabeads Human T-Activator CD3/CD28 in the presence of the humanized anti-LAG-3 antibody hLA212_H4/L2 (final concentration: 10, 1, and 0.1 µg/mL), a control antibody (final concentration: 10 µg/mL), tacrolimus (Tac), or dexamethasone (Dex) for 4 days were analyzed by flow cytometry (multiple staining). Results when PBMCs derived from two donors were used are shown (PBMC1 and PBMC2). FIG. 106A shows the number of CD28 negative CD4 T cells, and FIG. 106B shows the number of CD28 negative CD8 T cells.

FIG. 107 is a diagram showing that the LAG-3 antibody depletes CD57 positive T cells. Cells obtained by stimulating human PBMCs with Dynabeads Human T-Activator CD3/CD28 in the presence of the humanized anti-LAG-3 antibody hLA212_H4/L2 (final concentration: 10, 1, and 0.1 µg/mL), a control antibody (final concentration: 10 µg/mL), tacrolimus (Tac), or dexamethasone (Dex) for 4 days were analyzed by flow cytometry (multiple staining). Results when PBMCs derived from two donors were used are shown (PBMC1 and PBMC2). FIG. 107A shows the number of CD57 positive CD4 T cells, and FIG. 107B shows the number of CD57 positive CD8 T cells.

DESCRIPTION OF EMBODIMENTS

1. Definition

Figure 1:
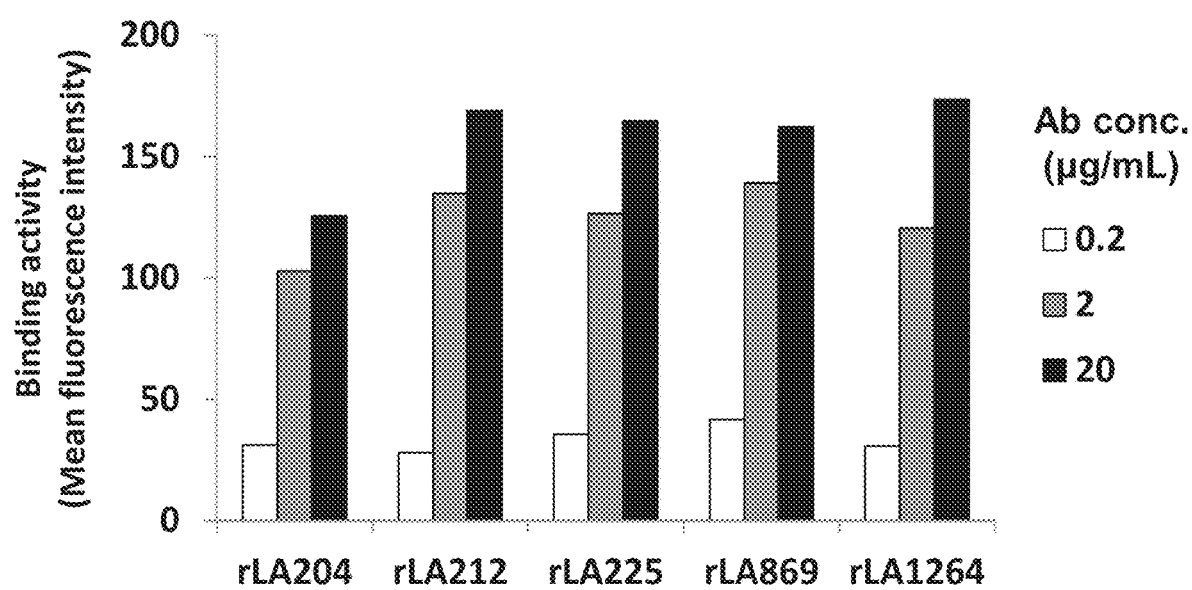
FIG. 1 is a diagram showing the results of testing, by flow cytometry, the binding activity of rat anti-LAG-3 antibodies (rLA204, rLA212, rLA225, rLA869, and rLA1264) to human PHA blasts expressing LAG-3. The vertical axis represents the mean fluorescence intensity measured by flow cytometry.

In the present invention, the term "gene" means a nucleic acid molecule comprising a nucleotide sequence encoding the amino acids of a protein, or its complementary strand. The term "gene" is meant to include, for example, a polynucleotide, an oligonucleotide, DNA, mRNA, cDNA, and cRNA comprising a nucleotide sequence encoding the amino acids of a protein or a nucleotide sequence complementary thereto. Such a gene is a single-stranded, double-stranded, or triple or more stranded nucleotide. The term "gene" is also meant to include an association of DNA and RNA strands, a mixture of ribonucleotides (RNAs) and deoxyribonucleotides (DNAs) on one nucleotide strand, and a double-stranded or triple or more stranded nucleotide comprising such a nucleotide strand. Examples of the "LAG-3 gene" of the present invention can include DNA, mRNA, cDNA, and cRNA comprising a nucleotide sequence encoding the amino acid sequence of the LAG-3 protein.

In the present invention, the term "nucleotide" has the same meaning as "nucleic acid" and "nucleic acid molecule", and is also meant to include, for example, DNA, RNA, a probe, an oligonucleotide, a polynucleotide, and a primer. Such a nucleotide is a single-stranded, double-stranded, or triple or more stranded nucleotide. The term "nucleotide" is also meant to include an association of DNA and RNA strands, a mixture of ribonucleotides (RNAs) and deoxyribonucleotides (DNAs) on one nucleotide strand, and an association of two strands or three or more strands comprising such a nucleotide strand.

In the present invention, the terms "polypeptide", "peptide", and "protein" have the same meaning.

In the present invention, the term "antigen" has the same meaning as "immunogen".

In the present invention, the term "cell" also includes, for example, various cells derived from individual animals, subcultured cells, primary cultured cells, cell lines, recombinant cells, and microbial cells.

In the present invention, each of an antibody that binds to LAG-3 and an antibody that recognizes LAG-3 may be referred to as an "anti-LAG-3 antibody" or abbreviated as a "LAG-3 antibody". The anti-LAG-3 antibody includes monoclonal antibodies, chimerized antibodies, humanized antibodies, human antibodies, chimeric antibodies, and the like.

The term "binding fragment of an antibody" in the present invention means an antibody fragment that exerts at least a part of the functions exerted by the original antibody. Examples of the "binding fragment of the antibody" can include, but are not limited to, Fab, F(ab')2, scFv, Fab', and single chain immunoglobulin. Such a binding fragment of the antibody may be obtained by treating a full-length molecule of the antibody protein with an enzyme such as papain or pepsin or may be a recombinant protein produced in an appropriate host cell using a recombinant gene.

In the present invention, the "site" to which an antibody binds, i.e., the "site" recognized by an antibody, means a partial peptide or a partial conformation on an antigen that is bound or recognized by the antibody. In the present invention, such a site is also referred to as an epitope or an antibody binding site. Examples of the site on the LAG-3 protein that is bound or recognized by the anti-LAG-3 antibody can include a partial peptide or a partial conformation on the LAG-3 protein.

The heavy and light chains of an antibody molecule are known to each have three complementarity determining regions (CDRs). The complementarity determining regions are also called hypervariable domains. These regions are located in the variable regions of the antibody heavy and light chains. These sites have a particularly highly variable primary structure and are usually separated into three positions on the respective primary structures of the heavy and light chain polypeptide strands. In the present invention, the complementarity determining regions of the antibody are referred to as CDRH1, CDRH2, and CDRH3 from the amino terminus of the heavy chain amino acid sequence for the complementarity determining regions of the heavy chain and as CDRL1, CDRL2, and CDRL3 from the amino terminus of the light chain amino acid sequence for the complementarity determining regions of the light chain. These sites are proximal to each other on the three-dimensional structure and determine the specificity for the antigen to be bound. The portions other than CDRH1 to CDRH3 in the heavy chain variable region amino acid sequence are called frameworks (Framework Regions: hereinafter, FR), and the portions from the amino terminus up to but not including CDRH1, from just after CDRH1 up to but not including CDRH2, from just after CDRH2 up to but not including CDRH3, and from just after CDRH3 to the carboxyl terminus are respectively called FRH1 to FRH4. Likewise, the portions other than CDRL1 to CDRL3 in the light chain variable region amino acid sequence are also FRs, and the portions from the amino terminus up to but not including CDRL1, from just after CDRL1 up to but not including CDRL2, from just after CDRL2 up to but not including CDRL3, and from just after CDRL3 to the carboxyl terminus are respectively called FRL1 to FRL4. That is, in (the amino acid sequence(s) of) the heavy chain and light chain variable regions, FRH1-CDRH1-FRH2-CDRH2-FRH3-CDRH3-FRH4 and FRL1-CDRL1-FRL2-CDRL2-FRL3-CDRL3-FRL4 are continuously aligned from the amino terminal side toward the carboxyl terminus in this order.

In the present invention, the term "antibody mutant" means a polypeptide that has an amino acid sequence derived from the amino acid sequence of the original antibody by the substitution, deletion, addition, and/or insertion (hereinafter, collectively referred to as a "mutation") of amino acid(s) and binds to the LAG-3 protein. The number of mutated amino acids in the antibody mutant is 1, 1 to 2, 1 to 3, 1 to 4, 1 to 5, 1 to 6, 1 to 7, 1 to 8, 1 to 9, 1 to 10, 1 to 12, 1 to 15, 1 to 20, 1 to 25, 1 to 30, 1 to 40, or 1 to 50. The antibody mutant is also encompassed by the "antibody" of the present invention.

In the present invention, the term "several" in "1 to several" refers to 3 to 10.

In the present invention, examples of activities or properties exerted by the LAG-3 antibody can include biological activities or physicochemical properties and can specifically include various biological activities, binding activity against an antigen or an epitope, stability during production or storage, and thermal stability.

In the present invention, the phrase "hybridizing under stringent conditions" means hybridization under conditions involving hybridization at 65° C. in a solution containing 5×SSC, followed by washing at 65° C. for 20 minutes in an aqueous solution containing 2×SSC-0.1% SDS, at 65° C. for 20 minutes in an aqueous solution containing 0.5×SSC-0.1% SDS, and at 65° C. for 20 minutes in an aqueous solution containing 0.2×SSC-0.1% SDS, or hybridization under conditions equivalent thereto. SSC means an aqueous solution of 150 mM NaCl-15 mM sodium citrate, and "n×SSC" means SSC with an n-fold concentration.

In the present invention, the term "cytotoxicity" refers to some pathological change brought about to cells and means not only direct trauma but every type of structural or functional damage to cells, including DNA cleavage, formation of base dimers, chromosomal breakage, damage to mitotic apparatus, and reduction in the activities of various enzymes.

In the present invention, the term "cytotoxic activity" means an activity that causes the cytotoxicity mentioned above.

In the present invention, the term "antibody-dependent cell-mediated cytotoxic activity", also called "antibody-dependent cellular cytotoxic activity" or "ADCC activity", means the effect or activity of damaging target cells by NK cells or the like via antibodies.

In the present invention, the term "host-versus-graft reaction" means the hyperimmune state of a recipient observed after organ transplantation, and the damage to the transplanted organ by such a state.

In the present invention, the term "graft-versus-host disease" means symptoms, caused by immunological attack by the transplanted cells to a recipient after transplantation of hematopoietic cells.

In the present invention, the term "depletion" refers to a state where the number of cells included in a particular cell group has been reduced or has not been increased by cytotoxic activity or the like. Likewise, the term "deplete" refers to decreasing or not increasing the number of cells included in a particular cell group by cytotoxic activity or the like.

In the present invention, the term "cytotoxic T cell" means a T cell having cytotoxicity to cells included in a particular cell group, and examples thereof can include T cell subsets such as CD4+(positive) CD28-(negative) T cells, CD8+ CD28− T cells, CD4+CD57+ T cells, CD8+CD57+ T cells, perforin+ T cells, and granzyme B+ T cells. Such cytotoxic T cells have been reported as one of the main inflammatory cells involved in diseases of the immune system or autoimmune diseases, such as asthma and severe asthma (hereinafter, collectively referred to as "asthma") or chronic obstructive pulmonary disease (COPD) (Non Patent Literatures 12 and 15), and have a high cytotoxic action, while resistance to the anti-inflammatory action brought about by steroid treatment or resistance to apoptosis induction has been reported (Non Patent Literature 16).

2. Antigen Protein (2-1) Properties

The LAG-3 protein (which may be hereinafter referred to simply as "LAG-3") is a transmembrane receptor protein and is composed of an extracellular region, composed of immunoglobulin-like domains (IgD1 to 4), which contains a ligand binding site, a type-I single-pass transmembrane region, and an intracellular region. LAG-3 has the same meaning as CD223.

In the present invention, LAG-3 is derived from vertebrates, preferably derived from mammals, more preferably derived from humans.

The LAG-3 protein has the following properties:
(i) binding to major histocompatibility complex (MHC) class II molecules on antigen presenting cells;
(ii) binding to MHC class II molecules and transmitting inhibitory signals to T cells expressing such molecules, to regulate T cell function negatively;
(iii) the LAG-3 protein in the present invention comprises an amino acid sequence (which will be hereinafter referred to as the "LAG-3 amino acid sequence") according to any one of (a) to (d) below, consists of an amino acid sequence comprising the LAG-3 amino acid sequence, or consists of the LAG-3 amino acid sequence:
(a) the amino acid sequence represented by SEQ ID No: 86 (FIG. 101);
(b) an amino acid sequence that exhibits 80% or higher, 82% or higher, 84% or higher, 86% or higher, 88% or higher, 90% or higher, 92% or higher, 94% or higher, 96% or higher, 98% or higher, or 99% or higher sequence identity to the amino acid sequence represented by SEQ ID No: 86 (FIG. 101) and is comprised in a polypeptide having MHC class II molecule binding activity;
(c) an amino acid sequence that is derived from the amino acid sequence represented by SEQ ID No: 86 (FIG. 101) by the substitution, deletion, addition, or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid and is comprised in a polypeptide having MHC class II molecule binding activity; and
(d) an amino acid sequence that is encoded by the nucleotide sequence of a polynucleotide (nucleic acid molecule) hybridizing under stringent conditions to a polynucleotide (nucleic acid molecule) having a nucleotide sequence complementary to a nucleotide sequence encoding the amino acid sequence represented by SEQ ID No: 86 (FIG. 101) and is comprised in a polypeptide having MHC class II molecule binding activity.

The polypeptide according to any one of (b) to (d) may have other activities of LAG-3 in addition to the MHC class II molecule binding activity.

(iv) The LAG-3 protein can be obtained from LAG-3-expressing cells, tissues, or cancer tissues, cells derived from the tissues, cultures of the cells, and the like, of a vertebrate, preferably of a mammal, more preferably of a rodent, such as a mouse or a rat, and a human, even more preferably of a human, a rat, or a mouse.

The expression of LAG-3 is observed in activated T cells, inflammation sites and the like in vivo, and almost no expression or a very low level of expression is seen in cells of normal tissues.

The LAG-3 protein may be a native (non-recombinant) or recombinant protein. The LAG-3 protein is also intended to include fusion products with another peptide or protein such as a carrier or a tag. The LAG-3 protein is further intended to include forms provided with a chemical modification including the addition of a polymer such as PEG and/or with a biological modification including a sugar chain modification. Moreover, the LAG-3 protein is intended to include a LAG-3 protein fragment. Of the LAG-3 protein fragments, those having the properties described in (i) and/or (ii) above are called LAG-3 protein binding fragments.

(2-2) Antigen Gene

The LAG-3 gene in the present invention comprises a nucleotide sequence (which will be hereinafter referred to as the "LAG-3 gene sequence") according to any one of (a) to (c) below, consists of a nucleotide sequence comprising the LAG-3 gene sequence, or consists of the LAG-3 gene sequence:
(a) a nucleotide sequence encoding the amino acid sequence represented by SEQ ID No: 86 (FIG. 101);
(b) the nucleotide sequence of a polynucleotide (nucleic acid molecule) that hybridizes under stringent conditions to a polynucleotide (nucleic acid molecule) consisting of a nucleotide sequence complementary to the nucleotide sequence encoding the amino acid sequence represented by SEQ ID No: 86 (FIG. 101) and encodes an amino acid sequence of a polypeptide having MHC class II molecule binding activity; and
(c) a nucleotide sequence that encodes an amino acid sequence derived from the amino acid sequence represented by SEQ ID No: 86 (FIG. 101) by the substitution, deletion, addition, or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 base and encodes an amino acid sequence of a polypeptide having MHC class II molecule binding activity.

The polypeptide having the amino acid sequence encoded by the nucleotide sequence according to (b) or (c) may have other activities of LAG-3 in addition to the MHC class II molecule binding activity.

The expression and the expression level of the LAG-3 gene may be assayed with either a LAG-3 gene transcript or the LAG-3 protein as an index. The former index can be determined by RT-PCR, Northern blot hybridization, or the like, while the latter index can be determined by an immunoassay such as flow cytometry, Western blotting, immunohistochemical staining, or the like, respectively.

(2-3) Preparation of Antigenic Protein

The LAG-3 protein can be prepared by purification or isolation from animal tissues (including body fluids), cells derived from the tissues, or cultures of the cells, gene recombination, in vitro translation, chemical synthesis, etc.

(2-3-1) Purification or isolation of non-recombinant LAG-3

The non-recombinant LAG-3 protein can be purified or isolated from LAG-3-expressing cells. Examples of the LAG-3-expressing cells can include those described in (iv) of (2-1), but the origin of the non-recombinant LAG-3 protein is not limited thereto.

The purification or isolation from such tissues, cells, cell cultures, or the like, can be performed by a combination of approaches well known by those skilled in the art, such as fractionation and chromatography.

(2-3-2) Preparation of Recombinant LAG-3 Protein

The LAG-3 protein can also be prepared in a recombinant form. Specifically, host cells are transfected with a gene encoding the amino acid sequence of the LAG-3 protein or a LAG-3 protein fragment, and the LAG-3 protein can be recovered from cultures of the cells. Also, the LAG-3 protein can be expressed not only as a molecule having the same amino terminus (N terminus) and/or carboxy terminus (C terminus) as native ones, but also as a fusion protein with a secretory signal, an intracellular localization signal, a tag for affinity purification, or a partner peptide. The LAG-3 protein can be purified or isolated from such recombinant cell cultures by an appropriate combination of methods such as fractionation and chromatography described in (2-3-1) Purification or isolation of non-recombinant LAG-3 protein. Further, the LAG-3 protein-containing solution can be subjected to buffer exchange and/or concentration using gel filtration or a concentrator such as Centriprep.

(2-3-3) In Vitro Translation

The LAG-3 protein can also be prepared by in vitro translation. Such a translation method is not particularly limited as long as the method employs a cell-free translation system involving: enzymes necessary for transcription and translation, substrates, and energy substances. Examples thereof can include a method using the Rapid Translation System (RTS) manufactured by Roche Diagnostics K.K.

(2-3-4) Chemical Synthesis

The LAG-3 protein can also be prepared by chemical synthesis. Examples of the chemical synthesis method can include solid-phase peptide synthesis methods such as Fmoc and Boc synthesis methods.

3. Antibody (3-1) Classification of Antibody

In the present invention, the LAG-3 antibody may be either a monoclonal or a polyclonal antibody. Examples of the monoclonal antibody can include non-human animal-derived antibodies (non-human animal antibodies), human-derived antibodies (human antibodies), chimerized antibodies (chimeric antibodies), and humanized antibodies.

Examples of the non-human animal antibody can include antibodies derived from vertebrates such as mammals and birds. Examples of the mammal-derived antibody can include rodent-derived antibodies such as mouse antibodies and rat antibodies. Examples of the bird-derived antibody can include chicken antibodies. Examples of the anti-human LAG-3 rat monoclonal antibody can include, but are not limited to, rLA204, rLA212, rLA225, 4LA869, and rLA1264.

Examples of the chimerized antibody can include, but are not limited to, an antibody comprising non-human animal antibody-derived variable regions bound to human antibody (human immunoglobulin) constant regions. Examples of the chimerized antibody comprising non-human animal antibody-derived variable regions bound to human antibody constant regions can include those having heavy and light chain variable regions derived from the rat monoclonal antibody rLA204, rLA212, rLA225, 4LA869, or rLA1264, and having human heavy and light chain constant regions (which are referred to as "cLA204", "cLA212", "cLA225", "cLA869", or "cLA1264", respectively).

Examples of the humanized antibody can include, but are not limited to, a human antibody (human immunoglobulin variable regions) grafted with CDRs in the variable regions of a non-human animal antibody, a human antibody grafted with the CDRs as well as with partial sequences of FRs of a non-human animal antibody, and an antibody having human antibody amino acids or other amino acids substituted for one or two or more non-human animal antibody-derived amino acids in any of these human (humanized) antibodies. Examples of the CDRs in the variable regions of a non-human animal antibody can include CDRH1 to CDRH3 in the heavy chain variable region and CDRL1 to CDRL3 in the light chain variable region derived from rLA204, rLA212, rLA225, rLA869, or rLA1264 mentioned above. Examples of the humanized antibody comprising CDRH1 to CDRH3 in the heavy chain variable region and CDRL1 to CDRL3 in the light chain variable region derived from rLA212 can include hLA212_H2/L1 to H2/L5, hLA212_H3/L1 to H3/L5, and hLA212_H4/L2.

The human antibody is not specifically limited, as long as the antibody recognizes LAG-3 protein, but examples thereof can include a human antibody binding to the same site as an antibody having the CDRs of the LAG-3 antibody, and a human antibody binding to the same site on LAG-3 as any one of the non-human animal antibodies, the chimeric antibodies, the humanized antibodies, and the like, and an antibody competing with any one of such antibodies for binding to LAG-3.

The antibody according to the present invention may be comprised of portions derived from a plurality of different antibodies as long as the antibody has LAG-3 binding activity. Examples of such an antibody can include an antibody comprising heavy and/or light chains exchanged among a plurality of different antibodies, an antibody comprising full-length heavy and/or light chains exchanged thereamong, an antibody comprising variable or constant regions exchanged thereamong, and an antibody comprising all or some CDRs exchanged thereamong. The heavy and light chain variable regions of the chimeric antibody may be derived from different LAG-3 antibodies. CDRH1 to CDRH3 and CDRL1 to CDRL3 in the heavy and light chain variable regions of the humanized antibody may be derived from two or more different LAG-3 antibodies. CDRH1 to CDRH3 and CDRL1 to CDRL3 in the heavy and light chain variable regions of the human antibody may be a combination of CDRs carried by two or more different LAG-3 antibodies. The antibody or the binding fragment thereof composed of such portions derived from a plurality of different antibodies each has the following properties, functions, activities, etc., described in (3-2) and (3-3), preferably (3-4) in addition to the above, more preferably (3-5) in addition to the above, further more preferably all of (3-2) to (3-8).

Examples of the isotype of the monoclonal antibody can include, but are not particularly limited to, IgG such as IgG1, IgG2, IgG3, and IgG4, IgM, IgA such as IgA1 and IgA2, IgD, and IgE and can preferably include IgG and IgM. The isotype and subclass of the monoclonal antibody can be determined by, for example, an Ouchterlony test, an enzyme-linked immuno-sorbent assay (hereinafter, referred to as "ELISA"), or a radio immunoassay (hereinafter, referred to as "RIA"). A commercially available kit for identification (e.g., Mouse Typer Kit; Bio-Rad Laboratories, Inc., and RAT MONOCLONAL ANTIBODY ISOTYPING TEST KIT: AbD Serotec) also may be used.

(3-2) Binding Specificity of Antibody

In the present invention, the LAG-3 antibody recognizes LAG-3 protein. In other words, the LAG-3 antibody binds to LAG-3 protein. Such an antibody is also expressed as an "anti-LAG-3 antibody". Preferably, the antibody used in the present invention specifically recognizes LAG-3 protein. In other words, the antibody used in the present invention preferably specifically binds to LAG-3 protein (the above properties will be collectively referred to as "LAG-3 binding activity" of the antibody). More preferably, the antibody used in the present invention specifically binds to the extracellular region(s) of LAG-3 protein, further more preferably, the antibody specifically binds to the immunoglobulin-like domains (which will be hereinafter referred to as "Ig-like domains") of LAG-3 protein, still further more preferably, the antibody specifically binds to Ig-like domain 3.

In the present invention, the term "specific recognition", i.e., "specific binding", means binding which is not non-specific adsorption. Examples of criteria for determination of whether binding is specific or not can include a dissociation constant (hereinafter, referred to as "KD"). Preferably, the antibody used in the present invention has a KD value of $1 \times 10^{-5}$ or lower, $5 \times 10^{-6}$ or lower, $2 \times 10^{-6}$ or lower, or $1 \times 10^{-6}$ or lower, more preferably $5 \times 10^{-7}$ or lower, $2 \times 10^{-7}$ or lower, or $1 \times 10^{-7}$ or lower, even more preferably $5 \times 10^{-8}$ or lower, $2 \times 10^{-8}$ or lower, or $1 \times 10^{-8}$ or lower, further more preferably $5 \times 10^{-9}$ or lower, $2 \times 10^{-9}$ or lower, or $1 \times 10^{-9}$ or lower, most preferably $5 \times 10^{-10}$ or lower, $2 \times 10^{-10}$ or lower, or $1 \times 10^{-10}$ or lower for the LAG-3 protein.

In the present invention, the binding of the antibody to the antigen can be assayed or determined by ELISA, RIA, surface plasmon resonance (hereinafter, referred to as "SPR") analysis, or the like. Examples of equipment used in the SPR analysis can include BIAcore™ (manufactured by GE Healthcare Bio-Sciences Corp.), ProteOn™ (manufactured by Bio-Rad Laboratories, Inc.), SPR-Navi™ (manufactured by BioNavis Oy Ltd.), Spreeta™ (manufactured by Texas Instruments Inc.), SPRi-Plex II™ (manufactured by Horiba, Ltd.), and Autolab SPR™ (manufactured by Metrohm Japan Ltd.). The binding of the antibody to the antigen expressed on a cell surface can be assayed by flow cytometry, Cell-ELISA, or the like.

(3-3) Cytotoxic Activity of Antibody

According to an aspect, the anti-LAG-3 antibody used in the present invention has antibody-dependent cellular cytotoxic (ADCC) activity, preferably has ADCC activity in vitro, more preferably has ADCC activity against LAG-3-expressing T cells. The anti-LAG-3 antibody used in the present invention may have complement-dependent cytotoxic (CDC) activity and/or antibody-dependent cellular phagocytosis (ADCP) activity in addition to the ADCC activity. In the present invention, the term "in vitro ADCC activity" is also simply referred to as "ADCC activity".

The ADCC activity can be assayed by a known method. Cells expressing the antigen of interest (target cells) and effector cells capable of killing the target cells are used in the ADCC activity assay. The effector cells recognize the Fc regions of antibodies binding to the target cells via Fcγ receptors. The effector cells kill the target cells by signals transduced from the Fcγ receptors. In the case of assaying the ADCC activity of an antibody having a human-derived Fc region, human NK cells are used as the effector cells. The human NK cells can be prepared from human peripheral blood mononuclear cells (PBMCs) by a method known in the art. Alternatively, PBMCs may be used directly as the effector cells.

(3-4) In Vivo LAG-3 Positive Cell Number Reducing Activity of Antibody

In the present invention, according to an aspect, the LAG-3 antibody reduces the number of LAG-3 positive cells, preferably reduces the number of LAG-3 positive cells in vivo, and more preferably reduces the number of LAG-3 positive cells in vivo in a low fucose form.

The LAG-3 positive cells include cells forced to express LAG-3 and cells having LAG-3 expression induced by stimulation, but are not limited thereto, as long as they are cells expressing LAG-3.

The number of LAG-3 positive cells can be counted by a conventional method such as flow cytometry.

In the present invention, the term "low fucose form" means a state where (i) the amount of fucose (fucose residues) binding to an antibody or a binding fragment thereof in N-glycoside-linked complex-type sugar chains is smaller than the amount of fucose (fucose residues) binding to the original (parent) antibody or a binding fragment thereof in N-glycoside-linked complex-type sugar chains, (ii) the amount of fucose (fucose residues) binding to an antibody or a binding fragment thereof in N-glycoside-linked complex-type sugar chains is smaller than the amount of fucose (fucose residues) naturally binding to an antibody or a binding fragment thereof in N-glycoside-linked complex-type sugar chains, or (iii) the amount of fucose (fucose residues) or sugar chains comprising fucose (fucose residues) binding to an antibody or a binding fragment thereof in N-glycoside-linked complex-type sugar chains is at or below the detection limit in a physical or chemical analysis (preferably mass spectrometry). In the case where the amount of fucose (fucose residues) binding to a modified antibody or a binding fragment thereof in N-glycoside-linked complex-type sugar chains is smaller than that before the modification, the modified antibody or the binding fragment thereof is understood to be in a "low fucose form". The modified form of hLA212_H4/L2 described below, which is a humanized antibody, is an aspect of the antibody in a low fucose form. An antibody or a binding fragment in a low fucose form has higher affinity for Fcγ receptors IIIA and stronger ADCC activity than when not in a low fucose form.

(3-5) In Vivo Experimental Autoimmune Encephalomyelitis Inhibitory Activity of Antibody In the present invention, according to an aspect, the LAG-3 antibody has encephalomyelitis inhibitory activity, preferably has experimental autoimmune encephalomyelitis inhibitory activity in vivo, more preferably has experimental autoimmune encephalomyelitis inhibitory activity in vivo in a low fucose form.

In the present invention, experimental autoimmune encephalomyelitis means encephalomyelitis induced by injection of a peptide derived from MOG (Myelin Oligodendrocyte Glycoprotein) which is one of the central nervous myelin component proteins, to mice together with Freund's Adjuvant.

Experimental autoimmune encephalomyelitis inhibitory activity can be assayed by daily observation of clinical scores that reflect the degrees of paralysis. The clinical score can be set, for example, as follows:
Score 0: Asymptomatic;
Score 1: Limp tail;
Score 2: Abnormal gait or loss of righting reflex;
Score 3: Hind leg paralysis;
Score 4: Partial paralysis of forelimbs; and
Score 5: Death or euthanasia.

(3-6) Activated Human T Cell Binding Activity of Antibody

In the present invention, according to an aspect, the LAG-3 antibody binds to activated human T cells, preferably binds to LAG-3 positive activated human T cells. The binding of the antibody to the activated human T cells can be assayed or detected, for example, by flow cytometry.

(3-7) Presence of Antibody Allowing Human LAG-3 to Bind to Human MHC Class II Molecules According to an aspect of the present invention, human LAG-3 can bind to human MHC class II molecules in the presence of the antibody, or in the present invention, the LAG-3 antibody does not inhibit binding of human LAG-3 to human MHC class II molecules.

The binding of fusion proteins of the extracellular region of the LAG-3 molecule and the Fc part of IgG to Raji cells that endogenously highly express MHC class II molecules can be evaluated, for example, by assay or detection by flow cytometry.

(3-8) Presence of Antibody Allowing Human LAG-3 to Exert Human T Cell Suppression Function According to another aspect, human LAG-3 exerts a human T cell suppression function in the presence of the LAG-3 antibody of the present invention.

The term "T cell suppression function" in the present invention means to reduce or suppress the amount of cytokine produced upon stimulation of T cells.

The T cell suppression function by human LAG-3 can be assayed, for example, by quantitating cytokines produced when human T cells are stimulated to induce LAG-3 expression.

In the present invention, the stimulation of human T cells is not specifically limited, but examples thereof can include stimulation with specific antigens, anti-CD3 antibodies, combinations of anti-CD3 antibodies and anti-CD28 antibodies, super antigens, cells derived from other donors, preferably stimulation with Staphylococcal Enterotoxin B, cells derived from other donors having different MHC, and the like.

Examples of the cytokines can include cytokines produced from activated T cells, preferably various interleukins and interferons, more preferably interleukin 2 (IL-2) and interferon γ.

(3-9) Monoclonal Antibody

The present invention provides an anti-LAG-3 monoclonal antibody and a binding fragment thereof. The monoclonal antibody includes monoclonal antibodies derived from non-human animals such as rat antibodies, mouse antibodies, rabbit antibodies, chicken antibodies, and fish antibodies, chimeric antibodies, humanized antibodies, human antibodies, binding fragments thereof, and modified forms thereof. Out of these, examples of the rat monoclonal antibody can include rLA204, rLA212, rLA225, rLA869, and rLA1264.

rLA204 is an anti-human LAG-3 rat monoclonal antibody obtained by the method described in Example 1. The nucleotide sequence of the heavy chain variable region of rLA204 is described in SEQ ID No: 1 (FIG. 16), and its amino acid sequence is described in SEQ ID No: 2 (FIG. 17). The nucleotide sequence of the light chain variable region of rLA204 is described in SEQ ID No: 3 (FIG. 18), and its amino acid sequence is described in SEQ ID No: 4 (FIG. 19). The amino acid sequence of CDRH1 of rLA204 is described in SEQ ID No: 41 (FIG. 56), the amino acid sequence of CDRH2 thereof is described in SEQ ID No: 42 (FIG. 57), the amino acid sequence of CDRH3 thereof is described in SEQ ID No: 43 (FIG. 58), the amino acid sequence of CDRL1 thereof is described in SEQ ID No: 44 (FIG. 59), the amino acid sequence of CDRL2 thereof is described in SEQ ID No: 45 (FIG. 60), and the amino acid sequence of CDRL3 thereof is described in SEQ ID No: 46 (FIG. 61), respectively.

The rLA212 is an anti-human LAG-3 rat monoclonal antibody obtained according to the method described in Example 1. The nucleotide sequence of the heavy chain variable region of rLA212 is described in SEQ ID No: 5 (FIG. 20), and its amino acid sequence is described in SEQ ID No: 6 (FIG. 21). The nucleotide sequence of the light chain variable region of rLA212 is described in SEQ ID No: 7 (FIG. 22), and its amino acid sequence is described in SEQ ID No: 8 (FIG. 23). The amino acid sequence of CDRH1 of rLA212 is described in SEQ ID No: 47 (FIG. 62), the amino acid sequence of CDRH2 thereof is described in SEQ ID No: 48 (FIG. 63), the amino acid sequence of CDRH3 thereof is described in SEQ ID No: 49 (FIG. 64), the amino acid sequence of CDRL1 thereof is described in SEQ ID No: 50 (FIG. 65), the amino acid sequence of CDRL2 thereof is described in SEQ ID No: 51 (FIG. 66), and the amino acid sequence of CDRL3 thereof is described in SEQ ID No: 52 (FIG. 67), respectively.

The rLA225 is an anti-human LAG-3 rat monoclonal antibody obtained according to the method described in Example 1. The nucleotide sequence of the heavy chain variable region of rLA225 is described in SEQ ID No: 9 (FIG. 24), and its amino acid sequence is described in SEQ ID No: 10 (FIG. 25). The nucleotide sequence of the light chain variable region of rLA225 is described in SEQ ID No: 11 (FIG. 26), and its amino acid sequence is described in SEQ ID No: 12 (FIG. 27). The amino acid sequence of CDRH1 of rLA225 is described in SEQ ID No: 53 (FIG. 68), the amino acid sequence of CDRH2 thereof is described in SEQ ID No: 54 (FIG. 69), the amino acid sequence of CDRH3 thereof is described in SEQ ID No: 55 (FIG. 70), the amino acid sequence of CDRL1 thereof is described in SEQ ID No: 56 (FIG. 71), the amino acid sequence of CDRL2 thereof is described in SEQ ID No: 57 (FIG. 72), and the amino acid sequence of CDRL3 thereof is described in SEQ ID No: 58 (FIG. 73).

The rLA869 is an anti-human LAG-3 rat monoclonal antibody obtained according to the method described in Example 1. The nucleotide sequence of the heavy chain variable region of rLA869 is described in SEQ ID No: 13 (FIG. 28), and its amino acid sequence is described in SEQ ID No: 14 (FIG. 29). The nucleotide sequence of the light chain variable region of rLA869 is described in SEQ ID No: 15 (FIG. 30), and its amino acid sequence is described in SEQ ID No: 16 (FIG. 31). The amino acid sequence of CDRH1 of rLA869 is described in SEQ ID No: 59 (FIG. 74), the amino acid sequence of CDRH2 thereof is described in SEQ ID No: 60 (FIG. 75), the amino acid sequence of CDRH3 thereof is described in SEQ ID No: 61 (FIG. 76), the amino acid sequence of CDRL1 thereof is described in SEQ ID No: 62 (FIG. 77), the amino acid sequence of CDRL2 thereof is described in SEQ ID No: 63 (FIG. 78), and the amino acid sequence of CDRL3 thereof is described in SEQ ID No: 64 (FIG. 79).

The rLA1264 is an anti-human LAG-3 rat monoclonal antibody obtained according to the method described in Example 1. The nucleotide sequence of the heavy chain variable region of rLA1264 is described in SEQ ID No: 17 (FIG. 32), and its amino acid sequence is described in SEQ ID No: 18 (FIG. 33). The nucleotide sequence of the light chain variable region of rLA1264 is described in SEQ ID No: 19 (FIG. 34), and its amino acid sequence is described in SEQ ID No: 20 (FIG. 35). The amino acid sequence of CDRH1 of rLA1264 is described in SEQ ID No: 65 (FIG. 80), the amino acid sequence of CDRH2 thereof is described in SEQ ID No: 66 (FIG. 81), the amino acid sequence of CDRH3 thereof is described in SEQ ID No: 67 (FIG. 82), the amino acid sequence of CDRL1 thereof is described in SEQ ID No: 68 (FIG. 83), the amino acid sequence of CDRL2 thereof is described in SEQ ID No: 69 (FIG. 84), and the amino acid sequence of CDRL3 thereof is described in SEQ ID No: 70 (FIG. 85).

Other examples of the anti-human LAG-3 monoclonal antibody can include the anti-human LAG-3 mouse antibody A9H12 (see WO2008/132601).

In the present invention, an antibody mutant preferably exhibits, for example, reduced sensitivity to protein degradation or oxidation, an improved biological activity, an improved ability to bind to the antigen, or impartation of certain physicochemical or functional properties thereto. Examples of such an antibody mutant can include an antibody having an amino acid sequence derived from the amino acid sequence of the original antibody by a conservative amino acid substitution of 1 or 2 or more, preferably 1 to several amino acids. The conservative amino acid substitution is a substitution that occurs in an amino acid group having related amino acid side chains.

Preferred amino acid groups are as follows: an acidic group including aspartic acid and glutamic acid; a basic group including lysine, arginine, and histidine; a nonpolar group including alanine, valine, leucine, isoleucine, proline, phenylalanine, methionine, and tryptophan; and an uncharged polar family including glycine, asparagine, glutamine, cysteine, serine, threonine, and tyrosine. Other preferred amino acid groups are as follows: an aliphatic hydroxy group including serine and threonine; an amide-containing group including asparagine and glutamine; an aliphatic group including alanine, valine, leucine, and isoleucine; and an aromatic group including phenylalanine, tryptophan, and tyrosine. Such an amino acid substitution in the antibody mutant is preferably performed without reducing the antigen binding activity of the original (parent) antibody.

Aspartic acid contained in a protein is easily converted to isoaspartic acid by isomerization when an amino acid linked thereto on the C terminal side has a small side chain. On the other hand, asparagine is easily converted to aspartic acid by deamidation and may be further converted to isoaspartic acid by isomerization. The progression of such isomerization or deamidation may influence the stability of the protein. Accordingly, aspartic acid or asparagine in the protein or, for example, an amino acid adjacent thereto, can be substituted for a different amino acid in order to avoid such isomerization or deamidation. Preferably, an antibody mutant having such an amino acid substitution maintains the antigen binding activity of the original antibody.

The present invention also encompasses, for example: an antibody mutant having an amino acid sequence derived from the amino acid sequence of rLA204, rLA212, rLA225, rLA869, rLA1264, or A9H12 of the present invention by conservative amino acid substitution; and a mouse antibody, a rat antibody, a chimerized antibody, a humanized antibody, or a human antibody comprising a CDR having an amino acid sequence in which a conservative amino acid mutation is introduced in the amino acid sequence of any of CDRH1 to CDRH3 and CDRL1 to CDRL3 derived from rLA204, rLA212, rLA225, rLA869, rLA1264, or A9H12.

The mutant of the antibody of the present invention encompasses a human LAG-3-binding antibody mutant comprising CDRH1 to CDRH3 and CDRL1 to CDRL3 having amino acid sequences where 1 to several, preferably 1 to 3, more preferably 1 or 2, most preferably 1 amino acid(s) is substituted for a different amino acid(s) in the amino acid sequences of any one or two or more of CDRH1 to CDRH3 and CDRL1 to CDRL3 derived from rLA204, rLA212, rLA225, rLA869, rLA1264, or A9H12 of the present invention.

The antibody mutant also includes an antibody having CDRH1 to CDRH3 and CDRL1 to CDRL3 derived from a plurality of antibodies. Examples of such a mutant can include an antibody mutant comprising CDRH3 derived from a certain antibody and CDRH1, CDRH2, and CDRL1 to CDRL3 derived from another antibody.

The "antibody" according to the present invention also encompasses these antibody mutants.

The constant regions of the antibody of the present invention are not particularly limited. Preferably, constant regions derived from a human antibody are used in the LAG-3 antibody for cytotoxic T cell depletion. Examples of the heavy chain constant region of the human antibody can include Cγ1, Cγ2, Cγ3, Cγ4, Cμ, Cδ, Cα1, Cα2, and Cε. Examples of the light chain constant region of the human antibody can include Cκ and Cλ.

(3-10) Chimeric Antibody

The anti-LAG-3 chimerized antibody or the binding fragment thereof used in the present invention has the properties, functions, activities, etc., described in (3-2) and (3-3), preferably (3-4) in addition to the above, more preferably (3-5) in addition to the above, further more preferably all of (3-2) to (3-8).

The nucleotide sequence and amino acid sequence of the heavy chain of cLA212 exemplified as the rat-human chimeric antibody of the present invention and the nucleotide sequence and amino acid sequence of the light chain thereof are respectively shown in SEQ ID No: 23, 24, 25, and 26 (FIGS. 38, 39, 40, and 41). Nucleotide positions 1 to 57 in the nucleotide sequence of the heavy chain and amino acid positions 1 to 19 in the amino acid sequence of the heavy chain each represent a signal sequence, which is normally not contained in the nucleotide sequences and amino acid sequences of most mature heavy chains. Likewise, nucleotide positions 1 to 60 in the nucleotide sequence of the light chain and amino acid positions 1 to 20 in the amino acid sequence of the light chain each represent a signal sequence, which is normally not contained in the nucleotide sequences and amino acid sequences of most mature light chains.

Rat-human chimeric antibodies cLA204, cLA225, cLA869, and cLA1264 are described elsewhere.

Other examples of the chimeric antibody of the present invention can include IMP731 (chimera type A9H12; see WO2008/132601), which is a mouse-human chimeric antibody of the anti-human LAG-3 mouse antibody A9H12.

(3-11) Binding Fragment of Antibody

According to one aspect, the antibody used in the present invention may be a binding fragment of the anti-LAG-3 antibody. The binding fragment of the antibody means a fragment that maintains at least a part of the functions of the antibody. Examples of such functions of the antibody can generally include antigen binding activity, antigen activity-regulating activity, and antibody-dependent cellular cytotoxic (ADCC) activity. Preferably, the binding fragment of the anti-LAG-3 antibody used in the present invention has the properties, functions, activities, etc., described in (3-2) and (3-3), preferably (3-4) in addition to the above, more preferably (3-5) in addition to the above, further more preferably all of (3-2) to (3-8).

The binding fragment of the antibody is not particularly limited as long as the fragment of the antibody maintains at least a portion of the activities of the antibody. Examples thereof can include, but are not limited to, Fab, F(ab')2, Fv, single chain Fv (scFv) comprising heavy and light chain Fvs linked via an appropriate linker, diabodies, linear antibodies, multispecific antibodies formed from antibody fragments, and Fab', which is a monovalent fragment of antibody variable regions obtained by the treatment of F(ab')2 under reducing conditions. The binding fragment of the antibody is also meant to include a molecule comprising the fragment of the antibody as well as other portions, such as scFv retaining a linker portion.

A molecule that is derived from the antibody protein by the deletion of 1 to several or more amino acid(s) at its amino terminus and/or carboxy terminus and maintains at least a portion of the functions of the antibody is also encompassed within the meaning of the binding fragment of the antibody. For example, the heavy chain of an antibody produced by cultured mammalian cells is known to lack a lysine residue at the carboxy terminus (Journal of Chromatography A, 705: 129-134 (1995)). Also, the heavy chain of such an antibody is known to lack two amino acid residues (glycine and lysine) at the carboxy terminus and instead have an amidated proline residue at the carboxy terminus (Analytical Biochemistry, 360: 75-83 (2007)). The deletion and the modification in these heavy chain sequences, however, do not influence the ability of the antibody to bind to the antigen or its effector functions (complement activation, antibody-dependent cellular cytotoxic effects, etc.). Such a modified form of the binding fragment of the antibody is also encompassed by the antibody or the binding fragment thereof, or a modified form (described later) thereof.

In the present invention, the antibody or the binding fragment thereof may be a multispecific antibody having specificity for at least 2 types of different antigens. The multispecific antibody is not limited to a bispecific antibody, which binds to 2 types of different antigens, and an antibody having specificity for 3 or more types of different antigens is also encompassed within the meaning of the term "multispecific antibody" of the present invention.

The multispecific antibody of the present invention may be a full-length antibody or a binding fragment thereof (e.g., bispecific F(ab')2 antibody). The bispecific antibody can also be prepared by linking the heavy and light chains (HL pairs) of two types of antibodies. Alternatively, the bispecific antibody may be obtained by fusing two or more types of monoclonal antibody-producing hybridomas to prepare bispecific antibody-producing fusion cells (Millstein et al., Nature (1983) 305, p. 537-539). The multispecific antibody can also be prepared in the same way as above.

According to one aspect, the LAG-3 antibody of the present invention is a single chain antibody (single chain Fv; hereinafter, referred to as "scFv"). An scFv is obtained by linking the heavy and light chain V regions of the antibody via a polypeptide linker (Pluckthun, The Pharmacology of Monoclonal Antibodies, 113, Rosenburg and Moore, ed., Springer Verlag, New York, p. 269-315 (1994); and Nature Biotechnology (2005), 23, p. 1126-1136). Also, a bi-scFv comprising two scFvs linked via a polypeptide linker can be used as a bispecific antibody. Alternatively, a multi-scFv comprising three or more scFvs may be used as a multispecific antibody.

The present invention includes a single chain immunoglobulin comprising full-length heavy and light chain sequences of the antibody linked via an appropriate linker (Lee, H-S, et al., Molecular Immunology (1999), 36, p. 61-71; and Schirrmann, T. et al., mAbs (2010), 2 (1) p. 73-76). Such a single chain immunoglobulin can be dimerized to thereby maintain a structure and activities similar to those of the antibody, which was originally a tetramer. In the present invention, the antibody may be an antibody that has a single heavy chain variable region and has no light chain sequence. Such an antibody, called a single domain antibody (sdAb) or a nanobody, has been reported to maintain the ability to bind to an antigen (Muyldermans S. et al., Protein Eng. (1994), 7 (9), 1129-35; and Hamers-Casterman C. et al., Nature (1993), 363 (6428), 446-8). These antibodies are also encompassed within the meaning of the functional fragment of the antibody.

(3-12) Humanized Antibody and Human Antibody

According to one aspect, the present invention provides a humanized antibody or a binding fragment thereof.

Preferably, the humanized anti-LAG-3 antibody or the binding fragment thereof used in the present invention has the properties, functions, activities, etc., described in (3-2) and (3-3), preferably (3-4) in addition to the above, more preferably (3-5) in addition to the above, further more preferably all of (3-2) to (3-8).

Preferred examples of the humanized antibody used in the present invention can include humanized antibodies having the heavy chain CDRH1 to CDRH3 and the light chain CDRL1 to CDRL3 of rLA204, rLA212, rLA225, rLA869, rLA1264, A9H12, or H5L7 as described below in A to F.

(A. Humanized Antibody Having Heavy Chain CDRH1 to CDRH3 and Light Chain CDRL1 to CDRL3 of rLA204 Antibody)

Examples of the humanized anti-LAG-3 antibody or the binding fragment thereof of the present invention can include a humanized antibody that consists of a heavy chain having a variable region comprising CDRH1 consisting of the amino acid sequence represented by SEQ ID No: 41 (FIG. 56), CDRH2 consisting of the amino acid sequence represented by SEQ ID No: 42 (FIG. 57), and CDRH3 consisting of the amino acid sequence represented by SEQ ID No: 43 (FIG. 58), and a light chain having a variable region comprising CDRL1 consisting of the amino acid sequence represented by SEQ ID No: 44 (FIG. 59), CDRL2 consisting of the amino acid sequence represented by SEQ ID No: 45 (FIG. 60), and CDRL3 consisting of the amino acid sequence represented by SEQ ID No: 46 (FIG. 61), and recognizes the LAG-3 protein, a binding fragment thereof, or a mutant thereof.

(B. Humanized Antibody Having Heavy Chain CDRH1 to CDRH3 and Light Chain CDRL1 to CDRL3 of rLA212 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 47 (FIG. 62), CDRH2 consisting of the amino acid sequence represented by SEQ ID No: 48 (FIG. 63), and CDRH3 consisting of the amino acid sequence represented by SEQ ID No: 49 (FIG.

64), and a light chain having a variable region comprising CDRL1 consisting of the amino acid sequence represented by SEQ ID No: 50 (FIG. 65), CDRL2 consisting of the amino acid sequence represented by SEQ ID No: 51 (FIG. 66), and CDRL3 consisting of the amino acid sequence represented by SEQ ID No: 52 (FIG. 67), and recognizes the LAG-3 protein, a binding fragment thereof, or a mutant thereof.

(C. Humanized Antibody Having Heavy Chain CDRH1 to CDRH3 and Light Chain CDRL1 to CDRL3 of rLA225 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 53 (FIG. 68), CDRH2 consisting of the amino acid sequence represented by SEQ ID No: 54 (FIG. 69), and CDRH3 consisting of the amino acid sequence represented by SEQ ID No: 55 (FIG. 70), and a light chain having a variable region comprising CDRL1 consisting of the amino acid sequence represented by SEQ ID No: 56 (FIG. 71), CDRL2 consisting of the amino acid sequence represented by SEQ ID No: 57 (FIG. 72), and CDRL3 consisting of the amino acid sequence represented by SEQ ID No: 58 (FIG. 73), and recognizes the LAG-3 protein, a binding fragment thereof, or a mutant thereof.

(D. Humanized Antibody Having Heavy Chain CDRH1 to CDRH3 and Light Chain CDRL1 to CDRL3 of rLA869 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 59 (FIG. 74), CDRH2 consisting of the amino acid sequence represented by SEQ ID No: 60 (FIG. 75), and CDRH3 consisting of the amino acid sequence represented by SEQ ID No: 61 (FIG. 76), and a light chain having a variable region comprising CDRL1 consisting of the amino acid sequence represented by SEQ ID No: 62 (FIG. 77), CDRL2 consisting of the amino acid sequence represented by SEQ ID No: 63 (FIG. 78), and CDRL3 consisting of the amino acid sequence represented by SEQ ID No: 64 (FIG. 79), and recognizes the LAG-3 protein, a binding fragment thereof, or a mutant thereof.

(E. Humanized Antibody Having Heavy Chain CDRH1 to CDRH3 and Light Chain CDRL1 to CDRL3 of rLA1264 Antibody)

Alternative examples of the humanized anti-LAG-3 antibody or the binding fragment thereof can include a humanized antibody that consists of a heavy chain having a variable region comprising CDRH1 consisting of the amino acid sequence represented by SEQ ID No: 65 (FIG. 80), CDRH2 consisting of the amino acid sequence represented by SEQ ID No: 66 (FIG. 81), and CDRH3 consisting of the amino acid sequence represented by SEQ ID No: 67 (FIG. 82), and a light chain having a variable region comprising CDRL1 consisting of the amino acid sequence represented by SEQ ID No: 68 (FIG. 83), CDRL2 consisting of the amino acid sequence represented by SEQ ID No: 69 (FIG. 84), and CDRL3 consisting of the amino acid sequence represented by SEQ ID No: 70 (FIG. 85), and recognizes the LAG-3 protein, a binding fragment thereof, or a mutant thereof.

(F. Humanized Antibody Having Heavy Chain CDRH1 to CDRH3 and Light Chain CDRL1 to CDRL3 of A9H12 Antibody or H5L7 Antibody)

Alternative examples thereof can include a humanized antibody that comprises CDRH1 to CDRH3 and CDRL1 to CDRL3 of the A9H12 antibody or the H5L7 antibody, and recognizes the LAG-3 protein, a binding fragment thereof, or a mutant thereof.

Preferred examples of the humanized antibody used in the present invention include those described in A to F above. More preferred examples of the humanized antibody can include, but are not limited to, hLA212_H2/L1 to hLA212_H2/L5, hLA212_H3/L1 to hLA212_H3/L5, and hLA212_H4/L2 (see [i] to [x] below) and the humanized IMP731 antibodies H5L7, H1L7, J7L7, H4L7, J11L7, H2L7, J13L7, H7L7, JOL7, HOL7, and H5L7BW (Patent Literature 2). For example, the more preferred examples of the humanized antibody used in the present invention also include an antibody comprising a heavy chain comprising the heavy chain variable region of any one of the humanized antibodies hLA212_H2/L1 to hLA212_H2/L5, hLA212_H3/L1 to hLA212_H3/L5, hLA212_H4/L2, H5L7, and H5L7BW and a light chain comprising the light chain variable region of any one of the humanized antibodies hLA212_H2/L1 to hLA212_H2/L5, hLA212_H3/L1 to hLA212_H3/L5, hLA212_H4/L2, H5L7, and H5L7BW.

[i]

[i-1] hLA212_H3/L2 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 33 (FIG. 48) (where the variable region is 61 to 387), and its amino acid sequence comprises amino acid positions 21 to 234 of SEQ ID No: 34 (FIG. 49) (where the variable region is 21 to 129). It can be evaluated by the methods described in the Examples that the antibody has physical properties that are suitable for the composition for cytotoxic T cell depletion, the method for treating or preventing a disease associated with cytotoxic T cells, the use for treatment or prevention, etc., of the present invention (data not shown), has the LAG-3 binding activity and the in vitro ADCC activity described in (3-2) and (3-3), the property described in (3-8), that is, the presence of the antibody allowing the human LAG-3 to exert a human T cell suppression function (see the Examples), and has the activities, the properties, etc., described in (3-4) to (3-7).

[i-2] hLA212_H4/L2 is a humanized antibody which was obtained in Example 8 and whose sugar chain modification is adjusted, and is a low fucose form of hLA212_H3/L2. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 33 (FIG. 48) (where the variable region is 61 to 387), and its amino acid sequence comprises amino acid positions 21 to 234 of SEQ ID No: 34 (FIG. 49) (where the variable region is 21 to 129). It can be evaluated by the methods described in the Examples that the antibody has physical properties that are suitable for the composition for cytotoxic T cell depletion, the method for treating or preventing a disease associated with cytotoxic T cells, the use for treatment or prevention, etc., of the present invention (data not shown), has the LAG-3 binding activity, the in vitro ADCC activity, the LAG-3 positive cell number reducing activity, the experimental autoimmune encephalomyelitis inhibitory activity, and the activated human T cell binding activity described in (3-2) to (3-6), has the properties described in (3-7), that is, the presence of the antibody allowing human LAG-3 to bind to human MHC class II molecules (see the Examples), and has the properties described in (3-8), that is, the presence of the antibody allowing human LAG-3 to exert a human T cell suppression function.

[ii] hLA212_H2/L1 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 31 (FIG. 46) (where the variable region is 61 to 387), and its amino acid sequence comprises amino acid positions 21 to 234 of SEQ ID No: 32 (FIG. 47) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[iii] hLA212_H3/L3 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 35 (FIG. 50) (where the variable region is 61 to 387), and its amino acid sequence comprises amino acid positions 21 to 234 of SEQ ID No: 36 (FIG. 51) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[iv] hLA212_H2/L2 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 33 (FIG. 48) (where the variable region is 61 to 387), and its amino acid sequence comprises amino acid positions 21 to 234 of SEQ ID No: 34 (FIG. 49) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[v] hLA212_H2/L3 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 35 (FIG. 50) (where the variable region is 61 to 387), and its amino acid sequence comprises amino acid positions 21 to 234 of SEQ ID No: 36 (FIG. 51) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[vi] hLA212_H2/L4 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 37 (FIG. 52) (where the variable region is 61 to 387), and its amino acid sequence comprises amino acid positions 21 to 234 of SEQ ID No: 38 (FIG. 53) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see Examples), and has the activities, the properties, etc., described in (3-4) to (3-8).

[vii] hLA212_H2/L5 is the humanized antibody obtained in Example 6. The nucleotide sequence of the heavy chain of this antibody comprises nucleotide positions 58 to 1410 of SEQ ID No: 27 (FIG. 42) (where the variable region is 58 to 420), and its amino acid sequence comprises amino acid positions 20 to 470 of SEQ ID No: 28 (FIG. 43) (where the variable region is 20 to 140). The nucleotide sequence of the light chain thereof comprises nucleotide positions 61 to 702 of SEQ ID No: 39 (FIG. 54) (where the variable region is 61 to 387), and its amino acid sequence comprises amino acid positions 21 to 234 of SEQ ID No: 40 (FIG. 55) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[viii] hLA212_H3/L1 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 31 (FIG. 46) (where the variable region is 61 to 387), and its amino acid sequence comprises amino acid positions 21 to 234 of SEQ ID No: 32 (FIG. 47) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[ix] hLA212_H3/L4 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 37 (FIG. 52) (where the variable region is 61 to 387), and its amino acid sequence comprises amino acid positions 21 to 234 of SEQ ID No: 38 (FIG. 53) (where the variable region is 21 to 129). It can be evaluated by the methods described in the Examples that the antibody has physical properties that are suitable for the composition, the treatment or prevention, etc., of the present invention (data not shown), has the LAG-3 binding activity and the in vitro ADCC activity described in (3-2) and (3-3) (see the Examples), and has the activities, the properties, etc., described in (3-4) to (3-8).

[x] hLA212_H3/L5 is the humanized antibody obtained in Example 6. The nucleotide sequence of the heavy chain of this antibody comprises nucleotide positions 58 to 1410 of SEQ ID No: 29 (FIG. 44) (where the variable region is 58 to 420), and its amino acid sequence comprises amino acid positions 20 to 470 of SEQ ID No: 30 (FIG. 45) (where the variable region is 20 to 140). The nucleotide sequence of the light chain thereof comprises nucleotide positions 61 to 702 of SEQ ID No: 39 (FIG. 54) (where the variable region is 61 to 387), and its amino acid sequence comprises amino acid positions 21 to 234 of SEQ ID No: 40 (FIG. 55) (where the variable region is 21 to 129). It can be evaluated by the methods described in the Examples that the antibody has physical properties that are suitable for the composition, the treatment or prevention, etc., of the present invention (data not shown), has the LAG3-binding activity and the in vitro ADCC activity described in (3-2) and (3-3) (see the Examples), and has the activities, the properties, etc., described in (3-4) to (3-8).

In [i] to [x] above, the activities described in (3-4) and (3-5) can be preferably evaluated in a low fucose form. In the present invention, the term "physical properties" means the stability of the antibody and the binding fragment thereof used in the present invention as a physical form, which can be evaluated using a known index. Examples of the stability as a physical form can include thermostability and storage stability, and examples of their indices can include Tm values obtained from thermograms and changes in antigen binding activity under storage conditions or accelerated deterioration conditions or changes over time.

Further, the hLA212 antibody_H4/L2 was administered to the human LAG-3/human FcγRIIIA double transgenic mice of Example 10 in a single dose, as a result of which, weight loss and other notable toxic events were not observed. Thus, the antibody used in the present invention advantageously possesses safety that is suitable for cytotoxic T cell depletion, and for methods for the treatment or prevention of diseases associated with cytotoxic T cells (defined elsewhere), etc.

Of the more preferred examples of the humanized anti-LAG-3 antibody and the binding fragment thereof used in the present invention described above, hLA212_H3/L2, hLA212_H2/L1, hLA212_H3/L3, hLA212_H3/L6, hLA212_H4/L2, H5L7, and H5L7BW are further more preferable.

The hLA212_H2/L1 to H2/L5, hLA212_H3/L1 to H3/L5, hLA212_H4/L2, H5L7, H5L7BW etc., included in the more preferred range of the humanized anti-LAG-3 antibody used in the present invention can comprise a heavy chain consisting of an amino acid sequence in which 1 to several, preferably 1 or 2 amino acids are substituted with other amino acids in FRH1 to FRH4 of the amino acid sequence of the heavy chain and a light chain consisting of an amino acid sequence in which 1 or more, preferably any number of amino acids selected from 1 to 14 are substituted with other amino acids in FRL1 to FRL4 of the amino acid sequence of the light chain.

More preferably, in the light chain of the humanized antibody such as hLA212_H2/L1 to H2/L5, hLA212_H3/L1 to H3/L5, or hLA212_H4/L2, amino acid 1 of FRL1, that is, amino acid 1 in the mature variable region (the amino acid corresponding to position 21 of SEQ ID No: 32 or FIG. 47) is Asp or Asn, amino acid 11 of FRL1, that is, amino acid 11 of the mature variable region (the amino acid corresponding to position 31 of SEQ ID No: 32 or FIG. 47) is Leu or Met, amino acid 13 of FRL1, that is, amino acid 13 of the mature variable region (the amino acid corresponding to position 33 of SEQ ID No: 32 or FIG. 47) is Ala or Ile, amino acid 21 of FRL1, that is, amino acid 21 of the mature variable region (the amino acid corresponding to position 41 of SEQ ID No: 32 or FIG. 47) is Ile or Met, amino acid 4 of FRL2, that is, amino acid 38 of the mature variable region (the amino acid corresponding to position 58 of SEQ ID No: 32 or FIG. 47) is Gln or Lys, amino acid 9 of FRL2, that is, amino acid 43 of the mature variable region (the amino acid corresponding to position 63 of SEQ ID No: 32 or FIG. 47) is Ala or Ser, amino acid 4 of FRL3, that is, amino acid 60 of the mature variable region (the amino acid corresponding to position 80 of SEQ ID No: 32 or FIG. 47) is Ser or Asp, amino acid 9 of FRL3, that is, amino acid 65 of the mature variable region (the amino acid corresponding to position 85 of SEQ ID No: 32 or FIG. 47) is Ser or Gly, amino acid 11 of FRL3, that is, amino acid 67 of the mature variable region (the amino acid corresponding to position 87 of SEQ ID No: 32 or FIG. 47) is Ser or Tyr, amino acid 22 of FRL3, that is, amino acid 78 of the mature variable region (the amino acid corresponding to position 98 of SEQ ID No: 32 or FIG. 47) is Leu or Val, amino acid 27 of FRL3, that is, amino acid 83 of the mature variable region (the amino acid corresponding to position 103 of SEQ ID No: 32 or FIG. 47) is Phe or Ala, amino acid 29 of FRL3, that is, amino acid 85 of the mature variable region (the amino acid corresponding to position 105 of SEQ ID No: 32 or FIG. 47) is Thr or Phe, amino acid 7 of FRL4, that is, amino acid 104 of the mature variable region (the amino acid corresponding to position 124 of SEQ ID No: 32 or FIG. 47) is Val or Leu, and amino acid 9 of FRL4, that is, amino acid 106 of the mature variable region (the amino acid corresponding to position 126 of SEQ ID No: 32 or FIG. 47) is Ile or Leu.

More preferably, in the heavy chain of the humanized antibody such as hLA212_H2/L1 to H2/L5, hLA212_H3/L1 to H3/L5, or hLA212_H4/L2, amino acid 14 of FRH2, that is, amino acid 49 of the mature variable region (the amino acid corresponding to position 68 of SEQ ID No: 28 or FIG. 43) is Gly or Ala, and amino acid 25 of FRH3, that is, amino acid 84 of the mature variable region (the amino acid corresponding to position 103 of SEQ ID No: 28 or FIG. 43) is Asn or Asp.

The present invention also encompasses an antibody that comprises a heavy chain and/or a light chain comprising an amino acid sequence having 80% or higher, 82% or higher, 84% or higher, 86% or higher, 88% or higher, 90% or higher, 92% or higher, 94% or higher, 96% or higher, 98% or higher, or 99% or higher identity to the amino acid sequence of the full length or the variable regions of the heavy chain and/or the light chain of any one of the rLA204, rLA212, rLA225, rLA869, rLA1264, cLA204, cLA212, cLA225, cLA869, rLA1264, and A9H12 antibodies, and the humanized hLA212_H2/L1 to hLA212_H2/L5, hLA212_H3/L1 to hLA212_H3/L5, hLA212_H4/L2, H5L7, and H5L7BW antibodies of the present invention, and binds to LAG-3, or a binding fragment thereof. Such sequence identity is preferably 94% or higher, more preferably 96% or higher, further more preferably 98% or higher, optimally 99% or higher. Further, the antibody or the binding fragment thereof has the properties, functions, activities, etc., described in (3-2) and (3-3), preferably (3-4) in addition to the above, more preferably (3-5) in addition to the above, further more preferably all of (3-2) to (3-8).

The identity or homology between two types of amino acid sequences can be determined using the default parameters of the Blast algorithm version 2.2.2 (Altschul, Stephen F., Thomas L. Madden, Alejandro A. Schaffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm is also available, for example, by Internet access at http://blast.ncbi.nlm.nih.gov/.

The present invention also encompasses an antibody that comprises a heavy chain and/or a light chain comprising an amino acid sequence that is derived from the full-length or variable-region amino acid sequence of the heavy chain and/or the light chain of any one of the rLA204, rLA212, rLA225, rLA869, rLA1264, cLA204, cLA212, cLA225, cLA869, cLA1264, and A9H12 antibodies, and the hLA212_H2/L1 to hLA212_H2/L5, hLA212_H3/L1 to hLA212_H3/L5, hLA212_H4/L2, H5L7, and H5L7BW antibodies of the present invention by the substitution, deletion, addition, and/or insertion of 1 to 50, 1 to 45, 1 to 40, 1 to 35, 1 to 30, 1 to 25, 1 to 20, 1 to 15, 1 to 10, 1 to 8, 1 to 6, 1 to 5, 1 to 4, 1 to 3, 1 or 2, or 1 amino acid, and binds to LAG-3, or a binding fragment thereof. Such an amino acid mutation is preferably a substitution. The number of amino acids mutated is preferably 1 to 5, more preferably 1 to 4, even more preferably 1 to 3, further more preferably 1 or 2, most preferably 1. Further, the antibody or the binding fragment thereof has the properties, functions, activities, etc., described in (3-2) and (3-3), preferably (3-4) in addition to the above, more preferably (3-5) in addition to the above, further more preferably all of (3-2) to (3-8).

The present invention also encompasses an antibody that comprises a heavy chain and/or light chain comprising an amino acid sequence encoded by a nucleotide sequence of a nucleotide that hybridizes under stringent conditions to a nucleotide having a nucleotide sequence complementary to a nucleotide sequence encoding the full-length or variable-region amino acid sequence of the heavy chain and/or the light chain of any one of the rLA204, rLA212, rLA225, rLA869, rLA1264, cLA204, cLA212, cLA225, cLA869, cLA1264, and A9H12 antibodies, and the hLA212_H2/L1 to hLA212_H2/L5, hLA212_H3/L1 to hLA212_H3/L5, hLA212_H4/L2, H5L7, and H5L7BW antibodies of the present invention, and binds to LAG-3, or a binding fragment thereof. The antibody or the binding fragment thereof has the properties, functions, activities, etc., described in (3-2) and (3-3), preferably (3-4) in addition to the above, more preferably (3-5) in addition to the above, further more preferably all of (3-2) to (3-8).

According to another aspect, the present invention provides a human antibody or a binding fragment thereof. The human antibody or the binding fragment thereof is not specifically limited, as long as it is a human-derived antibody that binds to LAG-3 or a binding fragment thereof, but has the properties, functions, activities, etc., described in (3-2) and (3-3), preferably (3-4) in addition to the above, more preferably (3-5) in addition to the above, further more preferably all of (3-2) to (3-8).

(3-13) Antibody Binding to Epitope

An "antibody binding to the same site" as in the case of the antibody used in the present invention can also be used in the present invention. An "antibody binding to the same site" as a certain antibody means a different antibody that binds to a site on an antigen molecule recognized by the antibody. If a second antibody binds to a partial peptide or a partial three-dimensional structure on an antigen molecule bound by a first antibody, the first and second antibodies are determined as binding to the same site. Alternatively, the first and second antibodies are determined as binding to the same site by confirming that the second antibody competes with the first antibody for binding to the antigen, i.e., the second antibody interferes with the binding of the first antibody to the antigen, even if the peptide sequence or three-dimensional structure of the specific binding site is not determined. When the first and second antibodies bind to the same site, and the first antibody has an effect such as ADCC activity, the second antibody also has an exceedingly high probability of having the same activity thereas. Thus, if a second anti-LAG-3 antibody binds to a site bound by a first anti-LAG-3 antibody, the first and second antibodies are determined as binding to the same site on the LAG-3 protein. Alternatively, the first and second anti-LAG-3 antibodies are determined as binding to the same site on the LAG-3 protein by confirming that the second anti-LAG-3 antibody competes with the first anti-LAG-3 antibody for binding to the LAG-3 protein.

In the present invention, an antibody binding to a site on the LAG-3 protein recognized by the monoclonal antibody is also included in the antibody that can be used in the present invention. The antibody and the binding fragment thereof has the properties, functions, activities, etc., described in (3-2) and (3-3), preferably (3-4) in addition to the above, more preferably (3-5) in addition to the above, further more preferably all of (3-2) to (3-8).

The antibody binding site can be determined by a method well known by those skilled in the art, such as an immunoassay. For example, a series of peptides are prepared by appropriate sequential cleavage of the amino acid sequence of the antigen from its C terminus or N terminus, and the reactivity of the antibody thereto is studied to determine roughly a recognition site. Then, shorter peptides are synthesized, and the reactivity of the antibody to these peptides can be studied thereby to determine the binding site. The antigen fragment peptides can be prepared using a technique such as gene recombination or peptide synthesis.

When the antibody binds to or recognizes a partial conformation of the antigen, the binding site for the antibody can be determined by identifying amino acid residues on the antigen adjacent to the antibody using X-ray structural analysis. For example, the antibody or its fragment and the antigen or its fragment can be bound to each other and crystallized, followed by structural analysis to identify each amino acid residue on the antigen having an interaction distance with the antibody. The interaction distance is 8 angstroms or shorter, preferably 6 angstroms or shorter, more preferably 4 angstroms or shorter. One or more of such amino acid residues having an interaction distance with the antibody can constitute a site (epitope) on the antigen to which the antibody binds. Two or more of such amino acid residues may not be adjacent to each other on the primary sequence.

The epitope of the LAG-3 antibody of the present invention is present in human LAG-3 or its amino acid sequence. The antibody or the binding fragment thereof that can be used in the present invention, or the modified form thereof also encompasses an antibody, a binding fragment thereof, or a modified form thereof binding to this epitope, competing with the antibody used in the present invention for binding to the epitope, or having an interaction distance with these amino acid residues.

(3-14) Modified Form of Antibody

The present invention provides a composition comprising a modified form of the antibody or the binding fragment thereof. The modified form of the antibody or the binding fragment thereof means that the antibody or the binding fragment thereof is provided with a chemical or a biological modification. The chemically modified form includes, for example, a form having an amino acid skeleton conjugated with a chemical moiety, and a form having a chemically modified N-linked or O-linked carbohydrate chain. The biologically modified form includes, for example, a form that has undergone post-translational modification (e.g., N-linked or O-linked glycosylation, N-terminal or C-terminal processing, deamidation, isomerization of aspartic acid, or oxidation of methionine), and a form containing a methionine residue added to the N-terminus by expression using prokaryotic host cells. Such a modified form is also meant to include a form labeled to permit detection or isolation of the antibody or the antigen, for example, an enzyme-labeled form, a fluorescently-labeled form, or an affinity-labeled form. Such a modified form of the antibody or the binding fragment thereof is useful for improving the stability or blood retention of the original antibody or the original binding fragment thereof, reducing antigenicity, or for the detection or isolation of the antibody or the antigen, etc.

Examples of the chemical moiety contained in the chemically modified form can include water-soluble polymers such as polyethylene glycol, ethylene glycol/propylene glycol copolymers, carboxymethylcellulose, dextran, and polyvinyl alcohol.

Examples of the biologically modified form can include a form modified by enzymatic treatment, cell treatment, or the like, a form fused with another peptide, such as a tag, added by gene recombination, and a form prepared from host cells expressing an endogenous or exogenous sugar chain-modifying enzyme.

The antibody-dependent cellular cytotoxic activity of the antibody or the binding fragment thereof may be enhanced by regulating the modification (glycosylation, defucosylation, etc.) of the sugar chain bound to the antibody or the binding fragment. For example, methods described in WO99/54342, WO00/61739, and WO02/31140 are known as such a technique of regulating the sugar chain modification of the antibody, though this technique is not limited thereto. In the present invention, the modified form of the antibody also includes an antibody that has undergone the sugar chain modification thus regulated.

Such a modification may be made at an arbitrary position or a desired position in the antibody or binding fragment thereof. The same or two or more different modifications may be made at one or two or more positions therein.

In the present invention, the term "modified form of the antibody fragment" is also meant to include even a "fragment of the modified form of the antibody".

In the present invention, the modified form of the antibody or the modified form of the binding fragment thereof is also simply referred to as an "antibody" or a "binding fragment of the antibody".

As described above, hLA212_H4/L2 is the humanized antibody which was obtained in Example 8 and whose sugar chain modification is adjusted. This humanized antibody is also encompassed by the antibody that can be used in the present invention.

The antibody or the binding fragment thereof that can be used in the present invention, and the modified forms thereof as described above preferably have physical properties, pharmacokinetics, blood retention, safety, etc., that are suitable for the composition for cytotoxic T cell depletion, the method for treating or preventing a disease associated with cytotoxic T cells, the use for treatment or prevention, etc., of the present invention.

(3-15) Depletion Activity Against Cytotoxic T Cell

The LAG-3 antibody that can be used for cytotoxic T cell depletion is preferably an antibody that exhibits cytotoxic activity such as ADCC activity, CDC activity, and/or ADCP activity against LAG-3-expressing cells, more preferably a LAG-3 antibody having enhanced ADCC activity, CDC activity, and/or ADCP activity. Examples of the low-fucose or afucosylated LAG-3 antibody having enhanced ADCC activity, that is, the LAG-3 antibody in a low fucose form, can include hLA212_H4/L2 and H5L7BW.

The depletion activity exerted by the LAG-3 antibody against cytotoxic T cells can be evaluated on the basis of an assay known in the art. Examples of an in vitro assay can include those described in Examples 13 and 14, and examples of an in vivo assay can include those described in Example 11-1), though the assay is not limited thereto.

4. Method for Producing Antibody (4-1) Method Using Hybridoma

The anti-LAG-3 antibody can be prepared according to the method of Kohler and Milstein (Kohler and Milstein, Nature (1975), 256, p. 495-497; and Kennet, R. ed., Monoclonal Antibodies, p. 365-367, Plenum Press, N.Y. (1980)). Thus, anti-LAG-3 antibody-producing cells are isolated from the spleens of animals immunized with the LAG-3 protein or its soluble form and the cells are fused with myeloma cells thereby establishing hybridomas. Monoclonal antibodies can be obtained from cultures of these hybridomas.

(4-1-1) Preparation of Antigen

The antigen for the preparation of the anti-LAG-3 antibody can be obtained according to, for example, the method for preparing a native or recombinant LAG-3 protein described in other paragraphs of the present invention. Examples of the antigen that may be thus prepared can include the LAG-3 protein, a LAG-3 protein fragment comprising a partial sequence with at least 6 consecutive amino acids of the LAG-3 protein, and derivatives thereof further comprising an arbitrary amino acid sequence or a carrier added thereto (hereinafter, collectively referred to as a "LAG-3 antigen"; which has the same meaning as "LAG-3 protein").

The recombinant LAG-3 antigen can be prepared by transfecting host cells with a gene comprising a nucleotide sequence encoding the amino acid sequence of the LAG-3 antigen, and recovering the antigen from cultures of the cells. Such a recombinant antigen may be a fusion protein with another protein such as an immunoglobulin Fc region. A LAG-3 antigen obtained in a cell-free in vitro translation system from a gene comprising a nucleotide sequence encoding the amino acid sequence of the LAG-3 antigen is also included in the recombinant LAG-3 antigen. The non-recombinant LAG-3 antigen can be purified and isolated from LAG-3-expressing cells or the like.

In order to obtain an anti-LAG-3 monoclonal antibody, the presence of which allows LAG-3 to exert a T cell action-suppressing function, or which does not suppress or inhibit the T cell action-suppressing function of LAG-3, a LAG-3 mutant in which immunoglobulin-like domains 1 and 2 are deleted, for example, can be used as a preferable immunogen.

(4-1-2) Production of Anti-LAG-3 Monoclonal Antibody

The monoclonal antibody is typically produced through the following steps of:
(a) preparing an antigen,
(b) preparing antibody-producing cells,
(c) preparing myeloma cells (hereinafter, referred to as "myelomas"),
(d) fusing the antibody-producing cells with the myelomas,
(e) screening for a hybridoma group producing the antibody of interest, and
(f) obtaining single cell clones (cloning).

This production method further involves the steps of (g) culturing the hybridomas, raising hybridoma-transplanted animals, etc., and (h) assaying or determining the biological activity of the monoclonal antibody, etc., if necessary.

Hereinafter, the method for preparing the monoclonal antibody will be described in detail with reference to these steps. However, the method for preparing the antibody is not limited to those steps, and antibody-producing cells other than spleen cells, for example, may be used.

(a) Purification of Antigen

This step is performed according to the method for preparing the LAG-3 protein described above in (2-3).

(b) Step of Preparing Antibody-Producing Cell

The antigen obtained in step (a) is mixed with an adjuvant such as a complete or incomplete Freund's adjuvant or potassium aluminum sulfate, and laboratory animals are immunized with the resulting immunogen. Any laboratory animal used in a hybridoma preparation method known in the art can be used without limitations. Specifically, for example, mice, rats, goats, sheep, cattle, or horses can be used. From the viewpoint of readily available myeloma cells to be fused with isolated antibody-producing cells, etc., the animals to be immunized are preferably mice or rats.

The strain of mice or rats actually used is not particularly limited. In the case of mice, for example, A, AKR, BALB/c, BALB/cAnNCrj, BDP, BA, CE, C3H, 57BL, C57BL, C57L, DBA, FL, HTH, HT1, LP, NZB, NZW, RF, R III, SJL, SWR, WB, or 129 can be used. In the case of rats, for example, Wistar, Low, Lewis, Sprague-Dawley, ACI, BN, or Fischer can be used.

These mice and rats are available from laboratory animal breeders or distributors, for example, CLEA Japan, Inc. or Charles River Laboratories Japan Inc.

Of those mice and rats, a BALB/c mouse strain or Wistar and Low rat strains are particularly preferred as animals to be immunized in consideration of fusion compatibility with the myeloma cells described later.

Also, in consideration of the homology between human and mouse antigens, mice whose biological mechanism to remove autoantibodies has been reduced, i.e., autoimmune disease mice, are also preferably used.

In this context, these mice or rats are preferably 5 to 12 weeks old, more preferably 6 to 8 weeks old, at the time of immunization.

The animals can be immunized with the LAG-3 protein using, for example, the method of Weir, D. M., Handbook of Experimental Immunology Vol. I. II. III., Blackwell Scientific Publications, Oxford (1987), Kabat, E. A. and Mayer, M. M., Experimental Immunochemistry, Charles C Thomas Publisher Springfield, Illinois (1964).

Examples of methods for determining antibody titers can include, but are not limited to, immunoassays such as RIA and ELISA.

Antibody-producing cells derived from spleen cells or lymphocytes isolated from the immunized animals, can be prepared according to a method known in the art, for example, Kohler et al., Nature (1975) 256, p. 495; Kohler et al., Eur. J. Immnol. (1977) 6, p. 511; Milstein et al., Nature (1977), 266, p. 550; Walsh, Nature, (1977) 266, p. 495.

In the case of spleen cells, a general method can be adopted, which involves cutting up the spleens, filtering cells through a stainless mesh, and then suspending the resulting cells in an Eagle's minimum essential medium (MEM) or the like, to isolate antibody-producing cells.

(c) Step of Preparing Myeloma

The myeloma cells used in the cell fusion are not particularly limited and can be selected appropriately for use from cell lines known in the art. For example, a hypoxanthine-guanine phosphoribosyl transferase (HGPRT)-deficient line, i.e., mouse-derived X63-Ag8 (X63), NS1-ANS/1 (NS1), P3X63-Ag8.U1 (P3U1), X63-Ag8.653 (X63.653), SP2/0-Agl4 (SP2/0), MPC11-45.6TG1.7 (45.6TG), FO, S149/5XXO, or BU.1, rat-derived 210.RSY3.Ag.1.2.3 (Y3), or human-derived U266AR (SKO-007), GM1500-GTG-A12 (GM1500), UC729-6, LICR-LOW-HMy2 (HMy2), or 8226AR/NIP4-1 (NP41), and the like, whose screening procedures have already been established, is preferably used in consideration of convenience in the selection of hybridomas from the fused cells. These HGPRT-deficient lines are available from, for example, the American Type Culture Collection (ATCC).

These cell lines are subcultured in an appropriate medium, for example, an 8-azaguanine medium [RPMI-1640 medium supplemented with glutamine, 2-mercaptoethanol, gentamicin, and fetal bovine serum (hereinafter, referred to as "FBS") and further supplemented with 8-azaguanine], an Iscove's modified Dulbecco's medium (hereinafter, referred to as "IMDM"), or a Dulbecco's modified Eagle medium (hereinafter, referred to as "DMEM") and then subcultured in a normal medium [e.g., ASF104 medium (manufactured by Ajinomoto Co., Inc.) containing 10% FBS] for 3 to 4 days before cell fusion to ensure that the number of cells is equal to or greater than $2\times10^7$ cells on the day of cell fusion.

(d) Step of Fusing Antibody-Producing Cell with Myeloma Cell

The antibody-producing cells can be fused with the myeloma cells under conditions that prevent cell viability from being exceedingly reduced, according to any method known in the art (e.g., Weir, D. M., Handbook of Experimental Immunology Vol. I. II. III., Blackwell Scientific Publications, Oxford (1987), and Kabat, E. A. and Mayer, M. M., Experimental Immunochemistry, Charles C Thomas Publisher Springfield, Illinois (1964)). For example, a chemical method which involves mixing antibody-producing cells with myeloma cells in a high-concentration solution of a polymer such as polyethylene glycol, or a physical method using electrical stimulation can be used.

(e) Step of Screening for Hybridoma Group Producing Antibody of Interest

The method for selecting the hybridomas obtained by cell fusion is not particularly limited, and a hypoxanthine-aminopterin-thymidine (HAT) selection method (Kohler et al., Nature (1975) 256, p. 495; Milstein et al., Nature (1977) 266, p. 550) is typically used. This method is effective for obtaining hybridomas using an HGPRT-deficient myeloma cell line, which cannot survive in the presence of aminopterin. Specifically, unfused cells and hybridomas can be cultured in a HAT medium thereby to allow only hybridomas resistant to aminopterin to live and grow selectively.

(f) Step of Obtaining Single Cell Clone (Cloning)

The hybridomas can be cloned using any method known in the art, for example, a methylcellulose, soft agarose, or limiting dilution method (see e.g., Barbara, B. M. and Stanley, M. S.: Selected Methods in Cellular Immunology, W. H. Freeman and Company, San Francisco (1980)). The limiting dilution method is preferred.

(g) Step of Culturing Hybridoma and Step of Raising Hybridoma-Transplanted Animal The selected hybridomas can be cultured thereby to produce monoclonal antibodies. Preferably, the desired hybridomas are cloned and then subjected to antibody production.

The monoclonal antibody produced by such a hybridoma can be recovered from cultures of the hybridoma. Also, a recombinant antibody can be recovered from cultures of cells introduced with the monoclonal antibody gene. Alternatively, the hybridoma may be injected intraperitoneally to mice of the same strain (e.g., BALB/cAnNCrj described above) or Nu/Nu mice and allowed to grow. Then, the monoclonal antibody can be recovered from their ascites.

(h) Step of Assaying or Determining Biological Activity of Monoclonal Antibody

Various biological tests can be selected and applied thereto according to the objective.

(4-2) Cell Immunization Method

Cells expressing the native LAG-3 protein, cells expressing the recombinant LAG-3 protein or a fragment thereof, or the like, can be used as immunogens thereby to prepare an anti-LAG-3 antibody by the hybridoma method described above.

These LAG-3-expressing cells are used in an amount of $1\times10^5$ to $1\times10^9$ cells, preferably $1\times10^6$ to $1\times10^8$ cells, more preferably 0.5 to $2\times10^7$ cells, even more preferably $1\times10^7$ cells, per immunization shot. The number of cells used for immunization can be changed according to the expression level of the LAG-3 protein. The immunogens are generally administered intraperitoneally and may be administered through an intradermal route or the like. The hybridomas can be prepared by the application of the method described in paragraph (4-1-2).

(4-3) Gene Recombination

In order to prepare the antibody used in the present invention, a nucleotide (a heavy chain nucleotide) comprising a nucleotide sequence encoding the amino acid sequence of its heavy chain and a nucleotide (a light chain nucleotide) comprising a nucleotide sequence encoding the amino acid sequence of its light chain, or a vector having an insert of the heavy chain nucleotide and a vector having an insert of the light chain nucleotide are introduced into host cells, and then the cells are cultured, and the antibody can be recovered from the cultures. The heavy chain nucleotide and the light chain nucleotide may be inserted in one vector.

Prokaryotic or eukaryotic cells can be used as the host cells. In the case of using host eukaryotic cells, animal cells, plant cells, or eukaryotic microbes can be used.

Examples of the animal cells can include mammal-derived cells, i.e., monkey-derived COS cells (Gluzman, Y. Cell (1981), 23, p. 175-182, ATCC CRL-1650), mouse fibroblast NIH3T3 (ATCC No. CRL-1658), a mouse NS0 cell line (ECACC), Chinese hamster ovary cells (CHO cells, ATCC CCL-61), dihydrofolate reductase-deficient lines thereof (CHOdhfr-; Urlaub, G. and Chasin, L. A. Proc. Natl. Acad. Sci. U.S.A. (1980), 77, p. 4126-4220), CHOK1SV (Lonza Biologics), cells derived from birds such as chickens, and cells derived from insects.

Also, cells that are modified to adjust the sugar chain modification of proteins, such as antibodies, can be used as the hosts. For example, CHO cells modified such that fucose bound to N-acetylglucosamine at the reducing ends of sugar chains is reduced on or removed from complex-type N-glycoside-linked sugar chains binding to the Fc region of the antibody may be used for antibody expression thereby to prepare a low-fucose or defucosylated antibody (also referred to as a modified form of the antibody) (WO00/61739, WO02/31140, etc.).

Examples of the eukaryotic microbes can include yeasts.

Examples of the prokaryotic cells can include *E. coli* and *Bacillus subtilis.*

A signal peptide for the secretion of the antibody (a monoclonal antibody derived from any animal, a rat antibody, a mouse antibody, a chimeric antibody, a humanized antibody, a human antibody, etc.) is not limited to the secretory signal of an antibody of the same species, the same type, and the same subtype as the antibody of the present invention or to the antibody of the present invention's own secretory signal. Any secretory signal of an antibody of a different type or subtype therefrom or any secretory signal of a protein derived from a different eukaryotic species therefrom or a prokaryotic species can be selected and used.

(4-4) Methods for Designing and Preparing Humanized Antibody

Examples of the humanized antibody can include, but are not limited to, a human-derived antibody having CDRs replaced with the CDRs of a non-human animal antibody (see Nature (1986), 321, p. 522-525), a human antibody grafted with the CDR sequences and with some amino acid residues from the framework regions by CDR grafting (see WO90/07861 and U.S. Pat. N0. 6,972,323), and any of said humanized antibodies wherein one or two or more non-human animal antibody-derived amino acid(s) have been replaced with human antibody-derived amino acid(s).

(4-5) Method for Preparing Human Antibody

Further examples of the antibody that can be used in the present invention can include a human antibody. The anti-LAG-3 human antibody means an anti-LAG-3 antibody consisting of the amino acid sequence of a human-derived antibody. The anti-LAG-3 human antibody can be obtained by a method using human antibody-producing mice carrying human genomic DNA fragments comprising human antibody heavy and light chain genes (see e.g., Tomizuka, K. et al., Nature Genetics (1997) 16, p. 133-143; Kuroiwa, Y. et al., Nuc. Acids Res. (1998) 26, p. 3447-3448; Yoshida, H. et al., Animal Cell Technology: Basic and Applied Aspects vol. 10, p. 69-73 (Kitagawa, Y., Matuda, T. and Iijima, S. eds.), Kluwer Academic Publishers, 1999; and Tomizuka, K. et. al., Proc. Natl. Acad. Sci. USA (2000) 97, p. 722-727).

Specifically, such human antibody-producing animals may be any of: recombinant animals that are obtained by disrupting the endogenous immunoglobulin heavy and light chain gene loci of non-human mammals and instead introducing thereto human immunoglobulin heavy and light chain gene loci via yeast artificial chromosome (YAC) vectors or the like, and recombinant animals that are created by crossing these animals.

Alternatively, eukaryotic cells may be transfected (transformed) with cDNAs encoding the heavy and light chains, respectively, of such a human antibody, preferably with vectors comprising the cDNAs, by a gene recombination technique. The transfected (transformed) cells that produce the recombinant human monoclonal antibody can be cultured. This antibody can be obtained from the culture supernatant.

In this context, for example, eukaryotic cells, preferably mammalian cells such as CHO cells, lymphocytes, or myelomas, can be used as the hosts.

Also, a method for obtaining a phage display-derived human antibody selected from a human antibody library (see e.g., Wormstone, I. M. et. al, Investigative Ophthalmology & Visual Science. (2002) 43 (7), p. 2301-2308; Carmen, S. et. al., Briefings in Functional Genomics and Proteomics (2002), 1 (2), p. 189-203; and Siriwardena, D. et. al., Opthalmology (2002) 109 (3), p. 427-431) is known.

For example, a phage display method (Nature Biotechnology (2005), 23, (9), p. 1105-1116) can be used, which involves allowing the variable regions of a human antibody to be expressed as a single chain antibody (scFv) on a phage surface and selecting a phage binding to the antigen.

The phage selected on the basis of its ability to bind to the antigen can be subjected to gene analysis thereby to determine DNA sequences encoding the variable regions of the human antibody binding to the antigen.

If the DNA sequence of an scFv binding to the antigen is determined, an expression vector having this sequence can be prepared and introduced into appropriate hosts to allow them to express the human antibody (WO92/01047, WO92/20791, WO93/06213, WO93/11236, WO93/19172, WO95/01438, WO95/15388, Annu. Rev. Immunol (1994) 12, p. 433-455, and Nature Biotechnology (2005) 23 (9), p. 1105-1116).

(4-6) Method for Preparing Binding Fragment of Antibody

The method for preparing a single chain antibody is well known in the art (see e.g., U.S. Pat. Nos. 4,946,778, 5,260, 203, 5,091,513, and 5,455,030). In this scFv, a heavy chain variable region and a light chain variable region are linked via a linker that prevents them from forming a conjugate, preferably a polypeptide linker (Huston, J. S. et al., Proc. Natl. Acad. Sci. U.S.A. (1988), 85, p. 5879-5883). The heavy chain variable region and the light chain variable region in an scFv may be derived from the same antibody or may be derived from different antibodies.

For example, an arbitrary single chain peptide consisting of 12 to 19 residues is used as the polypeptide linker that links these variable regions.

In order to obtain scFv-encoding DNA, of the sequences of DNA encoding the heavy chain or heavy chain variable region of the antibody and DNA encoding the light chain or light chain variable region thereof, each DNA portion encoding the whole or desired amino acid sequence is used as a template and amplified by PCR using a primer pair flanking both ends of the template. Subsequently, DNA encoding the polypeptide linker moiety is further amplified in combination with a primer pair flanking both ends of the DNA so that the obtained fragment can be linked at its ends to the heavy and light chain DNAs, respectively.

The scFv-encoding DNA can be used thereby to prepare, according to a routine method, an expression vector containing the DNA and host cells can be transformed with the expression vector. In addition, the host cells can be cultured, and the scFv can be recovered from the cultures according to a routine method.

In addition, in order to obtain any other binding fragment of the antibody, a gene encoding the binding fragment is obtained according to the method described above and introduced into cells. The binding fragment of interest can be recovered from cultures of the cells.

The antibody may be multimerized thereby to increase its affinity for the antigen. In this case, antibodies of the same type may be multimerized, or a plurality of antibodies recognizing a plurality of epitopes, respectively, of the same antigen may be multimerized. Examples of methods for multimerizing these antibodies can include the binding of two scFvs to an IgG CH3 domain, the binding thereof to streptavidin, and the introduction of a helix-turn-helix motif.

The antibody may be a mixture of a plurality of types of anti-LAG-3 antibodies differing in amino acid sequence, i.e., a polyclonal antibody. Examples of the polyclonal antibody can include a mixture of a plurality of types of antibodies differing in a portion of or in the whole of their CDRs. Such a polyclonal antibody can be recovered from cultures of different antibody-producing cells that have been mixed-cultured (WO2004/061104). Alternatively, separately prepared antibodies may be mixed. Antiserum, which is one embodiment of the polyclonal antibody, can be prepared by immunizing animals with the desired antigen and recovering serum from the animals according to a standard method.

Antibodies conjugated with various molecules such as polyethylene glycol (PEG) can also be used as modified forms of the antibody.

The antibody may further be any of the conjugates formed by these antibodies with other drugs (immunoconjugates). Examples of such an antibody can include an antibody conjugated with a radioactive material or a compound having a pharmacological action (Nature Biotechnology (2005), 23, p. 1137-1146).

The antibody or the binding fragment thereof, and the modified forms thereof as exemplified or described in (3-11), (3-14), (4-6), etc., are also called "molecules comprising the antibody or the binding fragment thereof".

(4-7) Purification of Antibody

The obtained antibody can be purified to be homogeneous. Usual protein separation and purification methods can be used for the separation and purification of the antibody.

The antibody can be separated and purified by appropriately selected or combined approach(es), for example, chromatography columns, filters, ultrafiltration, salting out, dialysis, preparative polyacrylamide gel electrophoresis, and/or isoelectric focusing (Strategies for Protein Purification and Characterization: A Laboratory Course Manual, Daniel R. Marshak et al. eds., Cold Spring Harbor Laboratory Press (1996); and Antibodies: A Laboratory Manual. Ed Harlow and David Lane, Cold Spring Harbor Laboratory (1988)) though the separation and purification method is not limited thereto.

Examples of chromatography include affinity chromatography, ion-exchange chromatography, hydrophobic chromatography, gel filtration, reverse-phase chromatography, and adsorption chromatography.

These chromatography approaches can be performed using liquid-phase chromatography such as HPLC or FPLC.

Examples of columns used in affinity chromatography can include protein A, protein G, and antigen columns.

Examples of the protein A columns include Hyper D (manufactured by Pall Corp.), POROS (manufactured by Applied Biosystems, Inc.), and Sepharose F. F. (manufactured by GE Healthcare Bio-Sciences Corp.).

Also, the antibody may be purified using its binding activity against the antigen using an antigen-immobilized carrier.

(4-8) Nucleotides Encoding Antibody, Recombinant Vector, and Recombinant Cell

A nucleotide encoding the antibody or the binding fragment thereof, or the modified form thereof (hereinafter, this nucleotide is referred to as an "antibody gene"), a recombinant vector having an insert of the gene, a cell comprising the gene or the vector (hereinafter, this cell is referred to as an "antibody gene-transfected cell"), and a cell producing the antibody or the binding fragment thereof, or the modified form thereof (hereinafter, this cell is referred to as an "antibody-producing cell") are also used for preparing the composition of the present invention.

Preferably, the antibody gene comprises a nucleotide sequence described in any one of (a) to (e) below (hereinafter, referred to as an "antibody gene sequence"), consists of a nucleotide sequence comprising the antibody gene sequence, or consists of the antibody gene sequence:

(a) a combination of a nucleotide sequence encoding the amino acid sequence of the heavy chain of any one of the rat antibodies rLA204, rLA212, rLA225, rLA869, and rLA1264, and the mouse antibody A9H12, their chimeric antibodies cLA204, cLA212, cLA225, cLA869, cLA1264, and chimera type A9H12 (IMP731) in which the heavy chain and light chain constant regions are substituted with those of human antibodies, and their humanized antibodies hLA212_H2/L1 to hLA212_H2/L5, LA212_H3/L1 to hLA212_H3/L5, H5L7, and H5L7BW and a nucleotide sequence encoding the amino acid sequence of the light chain thereof;

(b) a combination of a nucleotide sequence encoding the amino acid sequence of the heavy chain comprising CDRH1 to CDRH3 of any one of the rat antibodies rLA204, rLA212, rLA225, rLA869, and rLA1264, and the mouse antibody A9H12, their chimeric antibodies cLA204, cLA212, cLA225, cLA869, cLA1264, and chimera type A9H12 (IMP731) in which the heavy chain and light chain constant regions are substituted with those of human antibodies, and their humanized antibodies hLA212_H2/L1 to hLA212_H2/L5, LA212_H3/L1 to hLA212_H3/L5, H5L7, and H5L7BW and a nucleotide sequence encoding the amino acid sequence of the light chain comprising CDRL1 to CDRL3 thereof;

(c) a combination of a nucleotide sequence encoding the amino acid sequence of the heavy chain comprising the amino acid sequence of the heavy chain variable region of any one of the rat antibodies rLA204, rLA212, rLA225, rLA869, and rLA1264, and the mouse antibody A9H12, their chimeric antibodies cLA204, cLA212, cLA225, cLA869, and cLA1264, and chimera type A9H12 (IMP731) in which the heavy chain and light chain constant regions are substituted with those of human antibodies, and their humanized antibodies hLA212_H2/L1 to hLA212_H2/L5, LA212_H3/L1 to hLA212_H3/L5, H5L7, and H5L7BW and a nucleotide sequence encoding the amino acid sequence of the light chain comprising the amino acid sequence of the light chain variable region;

(d) a nucleotide sequence that hybridizes under stringent conditions to a nucleotide consisting of a nucleotide sequence complementary to the nucleotide sequence according to any one of (a) to (c), and encodes the amino acid sequence of an antibody binding to LAG-3; and (e) a nucleotide sequence that encodes an amino acid sequence derived from the amino acid sequence according to any one of (a) to (c) by the substitution, deletion, addition, and/or insertion of 1 to 50, 1 to 45, 1 to 40, 1 to 30, 1 to 25, 1 to 20, 1 to 15, 1 to 10, 1 to 8, 1 to 6, 1 to 5, 1 to 4, 1 to 3, 1 or 2, or 1 base, and encodes an amino acid sequence of an antibody binding to LAG-3, where the antibody having an amino acid sequence encoded by the nucleotide sequence according to (d) or (e) has the properties, functions, activities, etc., described in (3-2) and (3-3), preferably one or more of (3-4) in addition to the above, more preferably (3-5) in addition to the above, further more preferably all of (3-2) to (3-8).

However, the antibody gene is not limited to the aforementioned (a) to (e).

The antibody of the present invention or the binding fragment thereof, or the modified form thereof can be obtained by a method for producing an antibody or a binding fragment thereof, or a modified form thereof, comprising the steps of culturing antibody gene-transfected cells and recovering an antibody or a binding fragment thereof, or a modified form thereof from the culture, as described in (4-3).

5. Composition

The present invention provides a composition for cytotoxic T cell depletion, comprising an anti-LAG-3 antibody or a binding fragment thereof, or a modified form thereof.

The composition of the present invention is capable of bringing about clinical benefits by depleting cytotoxic T cells in the medical care for diseases involving cytotoxic T cells (hereinafter, referred to as "diseases associated with cytotoxic T cells"), preferably the medical care for immunosuppressant resistant diseases associated with cytotoxic T cells. Examples of such a disease can include chronic obstructive pulmonary disease (COPD; Non Patent Literature 16), multiple sclerosis (Non Patent Literature 15), Graves' disease (Sun, Z. et al., J. Clin. Immunol., 2008; Vol. 28 (No. 5): p. 464-472), ankylosing spondylitis (Schirmer, M. et al., Arthritis. Res., 2002; Vol. 4 (No. 1): p. 71-76), pars planitis (Pedroza-Seres, M. et al., Br. J. Ophthalmol., 2007; Vol. 91 (No. 10): p. 1393-1398), asthma (Hamzaoui, A. et al., Mediators. Inflamm., 2005; No. 3: p. 160-166), rheumatoid arthritis (Wang, E C. et al., Arthritis. Rheum., 1997; Vol. 40 (No. 2): p. 237-248; and Scarsi, M. et al., J. Rheumatol., 2010; Vol. 37 (No. 5): p. 911-916), polymyositis or dermatomyositis (Fasth, A E. et al., J. Immunol., 2009; No. 183 (Vol. 7): p. 4792-4799), inclusion body myositis (Keller, C W. et al., Ann. Clin. Transl. Neurol., 2017; Vol. 4 (No. 6): p. 422-445), acute coronary syndrome (Non Patent Literature 15), systemic lupus erythematosus (Zabinska et al., 2016, J Immunol Res. 1058165), lupus nephritis (Zabinska et al., 2016, J Immunol Res. 1058165), scleroderma (Li et al., 2017, J Invest Dermatol. 137 (5): 1042-1050), Crohn's disease (Dai et al., 2017, Clin Res Hepatol Gastroenterol. 41 (6): 693-702), ulcerative colitis (Dai et al., 2017, Clin Res Hepatol Gastroenterol. 41 (6): 693-702), aplastic anemia (Kook et al., 2001, Exp Hematol. 29 (11): 1270-7), myelodysplastic syndrome (Kook et al., 2001, Exp Hematol. 29 (11): 1270-7), Sjogren's syndrome (Smolenska et al., 2012, Cell Immunol. 278 (1-2): 143-51), Wegener's granulomatosis (Lamprecht et al., 2001, Thorax. 56 (10): 751-7), psoriasis (Lima et al., 2015, Br J Dermatol. 173 (4): 998-1005), type 2 diabetes (Giubilato et al., 2011, Eur Heart J. 32 (10): 1214-26), host-versus-graft reaction (Mendes et al., 2008, Clinics (Sao Paulo). 63 (5): 667-76), chronic hepatitis B (Wang et al., 2009, Immunol Invest. 2009; 38 (5): 434-46), and sarcoidosis (Roberts et al., 2005, Sarcoidosis Vasc Diffuse Lung Dis. 22 (1): 13-9). That is, preferably, the composition of the present invention is useful for the treatment or prevention of immunosuppressant resistant COPD, immunosuppressant resistant Graves' disease, immunosuppressant resistant ankylosing spondylitis, immunosuppressant resistant pars planitis, immunosuppressant resistant asthma, immunosuppressant resistant rheumatoid arthritis, immunosuppressant resistant polymyositis or dermatomyositis, immunosuppressant resistant inclusion body myositis, immunosuppressant resistant acute coronary syndrome, immunosuppressant resistant systemic lupus erythematosus, immunosuppressant resistant lupus nephritis, immunosuppressant resistant scleroderma, immunosuppressant resistant Crohn's disease, immunosuppressant resistant ulcerative colitis, immunosuppressant resistant aplastic anemia, immunosuppressant resistant myelodysplastic syndrome, immunosuppressant resistant Sjogren's syndrome, immunosuppressant resistant Wegener's granulomatosis, immunosuppressant resistant psoriasis, immunosuppressant resistant type 2 diabetes, immunosuppressant resistant host-versus-graft reaction, immunosuppressant resistant chronic hepatitis B, immunosuppressant resistant sarcoidosis, and the like (hereinafter, collectively referred to as an "immunosuppressant resistant disease associated with cytotoxic T cells").

For example, cytotoxic T cells and the diseases associated with cytotoxic T cells have been reported as follows: a correlation between the number of CD4+CD28- T cells and a worsening of prognosis has been reported for idiopathic pulmonary fibrosis (Gilani et al., PLoS One 2010, 5 (1): e8959); the disease severity of ankylosing spondylitis correlates with the number of CD8+CD28- T cells in the blood (Schirmer, M. et al., Arthritis. Res., 2002; Vol. 4 (No. 1): p. 71-76); the involvement of CD8+CD28- T cells has been suggested in the exacerbation of systemic lupus erythematosus and lupus nephritis (Zabinska et al., 2016, J Immunol Res. 1058165); the involvement of CD8+CD28- T cells in pathological conditions at the initial stage of scleroderma has been suggested (Li et al., 2017, J Invest Dermatol. 137 (5): 1042-1050); CD28- T cells are involved in the pathological conditions of polymyositis or dermatomyositis (Fasth, A E. et al., J. Immunol., 2009; Vol. 183 (No. 7): p. 4792-4799); CD28- T cells are involved in the pathological conditions of inclusion body myositis (Pandya et al., 2010, Arthritis Rheum. 62 (11): 3457-66); prognosis in Crohn's disease and ulcerative colitis becomes poorer with an increase in the percentage of CD8+CD28- T cells (Dai et al., 2017, Clin Res Hepatol Gastroenterol. 41 (6): 693-702); patients with aplastic anemia or myelodysplastic syndrome have an increased number of CD8+CD28- T cells (Kook et al., 2001, Exp Hematol. 29 (11): 1270-7); the number of CD4+CD28- T cells serves as a prognostic factor for multiple sclerosis (Peeters et al., 2017, Front Immunol. 8: 1160); a correlation between the number of CD8+CD28- T cells and severity is found in Sjogren's syndrome (Smolenska et al., 2012, Cell Immunol. 278 (1-2): 143-51); CD28- T cells are involved in the pathological conditions of Wegener's granulomatosis (Lamprecht et al., 2001, Thorax. 56 (10): 751-7); CD4+CD28- T cells are involved in the pathological conditions of psoriasis (Lima et al., 2015, Br J Dermatol. 173 (4): 998-1005); CD4+CD28- T cells are involved in the pathological conditions of type 2 diabetes (Giubilato et al., 2011, Eur Heart J. 32 (10): 1214-26); Graves' disease exhibits an increased number of CD28- T cells (Sun, Z. et al., J. Clin. Immunol., 2008; Vol. 28 (No. 5): p. 464-472); a correlation between the number of CD8+CD28- T cells and onset of the disease is found in host-versus-graft reaction (Mendes et al., 2008, Clinics (Sao Paulo). 63 (5): 667-76); asthma exhibits an increased number of CD8+CD28- T cells (Hamzaoui, A. et al., Mediators. Inflamm., 2005; No. 3: p. 160-166); CD4+CD28- T cells are involved in the pathological conditions of chronic hepatitis B (Wang et al., 2009, Immunol Invest. 2009; 38 (5): 434-46); and sarcoidosis exhibits an increased number of CD4+CD28- T cells (Roberts et al., 2005, Sarcoidosis Vasc Diffuse Lung Dis. 22 (1): 13-9).

For example, immunosuppressant resistance has been reported as follows: abatacept-resistant rheumatoid arthritis involves a large number of CD8+CD28- T cells (Scarsi et al., 2011, J Rheumatol. 38 (10): 2105-11); and CD8+CD28- T cells are involved in the steroid resistance of COPD (Non Patent Literature 16).

In the present invention, the term "immunosuppressant" means a drug that acts to suppress the immune system and is used for treatment, etc. of autoimmune diseases, and includes, for example, antifolates, calcineurin inhibitors, corticosteroids (also simply referred to as "steroids"), antithymocyte globulins, nucleic acid antimetabolites, nucleic acid synthesis inhibitors, biologics targeting cell surface antigens, or biologics targeting cytokines or cytokine receptors. Specific examples thereof can include methotrexate that is an antifolate, cyclosporin and tacrolimus that are calcineurin inhibitors, methylprednisolone, prednisolone, and dexamethasone that are corticosteroids, cyclophosphamide and azathioprine that are nucleic acid synthesis inhibitors, zetbulin, lymphoglobuline, and thymoglobulin that are antithymocyte globulins, mycophenolate mofetil that is a nucleic acid antimetabolite, alemtuzumab, rituximab, abatacept, and denosumab that are biologics targeting cell surface antigens, and adalimumab, infliximab, etanercept, tocilizumab, and the S1PR1 (one of the sphingosine-1-phosphate receptors) agonist fingolimod that are biologics targeting cytokines or cytokine receptors.

In the present invention, the term "immunosuppressant resistance" refers to a state where the disease cannot be sufficiently controlled even by treatment with the immunosuppressant as described above, and includes, for example, the case where treatment with the immunosuppressant as described above is ineffective or insufficiently effective, the case where the disease recurs, and the case where treatment with the immunosuppressant is difficult to accomplish due to adverse reactions.

In the present invention, the treatment or prevention of a disease includes, but is not limited to, the prevention of the onset of the disease, preferably of the disease in an individual expressing the LAG-3 protein, the suppression or inhibition of exacerbation or progression thereof, the alleviation of one or two or more symptoms exhibited by an individual affected with the disease, the suppression or remission of exacerbation or progression thereof, the treatment or prevention of a secondary disease, etc.

The present invention provides a pharmaceutical composition comprising an anti-LAG-3 antibody or a binding fragment thereof, or a modified form thereof. The pharmaceutical composition of the present invention is preferably applicable to treatment and/or treatment of a disease associated with cytotoxic T cells. More preferably, a biological sample containing cytotoxic T cells or a cell membrane fraction thereof is determined to be perforin positive, granzyme B positive, CD28 negative and CD4 positive, CD28 negative and CD8 positive, CD57 positive and CD4 positive, and/or CD57 positive and CD8 positive, further more preferably perforin positive, granzyme B positive, CD28 negative and CD4 positive, CD28 negative and CD8 positive, CD57 positive and CD4 positive, and/or CD57 positive and CD8 positive. Still further more preferably, the biological sample is derived from an individual who suffers from the disease associated with cytotoxic T cells or for whom it is desired to avoid suffering from the disease associated with cytotoxic T cells. The biological sample is preferably a sample containing cytotoxic T cells derived from a lesion site or collected from a lesion site, more preferably a sample containing cytotoxic T cells infiltrated into a lesion site.

The disease associated with cytotoxic T cells that may be treated or prevented with the pharmaceutical composition of the present invention is preferably chronic obstructive pulmonary disease (COPD), multiple sclerosis, Graves' disease, ankylosing spondylitis, pars planitis, asthma, rheumatoid arthritis, polymyositis or dermatomyositis, inclusion body myositis, acute coronary syndrome, systemic lupus erythematosus, lupus nephritis, scleroderma, Crohn's disease, ulcerative colitis, aplastic anemia, myelodysplastic syndrome, Sjogren's syndrome, Wegener's granulomatosis, psoriasis, type 2 diabetes, host-versus-graft reaction, chronic hepatitis B, and/or sarcoidosis.

The disease associated with cytotoxic T cells that may be treated or prevented with the pharmaceutical composition of the present invention is preferably LAG-3 positive and is more preferably a disease associated with cytotoxic T cells for which a biological sample derived from an individual, who suffers from the disease or for whom it is desired to avoid suffering from the disease, is determined to be LAG-3 positive. The biological sample is preferably a sample containing cytotoxic T cells derived from a lesion site or collected from a lesion site, more preferably a sample containing cytotoxic T cells infiltrated into a lesion site.

The composition or the pharmaceutical composition of the present invention may be administered to an individual in a method for treating or preventing a disease associated with cytotoxic T cells. That is, the present invention also provides a method for treating or preventing a disease associated with perforin positive, granzyme B positive, CD28 negative and CD4 positive, CD28 negative and CD8 positive, CD57 positive and CD4 positive, and/or CD57 positive and CD8 positive cytotoxic T cells, comprising the step of administering the composition or the pharmaceutical composition of the present invention to an individual who suffers from the disease associated with cytotoxic T cells or for whom it is desired to avoid suffering from the disease associated with cytotoxic T cells. The scope of the phrase "it is desired to avoid suffering from the disease" also includes being subjected to prevention or preventive procedures, being intended to receive prevention or preventive procedures, and being scheduled to perform prevention or preventive procedures. The scope of the term "prevention" includes the prevention of onset, recurrence, or aggravation of symptoms, etc., and examples thereof can include the case of administering the composition or the pharmaceutical composition of the present invention to an individual with symptoms that have been improved or ameliorated by treatment or the like, for the purpose of maintaining the state or preventing recurrence. In the present invention, a delay in aggravation or progression of a disease, pathological conditions, or symptoms is also encompassed by the scope of the term "treatment or prevention".

The composition or the pharmaceutical composition of the present invention can comprise a therapeutically or prophylactically effective amount of the anti-LAG-3 antibody or the binding fragment of the antibody, and pharmaceutically acceptable diluents, vehicles (carriers), solubilizers, emulsifiers, preservatives, and/or additives.

The term "therapeutically or prophylactically effective amount" means an amount that exerts therapeutic or prophylactic effects on a particular disease by means of a particular dosage form and administration route and has the same meaning as a "pharmacologically effective amount".

The composition or the pharmaceutical composition of the present invention may comprise materials for changing, maintaining, or retaining pH, osmotic pressure, viscosity, transparency, color, isotonicity, sterility, or the stability, solubility, sustained release, absorbability, permeability, dosage form, strength, properties, shape, etc., of the composition or the antibody comprised therein (hereinafter, referred to as "pharmaceutical materials"). The pharmaceutical materials are not particularly limited as long as the materials are pharmacologically acceptable. For example, no or low toxicity is a property preferably possessed by these pharmaceutical materials.

Examples of pharmaceutical materials can include, but are not limited to, amino acids such as glycine, alanine, glutamine, asparagine, histidine, arginine, or lysine, antibacterial agents, anti-oxidizing agents such as ascorbic acid, sodium sulfate, or sodium bisulfite, buffers such as phosphophate, citrate, borate buffers, sodium bicarbonate, and tris-hydrochloric acid (Tris-HCl) solution, fillers such as mannitol and glycine, chelating agents such as ethylenediaminetetraacetic acid (EDTA), complexing agents such as caffeine, polyvinyl pyrrolidine, β-cyclodextrin, and hydroxypropyl-β-cyclodextrin, extenders such as glucose, mannose, or dextrin, monosaccharides, disaccharides, other carbohydrates such as glucose, mannose, and dextrin, coloring agents, flavoring agents, diluents, emulsifiers, preservatives such as hydrophilic polymers, e.g., polyvinyl pyrrolidine, low molecular weight polypeptides, salt-forming counterions, benzalkonium chloride, benzoic acid, salicylic acid, thimerosal, phenethyl alcohol, methylparaben, propylparaben, chlorhexidine, sorbic acid, or hydrogen peroxide, solvents such as glycerin, propylene glycol, or polyethylene glycol, sugar alcohols such as mannitol or sorbitol, suspending agents, surfactants such as PEG, sorbitan ester, polysorbates, e.g., polysorbate 20 and polysorbate 80, triton, tromethamine, lecithin, or cholesterol, stability enhancers such as sucrose and sorbitol, elasticity enhancers such as sodium chloride, potassium chloride, mannitol, and sorbitol, transport agents, diluents, excipients, and/or pharmaceutical additives.

The amount of these pharmaceutical materials that is added is 0.001 to 1000 times, preferably 0.01 to 100 times, more preferably 0.1 to 10 times the weight of the anti-LAG-3 antibody or the binding fragment thereof, or the modified form thereof.

A composition or a pharmaceutical composition comprising an immunoliposome comprising the anti-LAG-3 antibody or binding fragment thereof, or the modified form of the antibody or binding fragment encapsulated in a liposome, or a modified antibody form comprising the antibody conjugated with a liposome (U.S. Pat. No. 6,214,388, etc.) is also included in the composition or the pharmaceutical composition of the present invention.

The excipients or vehicles (carriers) are usually liquid or solid and are not particularly limited as long as they are materials used for oral or parenteral administration such as injectable water, saline, artificial cerebrospinal fluids, etc. Examples of saline can include neutral saline and serum albumin-containing saline.

Examples of buffers can include a Tris buffer adjusted to bring the final pH of the composition or the pharmaceutical composition to 7.0 to 8.5, an acetate buffer adjusted to bring the final pH thereof to 4.0 to 5.5, a citrate buffer adjusted to bring the final pH thereof to 5.0 to 8.0, and a histidine buffer adjusted to bring the final pH thereof to 5.0 to 8.0.

The composition or the pharmaceutical composition of the present invention is a solid, a liquid, a suspension, or the like. Another example of the composition or the pharmaceutical composition of the present invention can include freeze-dried preparations. The freeze-dried preparations can be formed using an excipient such as sucrose.

The administration route of the composition or the pharmaceutical composition of the present invention may be any of enteral administration, local administration, and parenteral administration. Examples thereof can include intravenous administration, intraarterial administration, intramuscular administration, intradermal administration, hypodermic administration, intraperitoneal administration, transdermal administration, intraosseous administration, and intraarticular administration.

The constitution of the composition or the pharmaceutical composition can be determined according to the administration method, the binding affinity of the antibody for the LAG-3 protein, etc. The anti-LAG-3 antibody or the binding fragment thereof, or the modified form thereof having higher affinity (lower KD value) for the LAG-3 protein can exert its efficacy at a lower dose.

The dose of the anti-LAG-3 antibody is not limited as long as the dose is a pharmacologically effective amount. The dose can be appropriately determined according to the species of an individual, the type of disease, symptoms, sex, age, pre-existing conditions, the binding affinity of the antibody for the LAG-3 protein or its biological activity, and other factors. A dose of usually 0.01 to 1000 mg/kg, preferably 0.1 to 100 mg/kg, can be administered between once every day and once every 180 days or twice or three or more times a day.

Examples of the form of the composition or the pharmaceutical composition can include injections (including freeze-dried preparations and drops), suppositories, transnasal absorption preparations, transdermal absorption preparations, sublingual formulations, capsules, tablets, ointments, granules, aerosols, pills, powders, suspensions, emulsions, eye drops, and biological implant formulations.

The composition or the pharmaceutical composition comprising the anti-LAG-3 antibody or the binding fragment thereof, or the modified form thereof as an active ingredient can be administered concurrently with or separately from an additional drug. For example, the composition or the pharmaceutical composition comprising the anti-LAG-3 antibody or the binding fragment thereof as an active ingredient may be administered after administration of the additional drug, or the additional drug may be administered after administration of the composition or the pharmaceutical composition. Alternatively, the composition or the pharmaceutical composition and the additional drug may be administered concurrently.

Examples of the additional drug that is used in combination with the composition or the pharmaceutical composition of the present invention can include antifolates, calcineurin inhibitors, corticosteroids, antithymocyte globulins, nucleic acid antimetabolites, nucleic acid synthesis inhibitors, biologics targeting cell surface antigens, and biologics targeting cytokines or cytokine receptors, and these are preferable for the treatment or prevention of autoimmune diseases and/or the rejection of transplants. Examples of the additional drug can include methotrexate that is an antifolate, cyclosporin and tacrolimus that are calcineurin inhibitors, methylprednisolone and prednisolone that are corticosteroids, cyclophosphamide and azathioprine that are nucleic acid synthesis inhibitors, zetbulin, lymphoglobuline, and thymoglobulin that are antithymocyte globulins, mycophenolate mofetil that is a nucleic acid antimetabolite, alemtuzumab, rituximab, abatacept, and denosumab that are biologics targeting cell surface antigens, and adalimumab, infliximab, etanercept, tocilizumab, and anti-Orail antibodies that are biologics targeting cytokines or cytokine receptors. Further, the composition or the pharmaceutical composition of the present invention can also be used for the treatment or prevention of autoimmune diseases and/or rejection of transplants in combination with intravenous immunoglobulin (IVIg), plasma exchange, etc. Such additional drugs and therapies can also be combined with the composition of the present invention for treating or preventing diseases other than autoimmune diseases and the rejection of transplants.

Examples of the drugs and therapies that can be combined with the composition or the pharmaceutical composition of the present invention in treating or preventing malignant tumors can include anticancer agents such as various molecular targeted drugs, chemotherapeutic agents, radiation therapies, and various cancer immunotherapeutic agents typified by the anti-PD-1 antibody, the anti-PD-Li antibody, and the anti-CTLA-4 antibody.

One of these additional drugs and therapies, or two, three, or more of them can be administered or received. These are collectively referred to as the "combined use of the additional drug" or the "combination with the additional drug". The present invention also encompasses the composition of the present invention comprising such an additional drug or used in combination with another therapy, in addition to the LAG-3 antibody or the binding fragment thereof, or the modified form thereof, as an aspect of the "combined use of the additional drug" or the "combination with the additional drug".

The present invention also provides a method for depleting cytotoxic T cells, use of a LAG-3 antibody for depleting cytotoxic T cells or for preparing a composition or a pharmaceutical composition for cytotoxic T cell depletion, use of a LAG-3 antibody for the treatment or prevention of a disease associated with cytotoxic T cells, a LAG-3 antibody for the treatment or prevention of a disease associated with cytotoxic T cells, and a LAG-3 antibody for use in the treatment or prevention of a disease associated with cytotoxic T cells. The present invention also includes a kit for cytotoxic T cell depletion and a kit for the treatment or prevention of a disease associated with cytotoxic T cells, comprising a LAG-3 antibody.

EXAMPLES

Hereinafter, the present invention will be described further, specifically with reference to the Examples. However, the present invention is not intended to be limited to them.

Procedures related to gene manipulation in the Examples below were performed according to the methods described in "Molecular Cloning" (Sambrook, J., Fritsch, E. F. and Maniatis, T., Cold Spring Harbor Laboratory Press, 1989) or according to the methods described in other experimental manuals used by those skilled in the art, or using commercially available reagents or kits according to the instruction manuals, unless otherwise specified.

Example 1. Preparation of Rat Anti-Human LAG-3 Antibody

1)-1 Immunization

A mutant deficient in the 1st and 2nd domains (a region of positions 23 to 262) from the N terminus out of the four extracellular immunoglobulin-like domains of human LAG-3 (SEQ ID No: 86: FIG. 101) was cloned into pcDNA3.1 (Life Technologies Corp.) to prepare a large amount of expression plasmid pcDNA3.1-hLAG-3_D3D4 using an EndoFree Plasmid Giga Kit (Qiagen N. V). After pretreatment of both lower legs of a female WKY/Izm rat (Japan SLC, Inc.) with Hyaluronidase (Sigma-Aldrich), the pcDNA3.1-hLAG-3_D3D4 was injected intramuscularly into the same sites. Subsequently, using ECM830 (BTX Global Logistics), the same sites were subjected to in vivo electroporation using a two-needle electrode. Once every two weeks, the same in vivo electroporation was repeated 3 or 5 times in total, and thereafter lymph nodes of the rat were collected to be used for development of hybridomas.

1)-2 Hybridoma Preparation

The lymph node cells or the spleen cells were electrically fused with mouse myeloma SP2/0-ag14 cells using the Hybrimune Hybridoma Production System (manufactured by Cyto Pulse Sciences, Inc.). The fused cells were diluted with ClonaCell-HY Selection Medium D (manufactured by StemCell Technologies Inc.) and cultured. Hybridoma colonies that appeared were recovered to prepare monoclonal hybridomas. Each hybridoma colony thus recovered was cultured, and the obtained hybridoma culture supernatant was used to screen for an anti-LAG-3 antibody-producing hybridoma.

1)-3 Antibody screening by Cell-ELISA

Expression plasmids (pcDNA3.1/hLAG-3 and pcDNA3.1/cynoLAG-3) constructed by cloning human or cynomolgus monkey LAG-3 into pcDNA3.1 or a control plasmid were introduced into HEK293 cells using Lipofectamine 2000 (manufactured by Life Technologies Corp.), and the cells were cultured in a 96-well microplate (manufactured by Corning Inc.) overnight under conditions of 37° C. and 5% $CO_2$ in a DMEM medium containing 10% FBS. After removal of the culture supernatant, each hybridoma culture supernatant was added, and the plate was left standing at 4° C. for 1 hour. The cells in the wells were washed once with PBS containing 5% FBS. Then, Anti-Rat IgG-Peroxidase antibody produced in rabbit (manufactured by Sigma-Aldrich Corp.) diluted 500-fold with PBS containing 5% FBS was added thereto, and the plate was left standing at 4° C. for 1 hour. The cells in the wells were washed 5 times with PBS containing 5% FBS. Then, an OPD chromogenic solution (prepared by dissolving o-phenylenediamine dihydrochloride (manufactured by Wako Pure Chemicals Industries, Ltd.) and $H_2O_2$ at concentrations of 0.4 mg/mL and 0.6% (v/v), respectively, in the OPD solvent (0.05 M trisodium citrate and 0.1 M disodium hydrogen phosphate dodecahydrate, pH 4.5)) was added thereto at 25 µL/well. Color reaction was performed with occasional stirring and stopped by adding L/well of 1 M HCl. Then, the absorbance was measured at 490 nm using a plate reader (ENVISION; PerkinElmer, Inc.). In order to select hybridomas producing an antibody that specifically binds to LAG-3 expressed on the cell membrane surface, hybridomas that yielded a culture supernatant exhibiting higher absorbance for the LAG-3 expression vector-transfected HEK293 cells than for the control plasmid-transfected HEK293 cells free from the LAG-3 gene were selected as anti-LAG-3 antibody production-positive hybridomas.

1)-4 Antibody Screening by Flow Cytometry

It was further confirmed by flow cytometry that the antibody produced by the hybridomas determined to be positive by the Cell-ELISA in Example 1)-3 binds to PHA (phytohemagglutinin) activated human T cells (PHA blasts), a more physiologically relevant cell type expressing LAG-3. To human PBMCs stimulated with 2 µg/mL of PHA (manufactured by Sigma-Aldrich) for three days, was added a hybridoma culture supernatant for suspension, followed by reaction at 4° C. for 30 minutes. After washing with a FACS buffer (PBS, 0.1% BSA, and 0.1% sodium azide), a secondary antibody such as an Anti-Rat IgG PE conjugate (manufactured by Jackson ImmunoResearch Laboratories, Inc.) diluted 200-fold with a FACS buffer comprising a LIVE/DEAD Fixable Dead Cell Stain Kit-near-IR fluorescent reactive dye (manufactured by Invitrogen Corp.) was added thereto for suspension, followed by standing at 4° C. for 30 minutes. After washing with a FACS buffer, the cells were resuspended in PBS containing 1 to 2% paraformaldehyde, followed by detection using a flow cytometer (CantoII: manufactured by Becton, Dickinson and Company or FC500: manufactured by Beckman Coulter Inc.). The data was analyzed using FlowJo (manufactured by Tree Star Inc). After removal of the LIVE/DEAD Fixable Dead Cell Stain Kit-near-IR fluorescent reactive dye-positive dead cells by gating, a histogram of the fluorescence intensity of the living cells was plotted.

1)-5 Screening by ADCC Assay

1)-5-1 Preparation of Target Cells

293FT cells (Invitrogen Corp.) were transfected with pLenti6/V5-GW/lacZ, and ViraPower™ Packaging Mix (Invitrogen Corp.) according to the accompanying protocols to prepare a recombinant lentivirus to express the β-galactosidase gene. 293T cells were infected by the obtained recombinant lentivirus according to the protocol of ViraPower Lentiviral Expression Systems (Invitrogen Corp). Virus-infected cells were selected using 10 μg/mL blasticidin (Invitrogen Corp.) to obtain a line stably expressing β-galactosidase. An expression plasmid of the full-length human LAG-3 was introduced into the 293T cells stably expressing β-galactosidase (hereinafter, referred to as 293T-lacZ) using Lipofectamine 2000 (manufactured by Invitrogen Corp.), and the cells were cultured for 1 day and then dissociated and recovered using TrypLExpress (manufactured by Invitrogen Corp). The cells were washed twice with phenol red-free RPMI1640 containing 5% FBS (hereinafter, referred to as a "medium for ADCC"). The number of live cells was counted by the trypan blue dye exclusion test. The cells were resuspended to $1 \times 10^5$ cells/ml in a medium for ADCC and used as target cells.

1)-5-2 Preparation of Effector Cells

PBMCs were separated from human peripheral blood by Ficoll centrifugation, and a suspension adjusted to a live cell density of $1.2 \times 10^6$ cells/mL in a medium for ADCC was used as effector cells.

1)-5-3 ADCC Assay

To a 96-well U-bottom microplate containing 50 μL/well of the hybridoma culture supernatant, was added 50 μL/well of the target cells of 1)-5-1, followed by standing at 4° C. for 30 minutes. After adding 150 μL/well of a medium for ADCC thereto, followed by stirring, the plate was centrifuged at room temperature at 1200 rpm for 5 minutes to remove 200 μL/well of the supernatant. Then, 125 μL/well of the effector cells of 1)-5-2 was added thereto, followed by centrifugation at room temperature at 1200 rpm for 5 minutes. Thereafter, the cells were cultured overnight under conditions of 37° C. and 5% $CO_2$. On the next day, 50 μL of the supernatant was recovered into a black plate (manufactured by Corning Inc). 50 μL of a β-Glo assay system (manufactured by Promega Corp.) solution was added thereto. The luminescence intensity was measured using a plate reader (ENVISION; manufactured by PerkinElmer, Inc). The percentage of cells lysed by ADCC activity was calculated according to the following formula.

Percentage of cells lysed (%)=$(A-B)/(C-B) \times 100$

A: Count of each sample well
B: Average of spontaneous release (wells without antibody added) counts (n=3)
When adding the antibody, 50 μL of a medium for ADCC was added thereto. Except for that, the same operation as in the sample well was performed.
C: Average of maximum release (wells containing target cells lysed with a surfactant) counts (n=3)
When adding the antibody and adding the effector cells, 50 μL and 75 μL of a medium for ADCC were added thereto respectively. For the assay, 175 μl of the β-Glo assay system solution was added to each well containing the target cells and mixed therewith. A 100 μl aliquot thereof was added to a black plate to carry out the assay.

1)-6 Screening by LAG-3/MHC Class II Binding Test

This was conducted according to a previous report (Non Patent Literature 8). That is, 20 μL/well of LAG-3-Fc (manufactured by R&D Systems, Inc.) diluted with RPMI1640 containing 10% FBS to 25 nM was added to a 96-well U-bottom microplate, and 20 μL/well of the hybridoma culture supernatant was added thereto, followed by stirring and standing at 4° C. for 20 minutes. Then, 10 L/well ($2.5 \times 10^5$ cells/well) of Raji cells, which endogenously highly express MHC class II molecules, was added thereto, followed by stirring and standing at 4° C. for a further 30 minutes. The cells were washed twice with PBS or a FACS buffer, then an Anti-Human IgG PE conjugate (manufactured by Jackson ImmunoResearch Laboratories, Inc.) diluted 200-fold with a FACS buffer was added thereto for suspension, followed by standing at 4° C. for 20 minutes. After washing with PBS or a FACS buffer, the cells were resuspended in PBS containing 1 to 2% paraformaldehyde, followed by detection using a flow cytometer (CantoII: manufactured by Becton, Dickinson and Company or FC500: manufactured by Beckman Coulter Inc). The data was analyzed using FlowJo (manufactured by Tree Star Inc.), and the percentage of inhibition was calculated by the following formula.

Percentage of inhibition (%)=$100-(A-B)/(C-B) \times 100$

A: Mean fluorescence intensity of each sample well
B: Mean fluorescence intensity of background
When adding LAG-3-Fc and the antibody, 20 μL of a medium was added each time. Except for that, the same operation as in the sample well was performed.
C: Mean fluorescence intensity of maximum binding
When adding the antibody, 20 μL of a medium was added thereto.

1)-7 Purification of Monoclonal Antibody

A rat anti-human LAG-3 monoclonal antibody was purified from the hybridoma culture supernatant. That is, the hybridoma culture supernatant was first applied to a ProteinG column (manufactured by GE Healthcare) equilibrated with PBS. After washing the column with PBS, antibody-containing fractions were collected by elution with a 0.1 M glycine/hydrochloric acid aqueous solution (pH 2.7). To the collected fractions, was added 1M Tris-HCl (pH 9.0) for adjustment to pH 7.0 to 7.5, and thereafter Centrifugal UF Filter Device VIVASPIN20 (fraction molecular weight UF30K, manufactured by Sartorius AG) was used to replace the buffer with PBS and concentrate the antibody to adjust to 2 mg/mL or more. Finally, filtration with a Minisart-Plus filter (manufactured by Sartorius AG) was performed to give a purified sample.

Example 2. In Vitro Evaluation of Rat Anti-Human LAG-3 Antibodies (rLA204, rLA212, rLA225, rLA869, and rLA1264)

2)-1 Binding Activity of the Obtained Rat Anti-LAG-3 Antibodies (rLA204, rLA212, rLA225, rLA869, and rLA1264) to Activated Human T Cells The binding activity of the rat anti-human LAG-3 antibodies rLA204, rLA212, rLA225, rLA869, and rLA1264 purified by the method described in Example 1)-7 to activated human T cells was investigated. As shown in FIG. 1, all of the rat anti-human LAG-3 antibodies bound to PHA blasts prepared as in vitro activated human T cells in a concentration-dependent manner.

2)-2 ADCC Activity of Obtained Rat Anti-LAG-3 Antibodies (rLA204, rLA212, rLA225, rLA869, and rLA1264)

The ADCC activity of the purified rat anti-human LAG-3 antibodies rLA204, rLA212, rLA225, rLA869, and rLA1264 was investigated by the following method. To a 96-well U-bottom microplate containing 50 μL/well of the antibody solution, was added 50 μL/well of the target cells (which will be hereinafter referred to as 293T-lacZ/hLAG-3 cells) of Example 1)-5-1, followed by standing at 4° C. for 30 minutes. Then, 75 μL/well of effector cells prepared as in Example 1)-5-2 (which was however suspended to $2 \times 10^6$ cells/mL) was added thereto, followed by centrifugation at room temperature at 1200 rpm for 5 minutes, and thereafter the cells were cultured overnight under conditions of 37° C. and 5% $CO_2$. On the next day, 50 μl of the supernatant was recovered into a black plate (manufactured by Corning Inc). A solution of β-Glo assay system (manufactured by Promega Corp.) was added thereto at 50 μl/well. The luminescence intensity was measured using a plate reader (ENVISION; manufactured by PerkinElmer, Inc). The percentage of cells lysed by ADCC activity was calculated according to the following formula.

Percentage of cells lysed (%)=$(A-B)/(C-B) \times 100$

A: Count of each sample well
B: Average of spontaneous release (wells without antibody added) counts (n=3)
When adding the antibody, 50 μL of a medium for ADCC was added thereto. Except for that, the same operation as in the sample well was performed.
C: Average of maximum release (wells containing target cells lysed with a surfactant) counts (n=3)
When adding the antibody and adding the effector cells, 50 μL and 75 μL of a medium for ADCC were added thereto respectively. For the assay, 175 μl of the β-Glo assay system solution was added to each well containing the target cells and mixed therewith. A 100 μl aliquot thereof was added to a black plate to carry out the assay.

Figure 2:
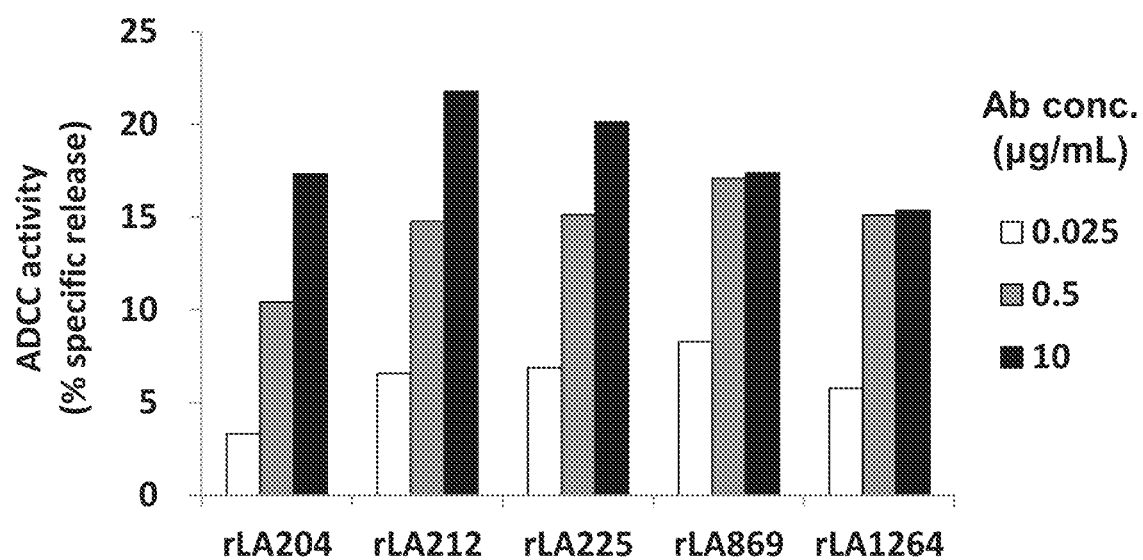
FIG. 2 is a diagram showing ADCC activity of rat anti-LAG-3 antibodies (rLA204, rLA212, rLA225, rLA869, and rLA1264). 293T-lacZ cells expressing human LAG-3 were used as target cells, and human PBMCs were used as effector cells.

As shown in FIG. 2, all the rat anti-human LAG-3 antibodies showed a concentration-dependent in vitro ADCC activity on the cells expressing human LAG-3. In contrast, these antibodies showed no ADCC activity on the 293T-lacZ cells into which the human LAG-3 gene was not transfected, so the action was specific.

2)-3 Investigation of Inhibitory Activity of Obtained Rat Anti-LAG-3 Antibodies (rLA204, rLA212, rLA225, rLA869, and rLA1264) in LAG-3/MHC Class II Binding Test It was investigated by the LAG-3/MHC class II binding test according to Example 1)-6 whether the purified anti-LAG-3 antibodies (rLA204, rLA212, rLA225, rLA869, and rLA1264) had an inhibitory activity against the binding of LAG-3 to MHC class II molecules, which were reported to be its ligands. As shown in FIG. 3A, the results revealed that all of the 5 clones of antibodies showed almost no inhibitory activity in the LAG-3/MHC class II binding test and had no influence on the binding to MHC class II molecules, which is considered to be necessary for LAG-3 to exert a T cell suppression function. In contrast, as shown in FIG. 3B, the human chimeric anti-LAG-3 antibody IMP731 (Patent Literature 1) that is a conventional antibody in the Citation List showed a powerful inhibitory activity in a concentration-dependent manner in the LAG-3/MHC class II binding test.

2)-4 Investigation of Inhibitory Activity of Obtained Rat Anti-LAG-3 Antibodies (rLA204, rLA212, rLA225, rLA869, and rLA1264) in 293T-hLAG-3/Raji Cell Adhesion Test In the LAG-3/MHC class II binding test according to Example 2)-3, the binding of the secondary antibody Anti-Human IgG PE conjugate for detecting binding of LAG-3-Fc to Raji cells could be inhibited by steric hindrance caused by binding of the anti-LAG-3 antibody to LAG-3-Fc, and thus the possibility of apparently showing a low fluorescence intensity cannot be completely excluded, despite the antibody not actually directly inhibiting the binding of LAG-3/MHC class II. Therefore, as an evaluation system without using a secondary antibody for detection, the following 293T-hLAG-3/Raji cell adhesion test system was constructed to evaluate the antibody.

Human LAG-3 expression plasmid pcDNA3.1/hLAG-3 was introduced into 293T cells using Lipofectamine 2000 (manufactured by Life Technologies Corp.), and the cells were inoculated onto a BioCoat poly-D-lysine-coated 96-well microplate (manufactured by Becton, Dickinson and Company) and cultured overnight. Meanwhile, Raji cells were labeled in a medium (RPMI1640 containing 10% FBS) with fluorescent dye BCECF-AM (manufactured by DOJINDO LABORATORIES, used at 10 μM) at 37° C. for 1 hour, followed by washing and then suspending in a medium to $1.6 \times 10^6$ cells/mL. After the transfection, the medium of the cells (293T-hLAG-3 cells) cultured overnight was removed, and 50 μL/well of a medium and 25 μL/well of an antibody solution were added thereto, followed by pre-incubation at 37° C. for 30 minutes. Thereafter, 25 μL/well of the BCECF-AM labeled Raji cells was added thereto, followed by centrifugation at 900 rpm for 30 seconds and incubation at 37° C. for 1 hour. After the reaction, the well was washed with medium two to three times to remove nonadherent cells, and the cells were lysed in 100 L/well of a Tris buffer (25 mM, pH 8.0) containing 0.1% NP-40, to measure the fluorescence intensity of the well with a plate reader (ENVISION: manufactured by PerkinElmer Inc). The percentage of inhibition was calculated by the following formula.

Percentage of inhibition (%)=100−(A−B)/(C−B)×100
A: Fluorescence intensity of each sample well
B: Fluorescence intensity of background When adding the Raji cells and the antibody, a medium was added thereto. Except for that, the same operation as in the sample well was performed.

C: Fluorescence intensity of maximum binding

When adding the antibody, a medium was added thereto.

Figure 4:
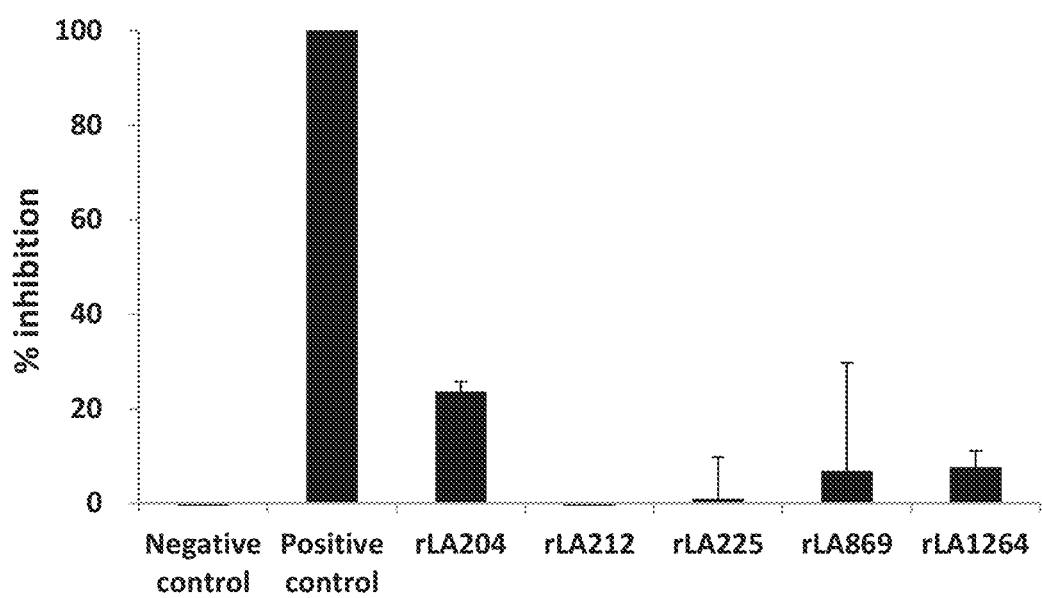
FIG. 4 is a diagram showing the inhibitory activity of the rat anti-LAG-3 antibodies (rLA204, rLA212, rLA225, rLA869, and rLA1264) in a 293T-hLAG-3/Raji cell adhesion test. Rat IgG2b was used as a negative control, and the rat anti-LAG-3 antibody (clone 6D7) that was developed in Example 2)-6 and recognized domain 1 of LAG-3 was used as a positive control, respectively. Each antibody was evaluated at 10 µg/mL.

As shown in FIG. 4, the results revealed that all of the purified rat anti-LAG-3 antibodies rLA204, rLA212, rLA225, rLA869, and rLA1264 showed almost no inhibitory activity in the 293T-hLAG-3/Raji cell adhesion test, further supporting the notion that the antibodies had no influence on binding to MHC class II molecules, which is considered to be necessary for LAG-3 to exert a T cell suppression function. In contrast, the human chimeric anti-LAG-3 antibody IMP731 (Patent Literature 1) that is a conventional antibody in the Citation List showed a powerful inhibitory activity with a percentage of inhibition of 90% at a concentration of 10 μg/mL in this test.

2)-5 Identification of Epitope of Obtained Rat Anti-LAG-3 Antibodies (rLA204, rLA212, rLA225, rLA869, and rLA1264)

Based on the fact that the rat anti-LAG-3 antibodies rLA204, rLA212, rLA225, rLA869, and rLA1264 are antibodies developed using a mutant deficient in the 1st and 2nd domains (which will be hereinafter referred to respectively as domains 1 and 2) from the N terminus out of the four immunoglobulin-like domains present in the extracellular region of LAG-3 as an immunogen, in order to reveal which of the remaining 3rd and 4th domains (which will be hereinafter referred to respectively as domains 3 and 4) from the N terminus these antibodies bind to, binding of the obtained rat anti-LAG-3 antibodies to cells expressing domains 3 and 4, or only domain 4, was investigated by flow cytometry.

Each expression plasmid (cloned into pcDNA3.1) of either domain 3 and onwards (263-525) or domain 4 and onwards (353-525) of human LAG-3 with a FLAG tag sequence (DYKDDDDK) (SEQ ID NO:87) added to the N terminus was introduced into HEK293T cells using Lipofectamine 2000 (manufactured by Life Technologies Corp.), and the cells were cultured for 1 day and then recovered, to investigate the binding activity of the antibodies by flow cytometry according to the method described in Example 1)-4. As to the results, all of the purified rat anti-LAG-3 antibodies rLA204, rLA212, and rLA225 bound to the cells expressing the construct containing domains 3 and 4, whereas none of them bound to the cells expressing the construct containing only domain 4, as shown in FIG. 5A. These results revealed that all the obtained rat anti-LAG-3 antibodies rLA204, rLA212, and rLA225 bound to domain 3 out of the four immunoglobulin-like domains present in the extracellular region of LAG-3.

The same type of experiment using a hybridoma culture supernatant revealed that the obtained rat anti-LAG-3 antibodies rLA869 and rLA1264 also bound to domain 3.

FIG. 5B shows the results of investigating the binding domain of the human-chimeric anti-human LAG-3 antibody IMP731 that is a conventional antibody in the Citation List by the same method. In addition to the two types of constructs in FIG. 5A, expression plasmids were used of domain 2 and onwards (amino acid positions 173-525 of the human LAG-3 amino acid sequence in SEQ ID No: 86, FIG. 101) of human LAG-3 with a FLAG tag sequence (DYKDDDDK) (SEQ ID NO:87) added to the N terminus and the full length of human LAG-3 (both were constructed using pcDNA3.1; the nucleotide sequence encoding the amino acid sequence of human LAG-3 is described in SEQ ID No: 85, FIG. 100). Both IMP731 and the rat anti-human LAG-3 antibody clone 6D7 developed in Example 2)-6 bound to the cells expressing the full length of human LAG-3 but did not bind to the mutants (FLAG-D2D3D4, FLAG-D3D4, and FLAG-D4) deficient in domain 1, thereby revealing that they bind to domain 1. That is, it was revealed that the obtained rat anti-LAG-3 antibodies rLA204, rLA212, rLA225, rLA869, and rLA1264, which bind to domain 3 out of the four immunoglobulin-like domains present in the extracellular region of LAG-3, recognize an epitope that is different from IMP731, which binds to domain 1.

2)-6 Obtaining Rat Anti-Human LAG-3 Antibody Using Purified LAG-3 Protein as Immunogen As an alternative immunization method to Example 1)-1, rat anti-human LAG-3 antibodies were obtained using a purified LAG-3 protein as an immunogen. An emulsion formed by mixing a protein with a His tag added to the C terminus of the extracellular region (1-450) of human LAG-3 with Freund's Complete Adjuvant (manufactured by Wako Pure Chemical Industries, Ltd.) (at a volume ratio of 1:2) was administered to the tail bases of 8 week-old female WKY/Izm rats (Japan SLC, Inc.) in an amount of 200 μg per mouse. Three weeks later, only an antigen protein was administered to the tail bases in an amount of 200 μg per mouse, and two further weeks later, lymph nodes were collected to develop hybridomas by the method of Example 1)-2. Screening by the methods of Example 1)-3 and 1)-4, etc., and analysis of the obtained monoclonal antibody epitope by the method of Example 2)-5 revealed that, out of the four immunoglobulin-like domains present in the extracellular region of LAG-3, 58% of the evaluated clones bound to domain 1, and 26% thereof bound to domain 2, so that monoclonal antibodies against portions close to the N terminus were preferentially obtained. Out of these, most of the clones that strongly bound to activated human T cells (PHA blasts) in flow cytometry, including clone 6D7, bound to domain 1 of LAG-3, and all of them showed strong inhibitory activity in the LAG-3/MHC class II binding test described in Example 2)-3. These results are fully consistent with the conventional finding (Non Patent Literature 4) that domains 1 and 2 of the N terminus out of the four extracellular immunoglobulin-like domains of LAG-3 are important for binding of LAG-3 to MHC class II molecules and indicate that, in order to obtain an antibody that does not inhibit the binding of LAG-3 to MHC class II molecules, that is, the T cell suppression function of LAG-3, it is necessary to develop a monoclonal antibody by devising such an immunization method as in Example 1)-1.

Example 3. Determination of Nucleotide Sequence of cDNA Encoding Variable Regions of Rat Anti-Human LAG-3 Antibodies (rLA204, rLA212, rLA225, rLA869, and rLA1264)

3)-1 Determination of Nucleotide Sequence of cDNA Encoding Variable Region of rLA204

3)-1-1 Preparation of Total RNA from Hybridoma Producing rLA204

In order to amplify cDNAs comprising the variable regions of rLA204, total RNA was prepared from the hybridoma producing rLA204 using TRIzol Reagent (Ambion/Thermo Fisher Scientific Inc.).

3)-1-2 Synthesis of cDNA (5'-RACE-Ready cDNA)

The cDNA (5'-RACE-Ready cDNA) was synthesized using about 1 μg of the total RNA prepared in Example 3)-1-1 and a SMARTer RACE cDNA Amplification Kit (Clontech Laboratories, Inc).

3)-1-3 5'-RACE PCR Amplification and Sequencing of cDNA Encoding Heavy Chain Variable Region of rLA204

The primers used for PCR amplification of the variable region-encoding cDNA of the heavy chain gene of rLA204 were oligonucleotides having the sequences of UPM (Universal Primer A Mix; provided with the SMARTer RACE cDNA Amplification Kit) and 5'-CTCCAGAGTTCCAGGT-CACGGTGACTGGC-3' (RG2AR3: SEQ ID NO: 71). The UPM used was provided with the SMARTer RACE cDNA Amplification Kit (Clontech Laboratories, Inc.), while RG2AR3 was designed from the sequences of rat heavy chain constant regions in a database.

cDNA comprising the heavy chain variable region of rLA204 was amplified by 5'-RACE PCR using this primer set and the cDNA (5'-RACE-Ready cDNA) synthesized in Example 3)-1-2 as a template. This PCR was carried out on the Touchdown PCR program according to the manual of the SMARTer RACE cDNA Amplification Kit (Clontech Laboratories, Inc.) using polymerase KOD-Plus—(Toyobo Co., Ltd.).

The heavy chain variable region-comprising cDNA amplified by 5'-RACE PCR was purified using a MinElute PCR Purification Kit (Qiagen N. V.) and then cloned using a Zero Blunt TOPO PCR Cloning Kit (Invitrogen Corp.). The cloned heavy chain variable region-comprising cDNA was analyzed by sequencing.

The sequencing primers used were an oligonucleotide having the sequence 5'-CTCCAGAGTTCCAGGT-CACGGTGACTGGC-3' (RG2AR3; SEQ ID No: 71) designed from the sequences of rat heavy chain constant regions in a database, and NUP (Nested Universal Primer A: provided with the SMART RACE cDNA Amplification Kit).

The determined nucleotide sequence of the cDNA encoding the heavy chain variable region of rLA204 is shown in SEQ ID NO: 1, and the amino acid sequence thereof is shown in SEQ ID NO: 2.

3)-1-4 5'-RACE PCR Amplification and Sequencing of cDNA Encoding Light Chain Variable Region of rLA204

The primers used for PCR amplification of the variable region-encoding cDNA of the light chain gene of rLA204 were UPM (Universal Primer A Mix; provided with the SMARTer RACE cDNA Amplification Kit) and an oligonucleotide having the sequence of 5'-TCAGTAACACTGTCCAGGACACCATCTC-3' (RKR5: SEQ ID NO: 72). The UPM used was provided with the SMARTer RACE cDNA Amplification Kit (Clontech Laboratories, Inc.), while RKR5 was designed from the sequences of rat light chain constant regions in a database.

cDNA comprising the light chain variable region of rLA204 was amplified by 5'-RACE PCR using this primer set and the cDNA (5'-RACE-Ready cDNA) synthesized in Example 3)-1-2 as a template. This PCR was carried out on the Touchdown PCR program according to the manual of the SMARTer RACE cDNA Amplification Kit (Clontech Laboratories, Inc.) using polymerase KOD-Plus—(Toyobo Co., Ltd.).

The light chain variable region-comprising cDNA amplified by 5'-RACE PCR was purified using a MinElute PCR Purification Kit (Qiagen N. V.) and then cloned using a Zero Blunt TOPO PCR Cloning Kit (Invitrogen Corp.). The cloned light chain variable region-encoding cDNA was analyzed by sequencing.

The sequencing primers used were an oligonucleotide having the sequence 5'-TCAGTAACACTGTCCAGGACACCATCTC-3' (RKR5; SEQ ID No: 72) designed from the sequences of rat light chain constant regions in a database, and NUP (Nested Universal Primer A: provided with the SMART RACE cDNA Amplification Kit).

The determined nucleotide sequence of the cDNA encoding the light chain variable region of rLA204 is shown in SEQ ID NO: 3, and the amino acid sequence thereof is shown in SEQ ID NO: 4.

3)-2 Determination of nucleotide sequence of cDNA encoding variable region of rLA212

The sequence was determined in the same manner as in Example 3)-1.

The determined nucleotide sequence of the cDNA encoding the heavy chain variable region of rLA212 is shown in SEQ ID NO: 5, and the amino acid sequence thereof is shown in SEQ ID NO: 6. The nucleotide sequence of the cDNA encoding the light chain variable region thereof is shown in SEQ ID NO: 7, and the amino acid sequence thereof is shown in SEQ ID NO: 8.

3)-3 Determination of Nucleotide Sequence of cDNA Encoding Variable Region of rLA225

The sequence was determined in the same manner as in Example 3)-1.

The determined nucleotide sequence of cDNA encoding the heavy chain variable region of rLA225 is shown in SEQ ID No: 9, and the amino acid sequence thereof is shown in SEQ ID No: 10. The nucleotide sequence of cDNA encoding the light chain variable region thereof is shown in SEQ ID No: 11, and the amino acid sequence thereof is shown in SEQ ID No: 12.

3)-4 Determination of nucleotide sequence of cDNA encoding variable region of rLA869

The sequence was determined in the same manner as in Example 3)-1.

The determined nucleotide sequence of cDNA encoding the heavy chain variable region of rLA869 is shown in SEQ ID No: 13, and the amino acid sequence thereof is shown in SEQ ID No: 14. The nucleotide sequence of cDNA encoding the light chain variable region thereof is shown in SEQ ID No: 15, and the amino acid sequence thereof is shown in SEQ ID No: 16.

3)-5 Determination of Nucleotide Sequence of cDNA Encoding Variable Region of rLA1264

The sequence was determined in the same manner as in Example 3)-1.

The determined nucleotide sequence of cDNA encoding the heavy chain variable region of rLA1264 is shown in SEQ ID No: 17, and the amino acid sequence thereof is shown in SEQ ID No: 18. The nucleotide sequence of cDNA encoding the light chain variable region thereof is shown in SEQ ID No: 19, and the amino acid sequence thereof is shown in SEQ ID No: 20.

Example 4. Development of Human Chimeric Anti-Human LAG-3 Antibody (cLA212)

4)-1 Construction of Chimeric and Humanized Antibody Light Chain Expression Vector pCMA-LK A plasmid pcDNA3.3-TOPO/LacZ (Invitrogen Corp.) was digested with restriction enzymes XbaI and PmeI. The obtained fragment of approximately 5.4 kb was ligated with a DNA fragment comprising a DNA sequence shown in SEQ ID No: 21 and encoding a human light chain secretory signal and a human κ chain constant region using an In-Fusion Advantage PCR cloning kit (Clontech Laboratories, Inc.) to prepare pcDNA3.3/LK.

PCR was performed with pcDNA3.3/LK as a template using the primer set shown below. The obtained fragment of approximately 3.8 kb was phosphorylated and then self-ligated to construct a chimeric and humanized antibody light chain expression vector pCMA-LK having a signal sequence, a cloning site, and a human light chain constant region, downstream of the CMV promoter.

Primer Set

```
5'-TATACCGTCGACCTCTAGCTAGAGCTTGGC-3'
(3.3-F1: SEQ ID NO: 73)

5'-GCTATGGCAGGGCCTGCCGCCCCGACGTTG-3'
(3.3-R1: SEQ ID NO: 74)
```

4)-2 Construction of chimeric and humanized antibody IgG1 Type Heavy Chain Expression Vector pCMA-G1

The obtained DNA fragment from which the light chain secretory signal and the human K chain constant region were removed by digesting pCMA-LK with XbaI and PmeI was bound to a DNA fragment comprising the DNA sequence shown in SEQ ID No: 22 and encoding the amino acids of a human heavy chain signal sequence and a human IgG1 constant region using an In-Fusion Advantage PCR cloning kit (Clontech Laboratories, Inc.) to construct a chimeric and humanized antibody IgG1 type heavy chain expression vector pCMA-G1 having a signal sequence, a cloning site, and a human IgG1 heavy chain constant region, downstream of the CMV promoter.

4)-3 Construction of cLA212 Heavy Chain Expression Vector

A DNA fragment comprising a heavy chain variable region-encoding cDNA was amplified with KOD-Plus— (Toyobo Co., Ltd.) and the primer set shown below, using the cDNA obtained in Example 3)-2 and comprising the heavy chain variable region of rLA212 as a template, and the amplified DNA fragment was inserted into the restriction enzyme BlpI-cleaved site of the chimeric and humanized IgG1 type heavy chain expression vector pCMA-G1 using an In-Fusion HD cloning kit (Clontech Laboratories, Inc.) to construct a cLA212 heavy chain expression vector. The obtained expression vector was designated as "pCMA-G1/cLA212". The nucleotide sequence of the cLA212 heavy chain is shown in SEQ ID No: 23, and the amino acid sequence thereof is shown in SEQ ID No: 24.

Primer Set for cLA212 Heavy Chain

```
5'-CCAGATGGGTGCTGAGCGAGGTGCAGCTGGTGGAGTCTGGGGGAG
G-3' (212H-F; SEQ ID No: 75)

5'-CTTGGTGGAGGCTGAGCTGACTGTGACCATGACTCCTTGGCCCCA
G-3' (212H-R; SEQ ID No: 76)
```

4)-4 Construction of cLA212 μLight Chain Expression Vector

A DNA fragment comprising a light chain variable region-encoding cDNA was amplified with KOD-Plus— (Toyobo Co., Ltd.) and the primer set shown below, using the cDNA obtained in Example 3)-2 and comprising the light chain variable region of rLA212 as a template, and the amplified DNA fragment was inserted into the restriction enzyme BsiWI-cleaved site of the chimeric and humanized light chain expression general vector pCMA-LK using an In-Fusion HD PCR cloning kit (Clontech Laboratories, Inc.) to construct a cLA212 μlight chain expression vector. The obtained expression vector was designated as "pCMA-LK/cLA212". The nucleotide sequence of the cLA212 light chain is shown in SEQ ID No: 25, and the amino acid sequence thereof is shown in SEQ ID No: 26.

Primer Set for cLA212 μLight Chain.

```
5'-ATCTCCGGCGCGTACGGCAACATTGTGATGACCCAGTCTCCCAAATC
C-3' (212L-F; SEQ ID No: 77)

5'-GGAGGGGGCGGCCACAGCCCGTTTCAGTTCCAGCTCGGTCCCAGC-3'
(212L-R; SEQ ID No: 78)
```

4)-5 Production of cLA212

FreeStyle 293F cells (Invitrogen Corp.) were subcultured and cultured according to the manual. $1.2 \times 10^9$ FreeStyle 293F cells (Invitrogen Corp.) in the logarithmic growth phase were inoculated into a 3-L Fernbach Erlenmeyer Flask (Corning Inc.), adjusted to $2.0 \times 10^6$ cells/ml by dilution with FreeStyle 293 expression medium (Invitrogen Corp.), and then shake-cultured at 90 rpm at 37° C. for 1 hour in an 8% $CO_2$ incubator. 1.8 mg of polyethyleneimine (Polysciences #24765) was dissolved in 20 ml of Opti-Pro SFM medium (Invitrogen Corp.). Next, each H chain expression vector (0.24 mg) and each L chain expression vector (0.36 mg) prepared using NucleoBond Xtra (Takara Bio Inc.) were added to 20 ml of Opti-Pro SFM medium (Invitrogen Corp.). 20 ml of the expression vector/Opti-Pro SFM mixed solution was added to 20 ml of the polyethyleneimine/Opti-Pro SFM mixed solution, and the mixture was gently stirred, left for 5 minutes, and then added to the FreeStyle 293F cells. The cells were shake-cultured at 90 rpm at 37° C. for 4 hours in an 8% $CO_2$ incubator. Then, 600 ml of EX-CELL VPRO medium (SAFC Biosciences), 18 ml of GlutaMAX I (GIBCO/Thermo Fisher Scientific Inc.), and 30 ml of Yeastolate Ultrafiltrate (GIBCO/Thermo Fisher Scientific Inc.) were added thereto. The cells were shake-cultured at 90 rpm at 37° C. for 7 days in an 8% $CO_2$ incubator, and the obtained culture supernatant was filtered through a Disposable Capsule Filter (Advantec #CCS-045-E1H).

The rLA212 human chimeric antibody obtained by the combination of pCMA-G1/cLA212 and pCMA-LK/cLA212 was designated as "cLA212".

4)-6 Purification of cLA212

The antibody was purified from the culture supernatant obtained in Example 4)-5 by rProtein A affinity chromatography (at 4 to 6° C.). The buffer replacement step after the rProtein A affinity chromatographic purification was carried out at 4 to 6° C. First, the culture supernatant was applied to a column filled with MabSelectSuRe (manufactured by GE Healthcare) equilibrated with PBS. After entry of the whole culture solution into the column, the column was washed with PBS in an amount of at least twice the column volume. Next, antibody-containing fractions were collected by elution with a 2 M arginine hydrochloride solution (pH 4.0). The fractions were buffer-replaced with HBSor (25 mM histidine and 5% sorbitol, pH 6.0) by dialysis (Thermo Fisher Scientific Inc., Slide-A-Lyzer Dialysis Cassette). Finally, the fractions were concentrated and adjusted to an IgG concentration of 25 mg/ml or higher using a Centrifugal UF Filter Device VIVASPIN 20 (molecular weight cutoff: UF10K, Sartorius AG, at 4° C.), and used as a purified sample. Finally, filtration with a Minisart-Plus filter (Sartorius AG) was performed to give a purified sample.

4)-7 Antigen Binding Activity of Human Chimeric Anti-LAG-3 Antibody (cLA212)

Figure 6:
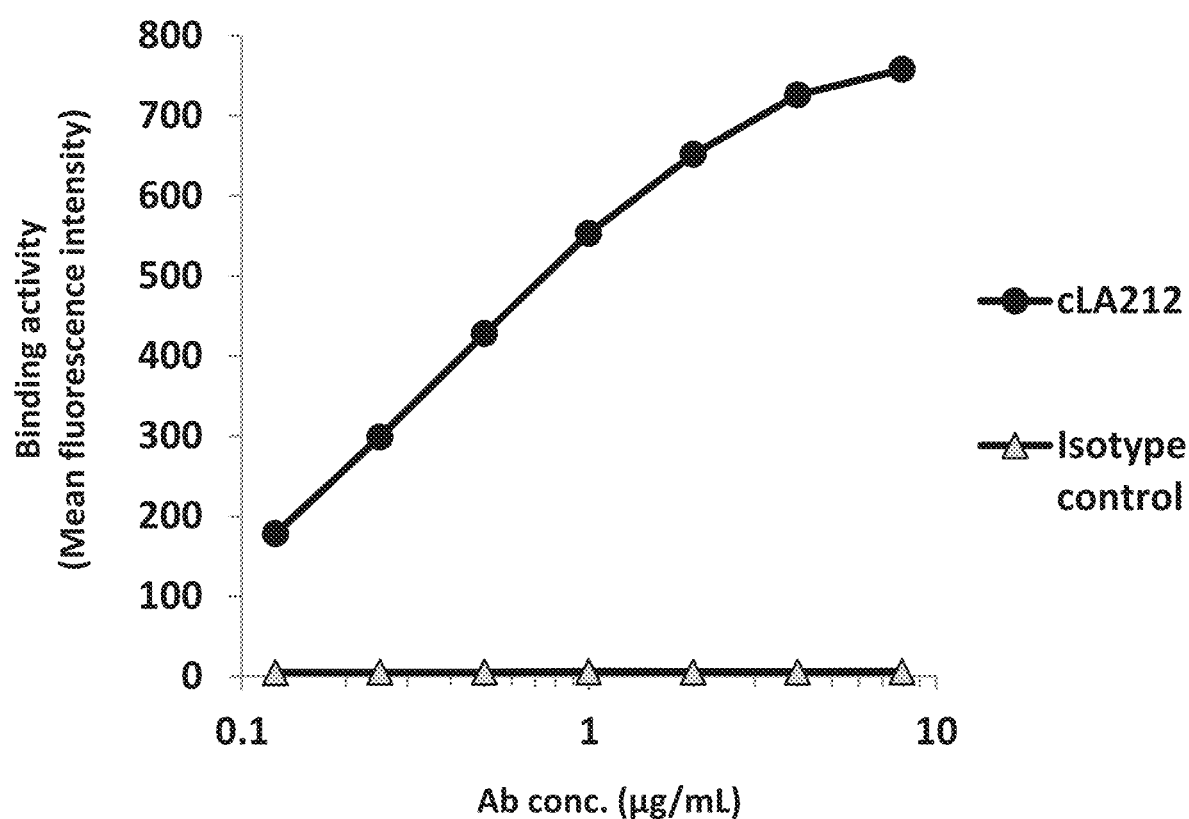
FIG. 6 is a diagram showing the results of testing the binding activity of the human chimeric anti-LAG-3 antibody cLA212 to 293T-lacZ cells expressing human LAG-3 by flow cytometry. The vertical axis represents the mean fluorescence intensity measured by flow cytometry.

The expression plasmid pcDNA3.1-hLAG-3 of human LAG-3 was introduced into the 293T-lacZ cells (described in Example 1)-5-1), using Lipofectamine 2000 (manufactured by Invitrogen Corp.), and the cells were cultured for 1 day and thereafter used for flow cytometry. The flow cytometry was performed according to the method described in Example 1)-4, except that an Anti-Human IgG PE conjugate (manufactured by Jackson ImmunoResearch Laboratories, Inc.) diluted 200-fold with a FACS buffer was used as the secondary antibody. As shown in FIG. 6, it was revealed that the human chimeric anti-LAG-3 antibody cLA212 bound to the 293T-lacZ cells expressing human LAG-3 in a concentration-dependent manner and thus also maintained binding activity after chimerization.

Example 5. Design of Humanized Version (hLA212) of Rat Anti-Human LAG-3 Antibody (rLA212)

5-1 Design of Humanized Rat Anti-Human LAG-3 Antibody rLA212

5)-1-1 Molecular Modeling of rLA212 Variable Regions

The molecular modeling of the rLA212 variable regions was carried out by a method known as homology modeling (Methods in Enzymology, 203, 121-153, (1991)). The variable regions of rLA212 determined in Example 3)-2 were compared with the primary sequences (three-dimensional structures derived from X-ray crystal structures are available) of human immunoglobulin variable regions registered in Protein Data Bank (Nuc. Acid Res. 35, D301-D303 (2007)). As a result, 2GHW and 2ARJ were selected as having the highest sequence homology to the heavy and light chain variable regions of rLA212. The three-dimensional structures of the framework regions were developed by obtaining "framework models" by combining the coordinates of 2GHW and 2ARJ corresponding to the heavy chain and the light chain of rLA212. Subsequently, the typical conformations of CDRs were incorporated into the framework models. Finally, an energy calculation for excluding disadvantageous interatomic contact was conducted in order to obtain possible molecular models of the rLA212 variable regions in terms of energy. These procedures were performed using the commercially available protein three-dimensional structural analysis program Discovery Studio (manufactured by Accelrys, Inc).

5)-1-2 Design of Amino Acid Sequences of Humanized Anti-Human LAG-3 Antibody hLA212

The humanized anti-human LAG-3 antibody hLA212 was constructed by a method generally known as CDR grafting (Proc. Natl. Acad. Sci. USA 86, 10029-10033 (1989)). An acceptor antibody was selected on the basis of the identity of amino acids in the framework regions.

The sequences of the framework regions of rLA212 were compared with the framework regions of the consensus sequences of human sub-groups and Germline sequences defined in KABAT et al. (Sequences of Proteins of Immunological Interest, 5th Ed. Public Health Service National Institutes of Health, Bethesda, MD. (1991)). As a result, the consensus sequence of the human gamma chain sub-group 3 for the heavy chain and the consensus sequence of the human kappa chain sub-group 1 for the light chain were selected respectively as acceptors because of having high sequence identity in the framework regions. The amino acid residues in the framework regions for the acceptors were aligned with the amino acid residues for rLA212 to identify the positions where different amino acids were used. The positions of these residues were analyzed using the three-dimensional model of rLA212 constructed in Example 5)-1-1. Then, the donor residues to be grafted onto the acceptors were selected according to the criteria provided by Queen et al. (Proc. Natl. Acad. Sci. USA 86, 10029-10033 (1989)). Some donor residues thus selected were transferred to the acceptor antibodies to construct the humanized hLA212 sequences as described in the Examples below.

5)-2 Humanization of rLA212 Heavy Chain

5)-2-1 Humanized hLA212_H2 Type Heavy Chain

A humanized hLA212 heavy chain designed by the replacement of arginine at amino acid position 16 with glycine, lysine at amino acid position 19 with arginine, threonine at amino acid position 42 with glycine, arginine at amino acid position 43 with lysine, alanine at amino acid position 49 with glycine, aspartic acid at amino acid position 84 with asparagine, serine at amino acid position 88 with alanine, threonine at amino acid position 93 with valine, valine at amino acid position 115 with threonine, and methionine at amino acid position 116 with leucine, in the heavy chain variable region of the chimeric cLA212 shown in SEQ ID No: 24 was designated as "humanized hLA212_H2 type heavy chain" (which may be referred to also as "hLA212_H2").

The amino acid sequence of the humanized hLA212_H2 type heavy chain is described in SEQ ID No: 28 of the Sequence Listing. In the amino acid sequence of SEQ ID No: 28, the sequence consisting of amino acid residues 1 to 19, the sequence consisting of amino acid residues 20 to 140, and the sequence consisting of amino acid residues 141 to 470 respectively correspond to the signal sequence, the heavy chain variable region, and the heavy chain constant region. The nucleotide sequence encoding the amino acid sequence of SEQ ID No: 28 is described in SEQ ID No: 27 of the Sequence Listing. In the nucleotide sequence of SEQ ID No: 27, the sequence consisting of nucleotides 1 to 57, the sequence consisting of nucleotides 58 to 420, and the sequence consisting of nucleotides 421 to 1410 respectively encode the signal sequence, the heavy chain variable region sequence, and the heavy chain constant region sequence. The nucleotide sequence of SEQ ID No: 27 and the amino acid sequence of SEQ ID No: 28 are also respectively described in FIGS. 42 and 43.

5)-2-2 Humanized hLA212_H3 Type Heavy Chain

A humanized hLA212 heavy chain designed by the replacement of arginine at amino acid position 16 with glycine, lysine at amino acid position 19 with arginine, threonine at amino acid position 42 with glycine, arginine at amino acid position 43 with lysine, serine at amino acid position 88 with alanine, threonine at amino acid position 93 with valine, valine at amino acid position 115 with threonine, and methionine at amino acid position 116 with leucine, in the heavy chain variable region of the chimeric cLA212 shown in SEQ ID No: 24 was designated as "humanized hLA212_H3 type heavy chain" (which may be referred to also as "hLA212_H3").

The amino acid sequence of the humanized hLA212_H3 type heavy chain is described in SEQ ID No: 30 of the Sequence Listing. In the amino acid sequence of SEQ ID No: 30, the sequence consisting of amino acid residues 1 to 19, the sequence consisting of amino acid residues 20 to 140, and the sequence consisting of amino acid residues 141 to 470 respectively correspond to the signal sequence, the heavy chain variable region, and the heavy chain constant region. The nucleotide sequence encoding the amino acid sequence of SEQ ID No: 30 is described in SEQ ID No: 29 of the Sequence Listing. In the nucleotide sequence of SEQ ID No: 29, the sequence consisting of nucleotides 1 to 57, the sequence consisting of nucleotides 58 to 420, and the sequence consisting of nucleotides 421 to 1410 respectively encode the signal sequence, the heavy chain variable region sequence, and the heavy chain constant region sequence. The nucleotide sequence of SEQ ID No: 29 and the amino acid sequence of SEQ ID No: 30 are also respectively described in FIGS. 44 and 45.

5)-3 Humanization of rLA212 μLight Chain

5)-3-1 Humanized hLA212_L1 Type Light Chain

A humanized hLA212 μlight chain designed by the replacement of asparagine at amino acid position 1 with aspartic acid, valine at amino acid position 3 with glutamine, lysine at amino acid position 9 with serine, methionine at amino acid position 11 with leucine, isoleucine at amino acid position 13 with alanine, methionine at amino acid position 21 with isoleucine, asparagine at amino acid position 22 with threonine, lysine at amino acid position 38 with glutamine, serine at amino acid position 43 with alanine, aspartic acid at amino acid position 60 with serine, threonine at amino acid position 63 with serine, glycine at amino acid position 65 with serine, tyrosine at amino acid position 67 with serine, asparagine at amino acid position 76 with serine, valine at amino acid position 78 with leucine, alanine at amino acid position 80 with proline, alanine at amino acid position 83 with phenylalanine, phenylalanine at amino acid position 85 with threonine, alanine at amino acid position 100 with glutamine, glutamic acid at amino acid position 103 with lysine, leucine at amino acid position 104 with valine, leucine at amino acid position 106 with isoleucine, and alanine at amino acid position 109 with threonine, in the light chain variable region of the chimeric cLA212 shown in SEQ ID No: 26 was designated as "humanized hLA212_L1 type light chain" (which may be referred to also as "hLA212_L1").

The amino acid sequence of the humanized hLA212_L1 type light chain is described in SEQ ID No: 32 of the Sequence Listing. In the amino acid sequence of SEQ ID No: 32, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 32 is described in SEQ ID No: 31 of the Sequence Listing. In the nucleotide sequence of SEQ ID No: 31, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 31 and the amino acid sequence of SEQ ID No: 32 are also respectively described in FIGS. 46 and 47.

5)-3-2 Humanized hLA212_L2 Type Light Chain

A humanized hLA212 μlight chain designed by the replacement of asparagine at amino acid position 1 with aspartic acid, valine at amino acid position 3 with glutamine, lysine at amino acid position 9 with serine, methionine at amino acid position 11 with leucine, isoleucine at amino acid position 13 with alanine, methionine at amino acid position 21 with isoleucine, asparagine at amino acid position 22 with threonine, lysine at amino acid position 38 with glutamine, aspartic acid at amino acid position 60 with serine, threonine at amino acid position 63 with serine, glycine at amino acid position 65 with serine, asparagine at amino acid position 76 with serine, valine at amino acid position 78 with leucine, alanine at amino acid position 80 with proline, alanine at amino acid position 83 with phenylalanine, phenylalanine at amino acid position 85 with threonine, alanine at amino acid position 100 with glutamine, glutamic acid at amino acid position 103 with lysine, leucine at amino acid position 104 with valine, leucine at amino acid position 106 with isoleucine, and alanine at amino acid position 109 with threonine, in the light chain variable region of the chimeric cLA212 shown in SEQ ID No: 26 was designated as "humanized hLA212_L2 type light chain" (which may be referred to also as "hLA212_L2").

The amino acid sequence of the humanized hLA212_L2 type light chain is described in SEQ ID No: 34 of the Sequence Listing. In the amino acid sequence of SEQ ID No: 34, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 34 is described in SEQ ID No: 33 of the Sequence Listing. In the nucleotide sequence of SEQ ID No: 33, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 33 and the amino acid sequence of SEQ ID No: 34 are also respectively described in FIGS. 48 and 49.

5)-3-3 Humanized hLA212_L3 Type Light Chain

A humanized hLA212 μlight chain designed by the replacement of valine at amino acid position 3 with glutamine, lysine at amino acid position 9 with serine, methionine at amino acid position 11 with leucine, isoleucine at amino acid position 13 with alanine, methionine at amino acid position 21 with isoleucine, asparagine at amino acid position 22 with threonine, threonine at amino acid position 63 with serine, asparagine at amino acid position 76 with serine, valine at amino acid position 78 with leucine, alanine at amino acid position 80 with proline, alanine at amino acid position 83 with phenylalanine, alanine at amino acid position 100 with glutamine, glutamic acid at amino acid position 103 with lysine, leucine at amino acid position 104 with valine, leucine at amino acid position 106 with isoleucine, and alanine at amino acid position 109 with threonine, in the light chain variable region of the chimeric cLA212 shown in SEQ ID No: 26 was designated as "humanized hLA212_L3 type light chain" (which may also be referred to as "hLA212_L3").

The amino acid sequence of the humanized hLA212_L3 type light chain is described in SEQ ID No: 36 of the Sequence Listing. In the amino acid sequence of SEQ ID No: 36, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 36 is described in SEQ ID No: 35 of the Sequence Listing. In the nucleotide sequence of SEQ ID No: 35, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 35 and the amino acid sequence of SEQ ID No: 36 are respectively described also in FIGS. 50 and 51.

5)-3-4 Humanized hLA212_L4 type light chain A humanized hLA212 μlight chain designed by the replacement of asparagine at amino acid position 1 with aspartic acid, valine at amino acid position 3 with glutamine, lysine at amino acid position 9 with serine, asparagine at amino acid position 22 with threonine, aspartic acid at amino acid position 60 with serine, threonine at amino acid position 63 with serine, glycine at amino acid position 65 with serine, tyrosine at amino acid position 67 with serine, asparagine at amino acid position 76 with serine, alanine at amino acid position 80 with proline, alanine at amino acid position 83 with phenylalanine, phenylalanine at amino acid position 85 with threonine, alanine at amino acid position 100 with glutamine, glutamic acid at amino acid position 103 with lysine, and alanine at amino acid position 109 with threonine, in the light chain variable region of the chimeric cLA212 shown in SEQ ID No: 26 was designated as "humanized hLA212_L4 type light chain" (which may also be referred to as "hLA212_L4").

The amino acid sequence of the humanized hLA212_L4 type light chain is described in SEQ ID No: 38 of the Sequence Listing. In the amino acid sequence of SEQ ID No: 38, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 38 is described in SEQ ID No: 37 of the Sequence Listing. In the nucleotide sequence of SEQ ID No: 37, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 37 and the amino acid sequence of SEQ ID No: 38 are respectively described also in FIGS. 52 and 53.

5)-3-5 Humanized hLA212_L5 Type Light Chain

A humanized hLA212 μlight chain designed by the replacement of valine at amino acid position 3 with glutamine, lysine at amino acid position 9 with serine, asparagine at amino acid position 22 with threonine, threonine at amino acid position 63 with serine, asparagine at amino acid position 76 with serine, alanine at amino acid position 80 with proline, alanine at amino acid position 100 with glutamine, glutamic acid at amino acid position 103 with lysine, and alanine at amino acid position 109 with threonine, in the light chain variable region of the chimeric cLA212 shown in SEQ ID No: 26 was designated as "humanized hLA212_L5 type light chain" (which may also be referred to as "hLA212_L5").

The amino acid sequence of the humanized hLA212_L5 type light chain is described in SEQ ID No: 40 of the Sequence Listing. In the amino acid sequence of SEQ ID No: 40, the sequence consisting of amino acid residues 1 to 20, the sequence consisting of amino acid residues 21 to 129, and the sequence consisting of amino acid residues 130 to 234 respectively correspond to the signal sequence, the light chain variable region, and the light chain constant region. The nucleotide sequence encoding the amino acid sequence of SEQ ID No: 40 is described in SEQ ID No: 39 of the Sequence Listing. In the nucleotide sequence of SEQ ID No: 39, the sequence consisting of nucleotides 1 to 60, the sequence consisting of nucleotides 61 to 387, and the sequence consisting of nucleotides 388 to 702 respectively encode the signal sequence, the light chain variable region sequence, and the light chain constant region sequence. The nucleotide sequence of SEQ ID No: 39 and the amino acid sequence of SEQ ID No: 40 are respectively described also in FIGS. 54 and 55.

5)-4 Design of Humanized hLA212 by Combination of Heavy Chain and Light Chain

An antibody consisting of the humanized hLA212_H2 type heavy chain and the humanized hLA212_L1 type light chain was designed and designated as "humanized hLA212_H2/L1" (which may also be referred to as "hLA212_H2/L1"). An antibody consisting of the humanized hLA212_H2 type heavy chain and the humanized hLA212_L2 type light chain was designed and designated as "humanized hLA212_H2/L2" (which may also be referred to as "hLA212_H2/L2"). An antibody consisting of the humanized hLA212_H2 type heavy chain and the humanized hLA212_L3 type light chain was designed and designated as "humanized hLA212_H2/L3" (which may also be referred to as "hLA212_H2/L3"). An antibody consisting of the humanized hLA212_H2 type heavy chain and the humanized hLA212_L4 type light chain was designed and designated as "humanized hLA212_H2/L4" (which may also be referred to as "hLA212_H2/L4"). An antibody consisting of the humanized hLA212_H2 type heavy chain and the humanized hLA212_L5 type light chain was designed and designated as "humanized hLA212_H2/L5" (which may also be referred to as "hLA212_H2/L5"). An antibody consisting of the humanized hLA212_H3 type heavy chain and the humanized hLA212_L1 type light chain was designed and designated as "humanized hLA212_H3/L1" (which may also be referred to as "hLA212_H3/L1"). An antibody consisting of the humanized hLA212_H3 type heavy chain and the humanized hLA212_L2 type light chain was designed and designated as "humanized hLA212_H3/L2" (which may also be referred to as "hLA212_H3/L2"). An antibody consisting of the humanized hLA212_H3 type heavy chain and the humanized hLA212_L3 type light chain was designed and designated as "humanized hLA212_H3/L3" (which may also be referred to as "hLA212_H3/L3"). An antibody consisting of the humanized hLA212_H3 type heavy chain and the humanized hLA212_L4 type light chain was designed and designated as "humanized hLA212_H3/L4" (which may also be referred to as "hLA212_H3/L4"). An antibody consisting of the humanized hLA212_H3 type heavy chain and the humanized hLA212_L5 type light chain was designed and designated as "humanized hLA212_H3/L5" (which may also be referred to as "hLA212_H3/L5"). The antibodies designed as above can be produced according to Example 6 and evaluated according to Example 7 and Example 8.

Example 6. Expression and Purification of Humanized Antibody (hLA212) of Human Chimeric Anti-LAG-3 Antibody cLA212

6)-1 Construction of hLA212 Heavy Chain Expression Vector

6)-1-1 Construction of hLA212_H2 Type Heavy Chain Expression Vector

A DNA fragment comprising the DNA sequence encoding the variable region of hLA212_H2 shown in nucleotide positions 36 to 437 of the nucleotide sequence of hLA212_H2 of SEQ ID No: 27 was synthesized (Strings DNA Fragments, Geneart AG). The synthesized DNA fragment was inserted into a site of the chimeric and humanized antibody IgG1 type heavy chain expression vector pCMA-G1 cleaved by restriction enzyme BlpI, using an In-Fusion HD PCR cloning kit (Clontech Laboratories, Inc.) to construct an hLA212_H2 expression vector. The obtained expression vector was designated as "pCMA/hLA212_H2".

6)-1-2 Construction of hLA212_H3 Type Heavy Chain Expression Vector

A DNA fragment comprising the DNA sequence encoding the variable region of hLA212_H3 shown in nucleotide positions 36 to 437 of the nucleotide sequence of hLA212_H3 of SEQ ID No: 29 was synthesized (Strings DNA Fragments, Geneart AG). In the same manner as in Example 6)-1-1, an hLA212_H3 expression vector was constructed. The obtained expression vector was designated as "pCMA/hLA212_H3".

6)-2 Construction of hLA212 μLight Chain Expression Vectors

6)-2-1 Construction of hLA212_L1 Type Light Chain Expression Vector

A DNA fragment comprising the DNA sequence encoding the variable region of hLA212_L1 shown in nucleotide positions 37 to 402 of the nucleotide sequence of hLA212_L1 of SEQ ID No: 31 was synthesized (Strings DNA Fragments, Geneart AG). The synthesized DNA fragment was inserted into a site of the chimeric and humanized antibody light chain expression vector pCMA-LK cleaved by restriction enzyme BsiWI, using an In-Fusion HD PCR cloning kit (Clontech Laboratories, Inc.) to construct an hLA212_L1 expression vector. The obtained expression vector was designated as "pCMA/hLA212_L1".

6)-2-2 Construction of hLA212_L2 Type Light Chain Expression Vector

A DNA fragment comprising the DNA sequence encoding the variable region of hLA212_L2 shown in nucleotide positions 37 to 402 of the nucleotide sequence of hLA212_L2 of SEQ ID No: 33 was synthesized (Strings DNA Fragments, Geneart AG). In the same manner as in Example 6)-2-1, an hLA212_L2 expression vector was constructed. The obtained expression vector was designated as "pCMA/hLA212_L2".

6)-2-3 Construction of hLA212_L3 Type Light Chain Expression Vector

A DNA fragment comprising the DNA sequence encoding the variable region of hLA212_L3 shown in nucleotide positions 37 to 402 of the nucleotide sequence of hLA212_L3 of SEQ ID No: 35 was synthesized (Strings DNA Fragments, Geneart AG). In the same manner as in Example 6)-2-1, an hLA212_L3 expression vector was constructed. The obtained expression vector was designated as "pCMA/hLA212_L3".

6)-2-4 Construction of hLA212_L4 Type Light Chain Expression Vector

A DNA fragment comprising the DNA sequence encoding the variable region of hLA212_L4 shown in nucleotide positions 37 to 402 in the nucleotide sequence of hLA212_L4 of SEQ ID No: 37 was synthesized (Strings DNA Fragments, Geneart AG). In the same manner as in Example 6)-2-1, an hLA212_L4 expression vector was constructed. The obtained expression vector was designated as "pCMA/hLA212_L4".

6)-2-5 Construction of hLA212_L5 Type Light Chain Expression Vector

A DNA fragment comprising the DNA sequence encoding the variable region of hLA212_L5 shown in nucleotide positions 37 to 402 in the nucleotide sequence of hLA212_L5 of SEQ ID No: 39 was synthesized (Strings DNA Fragments, Geneart AG). In the same manner as in Example 6)-2-1, an hLA212_L5 expression vector was constructed. The obtained expression vector was designated as "pCMA/hLA212_L5".

6)-3 Preparation of hLA212 Antibodies

6)-3-1 Production of hLA212 Antibodies

The production was carried out in the same manner as in Example 4)-5. That is, hLA212_H2/L1 was obtained by the combination of pCMA/hLA212_H2 and pCMA/hLA212_L1; hLA212_H2/L2 was obtained by the combination of pCMA/hLA212_H2 and pCMA/hLA212_L2; hLA212_H2/L3 was obtained by the combination of pCMA/hLA212_H2 and pCMA/hLA212_L3; hLA212_H2/L4 was obtained by the combination of pCMA/hLA212_H2 and pCMA/hLA212_L4; hLA212_H2/L5 was obtained by the combination of pCMA/hLA212_H2 and pCMA/hLA212_L5; hLA212_H3/L1 was obtained by the combination of pCMA/hLA212_H3 and pCMA/hLA212_L1; hLA212_H3/L2 was obtained by the combination of pCMA/hLA212_H3 and pCMA/hLA212_L2; hLA212_H3/L3 was obtained by the combination of pCMA/hLA212_H3 and pCMA/hLA212_L3; hLA212_H3/L4 was obtained by the combination of pCMA/hLA212_H3 and pCMA/hLA212_L4; and hLA212_H3/L5 was obtained by the combination of pCMA/hLA212_H3 and pCMA/hLA212_L5.

6)-3-2 Purification of hLA212 Antibody

The culture supernatant obtained in 6)-3-1 was subjected to purification in the same manner as in Example 4)-6.

Example 7. In Vitro Evaluation of Humanized Anti-Human LAG-3 Antibody (hLA212)

7)-1 Antigen Binding Activity Assay of Humanized Anti-Human LAG-3 Antibody (hLA212) Using Biacore FreeStyle 293F cells (Invitrogen Corp.) were used to express the C-terminally His-tagged protein, LAG-3_D3D4-His, comprising the 3rd and 4th (a region of positions 263-450) domains from the N terminus out of the four extracellular immunoglobulin-like domains of human LAG-3. The obtained culture supernatant was subjected to buffer replacement (20 mM HEPES, 300 mM NaCl, and pH 7.5), to purify the human LAG-3_D3D4-His protein using a HisTrap HP column (GE Healthcare) and a Superdex75 column (GE Healthcare). The final buffer was PBS.

The antibody was assayed for its dissociation constant for the antigen (LAG-3_D3D4-His) using Biacore T200 (GE Healthcare) by the capture method, which involves capturing the antibody as a ligand with an immobilized anti-human IgG(Fc) antibody (Human Antibody Capture kit, GE Healthcare) and assaying with the antigen as an analyte. The anti-human IgG(Fc) antibody was covalently bound to a CM5 sensor chip (GE Healthcare) by amine coupling, targeting approximately 1000 RU. Similarly, this antibody was immobilized onto a reference cell. The running buffer used was HBS-EP+ (10 mM HEPES (pH 7.4), 0.15 M NaCl, 3 mM EDTA, and 0.05% Surfactant P20). After each antibody was added for about 1 minute onto the anti-human IgG(Fc) antibody-immobilized chip, serial dilutions (0.06 to 20 nM) of the antigen were added thereto at a flow rate of 90 μl/minute for 300 seconds, and subsequently the dissociation phase was monitored for 3600 seconds. A 3M magnesium chloride solution was added thereto as a regenerating solution at a flow rate of 10 μl/minute for 30 seconds. The data was analyzed using a 1:1 binding model in analytical software (Biacore T200 Evaluation Software, version 1.0) to calculate an association rate constant ka, a dissociation rate constant kd, and a dissociation constant (KD; KD=kd/ka). FIG. 7 shows the dissociation constant.

Figure 8:
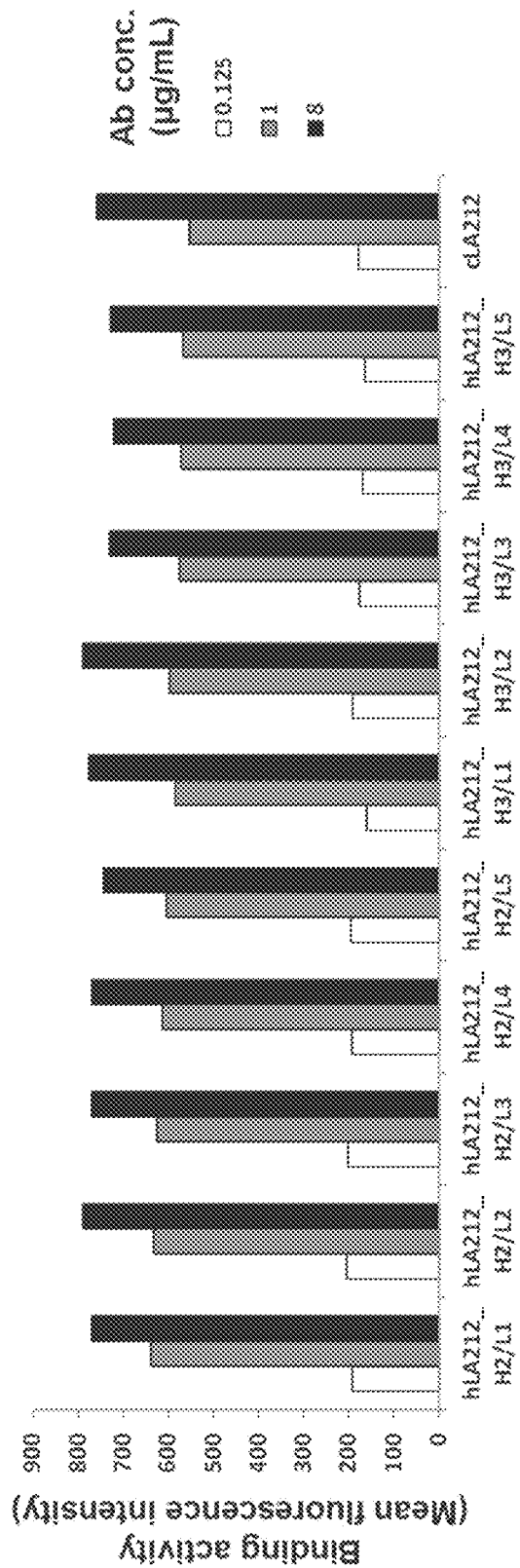
FIG. 8 is a diagram showing the results of testing the binding activity of 10 types of humanized anti-LAG-3 antibodies and the human chimeric anti-LAG-3 antibody cLA212 to 293T-lacZ cells expressing human LAG-3 by flow cytometry. The vertical axis represents the mean fluorescence intensity measured by flow cytometry.

7)-2 Investigation of Binding Activity of Humanized Anti-Human LAG-3 Antibody (hLA212) to Cells Expressing Human LAG-3 by Flow Cytometry The human LAG-3-expression plasmid pcDNA3.1/hLAG-3 was introduced into the 293T-lacZ cells (described in Example 1)-5-1), using Lipofectamine 2000 (manufactured by Invitrogen Corp.), and the cells were cultured for 1 day and thereafter used for flow cytometry. The flow cytometry was performed according to the method described in Example 1)-4, but an Anti-Human IgG PE conjugate (manufactured by Jackson ImmunoResearch Laboratories, Inc.) diluted 200-fold with a FACS buffer was used as the secondary antibody. As shown in FIG. 8, it was revealed that all 10 clones of the humanized anti-human LAG-3 antibodies (hLA212_H2/L1, hLA212_H2/L2, hLA212_H2/L3, hLA212_H2/L4, hLA212_H2/L5, hLA212_H3/L1, hLA212_H3/L2, hLA212_H3/L3, hLA212_H3/L4, and hLA212_H3/L5) exhibited concentration-dependent binding activity to the 293T-lacZ cells expressing human LAG-3, comparable to the human chimeric anti-LAG-3 antibody cLA212, and so maintained the binding activity even after humanization.

7)-3 ADCC Activity of Humanized Anti-Human LAG-3 Antibody (hLA212)

Figure 9:
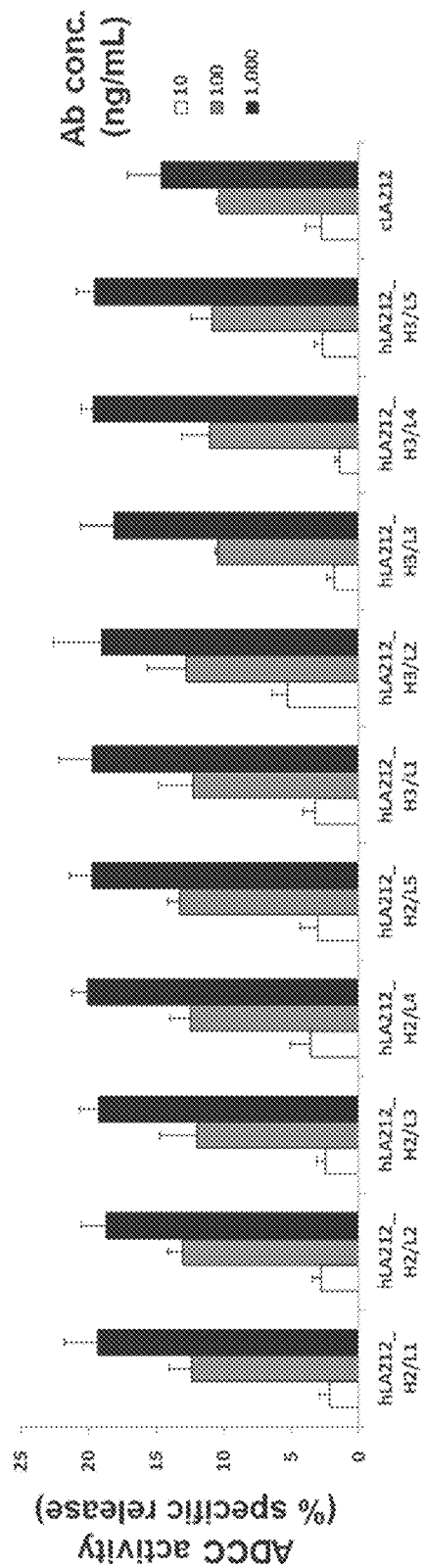
FIG. 9 is a diagram showing the ADCC activity of 10 types of humanized anti-LAG-3 antibodies and the human chimeric anti-LAG-3 antibody cLA212. 293T-lacZ cells expressing human LAG-3 were used as target cells, and human PBMCs were used as effector cells.

The ADCC activity of the humanized anti-human LAG-3 antibodies (hLA212) was investigated by the method described in Example 2)-2. As shown in FIG. 9, the results revealed that all 10 clones of the humanized anti-human LAG-3 antibodies (hLA212_H2/L1, hLA212_H2/L2, hLA212_H2/L3, hLA212_H2/L4, hLA212_H2/L5, hLA212_H3/L1, hLA212_H3/L2, hLA212_H3/L3, hLA212_H3/L4, and hLA212_H3/L5) exhibited concentration-dependent ADCC activity against the 293T-lacZ cells expressing human LAG-3, almost comparable to the human chimeric anti-LAG-3 antibody cLA212 and so maintained the ADCC activity even after humanization.

7)-4 Investigation of Influence of Humanized Anti-Human LAG-3 Antibody hLA212_H3/L2 on T Cell Suppression Function of LAG-3

It is known that LAG-3 binds to MHC class II molecules, thereby transmitting some inhibitory signals to T cells to regulate the T cell function negatively (Non Patent Literature 1). For binding of LAG-3 to MHC class II molecules, the N-terminal domains 1 and 2 of the four extracellular immunoglobulin-like domains of LAG-3 are considered to be important (Non Patent Literature 4). It was revealed in Example 2 that all 5 clones of the rat anti-human LAG-3 antibodies (rLA204, rLA212, rLA225, rLA869, and rLA1264) obtained by the method of Example 1 recognized domain 3 and exhibited no inhibitory activity in the LAG-3/MHC class II binding test and the 293T-hLAG-3/Raji cell adhesion test, whereas the human chimeric anti-human LAG-3 antibody IMP731 that is a conventional antibody in the Citation List recognized domain 1 and exhibited a powerful inhibitory activity in the LAG-3/MHC class II binding test and the 293T-hLAG-3/Raji cell adhesion test.

Figure 10:
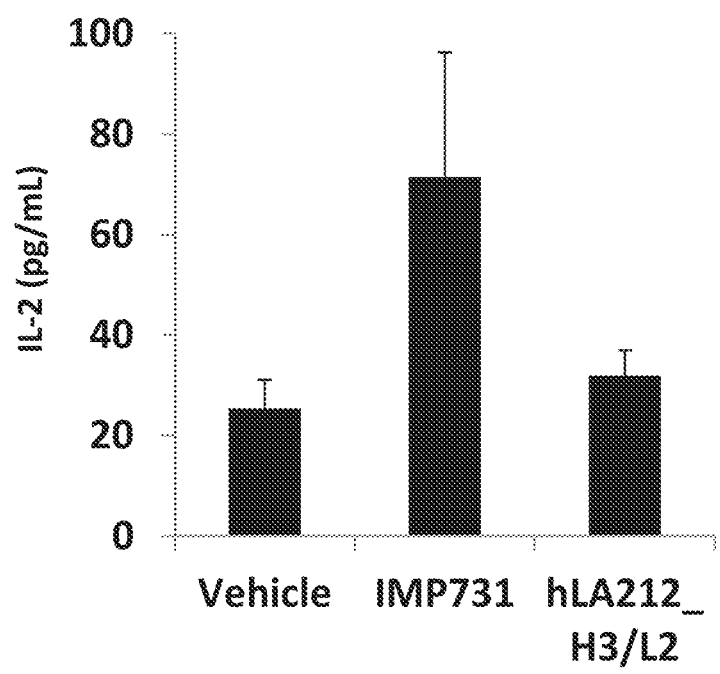
FIG. 10 is a diagram investigating the influence of the humanized anti-LAG-3 antibody hLA212_H3/L2 and the human chimeric anti-LAG-3 antibody IMP731 on the T cell suppression function of LAG-3. IL-2 production in culture supernatants was measured when human PBMCs were stimulated with SEB for 4 days in the presence of each antibody. Each antibody was evaluated at 10 µg/mL.

From these results, it was assumed that the clones obtained by the method of Example 1 and the humanized anti-human LAG-3 antibodies derived therefrom have no influence on the T cell suppression function inherent to LAG-3, whereas IMP731 inhibits it. In order to confirm this experimentally, the influence of the humanized anti-human LAG-3 antibody hLA212_H3/L2 on the T cell suppression function of LAG-3 was investigated according to a previous report (Non Patent Literature 9). PBMCs separated from the human peripheral blood by Ficoll centrifugation were disseminated in a 96-well microplate in an amount of $2 \times 10^5$ cells/well, and the antibody was added thereto, followed by pre-incubation at 37° C. for 30 minutes. The IL-2 concentration in the culture supernatant when SEB (Staphylococcal Enterotoxin B, manufactured by Sigma-Aldrich) was added thereto to a final concentration of 1 ng/mL, and the cells were cultured for 4 days was quantitated by a Human IL-2 Immunoassay kit (manufactured by PerkinElmer Inc). As a result, the developed humanized anti-human LAG-3 antibody hLA212_H3/L2 had almost no influence on IL-2 production, whereas IMP731 increased IL-2 production, as shown in FIG. 10. That is, as initially predicted, it was revealed that the developed humanized anti-human LAG-3 antibody hLA212_H3/L2 had no influence on the T cell suppression function of LAG-3, whereas IMP731 inhibited this, thereby risking adverse activation of the immune system.

Example 8. Preparation of Humanized Antibody in which its Sugar Chain Modification is Adjusted A humanized antibody comprising a heavy chain comprising amino acid positions 20 to 470 of the amino acid sequence represented by SEQ ID No: 30 (FIG. 45) and a light chain comprising amino acid positions 21 to 234 of the amino acid sequence represented by SEQ ID No: 34 (FIG. 49) was defucosylated according to a known method, to adjust the sugar chain modification binding to the antibody protein, and the obtained antibody was designated as hLA212_H4/L2. This modified form was subjected to mass spectrometry. As a result, the peak(s) derived from a fucose-containing H chain were equal to or lower than the detection limit. In the present invention, an antibody whose sugar chain modification is adjusted, such as hLA212_H4/L2, is also referred to as an "antibody" or a "modified form of the antibody".

Example 9. In Vitro Evaluation of Humanized Anti-Human LAG-3 Antibody hLA212_H4/L2

9)-1 Binding Activity of Humanized Anti-Human LAG-3 Antibody hLA212_H4/L2 to Cells Expressing LAG-3

Figure 11:
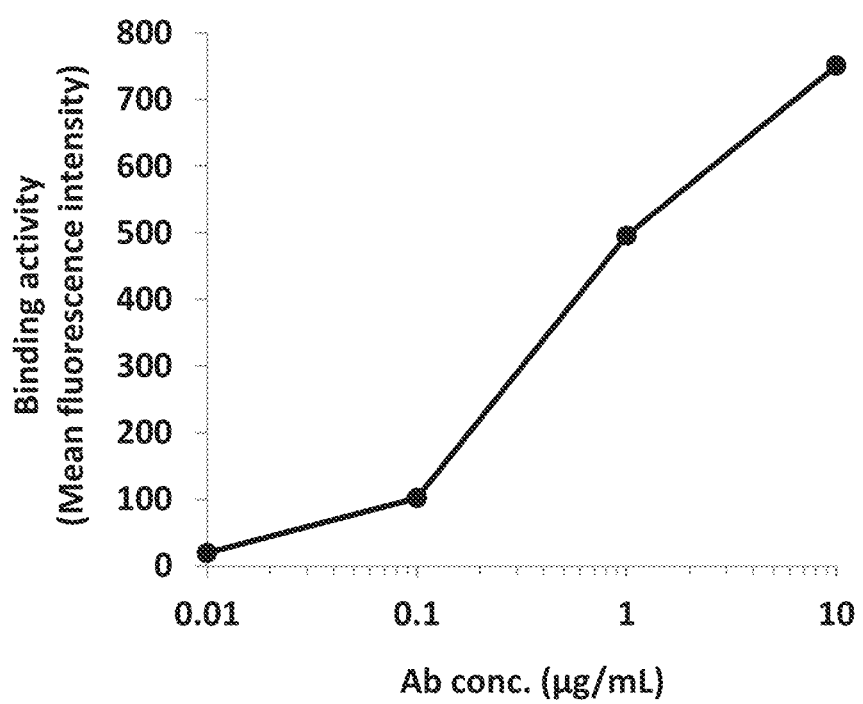
FIG. 11 is a diagram showing the results of testing the binding activity of the humanized anti-LAG-3 antibody hLA212_H4/L2 to 293T-lacZ cells expressing human LAG-3 by flow cytometry. The vertical axis represents the mean fluorescence intensity measured by flow cytometry.

The binding of the humanized anti-human LAG-3 antibody hLA212_H4/L2 to human LAG-3-expressing 293T-lacZ cells was investigated by flow cytometry according to the method described in Example 7)-2. As a result, concentration-dependent binding of hLA212_H4/L2 was observed, as shown in FIG. 11.

9)-2 In Vitro ADCC Activity of Humanized Anti-Human LAG-3 Antibody hLA212_H4/L2

Figure 12:
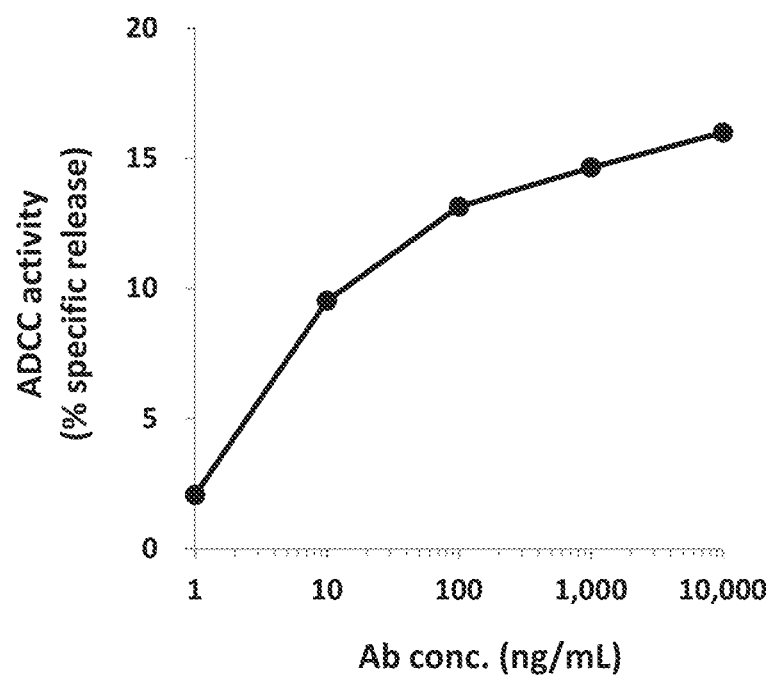
FIG. 12 is a diagram showing the ADCC activity of the humanized anti-LAG-3 antibody hLA212_H4/L2. 293T-lacZ cells expressing human LAG-3 were used as target cells, and human PBMCs were used as effector cells.

The in vitro ADCC activity of the humanized anti-human LAG-3 antibody hLA212_H4/L2 was evaluated by the method described in Example 7)-2. As a result, hLA212_H4/L2 exhibited a concentration-dependent ADCC activity against the 293T-lacZ cells expressing human LAG-3, as shown in FIG. 12. In contrast, it exhibited no ADCC activity on 293T-lacZ cells not expressing human LAG-3.

Example 10. Development of Human LAG-3/Human FcγRIIIA Double Transgenic Mice

It has been revealed that the humanized anti-human LAG-3 antibody hLA212_H4/L2 binds to human LAG-3, as shown in Example 9, but does not cross-react with LAG-3 of rodents. Therefore, to enable the in vivo evaluation of hLA212_H4/L2, BAC (Bacterial Artificial Chromosome) transgenic mice allowed to express human LAG-3 physiologically using the expression regulation mechanism of mouse LAG-3 were developed. Further, human FcγIIIA is necessary for ADCC activity to be enhanced by adjusting the sugar chain modification as in hLA212_H4/L2 (Junttila, T. T., et al., Cancer Res., Vol. 70 (No. 11): pp 4481-9(2010)), and thus BAC comprising the human FcγRIIIA gene was additionally introduced according to a previous report (Non Patent Literature 10).

10)-1 Construction of Recombinant BAC Expression Vector Using Red/ET Reaction

A recombinant BAC clone of human LAG-3 RecBAC was constructed using Red/ET Recombination Technology (Zhang Y et al, A new logic for DNA engineering using recombination in *E. Coli.*, Nature 20 (1998) 123-128), which is an active homologous recombination reaction in *Escherichia coli*.

BAC genome clones, RP11-101F21, and RP23-3001 each comprising a human LAG-3 or a mouse LAG-3 gene locus were obtained. As shown in the list below, the sequence of intron 5 of the human LAG-3 gene, the sequences at both ends of the genomic DNA sequence from the translation start codon to the stop codon of the human LAG-3 gene, and the 3' end and the 5' end of the genomic DNA sequence from the translation start codon to the stop codon of the LAG-3 gene of the mouse BAC clone were used as key sequences for the active homologous recombination reaction in *Escherichia coli*.

```
LAG-3-H1: Sequence near the start codon of the
human LAG-3 gene
                                    (SEQ ID No: 79)
[5']ATGTGGGAGGCTCAGTTCCTGGGCTTGCTGTTTC[3']

LAG-3-H2: Sequence near the stop codon of the
human LAG-3 gene
                                    (SEQ ID No: 80)
[5']GCCCGAGCCCGAGCCCGAGCCGGAGCAGCTCTGA[3']

LAG-3-H3: Rpsl-kan insertion site, the 5' side
                                    (SEQ ID No: 81)
[5']GAGTATGTGTTGACTGGTTGATAACTATCG[3']

LAG-3-H4: Rpsl-kan insertion site, the 3' side
                                    (SEQ ID No: 82)
[5']GCCATGACAGATTAGCCATGTCTGCAGCAC [3']

LAG-3-H5: 5'UTR of the mouse LAG-3 gene
                                    (SEQ ID No: 83)
[5']CAGGACCTTTTTCTAACCTCCCTTGGAGGGCTGGGGAGGCCCGGGCC
ATAGAGGAG[3']
```

-continued

LAG-3-H6: 3'UTR of the mouse LAG-3 gene
(SEQ ID No: 84)
[5']CCTGGAGCCGAGGCAGCCAGCAGGTCTCAGCAGCTCCGCCCGCCCGC

CCGCCCGCC[3']

First, in order to insert a positive/negative selection marker cassette (Rpsl-kan) into intron 5 of the LAG-3 gene of the human BAC clone, DNA fragment(s) connecting the LAG-3-H3 sequence, Rpsl-kan, and the LAG-3-H4 sequence in tandem were constructed by PCR using LA-Taq (Takara Bio Inc.) (LAG-3 Rpsl-Kan break-in fragment). The LAG-3 gene locus-containing human BAC clone and the LAG-3 Rpsl-Kan break-in fragment were introduced into Escherichia coli strains having Red/ET reaction ability to induce Red/ET reaction in the host Escherichia coli, and colonies with chloramphenicol resistance and kanamycin resistance were selected, thereby screening for a recombinant BAC clone in which the LAG-3 Rpsl-kan break-in fragment was inserted into intron 5 of the LAG-3 gene locus (human LAG-3 Intermediate). Then, in order to sub-clone the genomic DNA sequence of the human LAG-3 gene with the Rpsl-kan cassette inserted therein into a plasmid vector from the human LAG-3 Intermediate, a DNA cassette connecting H2-H6-SacBpBluescript-H5-H1 in tandem was constructed (LAG-3 pre-transfer plasmid). In the same manner as above, a linearized LAG-3 pre-transfer plasmid was introduced into Escherichia coli strains having Red/ET reaction ability together with the human LAG-3 Intermediate to induce Red/ET reaction in the host Escherichia coli, and ampicillin and kanamycin resistant colonies were selected, thereby screening for a plasmid having the genomic DNA sequence of the human LAG-3 gene with the Rpsl-kan cassette inserted therein (human LAG-3 transfer plasmid).

Next, the genomic DNA sequence of the human LAG-3 gene having the H5 sequence and the H6 sequence derived from a mouse genome sequence at both ends with the Rpsl-kan cassette inserted therein was excised from the human LAG-3 transfer plasmid vector by a restriction enzyme reaction (human LAG-3 transfer fragment). In the same manner as above, the human LAG-3 transfer fragment(s) were introduced into Escherichia coli strains having Red/ET reaction ability, together with the mouse LAG-3 BAC clone, to induce Red/ET reaction in the host Escherichia coli, and chloramphenicol and kanamycin resistant colonies were selected, thereby screening for a mouse LAG-3/human LAG-3 gene recombinant BAC clone in which the genomic DNA sequence from the translation start codon to the stop codon of the mouse LAG-3 gene was accurately replaced with the genomic DNA sequence from the translation start codon to the stop codon of the human LAG-3 transfer fragments (mouse LAG-3/human LAG-3 RecBAC Intermediate).

Finally, the intron 5 sequence of the human LAG-3 gene locus was amplified by PCR and used as a DNA sequence for removing Rpsl-Kan inserted into intron 5 of the human LAG-3 gene by negative selection (human LAG-3 repair fragments). In the same manner as above, the human LAG-3 repair fragment(s) was(were) introduced into Escherichia coli strains having Red/ET reaction ability together with the mouse LAG-3/human LAG-3 RecBAC Intermediate to induce Red/ET reaction in the host Escherichia coli, and chloramphenicol and streptomycin resistant colonies were selected, thereby constructing a mouse LAG-3/human LAG-3 gene recombinant BAC clone in which the genomic DNA sequence from the translation start codon to the stop codon of the mouse LAG-3 gene was accurately replaced with the genomic DNA sequence of the human LAG-3 gene from the translation start codon to the stop codon (human LAG-3 RecBAC). The genomic DNA sequences with Hi to H6 connected by the Red/ET reaction were checked by sequence analysis.

10)-2 Purification of High-Purity BAC DNA Fragments

DH10B cells transformed by the recombinant BAC clone that is a construct for expressing the human LAG-3 RecBAC gene were grown on an LB agar medium containing chloramphenicol, and a single colony was selected and shake-cultured in a liquid medium all night and all day.

The human LAG-3 RecBAC recombinant BAC clone was purified using a plasmid extraction kit (MACHEREY-NAGEL GmbH & Co. KG, Nucleobond BAC100 kit) according to the method of Abe, et al., with partial modification (Exp Anim. 2004 53 (4): 311-20. Establishment of an efficient BAC transgenesis protocol and its application to functional characterization of the mouse Brachyury locus. Abe K, Hazama M, Katoh H, Yamamura K, Suzuki M), followed by addition of PI-SceI, thereby allowing reaction at 37° C. for 16 hours for digestion.

The linearized human LAG-3 RecBAC recombinant BAC clone was applied to a 1% SeaKem GTG agarose gel (Takara Bio Inc.), and electrophoresis was performed under conditions of 6 v/cm, 0.1 to 40 sec, 15 hr, and 14° C. using a pulsed field electrophoresis apparatus (CHEF DR-II, Bio-Rad Laboratories, Inc). By visualizing a part of the sample as a guide marker using a UV transilluminator, the linearized human LAG-3 RecBAC recombinant BAC clone separated in the agarose gel was excised with a razor without UV irradiation. The obtained long chain DNA fragment was extracted from the agarose gel by the electroelution method and was dialyzed with a TE buffer prepared for microinjection at 4° C. for 2 hours. The purified DNA fragment was applied to pulsed field electrophoresis to confirm that the long chain DNA fragment was highly purified without fragmentation and the DNA concentration thereof was determined using a NanoDrop spectrophotometer (AGC TECHNO GLASS CO., LTD). A solution of the DNA fragment was diluted to 0.5 ng/μl to prepare a solution of an expression construct for transgenic mouse creation.

10-3) C57BL/6J Mouse Embryonic Microinjection

PMSG and hCG were administered to female C57BL/6J mice to induce superovulation, followed by mating with male mice of the same strain, and then fertilized eggs were collected.

Using a micromanipulator, the purified human LAG-3 RecBAC/human FcγR BAC expression constructs were directly injected into the male nuclei of pronuclear stage embryos of C57BL/6J mice. The DNA injected embryos were transplanted into the fallopian tubes of pseudopregnancy-induced recipient female mice.

10-4) Southern Screening of Founders

Progenies obtained by spontaneous delivery from the C57BL/6J mouse fertilized eggs with the human LAG-3 RecBAC/human FcγR BAC expression constructs injected therein were nursed to weaning. Human LAG-3 RecBAC/human FcγR BAC transgenic mice founder candidate individuals, were weaned at 3-weeks' old and ear tagged for identification of the individuals. Thereafter, their tail tissues were biopsied and stored at −80° C. until analysis.

The tail tissues of the candidate individuals of the human LAG-3 RecBAC/human FcγR BAC transgenic mice that had been stored at −80° C. were melted at room temperature, and a lysis buffer containing 1% SDS (Wako Pure Chemical Industries, Ltd.), 1 mg/ml actinase E (KAKEN PHARMACEUTICAL CO., LTD.) and 0.15 mg/ml proteinase K (Merck KGaA) was added thereto, followed by shaking at 55° C. for 16 hours to solubilize the tissues. Proteins binding to the genomic DNA and solubilized from the tissues were removed by phenol extraction and phenol/chloroform extraction. The RNA mixed in with the genomic DNA was degraded with RNase A (Sigma-Aldrich), and thereafter a polymer genomic DNA was precipitated by isopropanol precipitation. The precipitated genomic DNA was washed with 70% ethanol, air-dried, and thereafter redissolved in 50 μl of TE.

The DNA concentration of the genomic DNA solution prepared from each specimen was determined by absorption spectroscopy, and the volume of the genomic DNA solution equivalent to 5 μg of DNA was calculated from the value of the DNA concentration of each specimen.

To the genomic DNA prepared from each specimen, the positive control DNA (the genomic DNA of the control mice to which the expression construct used for microinjection was added), and the negative control DNA (the genomic DNA of the control mice), was added a restriction enzyme, followed by reaction at 37° C. for 16 hours. The fragments of the genomic DNA produced were precipitated by isopropanol precipitation, washed with 70% ethanol, air-dried, and thereafter redissolved in TE. The genomic DNA fragments were applied to a 1.2% agarose gel for electrophoresis, and the genomic DNA fragments separated in the agarose gel were visualized using a UV transilluminator and photographed with a scale.

The agarose gel was immersed in 0.25 N hydrochloric acid and gently shaken for 10 minutes. Thereafter, it was further immersed in 0.4 N sodium hydroxide and gently shaken for 10 minutes. The genomic DNA fragments separated in the agarose gel were transferred to a nylon membrane (Hybond-XL; GE Healthcare) at room temperature for 16 hours by the capillary method using 0.4 N sodium hydroxide. The nylon membrane with the genomic DNA fragments transferred therein was immersed in 2×SSC, gently shaken for 10 minutes, thereafter air-dried, and stored at room temperature until use for hybridization.

Using a DNA labeling kit (Megaprime DNA Labelling System; GE Healthcare), DNA fragments were [32P]-labeled by the random prime method. Using Sephadex spin columns (ProbeQuant G-50 Micro Columns; GE Healthcare), the [32P]-labeled fragments were purified to give [32P]-labeled probes.

The nylon membrane with the genomic DNA fragments transferred therein was put into a hybridization buffer, followed by preincubation at 65° C. for 1 hour. Thereafter, the [32P]-labeled probe denatured by heating at 95° C. for 5 minutes and immediate cooling with ice for 5 minutes was added thereto, followed by incubation at 65° C. for 4 hours. The nylon membrane was taken out after the completion of the incubation and washed with 0.1% SDS and 0.5×SSC at 65° C. for about 15 minutes. The radioactivity derived from the probe bound to the membrane was monitored with a survey meter, and the washing was repeated until the radioactivity became approximately constant.

The washed membrane was covered with Saran Wrap(R), laminated with an X-ray film (BioMax MS; Eastman Kodak Company) in a darkroom, and put into an autoradiography cassette. After exposure at 4° C. for 1 week, the X-ray film was developed. Specific signals derived from the human LAG-3 RecBAC/human FcγR BAC expression constructs were detected by autoradiography, and individuals giving the signals specific to hybridization with the [32P]-labeled probes were identified as the founder individuals of human LAG-3 RecBAC/human FcγR BAC transgenic mice.

10-5) Creation and Proliferation of F1 Mice

Progeny animals of the founder individuals were obtained and genotyped to obtain established Tg mouse lines. The Tg mouse founders identified by Southern analysis and wild-type C57BL/6J mice were in vitro fertilized or naturally mated to create F1 individuals. The established lines, where transfer of the transgenes to the F1 individuals was confirmed by genotyping, were proliferated by in vitro fertilization or natural mating with wild type C57BL/6J mice, and mice with both the human LAG-3 and the human FcγRIIIA heterozygously introduced therein, which was revealed by genotyping, were used for the experiments.

Figure 13:
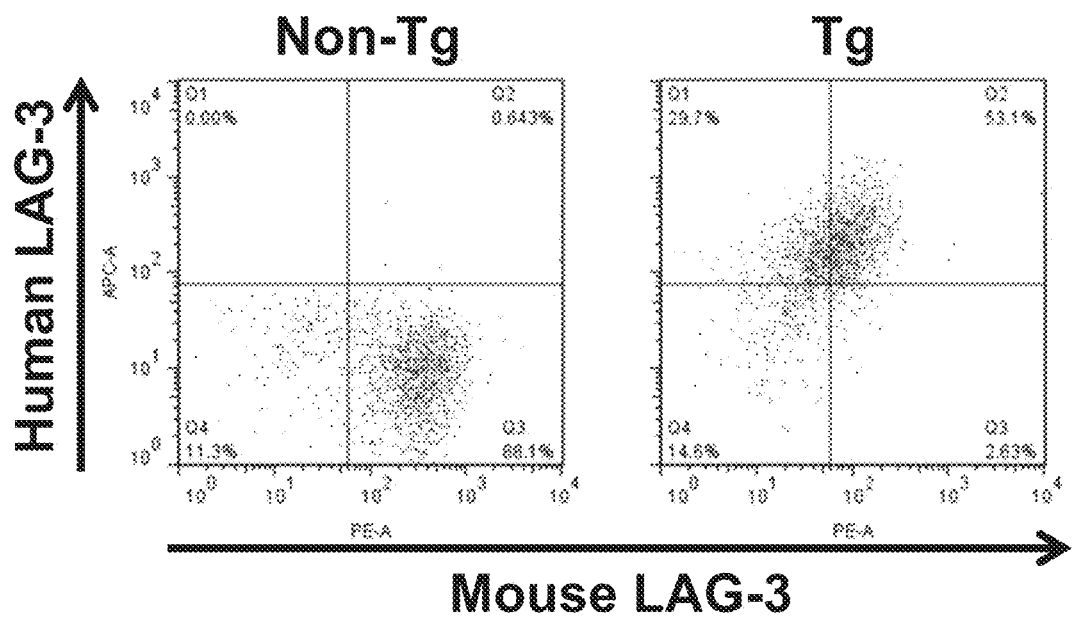
FIG. 13 is a diagram showing that the expression of human LAG-3 in human LAG-3/human FcγRIIIA double transgenic mice is consistent with the expression of mouse LAG-3. Human and mouse LAG-3 expression on activated T cells, obtained by stimulating white blood cells obtained from the peripheral blood of human LAG-3/human FcγRIIIA double transgenic mice (Tg) and control wild type mice (Non-Tg) with Con A, were investigated by flow cytometry (multiple staining). The results when CD3 positive T cells were gated for analysis are shown. The quadrants of the graph were set using samples free from staining antibodies to human and mouse LAG-3.

10-6) Confirmation of Phenotypes of Human LAG-3/Human FcγRIIIA Double Transgenic Mice The expression of the genes introduced into the obtained human LAG-3/human FcγRIIIA double transgenic mice was investigated by flow cytometry. The peripheral blood was collected from the tail vein of each mouse into a heparinized hematocrit capillary, and the red blood cells were hemolyzed by PharmLyse (manufactured by Becton, Dickinson and Company) to obtain white blood cells. The white blood cells were partially used for expression analysis of the human FcγRIIIA by flow cytometry, and the remainder was stimulated for 3 days with a medium containing 2 μg/mL Concanavalin A (Con A: Sigma-Aldrich) for inducing the expression of LAG-3 to obtain activated T cells. To the latter cells, were added a PE labeled anti-mouse LAG-3 antibody (manufactured by Becton, Dickinson and Company), an ATTO647 μlabeled anti-human LAG-3 antibody (manufactured by Enzo Life Sciences, Inc.), a FITC labeled anti-mouse CD3 antibody (manufactured by Becton, Dickinson and Company), and a LIVE/DEAD Fixable Dead Cell Stain Kit-near-IR fluorescent reactive dye (manufactured by Invitrogen Corp.) for suspension, followed by standing at 4° C. for 30 minutes. For use for identifying the positions of the negative populations, a control free from the PE labeled anti-mouse LAG-3 antibody and the ATTO647 μlabeled anti-human LAG-3 antibody was also prepared and treated in the same manner. After washing with a FACS buffer, the cells were resuspended in PBS containing 1% paraformaldehyde, followed by detection using a flow cytometer (CantoII: manufactured by Becton, Dickinson and Company). The data was analyzed using FlowJo (manufactured by Tree Star Inc). After removal of the LIVE/DEAD Fixable Dead Cell Stain Kit-near-IR fluorescent reactive dye-positive dead cells by gating, the living cells were analyzed. As a result, only the expression of mouse LAG-3 was found, and the expression of human LAG-3 was not found on Con A-activated T cells derived from the control wild-type mice, whereas the expression of both mouse LAG-3 and human LAG-3 was found on Con A-activated T cells derived from the human LAG-3/human FcγRIIIA double transgenic mice, and dots in the dot plot representing the individual cells were distributed almost diagonally, as shown in FIG. 13. Almost no expression of either mouse LAG-3 or human LAG-3 was found on resting T cells that were not activated. These results revealed that, in the developed human LAG-3/human FcγRIIIA double transgenic mice, human LAG-3 was expressed according to the endogenous expression pattern of mouse LAG-3, as initially planned, by using the BAC transgenic approach. Further, for the human FcγRIIIA, results comparable to a previous report (Non Patent Literature 10) were confirmed, in which the expression was observed on about 47% of peripheral blood NK cells (CD3-DX5+) of the developed human LAG-3/human FcγRIIIA double transgenic mice.

Example 11. In Vivo Evaluation of Humanized Anti-Human LAG-3 Antibody hLA212_H4/L2

11-1) LAG-3 Positive Cell Depletion Activity of Humanized Anti-Human LAG-3 Antibody hLA212_H4/L2

Figure 14:
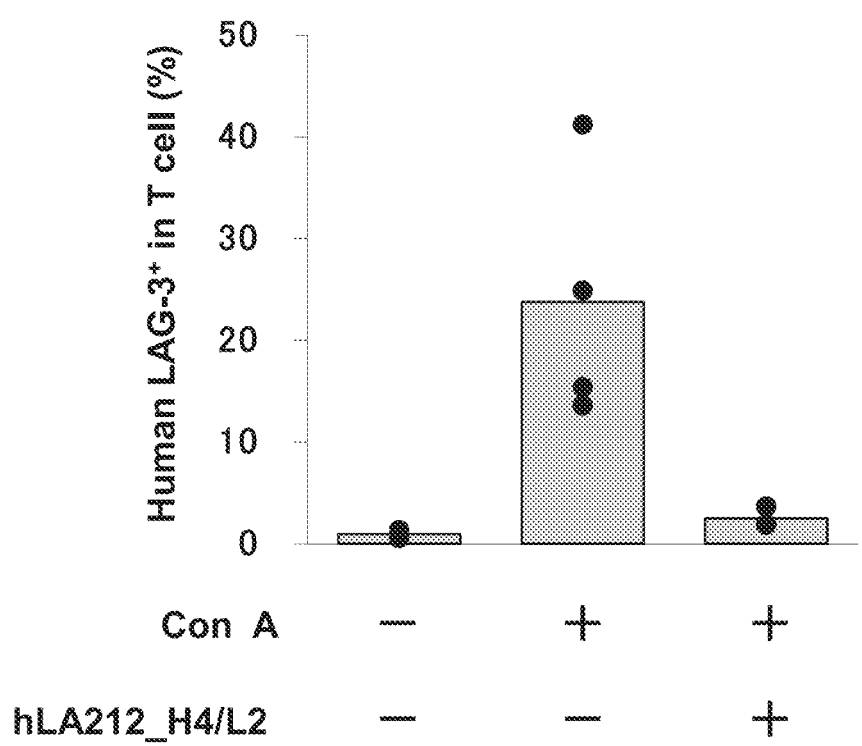
FIG. 14 is a diagram showing the depletion activity of the humanized anti-LAG-3 antibody hLA212_H4/L2 against LAG-3-expressing cells in vivo. The vertical axis represents human LAG-3 positivity in T cells of the peripheral blood of human LAG-3/human FcγRIIIA double transgenic mice two days after the administration of the antibody and Con A. The antibody was intraperitoneally administered at a dose of 30 mg/kg immediately before the administration of Con A.

Using the human LAG-3/human FcγRIIIA double transgenic mice of Example 10, it was investigated whether the obtained humanized anti-human LAG-3 antibody hLA212_H4/L2 has the activity of depleting LAG-3 positive cells in vivo. Immediately after the humanized anti-human LAG-3 antibody hLA212_H4/L2 (30 mg/kg) or a solvent was intraperitoneally administered to the human LAG-3/human FcγRIIIA double transgenic mice, Con A (manufactured by Sigma-Aldrich) having polyclonal T cell activating action was intravenously administered at a dose of 15 mg/kg. Red blood cells were hemolyzed from the blood collected 2 days thereafter with PharmLyse (manufactured by Becton, Dickinson and Company) to obtain white blood cells, and the white blood cells were used for flow cytometry. The white blood cells were allowed to react with FcBlock (manufactured by Becton, Dickinson and Company), and thereafter a PE labeled anti-mouse LAG-3 antibody (manufactured by Becton, Dickinson and Company), an ATTO647 μlabeled anti-human LAG-3 antibody (manufactured by Enzo Life Sciences, Inc.), a FITC labeled anti-mouse CD3 antibody (manufactured by Becton, Dickinson and Company), and a LIVE/DEAD Fixable Dead Cell Stain Kit-near-IR fluorescent reactive dye (manufactured by Invitrogen Corp.) were added thereto for suspension, followed by standing at 4° C. for 30 minutes. For use for identifying the positions of the negative populations, a control free from the PE labeled anti-mouse LAG-3 antibody and the ATTO647 μlabeled anti-human LAG-3 antibody was also prepared and treated in the same manner. After washing with a FACS buffer, the cells were resuspended in PBS containing 1% paraformaldehyde, followed by detection using a flow cytometer (CantoII: manufactured by Becton, Dickinson and Company). The data was analyzed using FlowJo (manufactured by Tree Star Inc). After removal of the LIVE/DEAD Fixable Dead Cell Stain Kit-near-IR fluorescent reactive dye-positive dead cells by gating, the living cells were analyzed. As a result of calculating the human LAG-3 positivity in CD3 positive T cells, as shown in FIG. 14, it was found that there were almost no human LAG-3 positive cells in the peripheral blood T cells of untreated human LAG-3/human FcγRIIIA double transgenic mice, whereas an average of 24% of the peripheral blood T cells in the antibody non-administration group became positive for human LAG-3 as a result of the administration of the Con A having polyclonal T cell activating action. In contrast, the human LAG-3 positivity in the peripheral blood T cells of the Con A-administered mice, to which hLA212_H4/L2 was administered, decreased in a remarkable manner. A similar tendency was observed in splenic T cells and in the peripheral blood T cells obtained one day after the administration of the Con A, and similar results were also obtained for the positivity of mouse LAG-3 and CD69, which is another activation marker. These results revealed that the obtained humanized anti-human LAG-3 antibody hLA212_H4/L2 had the activity of depleting LAG-3 positive cells in vivo.

11-2) Activity of Humanized Anti-Human LAG-3 Antibody hLA212_H4/L2 on T Cell-Dependent Autoimmune Disease Model In order to reveal whether the humanized anti-human LAG-3 antibody hLA212_H4/L2 having the activity of depleting LAG-3 positive cells in vivo is useful for treating autoimmune diseases, its efficacy against an EAE (experimental autoimmune encephalomyelitis) model (Non Patent Literature 11) that is a typical T cell-dependent autoimmune disease (multiple sclerosis) model was investigated.

Figure 15:
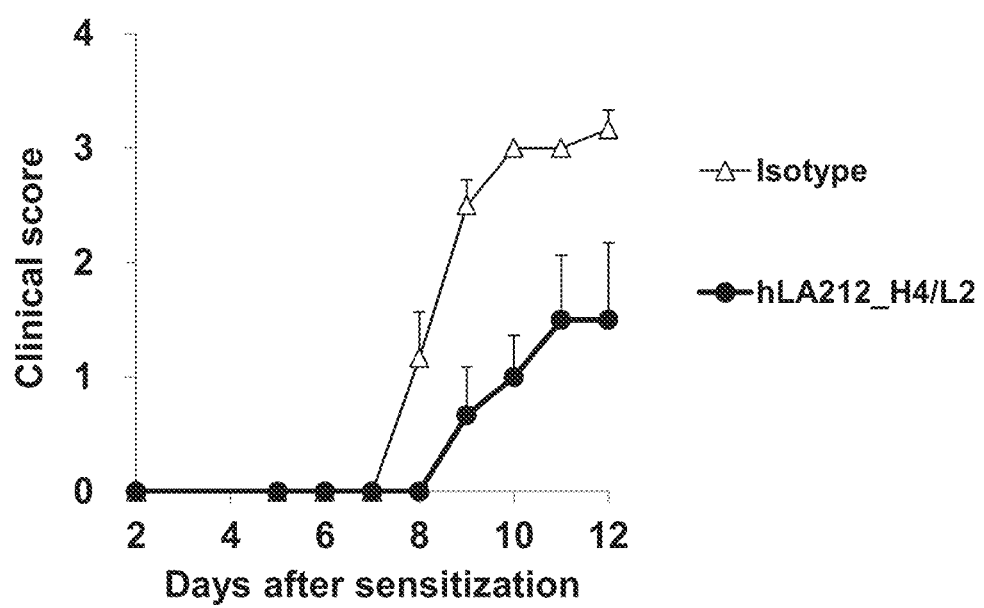
FIG. 15 is a diagram showing that the humanized anti-LAG-3 antibody hLA212_H4/L2 has an activity of suppressing an autoimmune disease model in vivo. The clinical scores of EAE in human LAG-3/human FcγRIIIA double transgenic mice in which EAE was induced and to which the humanized anti-LAG-3 antibody hLA212_H4/L2 or a control antibody was administered are shown over time. Each antibody was intravenously administered at a dose of 30 mg/kg on the day of sensitization and seven days thereafter.

A solution obtained by dissolving a peptide (amino acid 35-55, PEPTIDE INSTITUTE, INC.), derived from MOG (Myelin Oligodendrocyte Glycoprotein) that is one of the central nervous myelin component proteins, in normal saline at a concentration of 4 mg/mL was mixed with an 8 mg/mL mixture of Killed *Mycobacterium Tuberculosis* H37Ra (manufactured by Becton, Dickinson and Company) and Freund's Incomplete Adjuvant (manufactured by Wako Pure Chemical Industries, Ltd.) in equal amounts to give an emulsion. This emulsion was subcutaneously injected on Day 0 into both flanks of the human LAG-3/human FcγRIIIA double transgenic mice in an amount of 50 μL each, and 0.2 μg of pertussis toxin diluted with normal saline was further intravenously administered thereto, to induce EAE. Thereafter, the clinical scores of EAE were observed daily as follows. That is, Score 0: Asymptomatic; Score 1: Limp tail; Score 2: Abnormal gait and loss of righting reflex; Score 3: Hind leg paralysis; Score 4: Partial paralysis of forelimbs; and Score 5: Death or euthanasia. The humanized anti-human LAG-3 antibody hLA212_H4/L2 and a control antibody were intravenously administered each at a dose of 30 mg/kg on Days 0 and 7. As a result, the average of the EAE clinical scores in the humanized anti-human LAG-3 antibody hLA212_H4/L2-administered group was suppressed to 50% or less during the observation period, as compared with that in the control antibody-administered group, as shown in FIG. 15. Further, in the hLA212_H4/L2-administered group, the weight loss with EAE progression was also suppressed. These results revealed that the humanized anti-human LAG-3 antibody hLA212_H4/L2 having an activity to deplete LAG-3 positive cells in vivo suppresses EAE, which is a typical T cell-dependent autoimmune disease model, and can be a therapeutic medicine for human autoimmune diseases.

Example 12. Relationship Between LAG-3 and Perforin, CD28, or CD57 Expression in Activated Human T Cells PBMCs were separated from human peripheral blood by Ficoll centrifugation and added to a 96-well U-bottom microplate in an amount of $4 \times 10^5$ cells/well. Human IL-2 (PeproTech, Inc., final concentration: 100 ng/mL) and Dynabeads Human T-Activator CD3/CD28 (Life Technologies Corp., 4×105 beads/well) were added thereto, and T cells were activated by culture for 4 days. The obtained cells were recovered, suspended in a FACS buffer (PBS, 0.1% BSA, and 0.1% sodium azide), and then reacted with Human BD Fc Block (Becton, Dickinson and Company) at room temperature for 10 minutes. Subsequently, the cell surface was stained by reaction at 4° C. for 30 minutes with fluorescently labeled antibodies diluted with a FACS buffer containing a LIVE/DEAD Fixable Dead Cell Stain Kit-near-IR fluorescent reactive dye (manufactured by Invitrogen Corp.), followed by washing with a FACS buffer. The fluorescently labeled antibodies used were various combinations of a FITC-labeled anti-human CD8 antibody, a PerCP-Cy5.5-labeled anti-human CD3 antibody, an APC-labeled anti-human CD28 antibody, and a Pacific Blue-labeled anti-human CD57 antibody (all from Becton, Dickinson and Company), a PE-labeled anti-human CD28 antibody (BioLegend, Inc.), and an anti-human LAG-3 antibody and an isotype control antibody labeled using a PE labeling kit (Dojindo Laboratories). For some samples, intracellular perforin was also stained using a BD Cytofix/Cytoperm Fixation/Permeabilization Solution Kit (Becton, Dickinson and Company) and an APC-labeled anti-human perforin antibody (eBiosciences, Inc.). The cells thus washed were resuspended in PBS containing 1% paraformaldehyde, followed by detection using a flow cytometer (CantoII manufactured by Becton, Dickinson and Company or MACSQuantX manufactured by Miltenyi Biotech). The data was analyzed using FlowJo (manufactured by Tree Star Inc). After removal of the LIVE/DEAD Fixable Dead Cell Stain Kit-near-IR fluorescent reactive dye-positive dead cells by gating, only the living cells were analyzed by further gating CD3 positive and CD8 positive CD8 T cells.

Figure 102:
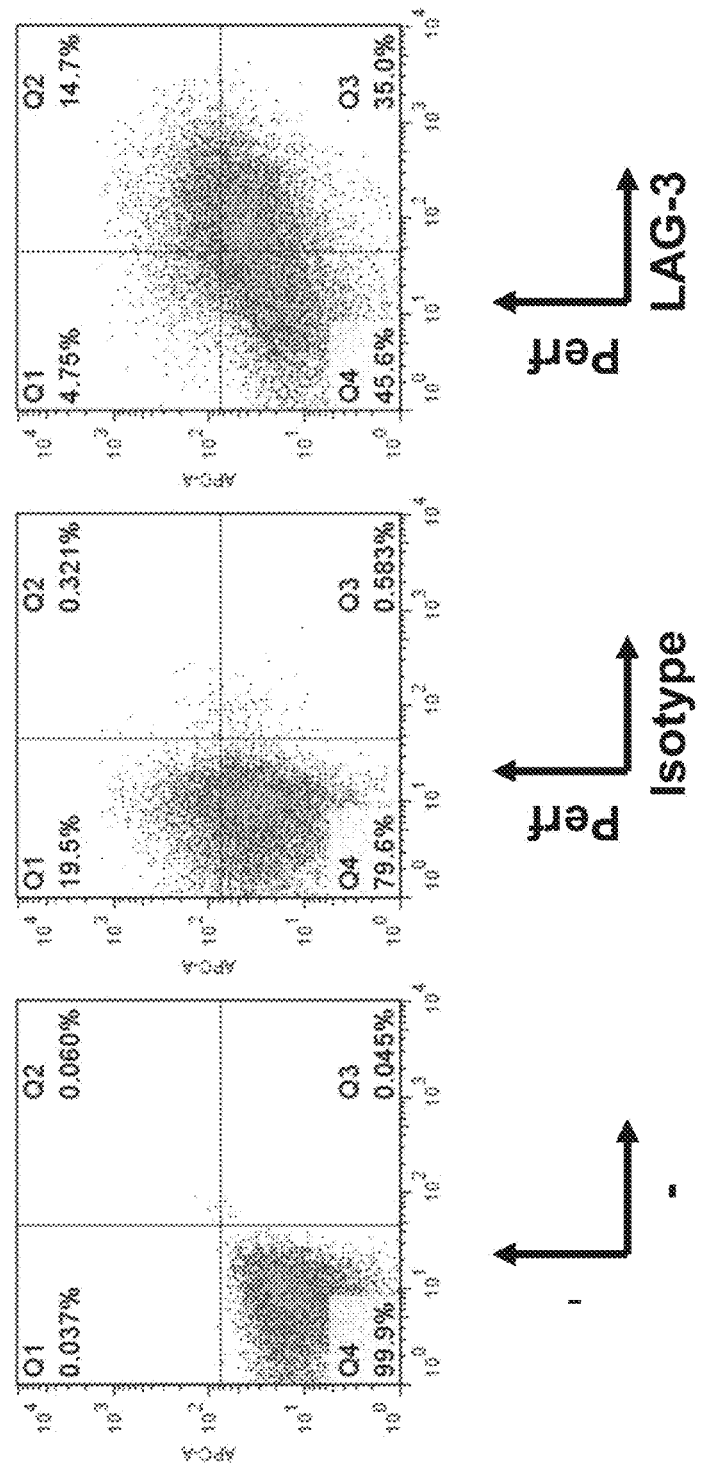
FIG. 102 is a diagram showing that in activated human CD8 T cells, the expression of human LAG-3 correlates with the expression of perforin. LAG-3 and perforin expression in human PBMC cells stimulated with Dynabeads Human T-Activator CD3/CD28 was investigated by flow cytometry (multiple staining). The results when CD3 positive and CD8 positive T cells were gated for analysis are shown. The quadrants of the graph were set using samples free from staining antibodies to human LAG-3 and human perforin (left most diagram).

Results of analyzing the relationship between LAG-3 and intracellular perforin expression are shown in FIG. 102. In the rightmost diagram, cell populations were distributed almost diagonally, revealing that in activated human CD8 T cells, LAG-3 and intracellular perforin are expressed almost in parallel. In this experiment, the PE-labeled isotype control (middle diagram) of the LAG-3 antibody exhibits a fluorescence intensity distribution in the horizontal axis direction this is rarely different from that of an unlabeled sample (leftmost diagram), confirming the staining specificity of human LAG-3.

Figure 103:
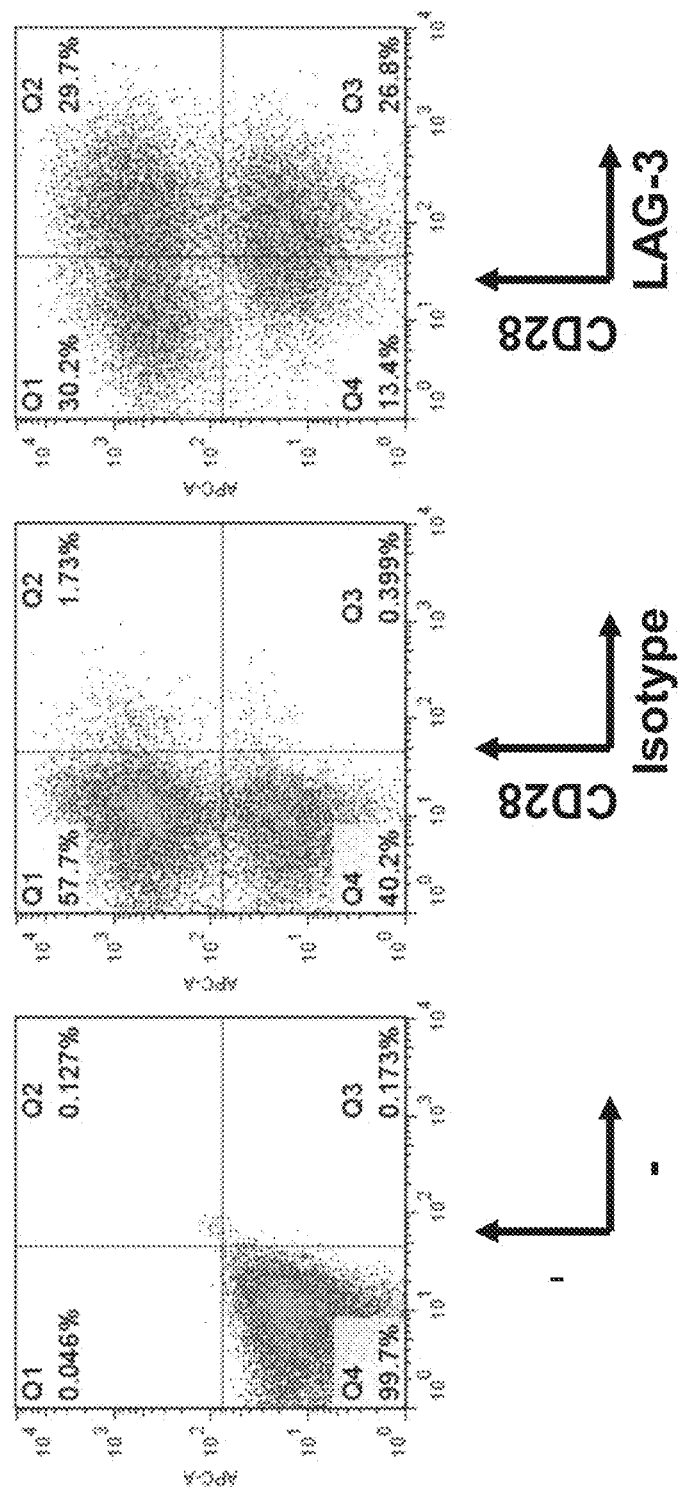
FIG. 103 is a diagram showing that in activated human CD8 T cells, most of CD28 negative cells express LAG-3. LAG-3 and CD28 expression on human PBMC cells stimulated with Dynabeads Human T-Activator CD3/CD28 was investigated by flow cytometry (multiple staining). The results when CD3 positive and CD8 positive T cells were gated for analysis are shown. The quadrants of the graph were set using samples free from staining antibodies to human LAG-3 and human CD28 (left most diagram).

FIG. 103 shows the results of analyzing the relationship between LAG-3 and CD28 expression. In the rightmost diagram, less than 50% of the CD28 positive cells were LAG-3 positive, whereas the cell population of CD28 negative cells shifted to the LAG-3 positive side as a whole, as compared with the CD28 positive cells, and ⅔ of the CD28 negative cells were LAG-3 positive, revealing that in activated human CD8 T cells, LAG-3 expression is more prevalent on CD28 negative cells than on CD28 positive cells.

Figure 104:
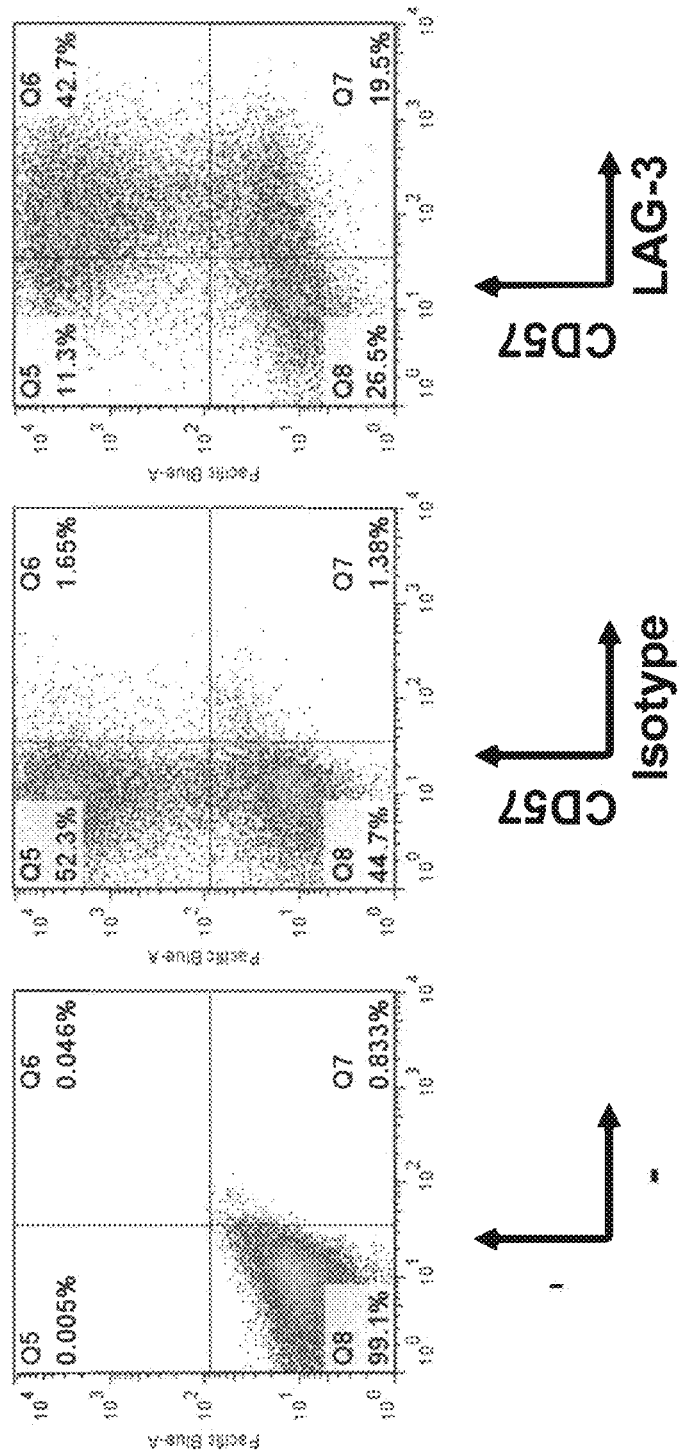
FIG. 104 is a diagram showing that in activated human CD8 T cells, most of CD57 positive cells express LAG-3. LAG-3 and CD57 expression on human PBMC cells stimulated with Dynabeads Human T-Activator CD3/CD28 was investigated by flow cytometry (multiple staining). The results when CD3 positive and CD8 positive T cells were gated for analysis are shown. The quadrants of the graph were set using samples free from staining antibodies to human LAG-3 and human CD57 (left most diagram).

FIG. 104 shows the results of analyzing the relationship between LAG-3 and CD57 expression. In the rightmost diagram, 42% of CD57 negative cells were LAG-3 positive, whereas the cell population of CD57 positive cells largely shifted to the LAG-3 positive side as a whole, as compared with the CD57 negative cells, and 79% of the CD57 positive cells were LAG-3 positive, revealing that in activated human CD8 T cells, LAG-3 expression is more prevalent on CD57 positive cells than on CD57 negative cells.

Example 13. Effect of LAG-3 Antibody on Perforin Positive CD8 T Cells

The effect of the humanized anti-human LAG-3 antibody hLA212_H4/L2, the calcineurin inhibitor tacrolimus, and the corticosteroid dexamethasone was investigated in the experimental system of Example 12. Human PBMCs were preincubated with hLA212_H4/L2 (final concentration: 10 µg/mL), a control human IgG antibody (Jackson ImmunoResearch Laboratories, Inc., final concentration: 10 µg/mL), tacrolimus (Focus Corp., final concentration: 10 nM), or dexamethasone (Enzo Life Sciences, Inc., final concentration: 1 µM) at 37° C. for 30 minutes and then cultured with Dynabeads Human T-Activator CD3/CD28 for 4 days as described in Example 12, and the obtained cells were subjected to flow cytometry. The concentrations of these antibodies and compounds were set to concentrations considered to exhibit the maximum efficacy on the basis of previous reports (Henderson, D J et al., Immunol., 1991; Vol. 73 (No. 3): p. 316-321; and Brunetti, M. et al., Pharmacol. Exp. Ther., 1998; Vol. 285 (No. 2): p. 915-919), etc.

The results are shown in FIG. 105. As shown in FIG. 105A, the addition of hLA212_H4/L2 or tacrolimus slightly reduced the total number of T cells after culture, as compared with the control, and results obtained by the addition of dexamethasone were rarely different from those of the control. This assay was conducted using PBMCs derived from two donors, and similar tendencies were observed (PBMC1 and PBMC2).

By contrast, as shown in FIG. 105B, the number of perforin positive CD8 T cells was evidently reduced by hLA212_H4/L2 compared with the control. On the other hand, results obtained by the addition of tacrolimus were rarely different from those of the control, and in the case of adding dexamethasone, the number of perforin positive CD8 T cells was increased in PBMC1, as compared with the control, and was at the same level as in the control for PBMC2. These results revealed that the humanized anti-human LAG-3 antibody hLA212_H4/L2 selectively depletes perforin positive CD8 T cells as compared with its influence on T cells as a whole, and the calcineurin inhibitor tacrolimus and the corticosteroid dexamethasone have no such effect. Although data is not shown, the humanized anti-human LAG-3 antibody hLA212_H4/L2 also reduced the number of granzyme positive CD8 T cells.

Example 14. Effect of LAG-3 Antibody on CD28 Negative T Cells and CD57 Positive T Cells The effect of the humanized anti-human LAG-3 antibody hLA212_H4/L2, the calcineurin inhibitor tacrolimus, and the corticosteroid dexamethasone on CD28 negative T cells and CD57 positive T cells was investigated in the assay system of Example 13. Human PBMCs were preincubated with hLA212_H4/L2 (final concentration: 10, 1, and 0.1 µg/mL), a control human IgG antibody (Jackson ImmunoResearch Laboratories, Inc., final concentration: 10 µg/mL), tacrolimus (Focus Corp., final concentration: 10 nM), or dexamethasone (Enzo Life Sciences, Inc., final concentration: 1 µM) at 37° C. for 30 minutes and then cultured with Dynabeads Human T-Activator CD3/CD28 for 4 days as described in Example 12, and the obtained cells were subjected to flow cytometry. Out of the living cells, a CD3 positive and CD8 negative fraction and a CD3 positive and CD8 positive fraction were analyzed as CD4 T cells and CD8 T cells, respectively.

Results of analyzing the effect on CD28 negative T cells are shown in FIG. 106. As shown in FIG. 106B, hLA212_H4/L2 evidently reduced the number of CD28 negative CD8 T cells, as in the perforin positive CD8 T cells of Example 13. This effect was dependent on the concentration of hLA212_H4/L2. Similar results were obtained using PBMCs derived from either of the two donors. By contrast, in the case of adding tacrolimus or dexamethasone, the evident reduction in the number of CD28 negative CD8 T cells as found for the LAG-3 antibody was not observed. As shown in FIG. 106A, the LAG-3 antibody hLA212_H4/L2 also reduced the number of CD28 negative CD4 T cells, albeit not as remarkably as observed in the CD28 negative CD8 T cells, whereas tacrolimus and dexamethasone were hardly effective or rather increased the cell number.

Results of analyzing the effect on CD57 positive T cells are shown in FIG. 107. As shown in FIG. 107B, hLA212_H4/L2 evidently reduced the number of CD57 positive CD8 T cells, as in the perforin positive CD8 T cells of Example 13 and the CD28 negative CD8 T cells. This effect was dependent on the concentration of hLA212_H4/L2. Similar results were obtained using PBMCs derived from either of the two donors. By contrast, in the case of adding tacrolimus or dexamethasone, the evident reduction in the number of CD57 positive CD8 T cells as found for the LAG-3 antibody was not observed. As shown in FIG. 107A, the LAG-3 antibody hLA212_H4/L2 also reduced the number of CD57 positive CD4 T cells, albeit not as remarkably as observed in the CD57 positive CD8 T cells, whereas such an effect was hardly observed in tacrolimus and dexamethasone.

The humanized anti-human LAG-3 antibody hLA212_H3/L2, the anti-human LAG-3 mouse-human chimeric antibody A9H12, and the anti-human LAG-3 rat-human chimeric antibody cLA212, which were not in a low fucose form, exhibited a tendency to reduce the number of CD28 negative T cells and the number of CD57 positive T cells (data not shown), albeit more weakly than hLA212_H4/L2, which is in a low fucose form.

These results revealed that the anti-LAG-3 antibody depletes cytotoxic CD28 negative T cells and CD57 positive T cells reportedly involved in the steroid resistance of diseases of the immune system, and the T cell depletion activity is enhanced in a low fucose form. This indicated the possibility that the anti-LAG-3 antibody could serve as a promising drug for cytotoxic T cell depletion in the medical care of immunosuppressant resistant diseases associated with cytotoxic T cells.

INDUSTRIAL APPLICABILITY

The compositions of the present invention are useful for cytotoxic T cell depletion.

Sequence Listing Free Text

SEQ ID No: 1: Nucleotide sequence encoding the amino acid sequence of the heavy chain variable region of the rLA204 antibody (FIG. 16)

SEQ ID No: 2: Amino acid sequence of the heavy chain variable region of the rLA204 antibody (FIG. 17)

SEQ ID No: 3: Nucleotide sequence encoding the amino acid sequence of the light chain variable region of the rLA204 antibody (FIG. 18)

SEQ ID No: 4: Amino acid sequence of the light chain variable region of the rLA204 antibody (FIG. 19)

SEQ ID No: 5: Nucleotide sequence encoding the amino acid sequence of the heavy chain variable region of the rLA212 antibody (FIG. 20)

SEQ ID No: 6: Amino acid sequence of the heavy chain variable region of the rLA212 antibody (FIG. 21)

SEQ ID No: 7: Nucleotide sequence encoding the amino acid sequence of the light chain variable region of the rLA212 antibody (FIG. 22)

SEQ ID No: 8: Amino acid sequence of the light chain variable region of the rLA212 antibody (FIG. 23)

SEQ ID No: 9: Nucleotide sequence encoding the amino acid sequence of the heavy chain variable region of the rLA225 antibody (FIG. 24)

SEQ ID No: 10: Amino acid sequence of the heavy chain variable region of the rLA225 antibody (FIG. 25)

SEQ ID No: 11: Nucleotide sequence encoding the amino acid sequence of the light chain variable region of the rLA225 antibody (FIG. 26)

SEQ ID No: 12: Amino acid sequence of the light chain variable region of the rLA225 antibody (FIG. 27)

SEQ ID No: 13: Nucleotide sequence encoding the amino acid sequence of the heavy chain variable region of the rLA869 antibody (FIG. 28)

SEQ ID No: 14: Amino acid sequence of the heavy chain variable region of the rLA869 antibody (FIG. 29)

SEQ ID No: 15: Nucleotide sequence encoding the amino acid sequence of the light chain variable region of the rLA869 antibody (FIG. 30)

SEQ ID No: 16: Amino acid sequence of the light chain variable region of the rLA869 antibody (FIG. 31)

SEQ ID No: 17: Nucleotide sequence of cDNA encoding the amino acid sequence of the heavy chain variable region of the rLA1264 antibody (FIG. 32)

SEQ ID No: 18: Amino acid sequence of the heavy chain variable region of the rLA1264 antibody (FIG. 33)

SEQ ID No: 19: Nucleotide sequence encoding the amino acid sequence of the light chain variable region of the rLA1264 antibody (FIG. 34)

SEQ ID No: 20: Amino acid sequence of the light chain variable region of the rLA1264 antibody (FIG. 35)

SEQ ID No: 21: Nucleotide sequence encoding the amino acid sequences of the human light chain secretion signal and the human K chain constant region (FIG. 36)

SEQ ID No: 22: Nucleotide sequence encoding the amino acid sequences of the human heavy chain secretion signal and the human IgG1 constant region (FIG. 37)

SEQ ID No: 23: Nucleotide sequence encoding the amino acid sequence of the heavy chain of the cLA212 antibody (FIG. 38)

SEQ ID No: 24: Amino acid sequence of the heavy chain of the cLA212 antibody (FIG. 39)

SEQ ID No: 25: Nucleotide sequence encoding the amino acid sequence of the light chain of the cLA212 antibody (FIG. 40)

SEQ ID No: 26: Amino acid sequence of the light chain of the cLA212 antibody (FIG. 41)

SEQ ID No: 27: Nucleotide sequence encoding the amino acid sequence of the heavy chain H2 of the hLA212 antibody (FIG. 42)

SEQ ID No: 28: Amino acid sequence of the heavy chain H2 of the hLA212 antibody (FIG. 43)

SEQ ID No: 29: Nucleotide sequence encoding the amino acid sequence of the heavy chain H3 of the hLA212 antibody (FIG. 44)

SEQ ID No: 30: Amino acid sequence of the heavy chain H3 of the hLA212 antibody (FIG. 45)

SEQ ID No: 31: Nucleotide sequence encoding the amino acid sequence of the light chain L1 of the hLA212 antibody (FIG. 46)

SEQ ID No: 32: Amino acid sequence of the light chain L1 of the hLA212 antibody (FIG. 47)

SEQ ID No: 33: Nucleotide sequence encoding the amino acid sequence of the light chain L2 of the hLA212 antibody (FIG. 48)

SEQ ID No: 34: Amino acid sequence of the light chain L2 of the hLA212 antibody (FIG. 49)

SEQ ID No: 35: Nucleotide sequence encoding the amino acid sequence of the light chain L3 of the hLA212 antibody (FIG. 50)

SEQ ID No: 36: Amino acid sequence of the light chain L3 of the hLA212 antibody (FIG. 51)

SEQ ID No: 37: Nucleotide sequence encoding the amino acid sequence of the light chain L4 of the hLA212 antibody (FIG. 52)

SEQ ID No: 38: Amino acid sequence of the light chain L4 of the hLA212 antibody (FIG. 53)

SEQ ID No: 39: Nucleotide sequence encoding the amino acid sequence of the light chain L5 of the hLA212 antibody (FIG. 54)

SEQ ID No: 40: Amino acid sequence of the light chain L5 of the hLA212 antibody (FIG. 55)

SEQ ID No: 41: Amino acid sequence of the heavy chain CDRH1 of the rLA204 antibody (FIG. 56)

SEQ ID No: 42: Amino acid sequence of the heavy chain CDRH2 of the rLA204 antibody (FIG. 57)

SEQ ID No: 43: Amino acid sequence of the heavy chain CDRH3 of the rLA204 antibody (FIG. 58)

SEQ ID No: 44: Amino acid sequence of the light chain CDRL1 of the rLA204 antibody (FIG. 59)

SEQ ID No: 45: Amino acid sequence of the light chain CDRL2 of the rLA204 antibody (FIG. 60)

SEQ ID No: 46: Amino acid sequence of the light chain CDRL3 of the rLA204 antibody (FIG. 61)

SEQ ID No: 47: Amino acid sequence of the heavy chain CDRH1 of the rLA212 antibody (FIG. 62)

SEQ ID No: 48: Amino acid sequence of the heavy chain CDRH2 of the rLA212 antibody (FIG. 63)

SEQ ID No: 49: Amino acid sequence of the heavy chain CDRH3 of the rLA212 antibody (FIG. 64)

SEQ ID No: 50: Amino acid sequence of the light chain CDRL1 of the rLA212 antibody (FIG. 65)

SEQ ID No: 51: Amino acid sequence of the light chain CDRL2 of the rLA212 antibody (FIG. 66)

SEQ ID No: 52: Amino acid sequence of the light chain CDRL3 of the rLA212 antibody (FIG. 67)

SEQ ID No: 53: Amino acid sequence of the heavy chain CDRH1 of the rLA225 antibody (FIG. 68)

SEQ ID No: 54: Amino acid sequence of the heavy chain CDRH2 of the rLA225 antibody (FIG. 69)

SEQ ID No: 55: Amino acid sequence of the heavy chain CDRH3 of the rLA225 antibody (FIG. 70)

SEQ ID No: 56: Amino acid sequence of the light chain CDRL1 of the rLA225 antibody (FIG. 71)

SEQ ID No: 57: Amino acid sequence of the light chain CDRL2 of the rLA225 antibody (FIG. 72)

SEQ ID No: 58: Amino acid sequence of the light chain CDRL3 of the rLA225 antibody (FIG. 73)

SEQ ID No: 59: Amino acid sequence of the heavy chain CDRH1 of the rLA869 antibody (FIG. 74)

SEQ ID No: 60: Amino acid sequence of the heavy chain CDRH2 of the rLA869 antibody (FIG. 75)

SEQ ID No: 61: Amino acid sequence of the heavy chain CDRH3 of the rLA869 antibody (FIG. 76)

SEQ ID No: 62: Amino acid sequence of the light chain CDRL1 of the rLA869 antibody (FIG. 77)

SEQ ID No: 63: Amino acid sequence of the light chain CDRL2 of the rLA869 antibody (FIG. 78)

SEQ ID No: 64: Amino acid sequence of the light chain CDRL3 of the rLA869 antibody (FIG. 79)

SEQ ID No: 65: Amino acid sequence of the heavy chain CDRH1 of the rLA1264 antibody (FIG. 80)

SEQ ID No: 66: Amino acid sequence of the heavy chain CDRH2 of the rLA1264 antibody (FIG. 81)

SEQ ID No: 67: Amino acid sequence of the heavy chain CDRH3 of the rLA1264 antibody (FIG. 82)

SEQ ID No: 68: Amino acid sequence of the light chain CDRL1 of the rLA1264 antibody (FIG. 83)

SEQ ID No: 69: Amino acid sequence of the light chain CDRL2 of the rLA1264 antibody (FIG. 84)

SEQ ID No: 70: Amino acid sequence of the light chain CDRL3 of the rLA1264 antibody (FIG. 85)

SEQ ID No: 71: Primer RG2AR3 (FIG. 86)

SEQ ID No: 72: Primer RKR5 (FIG. 87)

SEQ ID No: 73: Primer 3.3-F1 (FIG. 88)

SEQ ID No: 74: Primer 3.3-R1 (FIG. 89)

SEQ ID No: 75: Primer 212H-F (FIG. 90)

SEQ ID No: 76: Primer 212H-R (FIG. 91)

SEQ ID No: 77: Primer 212L-F (FIG. 92)

SEQ ID No: 78: Primer 212L-R (FIG. 93)

SEQ ID No: 79: Oligonucleotide LAG-3-H1 (FIG. 94)

SEQ ID No: 80: Oligonucleotide LAG-3-H2 (FIG. 95)

SEQ ID No: 81: Oligonucleotide LAG-3-H3 (FIG. 96)

SEQ ID No: 82: Oligonucleotide LAG-3-H4 (FIG. 97)

SEQ ID No: 83: Oligonucleotide LAG-3-H5 (FIG. 98)

SEQ ID No: 84: Oligonucleotide LAG-3-H6 (FIG. 99)

SEQ ID No: 85: Nucleotide sequence encoding the amino acid sequence of human LAG-3 (FIG. 100)

SEQ ID No: 86: Amino acid sequence of human LAG-3 (FIG. 101)

The invention claimed is:

1. A method for depleting cytotoxic T cells in a subject, comprising administering to a subject in need thereof an effective amount of an anti-LAG-3 antibody or a binding fragment thereof that binds to domain 3 of human LAG-3 and has the properties described in (i) to (vi) below:
   (i) having in vitro ADCC activity;
   (ii) reducing, in a low fucose form, the number of LAG-3 positive cells in vivo;
   (iii) binding to activated human T cells;
   (iv) suppressing, in a low fucose form, experimental autoimmune encephalomyelitis in vivo;
   (v) allowing human LAG-3 to bind to human major histocompatibility complex class II molecules in the presence of the antibody or the binding fragment thereof; and
   (vi) allowing human LAG-3 to exert a human T cell suppression function in the presence of the antibody or the binding fragment thereof,
   wherein the antibody or the binding fragment thereof comprises: a light chain comprising CDRL1 having the amino acid sequence represented by SEQ ID NO: 50, CDRL2 having the amino acid sequence represented by SEQ ID NO: 51 and CDRL3 having the amino acid sequence represented by SEQ ID NO: 52, and a heavy chain comprising CDRH1 having the amino acid sequence represented by SEQ ID NO: 47, CDRH2 having the amino acid sequence represented by SEQ ID NO: 48 and CDRH3 having the amino acid sequence represented by SEQ ID NO: 49.

2. The method according to claim 1, wherein the cytotoxic T cell is selected from the group consisting of: a perforin positive T cell, a granzyme B positive T cell, a CD28 negative and CD4 positive T cell, a CD28 negative and CD8 positive T cell, a CD57 positive and CD4 positive T cell, and a CD57 positive and CD8 positive T cell.

3. The method according to claim 1, wherein the antibody or the binding fragment thereof is a chimeric antibody, a humanized antibody, or a binding fragment thereof.

4. The method according to claim 1, wherein the antibody or the binding fragment thereof is a humanized antibody or a binding fragment thereof.

5. The method according to claim 4,
   wherein the anti-LAG-3 antibody comprises: a heavy chain amino acid sequence and a light chain amino acid sequence selected from the group consisting of [i] to [x] below:
   [i] a heavy chain amino acid sequence consisting of amino acid positions 20 to 470 of SEQ ID NO: 30 and a light chain amino acid sequence consisting of amino acid positions 21 to 234 of SEQ ID NO: 34;
   [ii] a heavy chain amino acid sequence consisting of amino acid positions 20 to 470 of SEQ ID NO: 28 and a light chain amino acid sequence consisting of amino acid positions 21 to 234 of SEQ ID NO: 32;
   [iii] a heavy chain amino acid sequence consisting of amino acid positions 20 to 470 of SEQ ID NO: 30 and a light chain amino acid sequence consisting of amino acid positions 21 to 234 of SEQ ID NO: 36;
   [iv] a heavy chain amino acid sequence consisting of amino acid positions 20 to 470 of SEQ ID NO: 28 and a light chain amino acid sequence consisting of amino acid positions 21 to 234 of SEQ ID NO: 34;
   [v] a heavy chain amino acid sequence consisting of amino acid positions 20 to 470 of SEQ ID NO: 28 and a light chain amino acid sequence consisting of amino acid positions 21 to 234 of SEQ ID NO: 36;
   [vi] a heavy chain amino acid sequence consisting of amino acid positions 20 to 470 of SEQ ID NO: 28 and a light chain amino acid sequence consisting of amino acid positions 21 to 234 of SEQ ID NO: 38;
   [vii] a heavy chain amino acid sequence consisting of amino acid positions 20 to 470 of SEQ ID NO: 28 and a light chain amino acid sequence consisting of amino acid positions 21 to 234 of SEQ ID NO: 40;
   [viii] a heavy chain amino acid sequence consisting of amino acid positions 20 to 470 of SEQ ID NO: 30 and a light chain amino acid sequence consisting of amino acid positions 21 to 234 of SEQ ID NO: 32;
   [ix] a heavy chain amino acid sequence consisting of amino acid positions 20 to 470 of SEQ ID NO: 30 and a light chain amino acid sequence consisting of amino acid positions 21 to 234 of SEQ ID NO: 38; and
   [x] a heavy chain amino acid sequence consisting of amino acid positions 20 to 470 of SEQ ID NO: 30 and a light chain amino acid sequence consisting of amino acid positions 21 to 234 of SEQ ID NO: 40.

6. The method according to claim 1, wherein the antibody or the binding fragment thereof is in a low fucose form.

7. The method according to claim 1, wherein the antibody or the binding fragment thereof is obtained by a method for producing the antibody or the binding fragment thereof, comprising the step of culturing a cell comprising a nucleic acid molecule comprising a nucleotide sequence encoding the amino acid sequence thereof or a vector comprising the nucleic acid molecule, or a cell producing the antibody or the binding fragment thereof.

8. The method according to claim 1, further comprising administering an additional drug to the subject.

9. The method according to claim 5, wherein the cytotoxic T cell is selected from the group consisting of: a perforin positive T cell, a granzyme B positive T cell, a CD28 negative and CD4 positive T cell, a CD28 negative and CD8 positive T cell, a CD57 positive and CD4 positive T cell, and a CD57 positive and CD8 positive T cell.

10. The method according to claim 5, further comprising administering an additional drug to the subject.

11. The method according to claim 5, wherein the antibody or the binding fragment thereof is in a low fucose form.

12. The method according to claim 5, wherein the antibody or the binding fragment thereof is obtained by a method for producing the antibody or the binding fragment thereof, comprising the step of culturing a cell comprising a nucleic acid molecule comprising a nucleotide sequence encoding the amino acid sequence thereof or a vector comprising the nucleic acid molecule, or a cell producing the antibody or the binding fragment thereof.

* * * * *

SEQUENCE LISTING

```
<160> NUMBER OF SEQ ID NOS: 87

<210> SEQ ID NO 1
<211> LENGTH: 366
<212> TYPE: DNA
<213> ORGANISM: Rattus norvegicus
<220> FEATURE:
<221> NAME/KEY: CDS
<222> LOCATION: (1)..(366)

<400> SEQUENCE: 1 gag gta gag ctg gtg gag tct ggg ggc ggc tta gtg cag cct gga agg      48
Glu Val Glu Leu Val Glu Ser Gly Gly Gly Leu Val Gln Pro Gly Arg
1               5                   10                  15 tcc atg aaa ctc tcc tgt gca gcc tca gga ttc act ttc aga acc tat      96
Ser Met Lys Leu Ser Cys Ala Ala Ser Gly Phe Thr Phe Arg Thr Tyr
```

```
                    20                  25                  30
ggc atg gcc tgg gtc cgc cag gct cca acg aag ggt ctg gag tgg gtc      144
Gly Met Ala Trp Val Arg Gln Ala Pro Thr Lys Gly Leu Glu Trp Val
        35                  40                  45 gca tcc att agt act ggt ggt ggt agc act tac tat cgc gac tcc gtg      192
Ala Ser Ile Ser Thr Gly Gly Gly Ser Thr Tyr Tyr Arg Asp Ser Val
 50                  55                  60 aag ggc cga ttc act atc tcc aga gat aat gca aaa agc acc cta tac      240
Lys Gly Arg Phe Thr Ile Ser Arg Asp Asn Ala Lys Ser Thr Leu Tyr
 65                  70                  75                  80 ctg caa atg gac agt ctg agg tct gag gac acg gcc act tat tac tgt      288
Leu Gln Met Asp Ser Leu Arg Ser Glu Asp Thr Ala Thr Tyr Tyr Cys
                 85                  90                  95 aca aca gat cta att aac tac ccg ggt ata ggg ggg ttt gct ttc tgg      336
Thr Thr Asp Leu Ile Asn Tyr Pro Gly Ile Gly Gly Phe Ala Phe Trp
            100                 105                 110 ggc caa ggc act ctg gtc act gtc tct tca                              366
Gly Gln Gly Thr Leu Val Thr Val Ser Ser
        115                 120
```

<210> SEQ ID NO 2
<211> LENGTH: 122
<212> TYPE: PRT
<213> ORGANISM: Rattus norvegicus

<400> SEQUENCE: 2

```
Glu Val Glu Leu Val Glu Ser Gly Gly Gly Leu Val Gln Pro Gly Arg
 1               5                  10                  15

Ser Met Lys Leu Ser Cys Ala Ala Ser Gly Phe Thr Phe Arg Thr Tyr
                20                  25                  30

Gly Met Ala Trp Val Arg Gln Ala Pro Thr Lys Gly Leu Glu Trp Val
        35                  40                  45

Ala Ser Ile Ser Thr Gly Gly Gly Ser Thr Tyr Tyr Arg Asp Ser Val
 50                  55                  60

Lys Gly Arg Phe Thr Ile Ser Arg Asp Asn Ala Lys Ser Thr Leu Tyr
 65                  70                  75                  80

Leu Gln Met Asp Ser Leu Arg Ser Glu Asp Thr Ala Thr Tyr Tyr Cys
                 85                 90                  95

Thr Thr Asp Leu Ile Asn Tyr Pro Gly Ile Gly Gly Phe Ala Phe Trp
            100                 105                 110

Gly Gln Gly Thr Leu Val Thr Val Ser Ser
        115                 120
```

<210> SEQ ID NO 3
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 3

```
aac att gtg atg acc cag tct ccc aaa tcc atg tcc ata tca gta gga       48
Asn Ile Val Met Thr Gln Ser Pro Lys Ser Met Ser Ile Ser Val Gly
 1               5                  10                  15 gac agg gtc acc atg aac tgc aag gcc agt cag aat gtg tat aat aat       96
Asp Arg Val Thr Met Asn Cys Lys Ala Ser Gln Asn Val Tyr Asn Asn
                20                  25                  30 ata gcc tgg tat caa cag aag cca ggg aaa tct cct aaa ctg ttg atc      144
Ile Ala Trp Tyr Gln Gln Lys Pro Gly Lys Ser Pro Lys Leu Leu Ile
```

```
                35                  40                  45
tac tat gca tct aac cgg tac act ggg gtc cct gat cgc ttc aca ggc      192
Tyr Tyr Ala Ser Asn Arg Tyr Thr Gly Val Pro Asp Arg Phe Thr Gly
        50                  55                  60 agt ggc tct ggg aca gat ttc act ctc acc atc cat agt gtg caa gct      240
Ser Gly Ser Gly Thr Asp Phe Thr Leu Thr Ile His Ser Val Gln Ala
 65                  70                  75                  80 gaa gat gca gcc ttt tat tac tgt cag cgt ctt tac aat tct cct ccg      288
Glu Asp Ala Ala Phe Tyr Tyr Cys Gln Arg Leu Tyr Asn Ser Pro Pro
                 85                  90                  95 acg ttc ggt gga ggc acc aag ctg gaa ttg aaa cgg gct                  327
Thr Phe Gly Gly Gly Thr Lys Leu Glu Leu Lys Arg Ala
                100                 105
```

<210> SEQ ID NO 4
<211> LENGTH: 109
<212> TYPE: PRT
<213> ORGANISM: Rattus norvegicus

<400> SEQUENCE: 4

```
Asn Ile Val Met Thr Gln Ser Pro Lys Ser Met Ser Ile Ser Val Gly
 1               5                  10                  15

Asp Arg Val Thr Met Asn Cys Lys Ala Ser Gln Asn Val Tyr Asn Asn
                20                  25                  30

Ile Ala Trp Tyr Gln Gln Lys Pro Gly Lys Ser Pro Lys Leu Leu Ile
            35                  40                  45

Tyr Tyr Ala Ser Asn Arg Tyr Thr Gly Val Pro Asp Arg Phe Thr Gly
        50                  55                  60

Ser Gly Ser Gly Thr Asp Phe Thr Leu Thr Ile His Ser Val Gln Ala
 65                  70                  75                  80

Glu Asp Ala Ala Phe Tyr Tyr Cys Gln Arg Leu Tyr Asn Ser Pro Pro
                 85                  90                  95

Thr Phe Gly Gly Gly Thr Lys Leu Glu Leu Lys Arg Ala
                100                 105
```

<210> SEQ ID NO 5
<211> LENGTH: 363
<212> TYPE: DNA
<213> ORGANISM: Rattus norvegicus
<220> FEATURE:
<221> NAME/KEY: CDS
<222> LOCATION: (1)..(363)

<400> SEQUENCE: 5

```
gag gtg cag ctg gtg gag tct ggg gga ggc tta gtg cag cct gga agg       48
Glu Val Gln Leu Val Glu Ser Gly Gly Gly Leu Val Gln Pro Gly Arg
 1               5                  10                  15 tcc ctg aaa ctc tcc tgt gca gcc tca gga ttc act tac cgt agc tat       96
Ser Leu Lys Leu Ser Cys Ala Ala Ser Gly Phe Thr Tyr Arg Ser Tyr
                20                  25                  30 gtc atg gcc tgg gtc cgc cag gct cca acg agg ggt ctg gag tgg gtc      144
Val Met Ala Trp Val Arg Gln Ala Pro Thr Arg Gly Leu Glu Trp Val
            35                  40                  45 gca tcc att agt act ggt ggt ggt aac act tac tat cga gac tcc gtg      192
Ala Ser Ile Ser Thr Gly Gly Gly Asn Thr Tyr Tyr Arg Asp Ser Val
        50                  55                  60 aag ggc cga ttc act atc tcc aga gat aat gca aag aac acc cta tac      240
Lys Gly Arg Phe Thr Ile Ser Arg Asp Asn Ala Lys Asn Thr Leu Tyr
 65                  70                  75                  80 cta caa atg gac agt ctg agg tct gag gac acg gcc act tat tac tgt      288
```

```
Leu Gln Met Asp Ser Leu Arg Ser Glu Asp Thr Ala Thr Tyr Tyr Cys
                85                  90                  95 gca gaa gac atg agt aat tcg gga tac ggg ctc ttt gat tac tgg ggc    336
Ala Glu Asp Met Ser Asn Ser Gly Tyr Gly Leu Phe Asp Tyr Trp Gly
            100                 105                 110 caa gga gtc atg gtc aca gtc tcc tca                                363
Gln Gly Val Met Val Thr Val Ser Ser
        115                 120

<210> SEQ ID NO 6
<211> LENGTH: 121
<212> TYPE: PRT
<213> ORGANISM: Rattus norvegicus

<400> SEQUENCE: 6

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Tyr Arg Ser Tyr
            20                  25                  30

Val Met Ala Trp Val Arg Gln Ala Pro Thr Arg Gly Leu Glu Trp Val
        35                  40                  45

Ala Ser Ile Ser Thr Gly Gly Gly Asn Thr Tyr Tyr Arg Asp Ser Val
    50                  55                  60

Lys Gly Arg Phe Thr Ile Ser Arg Asp Asn Ala Lys Asn Thr Leu Tyr
65                  70                  75                  80

Leu Gln Met Asp Ser Leu Arg Ser Glu Asp Thr Ala Thr Tyr Tyr Cys
                85                  90                  95

Ala Glu Asp Met Ser Asn Ser Gly Tyr Gly Leu Phe Asp Tyr Trp Gly
            100                 105                 110

Gln Gly Val Met Val Thr Val Ser Ser
        115                 120

<210> SEQ ID NO 7
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 7 aac att gtg atg acc cag tct ccc aaa tcc atg tcc ata tca gta gga    48
Asn Ile Val Met Thr Gln Ser Pro Lys Ser Met Ser Ile Ser Val Gly
1               5                   10                  15 gac agg gtc acc atg aac tgc aag gcc ggt cag aat gtg gat aat aat    96
Asp Arg Val Thr Met Asn Cys Lys Ala Gly Gln Asn Val Asp Asn Asn
            20                  25                  30 ata gcc tgg tat caa aag aaa cca ggg cag tct cct aaa ctg ttg atc    144
Ile Ala Trp Tyr Gln Lys Lys Pro Gly Gln Ser Pro Lys Leu Leu Ile
        35                  40                  45 tac tat gca tct aac cgg aac act ggg gtc cct gat cgc ttc aca ggc    192
Tyr Tyr Ala Ser Asn Arg Asn Thr Gly Val Pro Asp Arg Phe Thr Gly
    50                  55                  60 ggt gga tat ggg aca gat ttc act ctc acc atc aat agt gtg caa gct    240
Gly Gly Tyr Gly Thr Asp Phe Thr Leu Thr Ile Asn Ser Val Gln Ala
65                  70                  75                  80 gaa gat gca gcc ttt tat tac tgt cag cgt att tcc aat tct ccg tac    288
Glu Asp Ala Ala Phe Tyr Tyr Cys Gln Arg Ile Ser Asn Ser Pro Tyr
                85                  90                  95 acg ttt ggc gct ggg acc gag ctg gaa ctg aaa cgg gct                327
Thr Phe Gly Ala Gly Thr Glu Leu Glu Leu Lys Arg Ala
```

```
Thr Phe Gly Ala Gly Thr Glu Leu Glu Leu Lys Arg Ala
            100                 105
```

```
<210> SEQ ID NO 8
<211> LENGTH: 109
<212> TYPE: PRT
<213> ORGANISM: Rattus norvegicus

<400> SEQUENCE: 8
```

```
Asn Ile Val Met Thr Gln Ser Pro Lys Ser Met Ser Ile Ser Val Gly
1               5                   10                  15

Asp Arg Val Thr Met Asn Cys Lys Ala Gly Gln Asn Val Asp Asn Asn
            20                  25                  30

Ile Ala Trp Tyr Gln Lys Lys Pro Gly Gln Ser Pro Lys Leu Leu Ile
        35                  40                  45

Tyr Tyr Ala Ser Asn Arg Asn Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Ser Asn Ser Pro Tyr
                85                  90                  95

Thr Phe Gly Ala Gly Thr Glu Leu Glu Leu Lys Arg Ala
            100                 105
```

```
<210> SEQ ID NO 9
<211> LENGTH: 363
<212> TYPE: DNA
<213> ORGANISM: Rattus norvegicus
<220> FEATURE:
<221> NAME/KEY: CDS
<222> LOCATION: (1)..(363)

<400> SEQUENCE: 9
```

```
gag gtg cag ctg gtg gag tct ggg gga ggc tta gtg cag cct gga agg      48
Glu Val Gln Leu Val Glu Ser Gly Gly Gly Leu Val Gln Pro Gly Arg
1               5                   10                  15 tcc atg aaa ctc tcc tgt gta gcc tca gga ttc act ttc agt aac tat      96
Ser Met Lys Leu Ser Cys Val Ala Ser Gly Phe Thr Phe Ser Asn Tyr
            20                  25                  30 tac atg gcc tgg gtc cgc cag gct cca acg aag ggt ctg gag tgg gtc     144
Tyr Met Ala Trp Val Arg Gln Ala Pro Thr Lys Gly Leu Glu Trp Val
        35                  40                  45 gca tcc att agt act ggt ggt ggt aac act tac tat cga gac tcc gtg     192
Ala Ser Ile Ser Thr Gly Gly Gly Asn Thr Tyr Tyr Arg Asp Ser Val
    50                  55                  60 aag ggc cga ttc act atc tcc aga gat aat gca aaa agc acc cta tac     240
Lys Gly Arg Phe Thr Ile Ser Arg Asp Asn Ala Lys Ser Thr Leu Tyr
65                  70                  75                  80 ctg caa atg gac agt ctg agg tct gag gac acg gcc act tat tac tgt     288
Leu Gln Met Asp Ser Leu Arg Ser Glu Asp Thr Ala Thr Tyr Tyr Cys
                85                  90                  95 gca aga ccc cca tat ggc tat aac tac ggt tgg ttt act tac tgg ggc     336
Ala Arg Pro Pro Tyr Gly Tyr Asn Tyr Gly Trp Phe Thr Tyr Trp Gly
            100                 105                 110 caa ggc act ctg gtc act gtc tct tca                                 363
Gln Gly Thr Leu Val Thr Val Ser Ser
            115                 120
```

```
<210> SEQ ID NO 10
<211> LENGTH: 121
<212> TYPE: PRT
```

<213> ORGANISM: Rattus norvegicus

<400> SEQUENCE: 10

```
Glu Val Gln Leu Val Glu Ser Gly Gly Gly Leu Val Gln Pro Gly Arg
1               5                   10                  15

Ser Met Lys Leu Ser Cys Val Ala Ser Gly Phe Thr Phe Ser Asn Tyr
            20                  25                  30

Tyr Met Ala Trp Val Arg Gln Ala Pro Thr Lys Gly Leu Glu Trp Val
        35                  40                  45

Ala Ser Ile Ser Thr Gly Gly Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Arg Pro Pro Tyr Gly Tyr Asn Tyr Gly Trp Phe Thr Tyr Trp Gly
            100                 105                 110

Gln Gly Thr Leu Val Thr Val Ser Ser
            115                 120
```

<210> SEQ ID NO 11
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 11

```
gac atc cag atg aca cag tct cca gct tcc ctg tct gca tct ctg gga      48
Asp Ile Gln Met Thr Gln Ser Pro Ala Ser Leu Ser Ala Ser Leu Gly
1               5                   10                  15 gaa act gtc acc atc gaa tgt cga gca agt gag gac att cac aat ggt      96
Glu Thr Val Thr Ile Glu Cys Arg Ala Ser Glu Asp Ile His Asn Gly
            20                  25                  30 tta gta tgg tat cag cag aag cca ggg aaa tct cct cag ctc ctg atc     144
Leu Val Trp Tyr Gln Gln Lys Pro Gly Lys Ser Pro Gln Leu Leu Ile
        35                  40                  45 tat aat gca aat agt atg cat act ggg gtc cca tca cgg ttc agt ggc     192
Tyr Asn Ala Asn Ser Met His Thr Gly Val Pro Ser Arg Phe Ser Gly
    50                  55                  60 agt gga tct ggt aca cag tat tct ctc aag ata aac agc ctg cag tct     240
Ser Gly Ser Gly Thr Gln Tyr Ser Leu Lys Ile Asn Ser Leu Gln Ser
65                  70                  75                  80 gaa gat gtc gca agt tat ttc tgt caa cag tat tac aat tat cct cgg     288
Glu Asp Val Ala Ser Tyr Phe Cys Gln Gln Tyr Tyr Asn Tyr Pro Arg
                85                  90                  95 acg ttc ggt gga ggc acc aag ctg gaa ttg aaa cgg gct                 327
Thr Phe Gly Gly Gly Thr Lys Leu Glu Leu Lys Arg Ala
            100                 105
```

<210> SEQ ID NO 12
<211> LENGTH: 109
<212> TYPE: PRT
<213> ORGANISM: Rattus norvegicus

<400> SEQUENCE: 12

```
Asp Ile Gln Met Thr Gln Ser Pro Ala Ser Leu Ser Ala Ser Leu Gly
1               5                   10                  15

Glu Thr Val Thr Ile Glu Cys Arg Ala Ser Glu Asp Ile His Asn Gly
```

```
                    20                  25                  30
Leu Val Trp Tyr Gln Gln Lys Pro Gly Lys Ser Pro Gln Leu Leu Ile
            35                  40                  45

Tyr Asn Ala Asn Ser Met His Thr Gly Val Pro Ser Arg Phe Ser Gly
        50                  55                  60

Ser Gly Ser Gly Thr Gln Tyr Ser Leu Lys Ile Asn Ser Leu Gln Ser
 65                 70                  75                  80

Glu Asp Val Ala Ser Tyr Phe Cys Gln Gln Tyr Tyr Asn Tyr Pro Arg
                85                  90                  95

Thr Phe Gly Gly Gly Thr Lys Leu Glu Leu Lys Arg Ala
            100                 105

<210> SEQ ID NO 13
<211> LENGTH: 369
<212> TYPE: DNA
<213> ORGANISM: Rattus norvegicus
<220> FEATURE:
<221> NAME/KEY: CDS
<222> LOCATION: (1)..(369)

<400> SEQUENCE: 13 gag gtg cag ctg gtg gag tct ggg gga ggc tta gtg cag cct gga agg      48
Glu Val Gln Leu Val Glu Ser Gly Gly Gly Leu Val Gln Pro Gly Arg
 1               5                  10                  15 tcc ctg aaa ctc tcc tgt gca gcc tca gga ttc act tat cgt acc tat     96
Ser Leu Lys Leu Ser Cys Ala Ala Ser Gly Phe Thr Tyr Arg Thr Tyr
            20                  25                  30 gtc atg gcc tgg gtc cgc cag ggt cca acg cag ggt ctg gag tgg gtc    144
Val Met Ala Trp Val Arg Gln Gly Pro Thr Gln Gly Leu Glu Trp Val
        35                  40                  45 gca tcc att agt act ggt ggt gtt agc act tat tat cga gac tcc gtg    192
Ala Ser Ile Ser Thr Gly Gly Val Ser Thr Tyr Tyr Arg Asp Ser Val
    50                  55                  60 aag ggc cga ttc act atc tcc aga gat aat gca aaa aac acc cta tac    240
Lys Gly Arg Phe Thr Ile Ser Arg Asp Asn Ala Lys Asn Thr Leu Tyr
 65                 70                  75                  80 ttg caa atg gac agt ctg agg tct gag gac acg gcc act tat tac tgt    288
Leu Gln Met Asp Ser Leu Arg Ser Glu Asp Thr Ala Thr Tyr Tyr Cys
                85                  90                  95 gca aaa gac atg ttg aat ggt tat aac tct cag ggg ctt ttt gat tac    336
Ala Lys Asp Met Leu Asn Gly Tyr Asn Ser Gln Gly Leu Phe Asp Tyr
            100                 105                 110 tgg ggc caa gga gtc atg gtc aca gtc tcc tca                        369
Trp Gly Gln Gly Val Met Val Thr Val Ser Ser
        115                 120

<210> SEQ ID NO 14
<211> LENGTH: 123
<212> TYPE: PRT
<213> ORGANISM: Rattus norvegicus

<400> SEQUENCE: 14

Glu Val Gln Leu Val Glu Ser Gly Gly Gly Leu Val Gln Pro Gly Arg
 1               5                  10                  15

Ser Leu Lys Leu Ser Cys Ala Ala Ser Gly Phe Thr Tyr Arg Thr Tyr
            20                  25                  30

Val Met Ala Trp Val Arg Gln Gly Pro Thr Gln Gly Leu Glu Trp Val
        35                  40                  45

Ala Ser Ile Ser Thr Gly Gly Val Ser Thr Tyr Tyr Arg Asp Ser Val
    50                  55                  60
```

```
Lys Gly Arg Phe Thr Ile Ser Arg Asp Asn Ala Lys Asn Thr Leu Tyr
 65                  70                  75                  80

Leu Gln Met Asp Ser Leu Arg Ser Glu Asp Thr Ala Thr Tyr Tyr Cys
                 85                  90                  95

Ala Lys Asp Met Leu Asn Gly Tyr Asn Ser Gln Gly Leu Phe Asp Tyr
            100                 105                 110

Trp Gly Gln Gly Val Met Val Thr Val Ser Ser
        115                 120

<210> SEQ ID NO 15
<211> LENGTH: 327
<212> TYPE: DNA
<213> ORGANISM: Rattus norvegicus
<220> FEATURE:
<221> NAME/KEY: CDS
<222> LOCATION: (1)..(327)

<400> SEQUENCE: 15 aac att gtg atg acc cag tct ccc aaa tcc atg tcc ata tca gtg gga     48
Asn Ile Val Met Thr Gln Ser Pro Lys Ser Met Ser Ile Ser Val Gly
 1               5                  10                  15 gac agg gtc acc atg aac tgc agg gcc agt cag aat gtg gat aat act    96
Asp Arg Val Thr Met Asn Cys Arg Ala Ser Gln Asn Val Asp Asn Thr
            20                  25                  30 ata gcc tgg tat caa cag aaa cca ggg cag tct cct aaa ctg ttg atc   144
Ile Ala Trp Tyr Gln Gln Lys Pro Gly Gln Ser Pro Lys Leu Leu Ile
        35                  40                  45 tac ttt gca tct gac cgg tac act ggg gtc cct gat cgc ttc aca ggc   192
Tyr Phe Ala Ser Asp Arg Tyr Thr Gly Val Pro Asp Arg Phe Thr Gly
    50                  55                  60 ggt gga tat ggg aca gat ttc act ctc acc atc aat agt gtg caa gct   240
Gly Gly Tyr Gly Thr Asp Phe Thr Leu Thr Ile Asn Ser Val Gln Ala
65                  70                  75                  80 gaa gat gca gcc ttt tat tac tgt cag cgt att tac aat tct cca ctc   288
Glu Asp Ala Ala Phe Tyr Tyr Cys Gln Arg Ile Tyr Asn Ser Pro Leu
                85                  90                  95 acg ttc ggt tct ggg acc aag ctg gag atc aga cgg gct                327
Thr Phe Gly Ser Gly Thr Lys Leu Glu Ile Arg Arg Ala
            100                 105

<210> SEQ ID NO 16
<211> LENGTH: 109
<212> TYPE: PRT
<213> ORGANISM: Rattus norvegicus

<400> SEQUENCE: 16

Asn Ile Val Met Thr Gln Ser Pro Lys Ser Met Ser Ile Ser Val Gly
 1               5                  10                  15

Asp Arg Val Thr Met Asn Cys Arg Ala Ser Gln Asn Val Asp Asn Thr
            20                  25                  30

Ile Ala Trp Tyr Gln Gln Lys Pro Gly Gln Ser Pro Lys Leu Leu Ile
        35                  40                  45

Tyr Phe Ala Ser Asp Arg Tyr Thr Gly Val Pro Asp Arg Phe Thr Gly
    50                  55                  60

Gly Gly Tyr Gly Thr Asp Phe Thr Leu Thr Ile Asn Ser Val Gln Ala
65                  70                  75                  80

Glu Asp Ala Ala Phe Tyr Tyr Cys Gln Arg Ile Tyr Asn Ser Pro Leu
                85                  90                  95

Thr Phe Gly Ser Gly Thr Lys Leu Glu Ile Arg Arg Ala
```

<210> SEQ ID NO 17
<211> LENGTH: 357
<212> TYPE: DNA
<213> ORGANISM: Rattus norvegicus
<220> FEATURE:
<221> NAME/KEY: CDS
<222> LOCATION: (1)..(357)

<400> SEQUENCE: 17

| | | | | | | | | | | | | | | | | |
|---|---|---|---|---|---|---|---|---|---|---|---|---|---|---|---|---|
| gag | gtg | cag | ctg | gtg | gaa | tct | ggg | gga | ggc | tta | gtg | cag | cct | gga | agg | 48 |
| Glu | Val | Gln | Leu | Val | Glu | Ser | Gly | Gly | Gly | Leu | Val | Gln | Pro | Gly | Arg | |
| 1 | | | | 5 | | | | | 10 | | | | | 15 | | |
| tcc | ctg | aaa | ctc | tcc | tgt | gca | gcc | tca | gga | ttc | act | ttc | agt | tcc | tat | 96 |
| Ser | Leu | Lys | Leu | Ser | Cys | Ala | Ala | Ser | Gly | Phe | Thr | Phe | Ser | Ser | Tyr | |
| | | | 20 | | | | | 25 | | | | | 30 | | | |
| tac | atg | gcc | tgg | gtc | cgc | cag | gct | cca | acg | aag | ggt | ctg | gag | tgg | gtc | 144 |
| Tyr | Met | Ala | Trp | Val | Arg | Gln | Ala | Pro | Thr | Lys | Gly | Leu | Glu | Trp | Val | |
| | | 35 | | | | | 40 | | | | | 45 | | | | |
| gca | tac | atc | agt | aat | ggt | ggt | tat | agc | act | tac | tat | cga | gac | tcc | gtg | 192 |
| Ala | Tyr | Ile | Ser | Asn | Gly | Gly | Tyr | Ser | Thr | Tyr | Tyr | Arg | Asp | Ser | Val | |
| 50 | | | | | 55 | | | | | 60 | | | | | | |
| aag | ggc | cga | ttc | act | atc | tcc | aga | gaa | aat | gca | aaa | agc | acc | ctt | tac | 240 |
| Lys | Gly | Arg | Phe | Thr | Ile | Ser | Arg | Glu | Asn | Ala | Lys | Ser | Thr | Leu | Tyr | |
| 65 | | | | 70 | | | | | 75 | | | | | 80 | | |
| ctg | caa | atg | gac | agt | ctg | agg | tct | gag | gac | acg | gcc | act | tat | tac | tgt | 288 |
| Leu | Gln | Met | Asp | Ser | Leu | Arg | Ser | Glu | Asp | Thr | Ala | Thr | Tyr | Tyr | Cys | |
| | | | | 85 | | | | | 90 | | | | | 95 | | |
| aca | atc | aca | gat | cat | tcg | ggg | tac | agg | ttt | act | tac | tgg | ggc | caa | ggc | 336 |
| Thr | Ile | Thr | Asp | His | Ser | Gly | Tyr | Arg | Phe | Thr | Tyr | Trp | Gly | Gln | Gly | |
| | | | | 100 | | | | | 105 | | | | | 110 | | |
| act | ctg | gtc | act | gtc | tct | tca | | | | | | | | | | 357 |
| Thr | Leu | Val | Thr | Val | Ser | Ser | | | | | | | | | | |
| | | | | 115 | | | | | | | | | | | | |

<210> SEQ ID NO 18
<211> LENGTH: 119
<212> TYPE: PRT
<213> ORGANISM: Rattus norvegicus

<400> SEQUENCE: 18

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Ser Tyr
            20                  25                  30

Tyr Met Ala Trp Val Arg Gln Ala Pro Thr Lys Gly Leu Glu Trp Val
        35                  40                  45

Ala Tyr Ile Ser Asn Gly Gly Tyr Ser Thr Tyr Tyr Arg Asp Ser Val
    50                  55                  60

Lys Gly Arg Phe Thr Ile Ser Arg Glu Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Ile Thr Asp His Ser Gly Tyr Arg Phe Thr Tyr Trp Gly Gln Gly
            100                 105                 110

Thr Leu Val Thr Val Ser Ser
        115

<210> SEQ ID NO 19

```
<211> LENGTH: 324
<212> TYPE: DNA
<213> ORGANISM: Rattus norvegicus
<220> FEATURE:
<221> NAME/KEY: CDS
<222> LOCATION: (1)..(324)

<400> SEQUENCE: 19 gac atc cag atg acc cag tct cct tca ctc ctg tca gca tct gtg gga    48
Asp Ile Gln Met Thr Gln Ser Pro Ser Leu Leu Ser Ala Ser Val Gly
1               5                   10                  15 gac aga gtc act ctc agc tgc aaa gca agt cag agt att tac aac agc    96
Asp Arg Val Thr Leu Ser Cys Lys Ala Ser Gln Ser Ile Tyr Asn Ser
            20                  25                  30 tta gcc tgg tat cag caa aaa ctt gga gaa gct ccc aaa ctc ctc ata   144
Leu Ala Trp Tyr Gln Gln Lys Leu Gly Glu Ala Pro Lys Leu Leu Ile
        35                  40                  45 tat gat gca aac agt ttg caa acg ggc atc cca tca agg ttc agt ggc   192
Tyr Asp Ala Asn Ser Leu Gln Thr Gly Ile Pro Ser Arg Phe Ser Gly
50                  55                  60 agt gga tct ggt aca gat ttc aca ctc acc atc agc agc ctg cag cct   240
Ser Gly Ser Gly Thr Asp Phe Thr Leu Thr Ile Ser Ser Leu Gln Pro
65                  70                  75                  80 gaa gat gtt gcc aca tat ttc tgc cag aag tat tat agc ggg aac acg   288
Glu Asp Val Ala Thr Tyr Phe Cys Gln Lys Tyr Tyr Ser Gly Asn Thr
                85                  90                  95 ttt gga gct ggg acc aag ctg gaa ctg aaa cgg gct                   324
Phe Gly Ala Gly Thr Lys Leu Glu Leu Lys Arg Ala
            100                 105

<210> SEQ ID NO 20
<211> LENGTH: 108
<212> TYPE: PRT
<213> ORGANISM: Rattus norvegicus

<400> SEQUENCE: 20

Asp Ile Gln Met Thr Gln Ser Pro Ser Leu Leu Ser Ala Ser Val Gly
1               5                   10                  15

Asp Arg Val Thr Leu Ser Cys Lys Ala Ser Gln Ser Ile Tyr Asn Ser
            20                  25                  30

Leu Ala Trp Tyr Gln Gln Lys Leu Gly Glu Ala Pro Lys Leu Leu Ile
        35                  40                  45

Tyr Asp Ala Asn Ser Leu Gln Thr Gly Ile Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Lys Tyr Tyr Ser Gly Asn Thr
                85                  90                  95

Phe Gly Ala Gly Thr Lys Leu Glu Leu Lys Arg Ala
            100                 105

<210> SEQ ID NO 21
<211> LENGTH: 449
<212> TYPE: DNA
<213> ORGANISM: Homo sapiens

<400> SEQUENCE: 21
gcctccggac tctagagcca ccatggtgct gcagacccag gtgttcatct ccctgctgct    60
gtggatctcc ggcgcgtacg gcgatatcgt gatgattaaa cgtacggtgg ccgcccctc   120 cgtgttcatc ttccccccct ccgacgagca gctgaagtcc ggcaccgcct ccgtggtgtg   180
```

```
cctgctgaat aacttctacc ccagagaggc caaggtgcag tggaaggtgg acaacgccct        240
gcagtccggg aactcccagg agagcgtgac cgagcaggac agcaaggaca gcacctacag        300
cctgagcagc accctgaccc tgagcaaagc cgactacgag aagcacaagg tgtacgcctg        360
cgaggtgacc caccagggcc tgagctcccc cgtcaccaag agcttcaaca ggggggagtg        420
ttagggcccc gtttaaacgg gggaggcta                                          449
```

```
<210> SEQ ID NO 22
<211> LENGTH: 1132
<212> TYPE: DNA
<213> ORGANISM: Homo sapiens

<400> SEQUENCE: 22
gcctccggac tctagagcca ccatgaaaca cctgtggttc ttcctcctgc tggtggcagc         60
tcccagatgg gtgctgagcc aggtgcaatt gtgcaggcgg ttagctcagc ctccaccaag        120
ggcccaagcg tcttcccct ggcaccctcc tccaagagca cctctggcgg cacagccgcc        180
ctgggctgcc tggtcaagga ctacttcccc gaacccgtga ccgtgagctg gaactcaggc        240
gccctgacca gcggcgtgca caccttcccc gctgtcctgc agtcctcagg actctactcc        300
ctcagcagcg tggtgaccgt gccctccagc agcttgggca cccagaccta catctgcaac        360
gtgaatcaca gcccagcaa caccaaggtg gacaagagag ttgagcccaa atcttgtgac        420
aaaactcaca catgcccacc ctgcccagca cctgaactcc tggggggacc ctcagtcttc        480
ctcttccccc caaaacccaa ggacaccctc atgatctccc ggacccctga ggtcacatgc        540
gtggtggtgg acgtgagcca cgaagaccct gaggtcaagt tcaactggta cgtggacggc        600
gtggaggtgc ataatgccaa gacaaagccc cgggaggagc agtacaacag cacgtaccgg        660
gtggtcagcg tcctcaccgt cctgcaccag gactggctga atggcaagga gtacaagtgc        720
aaggtctcca acaaagccct cccagccccc atcgagaaaa ccatctccaa agccaaaggc        780
cagccccggg aaccacaggt gtacaccctg cccccatccc gggaggagat gaccaagaac        840
caggtcagcc tgacctgcct ggtcaaaggc ttctatccca gcgacatcgc cgtggagtgg        900
gagagcaatg ccagcccga gaacaactac aagaccaccc tcccgtgct ggactccgac        960 ggctccttct tcctctacag caagctcacc gtggacaaga gcaggtggca gcagggcaac       1020
gtcttctcat gctccgtgat gcatgaggct ctgcacaacc actacaccca gaagagcctc       1080
tccctgtctc ccggcaaatg agatatcggg cccgtttaaa cggggggaggc ta              1132
```

```
<210> SEQ ID NO 23
<211> LENGTH: 1410
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (1)..(1410)

<400> SEQUENCE: 23 atg aaa cac ctg tgg ttc ttc ctc ctg ctg gtg gca gct ccc aga tgg          48
Met Lys His Leu Trp Phe Phe Leu Leu Leu Val Ala Ala Pro Arg Trp
1               5                   10                  15 gtg ctg agc gag gtg cag ctg gtg gag tct ggg gga ggc tta gtg cag          96
Val Leu Ser Glu Val Gln Leu Val Glu Ser Gly Gly Gly Leu Val Gln
            20                  25                  30 cct gga agg tcc ctg aaa ctc tcc tgt gca gcc tca gga ttc act tac         144
```

-continued

| | | | | | | | | | | | | | | |
|---|---|---|---|---|---|---|---|---|---|---|---|---|---|---|
| Pro | Gly | Arg | Ser | Leu | Lys | Leu | Ser | Cys | Ala | Ala | Ser | Gly | Phe | Thr | Tyr |
| | | 35 | | | | 40 | | | | | 45 | | | | |

```
cgt agc tat gtc atg gcc tgg gtc cgc cag gct cca acg agg ggt ctg      192
Arg Ser Tyr Val Met Ala Trp Val Arg Gln Ala Pro Thr Arg Gly Leu
    50                  55                  60 gag tgg gtc gca tcc att agt act ggt ggt ggt aac act tac tat cga      240
Glu Trp Val Ala Ser Ile Ser Thr Gly Gly Gly Asn Thr Tyr Tyr Arg
65                  70                  75                  80 gac tcc gtg aag ggc cga ttc act atc tcc aga gat aat gca aag aac      288
Asp Ser Val Lys Gly Arg Phe Thr Ile Ser Arg Asp Asn Ala Lys Asn
                85                  90                  95 acc cta tac cta caa atg gac agt ctg agg tct gag gac acg gcc act      336
Thr Leu Tyr Leu Gln Met Asp Ser Leu Arg Ser Glu Asp Thr Ala Thr
            100                 105                 110 tat tac tgt gca gaa gac atg agt aat tcg gga tac ggg ctc ttt gat      384
Tyr Tyr Cys Ala Glu Asp Met Ser Asn Ser Gly Tyr Gly Leu Phe Asp
        115                 120                 125 tac tgg ggc caa gga gtc atg gtc aca gtc agc tca gcc tcc acc aag      432
Tyr Trp Gly Gln Gly Val Met Val Thr Val Ser Ser Ala Ser Thr Lys
    130                 135                 140 ggc cca agc gtc ttc ccc ctg gca ccc tcc tcc aag agc acc tct ggc      480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc      528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc      576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg      624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac      672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc      720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa      768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350
```

```
gcc ccc atc gag aaa acc atc tcc aaa gcc aaa ggc cag ccc cgg gaa      1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac      1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc      1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc      1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag      1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc      1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc      1392
Ser Val Met His Glu Ala Leu His Asn His Tyr Thr Gln Lys Ser Leu
    450                 455                 460 tcc ctg tct ccc ggc aaa                                              1410
Ser Leu Ser Pro Gly Lys
465                 470

<210> SEQ ID NO 24
<211> LENGTH: 470
<212> TYPE: PRT
<213> ORGANISM: Artificial Sequence
<220> FEATURE:
<223> OTHER INFORMATION: Synthetic Construct

<400> SEQUENCE: 24

Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
                20                  25                  30

Pro Gly Arg Ser Leu Lys Leu Ser Cys Ala Ala Ser Gly Phe Thr Tyr
            35                  40                  45

Arg Ser Tyr Val Met Ala Trp Val Arg Gln Ala Pro Thr Arg Gly Leu
        50                  55                  60

Glu Trp Val Ala Ser Ile Ser Thr Gly Gly Gly Asn Thr Tyr Tyr Arg
65                  70                  75                  80

Asp Ser Val Lys Gly Arg Phe Thr Ile Ser Arg Asp Asn Ala Lys Asn
                85                  90                  95

Thr Leu Tyr Leu Gln Met Asp Ser Leu Arg Ser Glu Asp Thr Ala Thr
            100                 105                 110

Tyr Tyr Cys Ala Glu Asp Met Ser Asn Ser Gly Tyr Gly Leu Phe Asp
        115                 120                 125

Tyr Trp Gly Gln Gly Val Met Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
```

```
                195                 200                 205
    Val Thr Val Pro Ser Ser Leu Gly Thr Gln Thr Tyr Ile Cys Asn
        210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 25
<211> LENGTH: 702
<212> TYPE: DNA
<213> ORGANISM: Artificial Sequence
<220> FEATURE:
<223> OTHER INFORMATION: chimeric
<220> FEATURE:
<221> NAME/KEY: CDS
<222> LOCATION: (1)..(702)

<400> SEQUENCE: 25 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc aac att gtg atg acc cag tct ccc aaa tcc atg tcc      96
Gly Ala Tyr Gly Asn Ile Val Met Thr Gln Ser Pro Lys Ser Met Ser
            20                  25                  30 ata tca gta gga gac agg gtc acc atg aac tgc aag gcc ggt cag aat     144
Ile Ser Val Gly Asp Arg Val Thr Met Asn Cys Lys Ala Gly Gln Asn
        35                  40                  45 gtg gat aat aat ata gcc tgg tat caa aag aaa cca ggg cag tct cct     192
```

```
Val Asp Asn Asn Ile Ala Trp Tyr Gln Lys Lys Pro Gly Gln Ser Pro
 50                  55                  60 aaa ctg ttg atc tac tat gca tct aac cgg aac act ggg gtc cct gat      240
Lys Leu Leu Ile Tyr Tyr Ala Ser Asn Arg Asn Thr Gly Val Pro Asp
 65                  70                  75                  80 cgc ttc aca ggc ggt gga tat ggg aca gat ttc act ctc acc atc aat      288
Arg Phe Thr Gly Gly Gly Tyr Gly Thr Asp Phe Thr Leu Thr Ile Asn
                     85                  90                  95 agt gtg caa gct gaa gat gca gcc ttt tat tac tgt cag cgt att tcc      336
Ser Val Gln Ala Glu Asp Ala Ala Phe Tyr Tyr Cys Gln Arg Ile Ser
                100                 105                 110 aat tct ccg tac acg ttt ggc gct ggg acc gag ctg gaa ctg aaa cgg      384
Asn Ser Pro Tyr Thr Phe Gly Ala Gly Thr Glu Leu Glu Leu Lys Arg
                115                 120                 125 gct gtg gcc gcc ccc tcc gtg ttc atc ttc ccc ccc tcc gac gag cag      432
Ala Val Ala Ala Pro Ser Val Phe Ile Phe Pro Pro Ser Asp Glu Gln
130                 135                 140 ctg aag tcc ggc acc gcc tcc gtg gtg tgc ctg ctg aat aac ttc tac      480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc      528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc      576
Gly Asn Ser Gln Glu Ser Val Thr Glu Gln Asp Ser Lys Asp Ser Thr
                180                 185                 190 tac agc ctg agc agc acc ctg acc ctg agc aaa gcc gac tac gag aag      624
Tyr Ser Leu Ser Ser Thr Leu Thr Leu Ser Lys Ala Asp Tyr Glu Lys
                195                 200                 205 cac aag gtg tac gcc tgc gag gtg acc cac cag ggc ctg agc tcc ccc      672
His Lys Val Tyr Ala Cys Glu Val Thr His Gln Gly Leu Ser Ser Pro
210                 215                 220 gtc acc aag agc ttc aac agg ggg gag tgt                              702
Val Thr Lys Ser Phe Asn Arg Gly Glu Cys
225                 230

<210> SEQ ID NO 26
<211> LENGTH: 234
<212> TYPE: PRT
<213> ORGANISM: Artificial Sequence
<220> FEATURE:
<223> OTHER INFORMATION: Synthetic Construct

<400> SEQUENCE: 26

Met Val Leu Gln Thr Gln Val Phe Ile Ser Leu Leu Leu Trp Ile Ser
 1               5                  10                  15

Gly Ala Tyr Gly Asn Ile Val Met Thr Gln Ser Pro Lys Ser Met Ser
                20                  25                  30

Ile Ser Val Gly Asp Arg Val Thr Met Asn Cys Lys Ala Gly Gln Asn
             35                  40                  45

Val Asp Asn Asn Ile Ala Trp Tyr Gln Lys Lys Pro Gly Gln Ser Pro
 50                  55                  60

Lys Leu Leu Ile Tyr Tyr Ala Ser Asn Arg Asn Thr Gly Val Pro Asp
 65                  70                  75                  80

Arg Phe Thr Gly Gly Gly Tyr Gly Thr Asp Phe Thr Leu Thr Ile Asn
                85                  90                  95

Ser Val Gln Ala Glu Asp Ala Ala Phe Tyr Tyr Cys Gln Arg Ile Ser
                100                 105                 110

Asn Ser Pro Tyr Thr Phe Gly Ala Gly Thr Glu Leu Glu Leu Lys Arg
```

```
            115                 120                 125
Ala Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 27
<211> LENGTH: 1410
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(1410)

<400> SEQUENCE: 27 atg aaa cac ctg tgg ttc ttc ctc ctg ctg gtg gca gct ccc aga tgg      48
Met Lys His Leu Trp Phe Phe Leu Leu Leu Val Ala Ala Pro Arg Trp
1               5                   10                  15 gtg ctg agc gaa gtg cag ctg gtg gaa tct ggc ggc gga ctg gtg cag      96
Val Leu Ser Glu Val Gln Leu Val Glu Ser Gly Gly Gly Leu Val Gln
            20                  25                  30 cct ggc gga tct ctg aga ctg agc tgt gcc gcc agc ggc ttc acc tac      144
Pro Gly Gly Ser Leu Arg Leu Ser Cys Ala Ala Ser Gly Phe Thr Tyr
        35                  40                  45 cgg tct tac gtg atg gcc tgg gtg cgc cag gcc cct gga aaa gga ctg      192
Arg Ser Tyr Val Met Ala Trp Val Arg Gln Ala Pro Gly Lys Gly Leu
    50                  55                  60 gaa tgg gtg gga tcc atc agc acc ggc gga ggc aac acc tac tac cgg      240
Glu Trp Val Gly Ser Ile Ser Thr Gly Gly Gly Asn Thr Tyr Tyr Arg
65                  70                  75                  80 gat agc gtg aag ggc cgg ttc acc atc agc cgg gac aac gcc aag aac      288
Asp Ser Val Lys Gly Arg Phe Thr Ile Ser Arg Asp Asn Ala Lys Asn
                85                  90                  95 acc ctg tac ctg cag atg aac agc ctg cgg gcc gag gac acc gcc gtg      336
Thr Leu Tyr Leu Gln Met Asn Ser Leu Arg Ala Glu Asp Thr Ala Val
            100                 105                 110 tac tat tgc gcc gag gat atg agc aac agc ggc tac ggc ctg ttc gac      384
Tyr Tyr Cys Ala Glu Asp Met Ser Asn Ser Gly Tyr Gly Leu Phe Asp
        115                 120                 125 tac tgg ggc cag gga acc ctc gtg acc gtc agc tca gcc tcc acc aag      432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc      480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc      528
Gly Thr Ala Ala Leu Gly Cys Leu Val Lys Asp Tyr Phe Pro Glu Pro
                165                 170                 175
```

-continued

```
gtg acc gtg agc tgg aac tca ggc gcc ctg acc agc ggc gtg cac acc      576
Val Thr Val Ser Trp Asn Ser Gly Ala Leu Thr Ser Gly Val His Thr
            180                 185                 190 ttc ccc gct gtc ctg cag tcc tca gga ctc tac tcc ctc agc agc gtg      624
Phe Pro Ala Val Leu Gln Ser Ser Gly Leu Tyr Ser Leu Ser Ser Val
        195                 200                 205 gtg acc gtg ccc tcc agc agc ttg ggc acc cag acc tac atc tgc aac      672
Val Thr Val Pro Ser Ser Ser Leu Gly Thr Gln Thr Tyr Ile Cys Asn
        210                 215                 220 gtg aat cac aag ccc agc aac acc aag gtg gac aag aga gtt gag ccc      720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa      768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac      816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac      864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc      912
Val Ser His Glu Asp Pro Glu Val Lys Phe Asn Trp Tyr Val Asp Gly
        290                 295                 300 gtg gag gtg cat aat gcc aag aca aag ccc cgg gag gag cag tac aac      960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg     1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca     1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa     1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac     1152
Pro Gln Val Tyr Thr Leu Pro Pro Ser Arg Glu Glu Met Thr Lys Asn
        370                 375                 380 cag gtc agc ctg acc tgc ctg gtc aaa ggc ttc tat ccc agc gac atc     1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc     1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag     1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc     1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc     1392
Ser Val Met His Glu Ala Leu His Asn His Tyr Thr Gln Lys Ser Leu
        450                 455                 460 tcc ctg tct ccc ggc aaa                                              1410
Ser Leu Ser Pro Gly Lys
465                 470
```

<210> SEQ ID NO 28

<211> LENGTH: 470
<212> TYPE: PRT
<213> ORGANISM: Artificial Sequence
<220> FEATURE:
<223> OTHER INFORMATION: Synthetic Construct

<400> SEQUENCE: 28

```
Met Lys His Leu Trp Phe Phe Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Tyr
            35                  40                  45

Arg Ser Tyr Val Met Ala Trp Val Arg Gln Ala Pro Gly Lys Gly Leu
    50                  55                  60

Glu Trp Val Gly Ser Ile Ser Thr Gly Gly Asn Thr Tyr Tyr Arg
65                  70                  75                  80

Asp Ser Val Lys Gly Arg Phe Thr Ile Ser Arg Asp Asn Ala Lys Asn
                85                  90                  95

Thr Leu Tyr Leu Gln Met Asn Ser Leu Arg Ala Glu Asp Thr Ala Val
            100                 105                 110

Tyr Tyr Cys Ala Glu Asp Met Ser Asn Ser Gly Tyr Gly Leu Phe Asp
            115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Glu Glu Met Thr Lys Asn
    370                 375                 380
```

```
Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 29
<211> LENGTH: 1410
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(1410)

<400> SEQUENCE: 29 atg aaa cac ctg tgg ttc ttc ctc ctg ctg gtg gca gct ccc aga tgg     48
Met Lys His Leu Trp Phe Phe Leu Leu Leu Val Ala Ala Pro Arg Trp
1               5                   10                  15 gtg ctg agc gaa gtg cag ctg gtg gaa tct ggc ggc gga ctg gtg cag     96
Val Leu Ser Glu Val Gln Leu Val Glu Ser Gly Gly Gly Leu Val Gln
            20                  25                  30 cct ggc gga tct ctg aga ctg agc tgt gcc gcc agc ggc ttc acc tac    144
Pro Gly Gly Ser Leu Arg Leu Ser Cys Ala Ala Ser Gly Phe Thr Tyr
        35                  40                  45 cgg tct tac gtg atg gcc tgg gtg cgc cag gcc cct gga aaa gga ctg    192
Arg Ser Tyr Val Met Ala Trp Val Arg Gln Ala Pro Gly Lys Gly Leu
    50                  55                  60 gaa tgg gtg gcc agc atc agc acc ggc gga ggc aac acc tac tac cgg    240
Glu Trp Val Ala Ser Ile Ser Thr Gly Gly Gly Asn Thr Tyr Tyr Arg
65                  70                  75                  80 gat agc gtg aag ggc cgg ttc acc atc agc cgg gac aac gcc aag aac    288
Asp Ser Val Lys Gly Arg Phe Thr Ile Ser Arg Asp Asn Ala Lys Asn
                85                  90                  95 acc ctg tac ctg cag atg gac agc ctg cgg gcc gag gat acc gcc gtg    336
Thr Leu Tyr Leu Gln Met Asp Ser Leu Arg Ala Glu Asp Thr Ala Val
            100                 105                 110 tac tac tgt gcc gag gac atg agc aac agc ggc tac ggc ctg ttc gac    384
Tyr Tyr Cys Ala Glu Asp Met Ser Asn Ser Gly Tyr Gly Leu Phe Asp
        115                 120                 125 tac tgg ggc cag gga acc ctc gtg acc gtc agc tca gcc tcc acc aag    432
Tyr Trp Gly Gln Gly Thr Leu Val Thr Val Ser Ser Ala Ser Thr Lys
    130                 135                 140 ggc cca agc gtc ttc ccc ctg gca ccc tcc tcc aag agc acc tct ggc    480
Gly Pro Ser Val Phe Pro Leu Ala Pro Ser Ser Lys Ser Thr Ser Gly
145                 150                 155                 160 ggc aca gcc gcc ctg ggc tgc ctg gtc aag gac tac ttc ccc gaa ccc    528
Gly Thr Ala Ala Leu Gly Cys Leu Val Lys Asp Tyr Phe Pro Glu Pro
                165                 170                 175 gtg acc gtg agc tgg aac tca ggc gcc ctg acc agc ggc gtg cac acc    576
Val Thr Val Ser Trp Asn Ser Gly Ala Leu Thr Ser Gly Val His Thr
            180                 185                 190
```

-continued

```
ttc ccc gct gtc ctg cag tcc tca gga ctc tac tcc ctc agc agc gtg    624
Phe Pro Ala Val Leu Gln Ser Ser Gly Leu Tyr Ser Leu Ser Ser Val
            195                 200                 205 gtg acc gtg ccc tcc agc agc ttg ggc acc cag acc tac atc tgc aac    672
Val Thr Val Pro Ser Ser Ser Leu Gly Thr Gln Thr Tyr Ile Cys Asn
    210                 215                 220 gtg aat cac aag ccc agc aac acc aag gtg gac aag aga gtt gag ccc    720
Val Asn His Lys Pro Ser Asn Thr Lys Val Asp Lys Arg Val Glu Pro
225                 230                 235                 240 aaa tct tgt gac aaa act cac aca tgc cca ccc tgc cca gca cct gaa    768
Lys Ser Cys Asp Lys Thr His Thr Cys Pro Pro Cys Pro Ala Pro Glu
                245                 250                 255 ctc ctg ggg gga ccc tca gtc ttc ctc ttc ccc cca aaa ccc aag gac    816
Leu Leu Gly Gly Pro Ser Val Phe Leu Phe Pro Pro Lys Pro Lys Asp
            260                 265                 270 acc ctc atg atc tcc cgg acc cct gag gtc aca tgc gtg gtg gtg gac    864
Thr Leu Met Ile Ser Arg Thr Pro Glu Val Thr Cys Val Val Val Asp
        275                 280                 285 gtg agc cac gaa gac cct gag gtc aag ttc aac tgg tac gtg gac ggc    912
Val Ser His Glu Asp Pro Glu Val Lys Phe Asn Trp Tyr Val Asp Gly
    290                 295                 300 gtg gag gtg cat aat gcc aag aca aag ccc cgg gag gag cag tac aac    960
Val Glu Val His Asn Ala Lys Thr Lys Pro Arg Glu Glu Gln Tyr Asn
305                 310                 315                 320 agc acg tac cgg gtg gtc agc gtc ctc acc gtc ctg cac cag gac tgg   1008
Ser Thr Tyr Arg Val Val Ser Val Leu Thr Val Leu His Gln Asp Trp
                325                 330                 335 ctg aat ggc aag gag tac aag tgc aag gtc tcc aac aaa gcc ctc cca   1056
Leu Asn Gly Lys Glu Tyr Lys Cys Lys Val Ser Asn Lys Ala Leu Pro
            340                 345                 350 gcc ccc atc gag aaa acc atc tcc aaa gcc aaa ggc cag ccc cgg gaa   1104
Ala Pro Ile Glu Lys Thr Ile Ser Lys Ala Lys Gly Gln Pro Arg Glu
        355                 360                 365 cca cag gtg tac acc ctg ccc cca tcc cgg gag gag atg acc aag aac   1152
Pro Gln Val Tyr Thr Leu Pro Pro Ser Arg Glu Glu Met Thr Lys Asn
    370                 375                 380 cag gtc agc ctg acc tgc ctg gtc aaa ggc ttc tat ccc agc gac atc   1200
Gln Val Ser Leu Thr Cys Leu Val Lys Gly Phe Tyr Pro Ser Asp Ile
385                 390                 395                 400 gcc gtg gag tgg gag agc aat ggc cag ccc gag aac aac tac aag acc   1248
Ala Val Glu Trp Glu Ser Asn Gly Gln Pro Glu Asn Asn Tyr Lys Thr
                405                 410                 415 acc cct ccc gtg ctg gac tcc gac ggc tcc ttc ttc ctc tac agc aag   1296
Thr Pro Pro Val Leu Asp Ser Asp Gly Ser Phe Phe Leu Tyr Ser Lys
            420                 425                 430 ctc acc gtg gac aag agc agg tgg cag cag ggc aac gtc ttc tca tgc   1344
Leu Thr Val Asp Lys Ser Arg Trp Gln Gln Gly Asn Val Phe Ser Cys
        435                 440                 445 tcc gtg atg cat gag gct ctg cac aac cac tac acc cag aag agc ctc   1392
Ser Val Met His Glu Ala Leu His Asn His Tyr Thr Gln Lys Ser Leu
    450                 455                 460 tcc ctg tct ccc ggc aaa                                            1410
Ser Leu Ser Pro Gly Lys
465                 470
```

<210> SEQ ID NO 30
<211> LENGTH: 470
<212> TYPE: PRT
<213> ORGANISM: Artificial Sequence
<220> FEATURE:

<223> OTHER INFORMATION: Synthetic Construct

<400> SEQUENCE: 30

```
Met Lys His Leu Trp Phe Phe Leu Leu Leu Val Ala Ala Pro Arg Trp
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Tyr
        35                  40                  45

Arg Ser Tyr Val Met Ala Trp Val Arg Gln Ala Pro Gly Lys Gly Leu
    50                  55                  60

Glu Trp Val Ala Ser Ile Ser Thr Gly Gly Asn Thr Tyr Tyr Arg
65                  70                  75                  80

Asp Ser Val Lys Gly Arg Phe Thr Ile Ser Arg Asp Asn Ala Lys Asn
                85                  90                  95

Thr Leu Tyr Leu Gln Met Asp Ser Leu Arg Ala Glu Asp Thr Ala Val
            100                 105                 110

Tyr Tyr Cys Ala Glu Asp Met Ser Asn Ser Gly Tyr Gly Leu Phe Asp
        115                 120                 125

Tyr Trp Gly Gln Gly Thr Leu Val Thr Val Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400
```

-continued

```
Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
        420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 31
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 31 atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
1               5                   10                  15 ggc gcg tac ggc gac atc cag atg acc cag agc cct agc agc ctg agc      96
Gly Ala Tyr Gly Asp Ile Gln Met Thr Gln Ser Pro Ser Ser Leu Ser
            20                  25                  30 gcc agc gtg ggc gac aga gtg acc atc acc tgt aaa gcc ggc cag aac     144
Ala Ser Val Gly Asp Arg Val Thr Ile Thr Cys Lys Ala Gly Gln Asn
        35                  40                  45 gtg gac aac aat atc gcc tgg tat cag cag aag ccc ggc cag gcc cct     192
Val Asp Asn Asn Ile Ala Trp Tyr Gln Gln Lys Pro Gly Gln Ala Pro
    50                  55                  60 aag ctg ctg atc tac tac gcc agc aac cgg aac acc ggc gtg ccc agc     240
Lys Leu Leu Ile Tyr Tyr Ala Ser Asn Arg Asn Thr Gly Val Pro Ser
65                  70                  75                  80 aga ttt tct ggc agc ggc tcc ggc acc gac ttc acc ctg aca atc agc     288
Arg Phe Ser Gly Ser Gly Ser Gly Thr Asp Phe Thr Leu Thr Ile Ser
                85                  90                  95 agc ctg cag ccc gag gac ttc gcc acc tac tac tgc cag aga atc agc     336
Ser Leu Gln Pro Glu Asp Phe Ala Thr Tyr Tyr Cys Gln Arg Ile Ser
            100                 105                 110 aac agc ccc tac acc ttc ggc cag ggc acc aag gtg gaa atc aag cgt     384
Asn Ser Pro Tyr Thr Phe Gly Gln Gly Thr Lys Val Glu Ile Lys Arg
        115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac     480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc     528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc     576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag     624
Tyr Ser Leu Ser Ser Thr Leu Thr Leu Ser Lys Ala Asp Tyr Glu Lys
        195                 200                 205
```

```
cac aag gtg tac gcc tgc gag gtg acc cac cag ggc ctg agc tcc ccc      672
His Lys Val Tyr Ala Cys Glu Val Thr His Gln Gly Leu Ser Ser Pro
    210                 215                 220 gtc acc aag agc ttc aac agg ggg gag tgt                              702
Val Thr Lys Ser Phe Asn Arg Gly Glu Cys
225                 230
```

<210> SEQ ID NO 32
<211> LENGTH: 234
<212> TYPE: PRT
<213> ORGANISM: Artificial Sequence
<220> FEATURE:
<223> OTHER INFORMATION: Synthetic Construct

<400> SEQUENCE: 32

```
Met Val Leu Gln Thr Gln Val Phe Ile Ser Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Lys Ala Gly Gln Asn
            35                  40                  45

Val Asp Asn Ile Ala Trp Tyr Gln Gln Lys Pro Gly Gln Ala Pro
    50                  55                  60

Lys Leu Leu Ile Tyr Tyr Ala Ser Asn Arg Asn Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Arg Ile Ser
                100                 105                 110

Asn Ser Pro Tyr Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 33
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 33

```
atg gtg ctg cag acc cag gtg ttc atc tcc ctg ctg ctg tgg atc tcc     48
Met Val Leu Gln Thr Gln Val Phe Ile Ser Leu Leu Leu Trp Ile Ser
```

```
     1               5                  10                 15
ggc gcg tac ggc gac atc cag atg acc cag agc cct agc agc ctg agc      96
Gly Ala Tyr Gly Asp Ile Gln Met Thr Gln Ser Pro Ser Ser Leu Ser
             20                  25                  30 gcc agc gtg ggc gac aga gtg acc atc acc tgt aaa gcc ggc cag aac     144
Ala Ser Val Gly Asp Arg Val Thr Ile Thr Cys Lys Ala Gly Gln Asn
             35                  40                  45 gtg gac aac aat atc gcc tgg tat cag cag aag ccc ggc cag agc ccc     192
Val Asp Asn Asn Ile Ala Trp Tyr Gln Gln Lys Pro Gly Gln Ser Pro
 50                  55                  60 aag ctg ctg atc tac tac gcc agc aac cgg aac acc ggc gtg ccc agc     240
Lys Leu Leu Ile Tyr Tyr Ala Ser Asn Arg Asn Thr Gly Val Pro Ser
 65                  70                  75                  80 aga ttt tcc ggc agc ggc tac ggc acc gac ttc acc ctg aca atc agc     288
Arg Phe Ser Gly Ser Gly Tyr Gly Thr Asp Phe Thr Leu Thr Ile Ser
                 85                  90                  95 agc ctg cag ccc gag gac ttc gcc acc tac tac tgc cag aga atc agc     336
Ser Leu Gln Pro Glu Asp Phe Ala Thr Tyr Tyr Cys Gln Arg Ile Ser
            100                 105                 110 aac agc ccc tac acc ttc ggc cag ggc acc aag gtg gaa atc aag cgt     384
Asn Ser Pro Tyr Thr Phe Gly Gln Gly Thr Lys Val Glu Ile Lys Arg
            115                 120                 125 acg gtg gcc gcc ccc tcc gtg ttc atc ttc ccc ccc tcc gac gag cag     432
Thr Val Ala Ala Pro Ser Val Phe Ile Phe Pro Pro Ser Asp Glu Gln
            130                 135                 140 ctg aag tcc ggc acc gcc tcc gtg gtg tgc ctg ctg aat aac ttc tac     480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc     528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc     576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag     624
Tyr Ser Leu Ser Ser Thr Leu Thr Leu Ser Lys Ala Asp Tyr Glu Lys
            195                 200                 205 cac aag gtg tac gcc tgc gag gtg acc cac cag ggc ctg agc tcc ccc     672
His Lys Val Tyr Ala Cys Glu Val Thr His Gln Gly Leu Ser Ser Pro
            210                 215                 220 gtc acc aag agc ttc aac agg ggg gag tgt                             702
Val Thr Lys Ser Phe Asn Arg Gly Glu Cys
225                 230

<210> SEQ ID NO 34
<211> LENGTH: 234
<212> TYPE: PRT
<213> ORGANISM: Artificial Sequence
<220> FEATURE:
<223> OTHER INFORMATION: Synthetic Construct

<400> SEQUENCE: 34

Met Val Leu Gln Thr Gln Val Phe Ile Ser Leu Leu Leu Trp Ile Ser
 1               5                  10                  15

Gly Ala Tyr Gly Asp Ile Gln Met Thr Gln Ser Pro Ser Ser Leu Ser
             20                  25                  30

Ala Ser Val Gly Asp Arg Val Thr Ile Thr Cys Lys Ala Gly Gln Asn
             35                  40                  45

Val Asp Asn Asn Ile Ala Trp Tyr Gln Gln Lys Pro Gly Gln Ser Pro
 50                  55                  60
```

```
Lys Leu Leu Ile Tyr Tyr Ala Ser Asn Arg Asn Thr Gly Val Pro Ser
 65                  70                  75                  80

Arg Phe Ser Gly Ser Gly Tyr Gly Thr Asp Phe Thr Leu Thr Ile Ser
                 85                  90                  95

Ser Leu Gln Pro Glu Asp Phe Ala Thr Tyr Tyr Cys Gln Arg Ile Ser
            100                 105                 110

Asn Ser Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 35
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 35

```
atg gtg ctg cag acc cag gtg ttc atc tcc ctg ctg ctg tgg atc tcc      48
Met Val Leu Gln Thr Gln Val Phe Ile Ser Leu Leu Leu Trp Ile Ser
  1               5                  10                  15 ggc gcg tac ggc aac atc cag atg acc cag agc ccc agc agc ctg tct      96
Gly Ala Tyr Gly Asn Ile Gln Met Thr Gln Ser Pro Ser Ser Leu Ser
                 20                  25                  30 gcc agc gtg ggc gac aga gtg acc atc aca tgc aag gcc ggc cag aac     144
Ala Ser Val Gly Asp Arg Val Thr Ile Thr Cys Lys Ala Gly Gln Asn
             35                  40                  45 gtg gac aac aat atc gcc tgg tat cag aag aag ccc ggc cag tcc ccc     192
Val Asp Asn Asn Ile Ala Trp Tyr Gln Lys Lys Pro Gly Gln Ser Pro
         50                  55                  60 aag ctg ctg atc tac tac gcc agc aac cgg aac acc ggc gtg ccc gac     240
Lys Leu Leu Ile Tyr Tyr Ala Ser Asn Arg Asn Thr Gly Val Pro Asp
 65                  70                  75                  80 aga ttt tcc ggc gga ggc tac ggc acc gac ttc acc ctg acc atc agc     288
Arg Phe Ser Gly Gly Gly Tyr Gly Thr Asp Phe Thr Leu Thr Ile Ser
                 85                  90                  95 tcc ctg cag ccc gag gac ttc gcc ttc tac tac tgt cag cgg atc agc     336
Ser Leu Gln Pro Glu Asp Phe Ala Phe Tyr Tyr Cys Gln Arg Ile Ser
            100                 105                 110 aac agc ccc tac acc ttc ggc cag ggc acc aag gtg gaa atc aag cgt     384
Asn Ser Pro Tyr Thr Phe Gly Gln Gly Thr Lys Val Glu Ile Lys Arg
        115                 120                 125
```

| | | | | | | | | | | | | | | | |
|---|---|---|---|---|---|---|---|---|---|---|---|---|---|---|---|
| acg | gtg | gcc | gcc | ccc | tcc | gtg | ttc | atc | ttc | ccc | ccc | tcc | gac | gag | cag | 432 |
| Thr | Val | Ala | Ala | Pro | Ser | Val | Phe | Ile | Phe | Pro | Pro | Ser | Asp | Glu | Gln | |
| | | 130 | | | | 135 | | | | 140 | | | | | | |

| | | | | | | | | | | | | | | | |
|---|---|---|---|---|---|---|---|---|---|---|---|---|---|---|---|
| ctg | aag | tcc | ggc | acc | gcc | tcc | gtg | gtg | tgc | ctg | ctg | aat | aac | ttc | tac | 480 |
| Leu | Lys | Ser | Gly | Thr | Ala | Ser | Val | Val | Cys | Leu | Leu | Asn | Asn | Phe | Tyr | |
| 145 | | | | | 150 | | | | | 155 | | | | | 160 | |

| | | | | | | | | | | | | | | | |
|---|---|---|---|---|---|---|---|---|---|---|---|---|---|---|---|
| ccc | aga | gag | gcc | aag | gtg | cag | tgg | aag | gtg | gac | aac | gcc | ctg | cag | tcc | 528 |
| Pro | Arg | Glu | Ala | Lys | Val | Gln | Trp | Lys | Val | Asp | Asn | Ala | Leu | Gln | Ser | |
| | | | | 165 | | | | | 170 | | | | | 175 | | |

| | | | | | | | | | | | | | | | |
|---|---|---|---|---|---|---|---|---|---|---|---|---|---|---|---|
| ggg | aac | tcc | cag | gag | agc | gtg | acc | gag | cag | gac | agc | aag | gac | agc | acc | 576 |
| Gly | Asn | Ser | Gln | Glu | Ser | Val | Thr | Glu | Gln | Asp | Ser | Lys | Asp | Ser | Thr | |
| | | | 180 | | | | | 185 | | | | | 190 | | | |

| | | | | | | | | | | | | | | | |
|---|---|---|---|---|---|---|---|---|---|---|---|---|---|---|---|
| tac | agc | ctg | agc | agc | acc | ctg | acc | ctg | agc | aaa | gcc | gac | tac | gag | aag | 624 |
| Tyr | Ser | Leu | Ser | Ser | Thr | Leu | Thr | Leu | Ser | Lys | Ala | Asp | Tyr | Glu | Lys | |
| | | | 195 | | | | | 200 | | | | | 205 | | | |

| | | | | | | | | | | | | | | | |
|---|---|---|---|---|---|---|---|---|---|---|---|---|---|---|---|
| cac | aag | gtg | tac | gcc | tgc | gag | gtg | acc | cac | cag | ggc | ctg | agc | tcc | ccc | 672 |
| His | Lys | Val | Tyr | Ala | Cys | Glu | Val | Thr | His | Gln | Gly | Leu | Ser | Ser | Pro | |
| 210 | | | | | 215 | | | | | 220 | | | | | | |

| | | | | | | | | |
|---|---|---|---|---|---|---|---|---|
| gtc | acc | aag | agc | ttc | aac | agg | ggg | gag | tgt | 702 |
| Val | Thr | Lys | Ser | Phe | Asn | Arg | Gly | Glu | Cys | |
| 225 | | | | | 230 | | | | | |

<210> SEQ ID NO 36
<211> LENGTH: 234
<212> TYPE: PRT
<213> ORGANISM: Artificial Sequence
<220> FEATURE:
<223> OTHER INFORMATION: Synthetic Construct

<400> SEQUENCE: 36

Met Val Leu Gln Thr Gln Val Phe Ile Ser Leu Leu Trp Ile Ser
1               5                   10                  15

Gly Ala Tyr Gly Asn Ile Gln Met Thr Gln Ser Pro Ser Ser Leu Ser
            20                  25                  30

Ala Ser Val Gly Asp Arg Val Thr Ile Thr Cys Lys Ala Gly Gln Asn
        35                  40                  45

Val Asp Asn Asn Ile Ala Trp Tyr Gln Lys Lys Pro Gly Gln Ser Pro
    50                  55                  60

Lys Leu Leu Ile Tyr Tyr Ala Ser Asn Arg Asn Thr Gly Val Pro Asp
65                  70                  75                  80

Arg Phe Ser Gly Gly Tyr Gly Thr Asp Phe Thr Leu Thr Ile Ser
                85                  90                  95

Ser Leu Gln Pro Glu Asp Phe Ala Phe Tyr Tyr Cys Gln Arg Ile Ser
            100                 105                 110

Asn Ser Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 37
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 37

| | | |
|---|---|---|
| atg gtg ctg cag acc cag gtg ttc atc tcc ctg ctg ctg tgg atc tcc<br>Met Val Leu Gln Thr Gln Val Phe Ile Ser Leu Leu Leu Trp Ile Ser<br>1               5                   10                  15 | 48 | |
| ggc gcg tac ggc gac atc cag atg acc cag agc ccc agc agc atg agc<br>Gly Ala Tyr Gly Asp Ile Gln Met Thr Gln Ser Pro Ser Ser Met Ser<br>            20                  25                  30 | 96 | |
| atc agc gtg ggc gac aga gtg acc atg acc tgc aag gcc ggc cag aac<br>Ile Ser Val Gly Asp Arg Val Thr Met Thr Cys Lys Ala Gly Gln Asn<br>        35                  40                  45 | 144 | |
| gtg gac aac aat atc gcc tgg tat cag aag aag ccc ggc cag tcc ccc<br>Val Asp Asn Asn Ile Ala Trp Tyr Gln Lys Lys Pro Gly Gln Ser Pro<br>    50                  55                  60 | 192 | |
| aag ctg ctg atc tac tac gcc agc aac cgg aac acc ggc gtg ccc agc<br>Lys Leu Leu Ile Tyr Tyr Ala Ser Asn Arg Asn Thr Gly Val Pro Ser<br>65                  70                  75                  80 | 240 | |
| aga ttt tct ggc agc ggc tcc ggc acc gac ttc acc ctg aca atc agc<br>Arg Phe Ser Gly Ser Gly Ser Gly Thr Asp Phe Thr Leu Thr Ile Ser<br>                85                  90                  95 | 288 | |
| agc gtg cag ccc gag gac ttc gcc acc tac tac tgc cag aga atc agc<br>Ser Val Gln Pro Glu Asp Phe Ala Thr Tyr Tyr Cys Gln Arg Ile Ser<br>            100                 105                 110 | 336 | |
| aac agc ccc tac acc ttc ggc cag ggc acc aag ctg gaa ctg aag cgt<br>Asn Ser Pro Tyr Thr Phe Gly Gln Gly Thr Lys Leu Glu Leu Lys Arg<br>        115                 120                 125 | 384 | |
| acg gtg gcc gcc ccc tcc gtg ttc atc ttc ccc ccc tcc gac gag cag<br>Thr Val Ala Ala Pro Ser Val Phe Ile Phe Pro Pro Ser Asp Glu Gln<br>    130                 135                 140 | 432 | |
| ctg aag tcc ggc acc gcc tcc gtg gtg tgc ctg ctg aat aac ttc tac<br>Leu Lys Ser Gly Thr Ala Ser Val Val Cys Leu Leu Asn Asn Phe Tyr<br>145                 150                 155                 160 | 480 | |
| ccc aga gag gcc aag gtg cag tgg aag gtg gac aac gcc ctg cag tcc<br>Pro Arg Glu Ala Lys Val Gln Trp Lys Val Asp Asn Ala Leu Gln Ser<br>                165                 170                 175 | 528 | |
| ggg aac tcc cag gag agc gtg acc gag cag gac agc aag gac agc acc<br>Gly Asn Ser Gln Glu Ser Val Thr Glu Gln Asp Ser Lys Asp Ser Thr<br>            180                 185                 190 | 576 | |
| tac agc ctg agc agc acc ctg acc ctg agc aaa gcc gac tac gag aag<br>Tyr Ser Leu Ser Ser Thr Leu Thr Leu Ser Lys Ala Asp Tyr Glu Lys<br>        195                 200                 205 | 624 | |
| cac aag gtg tac gcc tgc gag gtg acc cac cag ggc ctg agc tcc ccc<br>His Lys Val Tyr Ala Cys Glu Val Thr His Gln Gly Leu Ser Ser Pro<br>    210                 215                 220 | 672 | |
| gtc acc aag agc ttc aac agg ggg gag tgt<br>Val Thr Lys Ser Phe Asn Arg Gly Glu Cys<br>225                 230 | 702 | |

<210> SEQ ID NO 38

```
<211> LENGTH: 234
<212> TYPE: PRT
<213> ORGANISM: Artificial Sequence
<220> FEATURE:
<223> OTHER INFORMATION: Synthetic Construct

<400> SEQUENCE: 38

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Met Ser
            20                  25                  30

Ile Ser Val Gly Asp Arg Val Thr Met Thr Cys Lys Ala Gly Gln Asn
        35                  40                  45

Val Asp Asn Asn Ile Ala Trp Tyr Gln Lys Lys Pro Gly Gln Ser Pro
    50                  55                  60

Lys Leu Leu Ile Tyr Tyr Ala Ser Asn Arg Asn Thr Gly Val Pro Ser
65                  70                  75                  80

Arg Phe Ser Gly Ser Gly Ser Gly Thr Asp Phe Thr Leu Thr Ile Ser
                85                  90                  95

Ser Val Gln Pro Glu Asp Phe Ala Thr Tyr Tyr Cys Gln Arg Ile Ser
            100                 105                 110

Asn Ser Pro Tyr Thr Phe Gly Gln Gly Thr Lys Leu Glu Leu Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 39
<211> LENGTH: 702
<212> TYPE: DNA
<213> ORGANISM: Artificial Sequence
<220> FEATURE:
<223> OTHER INFORMATION: humanized
<220> FEATURE:
<221> NAME/KEY: CDS
<222> LOCATION: (1)..(702)

<400> SEQUENCE: 39 atg gtg ctg cag acc cag gtg ttc atc tcc ctg ctg ctg tgg atc tcc    48
Met Val Leu Gln Thr Gln Val Phe Ile Ser Leu Leu Leu Trp Ile Ser
1               5                   10                  15 ggc gcg tac ggc aac atc cag atg acc cag agc ccc agc agc atg agc    96
Gly Ala Tyr Gly Asn Ile Gln Met Thr Gln Ser Pro Ser Ser Met Ser
            20                  25                  30 atc agc gtg ggc gac aga gtg acc atg acc tgc aag gcc ggc cag aac   144
Ile Ser Val Gly Asp Arg Val Thr Met Thr Cys Lys Ala Gly Gln Asn
        35                  40                  45 gtg gac aac aat atc gcc tgg tat cag aag aag ccc ggc cag tcc ccc   192
```

```
                Val Asp Asn Asn Ile Ala Trp Tyr Gln Lys Pro Gly Gln Ser Pro
                    50                  55                  60 aag ctg ctg atc tac tac gcc agc aac cgg aac acc ggc gtg ccc gac        240
Lys Leu Leu Ile Tyr Tyr Ala Ser Asn Arg Asn Thr Gly Val Pro Asp
 65                  70                  75                  80 aga ttt tcc ggc gga ggc tac ggc acc gac ttc acc ctg aca atc agc        288
Arg Phe Ser Gly Gly Gly Tyr Gly Thr Asp Phe Thr Leu Thr Ile Ser
                 85                  90                  95 agc gtg cag ccc gag gac gcc gcc ttc tac tac tgt cag cgg atc agc        336
Ser Val Gln Pro Glu Asp Ala Ala Phe Tyr Tyr Cys Gln Arg Ile Ser
            100                 105                 110 aac agc ccc tac acc ttc ggc cag ggc acc aag ctg gaa ctg aag cgt        384
Asn Ser Pro Tyr Thr Phe Gly Gln Gly Thr Lys Leu Glu Leu Lys Arg
        115                 120                 125 acg gtg gcc gcc ccc tcc gtg ttc atc ttc ccc ccc tcc gac gag cag        432
Thr Val Ala Ala Pro Ser Val Phe Ile Phe Pro Pro Ser Asp Glu Gln
    130                 135                 140 ctg aag tcc ggc acc gcc tcc gtg gtg tgc ctg ctg aat aac ttc tac        480
Leu Lys Ser Gly Thr Ala Ser Val Val Cys Leu Leu Asn Asn Phe Tyr
145                 150                 155                 160 ccc aga gag gcc aag gtg cag tgg aag gtg gac aac gcc ctg cag tcc        528
Pro Arg Glu Ala Lys Val Gln Trp Lys Val Asp Asn Ala Leu Gln Ser
                165                 170                 175 ggg aac tcc cag gag agc gtg acc gag cag gac agc aag gac agc acc        576
Gly Asn Ser Gln Glu Ser Val Thr Glu Gln Asp Ser Lys Asp Ser Thr
            180                 185                 190 tac agc ctg agc agc acc ctg acc ctg agc aaa gcc gac tac gag aag        624
Tyr Ser Leu Ser Ser Thr Leu Thr Leu Ser Lys Ala Asp Tyr Glu Lys
        195                 200                 205 cac aag gtg tac gcc tgc gag gtg acc cac cag ggc ctg agc tcc ccc        672
His Lys Val Tyr Ala Cys Glu Val Thr His Gln Gly Leu Ser Ser Pro
    210                 215                 220 gtc acc aag agc ttc aac agg ggg gag tgt                                702
Val Thr Lys Ser Phe Asn Arg Gly Glu Cys
225                 230

<210> SEQ ID NO 40
<211> LENGTH: 234
<212> TYPE: PRT
<213> ORGANISM: Artificial Sequence
<220> FEATURE:
<223> OTHER INFORMATION: Synthetic Construct

<400> SEQUENCE: 40

Met Val Leu Gln Thr Gln Val Phe Ile Ser Leu Leu Leu Trp Ile Ser
 1               5                  10                  15

Gly Ala Tyr Gly Asn Ile Gln Met Thr Gln Ser Pro Ser Ser Met Ser
                20                  25                  30

Ile Ser Val Gly Asp Arg Val Thr Met Thr Cys Lys Ala Gly Gln Asn
            35                  40                  45

Val Asp Asn Asn Ile Ala Trp Tyr Gln Lys Lys Pro Gly Gln Ser Pro
        50                  55                  60

Lys Leu Leu Ile Tyr Tyr Ala Ser Asn Arg Asn Thr Gly Val Pro Asp
 65                  70                  75                  80

Arg Phe Ser Gly Gly Gly Tyr Gly Thr Asp Phe Thr Leu Thr Ile Ser
                 85                  90                  95

Ser Val Gln Pro Glu Asp Ala Ala Phe Tyr Tyr Cys Gln Arg Ile Ser
            100                 105                 110

Asn Ser Pro Tyr Thr Phe Gly Gln Gly Thr Lys Leu Glu Leu Lys Arg
```

```
                    115                 120                 125
Thr Val Ala Ala Pro Ser Val Phe Ile Phe Pro Ser Asp Glu Gln
    130                 135                 140
Leu Lys Ser Gly Thr Ala Ser Val Val Cys Leu Leu Asn Asn Phe Tyr
145                 150                 155                 160
Pro Arg Glu Ala Lys Val Gln Trp Lys Val Asp Asn Ala Leu Gln Ser
                165                 170                 175
Gly Asn Ser Gln Glu Ser Val Thr Glu Gln Asp Ser Lys Asp Ser Thr
            180                 185                 190
Tyr Ser Leu Ser Ser Thr Leu Thr Leu Ser Lys Ala Asp Tyr Glu Lys
        195                 200                 205
His Lys Val Tyr Ala Cys Glu Val Thr His Gln Gly Leu Ser Ser Pro
    210                 215                 220
Val Thr Lys Ser Phe Asn Arg Gly Glu Cys
225                 230

<210> SEQ ID NO 41
<211> LENGTH: 10
<212> TYPE: PRT
<213> ORGANISM: Rattus norvegicus

<400> SEQUENCE: 41

Gly Phe Thr Phe Arg Thr Tyr Gly Met Ala
1               5                   10

<210> SEQ ID NO 42
<211> LENGTH: 17
<212> TYPE: PRT
<213> ORGANISM: Rattus norvegicus

<400> SEQUENCE: 42

Ser Ile Ser Thr Gly Gly Gly Ser Thr Tyr Tyr Arg Asp Ser Val Lys
1               5                   10                  15
Gly

<210> SEQ ID NO 43
<211> LENGTH: 13
<212> TYPE: PRT
<213> ORGANISM: Rattus norvegicus

<400> SEQUENCE: 43

Asp Leu Ile Asn Tyr Pro Gly Ile Gly Gly Phe Ala Phe
1               5                   10

<210> SEQ ID NO 44
<211> LENGTH: 11
<212> TYPE: PRT
<213> ORGANISM: Rattus norvegicus

<400> SEQUENCE: 44

Lys Ala Ser Gln Asn Val Tyr Asn Asn Ile Ala
1               5                   10

<210> SEQ ID NO 45
<211> LENGTH: 7
<212> TYPE: PRT
<213> ORGANISM: Rattus norvegicus

<400> SEQUENCE: 45

Tyr Ala Ser Asn Arg Tyr Thr
1               5
```

```
<210> SEQ ID NO 46
<211> LENGTH: 9
<212> TYPE: PRT
<213> ORGANISM: Rattus norvegicus

<400> SEQUENCE: 46

Gln Arg Leu Tyr Asn Ser Pro Pro Thr
1               5

<210> SEQ ID NO 47
<211> LENGTH: 10
<212> TYPE: PRT
<213> ORGANISM: Rattus norvegicus

<400> SEQUENCE: 47

Gly Phe Thr Tyr Arg Ser Tyr Val Met Ala
1               5                   10

<210> SEQ ID NO 48
<211> LENGTH: 17
<212> TYPE: PRT
<213> ORGANISM: Rattus norvegicus

<400> SEQUENCE: 48

Ser Ile Ser Thr Gly Gly Gly Asn Thr Tyr Tyr Arg Asp Ser Val Lys
1               5                   10                  15

Gly

<210> SEQ ID NO 49
<211> LENGTH: 12
<212> TYPE: PRT
<213> ORGANISM: Rattus norvegicus

<400> SEQUENCE: 49

Asp Met Ser Asn Ser Gly Tyr Gly Leu Phe Asp Tyr
1               5                   10

<210> SEQ ID NO 50
<211> LENGTH: 11
<212> TYPE: PRT
<213> ORGANISM: Rattus norvegicus

<400> SEQUENCE: 50

Lys Ala Gly Gln Asn Val Asp Asn Asn Ile Ala
1               5                   10

<210> SEQ ID NO 51
<211> LENGTH: 7
<212> TYPE: PRT
<213> ORGANISM: Rattus norvegicus

<400> SEQUENCE: 51

Tyr Ala Ser Asn Arg Asn Thr
1               5

<210> SEQ ID NO 52
<211> LENGTH: 9
<212> TYPE: PRT
<213> ORGANISM: Rattus norvegicus

<400> SEQUENCE: 52

Gln Arg Ile Ser Asn Ser Pro Tyr Thr
1               5
```

<210> SEQ ID NO 53
<211> LENGTH: 10
<212> TYPE: PRT
<213> ORGANISM: Rattus norvegicus

<400> SEQUENCE: 53

Gly Phe Thr Phe Ser Asn Tyr Tyr Met Ala
1               5                   10

<210> SEQ ID NO 54
<211> LENGTH: 17
<212> TYPE: PRT
<213> ORGANISM: Rattus norvegicus

<400> SEQUENCE: 54

Ser Ile Ser Thr Gly Gly Gly Asn Thr Tyr Tyr Arg Asp Ser Val Lys
1               5                   10                  15

Gly

<210> SEQ ID NO 55
<211> LENGTH: 12
<212> TYPE: PRT
<213> ORGANISM: Rattus norvegicus

<400> SEQUENCE: 55

Pro Pro Tyr Gly Tyr Asn Tyr Gly Trp Phe Thr Tyr
1               5                   10

<210> SEQ ID NO 56
<211> LENGTH: 11
<212> TYPE: PRT
<213> ORGANISM: Rattus norvegicus

<400> SEQUENCE: 56

Arg Ala Ser Glu Asp Ile His Asn Gly Leu Val
1               5                   10

<210> SEQ ID NO 57
<211> LENGTH: 7
<212> TYPE: PRT
<213> ORGANISM: Rattus norvegicus

<400> SEQUENCE: 57

Asn Ala Asn Ser Met His Thr
1               5

<210> SEQ ID NO 58
<211> LENGTH: 9
<212> TYPE: PRT
<213> ORGANISM: Rattus norvegicus

<400> SEQUENCE: 58

Gln Gln Tyr Tyr Asn Tyr Pro Arg Thr
1               5

<210> SEQ ID NO 59
<211> LENGTH: 10
<212> TYPE: PRT
<213> ORGANISM: Rattus norvegicus

<400> SEQUENCE: 59

Gly Phe Thr Tyr Arg Thr Tyr Val Met Ala
1               5                   10

```
<210> SEQ ID NO 60
<211> LENGTH: 17
<212> TYPE: PRT
<213> ORGANISM: Rattus norvegicus

<400> SEQUENCE: 60

Ser Ile Ser Thr Gly Gly Val Ser Thr Tyr Tyr Arg Asp Ser Val Lys
1               5                   10                  15
Gly

<210> SEQ ID NO 61
<211> LENGTH: 14
<212> TYPE: PRT
<213> ORGANISM: Rattus norvegicus

<400> SEQUENCE: 61

Asp Met Leu Asn Gly Tyr Asn Ser Gln Gly Leu Phe Asp Tyr
1               5                   10

<210> SEQ ID NO 62
<211> LENGTH: 11
<212> TYPE: PRT
<213> ORGANISM: Rattus norvegicus

<400> SEQUENCE: 62

Arg Ala Ser Gln Asn Val Asp Asn Thr Ile Ala
1               5                   10

<210> SEQ ID NO 63
<211> LENGTH: 7
<212> TYPE: PRT
<213> ORGANISM: Rattus norvegicus

<400> SEQUENCE: 63

Phe Ala Ser Asp Arg Tyr Thr
1               5

<210> SEQ ID NO 64
<211> LENGTH: 9
<212> TYPE: PRT
<213> ORGANISM: Rattus norvegicus

<400> SEQUENCE: 64

Gln Arg Ile Tyr Asn Ser Pro Leu Thr
1               5

<210> SEQ ID NO 65
<211> LENGTH: 10
<212> TYPE: PRT
<213> ORGANISM: Rattus norvegicus

<400> SEQUENCE: 65

Gly Phe Thr Phe Ser Ser Tyr Tyr Met Ala
1               5                   10

<210> SEQ ID NO 66
<211> LENGTH: 17
<212> TYPE: PRT
<213> ORGANISM: Rattus norvegicus

<400> SEQUENCE: 66

Tyr Ile Ser Asn Gly Gly Tyr Ser Thr Tyr Tyr Arg Asp Ser Val Lys
1               5                   10                  15
```

Gly

<210> SEQ ID NO 67
<211> LENGTH: 10
<212> TYPE: PRT
<213> ORGANISM: Rattus norvegicus

<400> SEQUENCE: 67

Thr Asp His Ser Gly Tyr Arg Phe Thr Tyr
1               5                   10

<210> SEQ ID NO 68
<211> LENGTH: 11
<212> TYPE: PRT
<213> ORGANISM: Rattus norvegicus

<400> SEQUENCE: 68

Lys Ala Ser Gln Ser Ile Tyr Asn Ser Leu Ala
1               5                   10

<210> SEQ ID NO 69
<211> LENGTH: 7
<212> TYPE: PRT
<213> ORGANISM: Rattus norvegicus

<400> SEQUENCE: 69

Asp Ala Asn Ser Leu Gln Thr
1               5

<210> SEQ ID NO 70
<211> LENGTH: 8
<212> TYPE: PRT
<213> ORGANISM: Rattus norvegicus

<400> SEQUENCE: 70

Gln Lys Tyr Tyr Ser Gly Asn Thr
1               5

<210> SEQ ID NO 71
<211> LENGTH: 29
<212> TYPE: DNA
<213> ORGANISM: Artificial Sequence
<220> FEATURE:
<223> OTHER INFORMATION: primer

<400> SEQUENCE: 71
ctccagagtt ccaggtcacg gtgactggc                                    29

<210> SEQ ID NO 72
<211> LENGTH: 28
<212> TYPE: DNA
<213> ORGANISM: Artificial Sequence
<220> FEATURE:
<223> OTHER INFORMATION: primer

<400> SEQUENCE: 72
tcagtaacac tgtccaggac accatctc                                     28

<210> SEQ ID NO 73
<211> LENGTH: 30
<212> TYPE: DNA
<213> ORGANISM: Artificial Sequence
<220> FEATURE:
<223> OTHER INFORMATION: primer

```
<400> SEQUENCE: 73
tataccgtcg acctctagct agagcttggc                                    30

<210> SEQ ID NO 74
<211> LENGTH: 30
<212> TYPE: DNA
<213> ORGANISM: Artificial Sequence
<220> FEATURE:
<223> OTHER INFORMATION: primer

<400> SEQUENCE: 74
gctatggcag ggcctgccgc cccgacgttg                                    30

<210> SEQ ID NO 75
<211> LENGTH: 46
<212> TYPE: DNA
<213> ORGANISM: Artificial Sequence
<220> FEATURE:
<223> OTHER INFORMATION: primer

<400> SEQUENCE: 75
ccagatgggt gctgagcgag gtgcagctgg tggagtctgg gggagg                  46

<210> SEQ ID NO 76
<211> LENGTH: 46
<212> TYPE: DNA
<213> ORGANISM: Artificial Sequence
<220> FEATURE:
<223> OTHER INFORMATION: primer

<400> SEQUENCE: 76
cttggtggag gctgagctga ctgtgaccat gactccttgg ccccag                  46

<210> SEQ ID NO 77
<211> LENGTH: 48
<212> TYPE: DNA
<213> ORGANISM: Artificial Sequence
<220> FEATURE:
<223> OTHER INFORMATION: primer

<400> SEQUENCE: 77
atctccggcg cgtacggcaa cattgtgatg acccagtctc ccaaatcc                48

<210> SEQ ID NO 78
<211> LENGTH: 45
<212> TYPE: DNA
<213> ORGANISM: Artificial Sequence
<220> FEATURE:
<223> OTHER INFORMATION: primer

<400> SEQUENCE: 78 ggaggggcg gccacagccc gtttcagttc cagctcggtc ccagc                    45

<210> SEQ ID NO 79
<211> LENGTH: 34
<212> TYPE: DNA
<213> ORGANISM: Homo sapiens

<400> SEQUENCE: 79
atgtgggagg ctcagttcct gggcttgctg tttc                               34

<210> SEQ ID NO 80
<211> LENGTH: 34
<212> TYPE: DNA
<213> ORGANISM: Homo sapiens
```

```
<400> SEQUENCE: 80
gcccgagccc gagcccgagc cggagcagct ctga                            34

<210> SEQ ID NO 81
<211> LENGTH: 30
<212> TYPE: DNA
<213> ORGANISM: Artificial Sequence
<220> FEATURE:
<223> OTHER INFORMATION: oligonucleotide

<400> SEQUENCE: 81
gagtatgtgt tgactggttg ataactatcg                                 30

<210> SEQ ID NO 82
<211> LENGTH: 30
<212> TYPE: DNA
<213> ORGANISM: Artificial Sequence
<220> FEATURE:
<223> OTHER INFORMATION: oligonucleotide

<400> SEQUENCE: 82
gccatgacag attagccatg tctgcagcac                                 30

<210> SEQ ID NO 83
<211> LENGTH: 56
<212> TYPE: DNA
<213> ORGANISM: Mus musculus

<400> SEQUENCE: 83
caggaccttt ttctaacctc ccttggaggg ctggggaggc ccgggccata gaggag    56

<210> SEQ ID NO 84
<211> LENGTH: 56
<212> TYPE: DNA
<213> ORGANISM: Mus musculus

<400> SEQUENCE: 84
cctggagccg aggcagccag caggtctcag cagctccgcc cgcccgcccg cccgcc    56

<210> SEQ ID NO 85
<211> LENGTH: 1575
<212> TYPE: DNA
<213> ORGANISM: Homo sapiens
<220> FEATURE:
<221> NAME/KEY: CDS
<222> LOCATION: (1)..(1575)

<400> SEQUENCE: 85 atg tgg gag gct cag ttc ctg ggc ttg ctg ttt ctg cag ccg ctt tgg    48
Met Trp Glu Ala Gln Phe Leu Gly Leu Leu Phe Leu Gln Pro Leu Trp
1               5                   10                  15 gtg gct cca gtg aag cct ctc cag cca ggg gct gag gtc ccg gtg gtg    96
Val Ala Pro Val Lys Pro Leu Gln Pro Gly Ala Glu Val Pro Val Val
                20                  25                  30 tgg gcc cag gag ggg gct cct gcc cag ctc ccc tgc agc ccc aca atc   144
Trp Ala Gln Glu Gly Ala Pro Ala Gln Leu Pro Cys Ser Pro Thr Ile
            35                  40                  45 ccc ctc cag gat ctc agc ctt ctg cga aga gca ggg gtc act tgg cag   192
Pro Leu Gln Asp Leu Ser Leu Leu Arg Arg Ala Gly Val Thr Trp Gln
        50                  55                  60 cat cag cca gac agt ggc ccg ccc gct gcc gcc ccc ggc cat ccc ctg   240
His Gln Pro Asp Ser Gly Pro Pro Ala Ala Ala Pro Gly His Pro Leu
65                  70                  75                  80
```

```
gcc ccc ggc cct cac ccg gcg gcg ccc tcc tcc tgg ggg ccc agg ccc     288
Ala Pro Gly Pro His Pro Ala Ala Pro Ser Ser Trp Gly Pro Arg Pro
                85                  90                  95 cgc cgc tac acg gtg ctg agc gtg ggt ccc gga ggc ctg cgc agc ggg     336
Arg Arg Tyr Thr Val Leu Ser Val Gly Pro Gly Gly Leu Arg Ser Gly
            100                 105                 110 agg ctg ccc ctg cag ccc cgc gtc cag ctg gat gag cgc ggc cgg cag     384
Arg Leu Pro Leu Gln Pro Arg Val Gln Leu Asp Glu Arg Gly Arg Gln
        115                 120                 125 cgc ggg gac ttc tcg cta tgg ctg cgc cca gcc cgg gcg gac gcc         432
Arg Gly Asp Phe Ser Leu Trp Leu Arg Pro Ala Arg Ala Asp Ala
    130                 135                 140 ggc gag tac cgc gcc gcg gtg cac ctc agg gac cgc gcc ctc tcc tgc     480
Gly Glu Tyr Arg Ala Ala Val His Leu Arg Asp Arg Ala Leu Ser Cys
145                 150                 155                 160 cgc ctc cgt ctg cgc ctg ggc cag gcc tcg atg act gcc agc ccc cca     528
Arg Leu Arg Leu Arg Leu Gly Gln Ala Ser Met Thr Ala Ser Pro Pro
                165                 170                 175 gga tct ctc aga gcc tcc gac tgg gtc att ttg aac tgc tcc ttc agc     576
Gly Ser Leu Arg Ala Ser Asp Trp Val Ile Leu Asn Cys Ser Phe Ser
            180                 185                 190 cgc cct gac cgc cca gcc tct gtg cat tgg ttc cgg aac cgg ggc cag     624
Arg Pro Asp Arg Pro Ala Ser Val His Trp Phe Arg Asn Arg Gly Gln
        195                 200                 205 ggc cga gtc cct gtc cgg gag tcc ccc cat cac cac tta gcg gaa agc     672
Gly Arg Val Pro Val Arg Glu Ser Pro His His His Leu Ala Glu Ser
    210                 215                 220 ttc ctc ttc ctg ccc caa gtc agc ccc atg gac tct ggg ccc tgg ggc     720
Phe Leu Phe Leu Pro Gln Val Ser Pro Met Asp Ser Gly Pro Trp Gly
225                 230                 235                 240 tgc atc ctc acc tac aga gat ggc ttc aac gtc tcc atc atg tat aac     768
Cys Ile Leu Thr Tyr Arg Asp Gly Phe Asn Val Ser Ile Met Tyr Asn
                245                 250                 255 ctc act gtt ctg ggt ctg gag ccc cca act ccc ttg aca gtg tac gct     816
Leu Thr Val Leu Gly Leu Glu Pro Pro Thr Pro Leu Thr Val Tyr Ala
            260                 265                 270 gga gca ggt tcc agg gtg ggg ctg ccc tgc cgc ctg cct gct ggt gtg     864
Gly Ala Gly Ser Arg Val Gly Leu Pro Cys Arg Leu Pro Ala Gly Val
        275                 280                 285 ggg acc cgg tct ttc ctc act gcc aag tgg act cct cct ggg gga ggc     912
Gly Thr Arg Ser Phe Leu Thr Ala Lys Trp Thr Pro Pro Gly Gly Gly
    290                 295                 300 cct gac ctc ctg gtg act gga gac aat ggc gac ttt acc ctt cga cta     960
Pro Asp Leu Leu Val Thr Gly Asp Asn Gly Asp Phe Thr Leu Arg Leu
305                 310                 315                 320 gag gat gtg agc cag gcc cag gct ggg acc tac acc tgc cat atc cat    1008
Glu Asp Val Ser Gln Ala Gln Ala Gly Thr Tyr Thr Cys His Ile His
                325                 330                 335 ctg cag gaa cag cag ctc aat gcc act gtc aca ttg gca atc atc aca    1056
Leu Gln Glu Gln Gln Leu Asn Ala Thr Val Thr Leu Ala Ile Ile Thr
            340                 345                 350 gtg act ccc aaa tcc ttt ggg tca cct gga tcc ctg ggg aag ctg ctt    1104
Val Thr Pro Lys Ser Phe Gly Ser Pro Gly Ser Leu Gly Lys Leu Leu
        355                 360                 365 tgt gag gtg act cca gta tct gga caa gaa cgc ttt gtg tgg agc tct    1152
Cys Glu Val Thr Pro Val Ser Gly Gln Glu Arg Phe Val Trp Ser Ser
    370                 375                 380 ctg gac acc cca tcc cag agg agt ttc tca gga cct tgg ctg gag gca    1200
Leu Asp Thr Pro Ser Gln Arg Ser Phe Ser Gly Pro Trp Leu Glu Ala
```

```
                385                 390                 395                 400
cag gag gcc cag ctc ctt tcc cag cct tgg caa tgc cag ctg tac cag         1248
Gln Glu Ala Gln Leu Leu Ser Gln Pro Trp Gln Cys Gln Leu Tyr Gln
                    405                 410                 415 ggg gag agg ctt ctt gga gca gca gtg tac ttc aca gag ctg tct agc         1296
Gly Glu Arg Leu Leu Gly Ala Ala Val Tyr Phe Thr Glu Leu Ser Ser
            420                 425                 430 cca ggt gcc caa cgc tct ggg aga gcc cca ggt gcc ctc cca gca ggc         1344
Pro Gly Ala Gln Arg Ser Gly Arg Ala Pro Gly Ala Leu Pro Ala Gly
                    435                 440                 445 cac ctc ctg ctg ttt ctc atc ctt ggt gtc ctt tct ctg ctc ctt ttg         1392
His Leu Leu Leu Phe Leu Ile Leu Gly Val Leu Ser Leu Leu Leu Leu
            450                 455                 460 gtg act gga gcc ttt ggc ttt cac ctt tgg aga aga cag tgg cga cca         1440
Val Thr Gly Ala Phe Gly Phe His Leu Trp Arg Arg Gln Trp Arg Pro
465                 470                 475                 480 aga cga ttt tct gcc tta gag caa ggg att cac cct ccg cag gct cag         1488
Arg Arg Phe Ser Ala Leu Glu Gln Gly Ile His Pro Pro Gln Ala Gln
                    485                 490                 495 agc aag ata gag gag ctg gag caa gaa ccg gag ccg gag ccg gag ccg         1536
Ser Lys Ile Glu Glu Leu Glu Gln Glu Pro Glu Pro Glu Pro Glu Pro
            500                 505                 510 gaa ccg gag ccc gag ccc gag ccc gag ccg gag cag ctc                     1575
Glu Pro Glu Pro Glu Pro Glu Pro Glu Pro Glu Gln Leu
                515                 520                 525

<210> SEQ ID NO 86
<211> LENGTH: 525
<212> TYPE: PRT
<213> ORGANISM: Homo sapiens

<400> SEQUENCE: 86

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160

Arg Leu Arg Leu Arg Leu Gly Gln Ala Ser Met Thr Ala Ser Pro Pro
                165                 170                 175

Gly Ser Leu Arg Ala Ser Asp Trp Val Ile Leu Asn Cys Ser Phe Ser
            180                 185                 190

Arg Pro Asp Arg Pro Ala Ser Val His Trp Phe Arg Asn Arg Gly Gln
```

```
                195                 200                 205
Gly Arg Val Pro Val Arg Glu Ser Pro His His Leu Ala Glu Ser
210                 215                 220

Phe Leu Phe Leu Pro Gln Val Ser Pro Met Asp Ser Gly Pro Trp Gly
225                 230                 235                 240

Cys Ile Leu Thr Tyr Arg Asp Gly Phe Asn Val Ser Ile Met Tyr Asn
                245                 250                 255

Leu Thr Val Leu Gly Leu Glu Pro Pro Thr Pro Leu Thr Val Tyr Ala
                260                 265                 270

Gly Ala Gly Ser Arg Val Gly Leu Pro Cys Arg Leu Pro Ala Gly Val
                275                 280                 285

Gly Thr Arg Ser Phe Leu Thr Ala Lys Trp Thr Pro Pro Gly Gly Gly
                290                 295                 300

Pro Asp Leu Leu Val Thr Gly Asp Asn Gly Asp Phe Thr Leu Arg Leu
305                 310                 315                 320

Glu Asp Val Ser Gln Ala Gln Ala Gly Thr Tyr Thr Cys His Ile His
                325                 330                 335

Leu Gln Glu Gln Gln Leu Asn Ala Thr Val Thr Leu Ala Ile Ile Thr
                340                 345                 350

Val Thr Pro Lys Ser Phe Gly Ser Pro Gly Ser Leu Gly Lys Leu Leu
                355                 360                 365

Cys Glu Val Thr Pro Val Ser Gly Gln Glu Arg Phe Val Trp Ser Ser
370                 375                 380

Leu Asp Thr Pro Ser Gln Arg Ser Phe Ser Gly Pro Trp Leu Glu Ala
385                 390                 395                 400

Gln Glu Ala Gln Leu Leu Ser Gln Pro Trp Gln Cys Gln Leu Tyr Gln
                405                 410                 415

Gly Glu Arg Leu Leu Gly Ala Ala Val Tyr Phe Thr Glu Leu Ser Ser
                420                 425                 430

Pro Gly Ala Gln Arg Ser Gly Arg Ala Pro Gly Ala Leu Pro Ala Gly
                435                 440                 445

His Leu Leu Leu Phe Leu Ile Leu Gly Val Leu Ser Leu Leu Leu Leu
450                 455                 460

Val Thr Gly Ala Phe Gly Phe His Leu Trp Arg Arg Gln Trp Arg Pro
465                 470                 475                 480

Arg Arg Phe Ser Ala Leu Glu Gln Gly Ile His Pro Pro Gln Ala Gln
                485                 490                 495

Ser Lys Ile Glu Glu Leu Glu Gln Glu Pro Glu Pro Glu Pro Glu Pro
                500                 505                 510

Glu Pro Glu Pro Glu Pro Glu Pro Glu Pro Gln Leu
                515                 520                 525

<210> SEQ ID NO 87
<211> LENGTH: 8
<212> TYPE: PRT
<213> ORGANISM: Artificial sequence
<220> FEATURE:
<223> OTHER INFORMATION: Synthetic construct

<400> SEQUENCE: 87

Asp Tyr Lys Asp Asp Asp Asp Lys
1               5
```